US011253521B2

(12) United States Patent
Gahman et al.

(10) Patent No.: US 11,253,521 B2
(45) Date of Patent: Feb. 22, 2022

(54) 3-HYDROXY-QUINAZOLINE-2,4-DIONE DERIVATIVES AND THEIR USE AS NUCLEASE MODULATORS

(71) Applicant: Ludwig Institute for Cancer Research Ltd, Zurich (CH)

(72) Inventors: Timothy Gahman, Encinitas, CA (US); Andrew Shiau, San Diego, CA (US); Richard Kolodner, La Jolla, CA (US)

(73) Assignee: Ludwig Institute for Cancer Research Ltd, Zurich (CH)

( * ) Notice: Subject to any disclaimer, the term of this patent is extended or adjusted under 35 U.S.C. 154(b) by 796 days.

(21) Appl. No.: 15/762,527

(22) PCT Filed: Sep. 26, 2016

(86) PCT No.: PCT/IB2016/001473
§ 371 (c)(1),
(2) Date: Mar. 22, 2018

(87) PCT Pub. No.: WO2017/051251
PCT Pub. Date: Mar. 30, 2017

(65) Prior Publication Data
US 2020/0237763 A1 Jul. 30, 2020

Related U.S. Application Data

(60) Provisional application No. 62/233,110, filed on Sep. 25, 2015.

(51) Int. Cl.
| | |
|---|---|
| *A61K 31/519* | (2006.01) |
| *A61K 31/517* | (2006.01) |
| *A61K 45/06* | (2006.01) |
| *C07D 239/96* | (2006.01) |
| *C07D 403/12* | (2006.01) |
| *C07D 405/12* | (2006.01) |
| *C07D 409/12* | (2006.01) |
| *C07D 413/12* | (2006.01) |
| *C07D 417/12* | (2006.01) |
| *C07D 471/04* | (2006.01) |

(52) U.S. Cl.
CPC .......... *A61K 31/519* (2013.01); *A61K 31/517* (2013.01); *A61K 45/06* (2013.01); *C07D 239/96* (2013.01); *C07D 403/12* (2013.01); *C07D 405/12* (2013.01); *C07D 409/12* (2013.01); *C07D 413/12* (2013.01); *C07D 417/12* (2013.01); *C07D 471/04* (2013.01)

(58) Field of Classification Search
None
See application file for complete search history.

(56) References Cited

FOREIGN PATENT DOCUMENTS

| | | |
|---|---|---|
| CN | 105 669 653 A | 6/2016 |
| EP | 0 316 630 A1 | 5/1989 |
| WO | WO-99/21840 A1 | 5/1999 |
| WO | WO-01/70737 A2 | 9/2001 |
| WO | WO-01/70737 A3 | 9/2001 |
| WO | WO-2006/014647 A2 | 2/2006 |
| WO | WO-2006/014647 A3 | 2/2006 |
| WO | WO-2012/004731 A1 | 1/2012 |
| WO | WO-2012/047993 A2 | 4/2012 |
| WO | WO-2012/047993 A3 | 4/2012 |

OTHER PUBLICATIONS

Hurd et al., Journal of Organic Chemistry (1954), 19(7), pp. 1140-1149.*
Tserng et al., Journal of Heterocyclic Chemistry (1972), 9(6), pp. 1433-1435.*
Database Accession No. 1988:204459, "Novel 2-subsituted aminonicotinhydroxamic acids," 2 pages.
Database Accession No. 2015:1253756, "Transformation of benzoxazinone derivatives to some interesting heterocyclic compounds with expected biological activity," 1 page.
Database Accession No. 1991:164266, "Preparation of 3-substituted 4-imino-1,2,3,4-tetrahydroquinazoline-2-thiones," 2 pages.
Database Accession No. 2016:965098, "Preparation of heterocycle fused N-hydroxypyrimidinedione derivatives as antiviral agents,", 15 pages.
International Search Report dated Jan. 4, 2017, for PCT Application No. PCT/IB2016/001473, filed Sep. 26, 2016, 10 pages.
Chapman, T.M. et al. (Oct. 1, 2015, e-published Aug. 14, 2015). "N-Hydroxyimides and hydroxypyrimidinones as inhibitors of the DNA repair complex ERCC1-XPF," Bioorg Med Chem Lett 25(19):4104-4108.
Cianci, C. et al. (1996). "Identification of N-hydroxamic acid and N-hydroxy-imide compounds that inhibit the influenza virus polymerase," *Antiviral Chemistry & Chemotherapy* 7(6):353-360.
Colotta, V. et al. (May 3, 2004). "3-hydroxy-quinazoline-2,4-dione as a useful scaffold to obtain selective Gly/NMDA and AMPA receptor antagonists," *Bioorg Med Chem Lett* 14(9):2345-2349.

(Continued)

*Primary Examiner* — Brian J Davis
(74) *Attorney, Agent, or Firm* — Irina E. Britva; Mintz, Levin, Cohn, Ferris, Glovsky and Popeo, P.C.

(57) ABSTRACT

Described inter alia are compounds according to formula (I): or a pharmaceutically acceptable salt thereof, and uses in methods for the modulation of flap endonuclease 1 (FEN1), Xeroderma Pigmentosum Complementation Group G protein (XPG), Exonuclease 1 (EXO1) and/or GEN1.

20 Claims, 16 Drawing Sheets

(56) References Cited

OTHER PUBLICATIONS

Colotta, V. et al. (Oct. 5, 2006). "Structural investigation of the 7-chloro-3-hydroxy-1H-quinazoline-2,4-dione scaffold to obtain AMPA and kainate receptor selective antagonists. Synthesis, pharmacological, and molecular modeling studies," *J Med Chem* 49(20):6015-6026.

Colotta, V. et al. (Aug. 2012, e-published Jun. 4, 2012). "3-Hydroxy-1H-quinazoline-2,4-dione derivatives as new antagonists at ionotropic glutamate receptors: molecular modeling and pharmacological studies," *Eur J Med Chem* 54:470-482.

Exell, J.C. et al. (Oct. 2016, e-published Aug. 15, 2016). "Cellularly active N-hydroxyurea FEN1 inhibitors block substrate entry to the active site," *Nat Chem Biol* 12(10):815-821.

Ghoneim, K.E. et al. (1987). "Novel 2-substitued aminocotinhydroxamic acids" *Egyptian Journal of Pharmaceutical Sciences* 28(1-4):9-16.

Ji, F. et al. (Aug. 14, 2014, e-published Jun. 27, 2014). "One-pot synthesis of 2-amino-4(3H)-quinazolinones via ring-opening of isatoic anhydride and palladium-catalyzed oxidative isocyanide-insertion," *Org Biomol Chem* 12(30):5766-5772.

Khokhlov, P.S. et al. (Jan. 2011). "3-Hydroxy- and 3-alkoxy-2-sulfanylquinazolin-4(3H)-ones:synthesis and reactions with alkylating and acylating agents," *Russian Chemical Bulletin, International Edition* 60(1):153-156.

Lansdon, E.B. et al. (Jun. 2011, e-published Apr. 4, 2011). "Structural and binding analysis of pyrimidinol carboxylic acid and N-hydroxy quinazolinedione HIV-1 RNase H inhibitors," *Antimicrob Agents Chemother* 55(6):2905-2915.

Li, Y. et al. (Aug. 31, 2015, e-Collection Oct. 8, 2015). "Thioxo-dihydroquinazolin-one Compounds as Novel Inhibitors of Myeloperoxidase," *ACS Med Chem Lett* 6(10):1047-1052.

Marzouk, M.I. et al. (2015). "Transformation of Benzoxainone Derivatives to Some Interesting Heterocyclic Compounds with Expected Biological Activity," *Heterocycles* 91(7):1399-1416.

Tran, T.P. et al. (Sep. 6, 2004). "Synthesis and structural-activity relationships of 3-hydroxyquinazoline-2,4-dione antibacterial agents," *Bioorg Med Chem Lett* 14(17):4405-4409.

Tserng, K.-Y. et al. (Dec. 1972). "3-hydroxypyridopyrimidine-2,4(1H,3H)diones," *Journal of Heterocyclic Chemistry* 9(6):1433-1435.

Tumey, L.N et al. (Jan. 17, 2005). "The identification and optimization of a N-hydroxy urea series of flap endonuclease 1 inhibitors," *Bioorg Med Chem Lett* 15(2):277-281.

Written Opinion dated Jan. 4, 2017, for PCT Application No. PCT/IB2016/001473, filed Sep. 26, 2016, 10 pages.

* cited by examiner

| | | | |
|---|---|---|---|
| FEN1 | +++ | + | ++ | ++ |
| EXO1 | + | + | + | - |
| XPG | ++ | + | ++ | - |
| GEN1 | + | + | + | - |

| | | | |
|---|---|---|---|
| FEN1 | ++ | + | ++ | +++ |
| EXO1 | - | - | - | +++ |
| XPG | - | - | - | ++ |
| GEN1 | - | - | - | ++ |

| | | | |
|---|---|---|---|
| FEN1 | + | +++ | +++ | +++ |
| EXO1 | - | - | - | +++ |
| XPG | - | - | - | ++ |
| GEN1 | - | - | - | ++ |

| | | | |
|---|---|---|---|
| FEN1 | +++ | ++ | +++ | +++ |
| EXO1 | - | - | - | - |
| XPG | - | - | - | - |
| GEN1 | - | - | - | - |

| | | | |
|---|---|---|---|
| FEN1 | ++ | ++ | +++ | +++ |
| EXO1 | - | - | - | - |
| XPG | - | - | - | - |
| GEN1 | - | - | - | - |

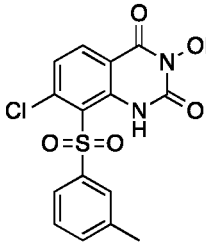

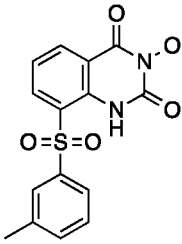

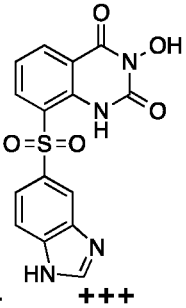

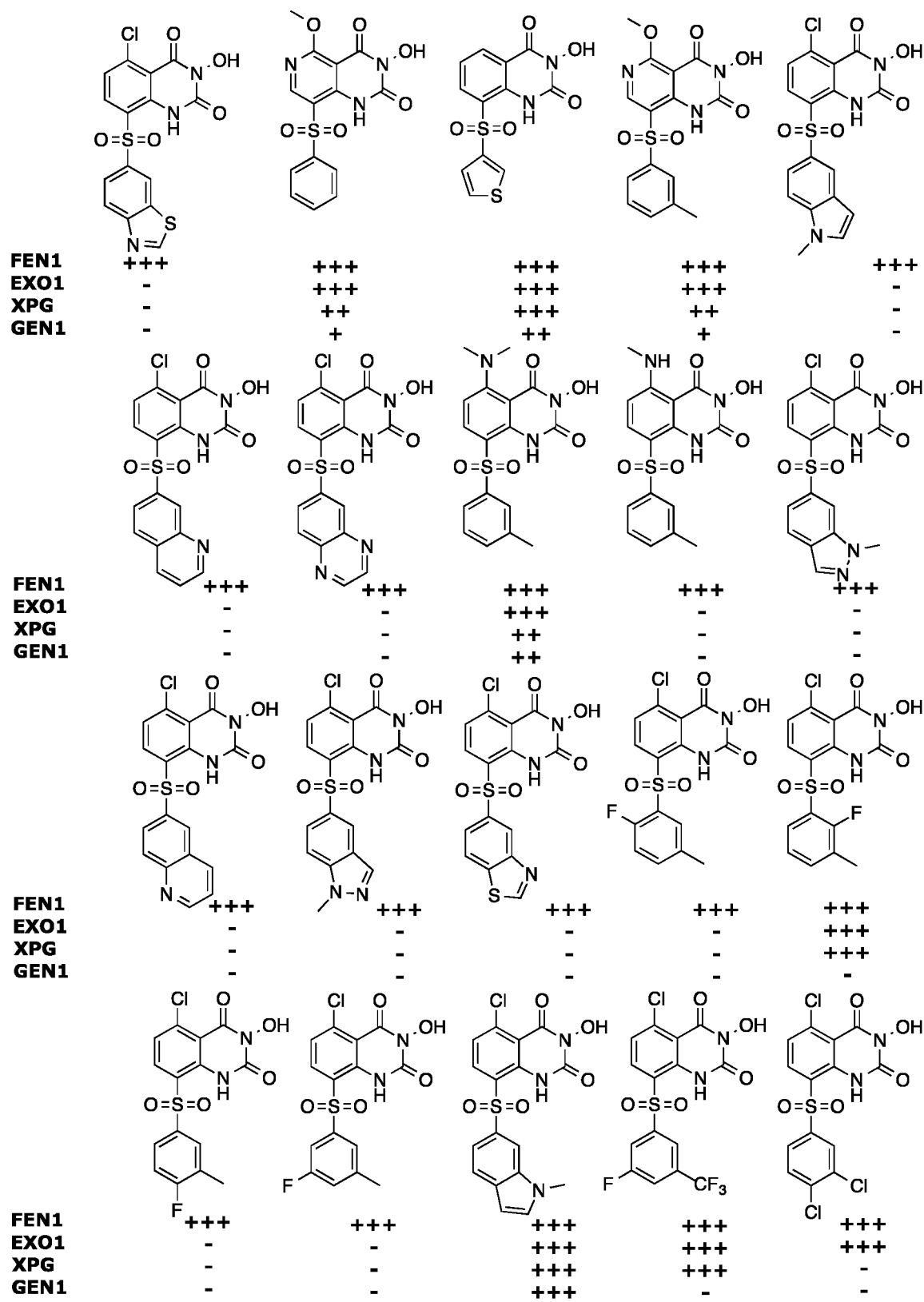

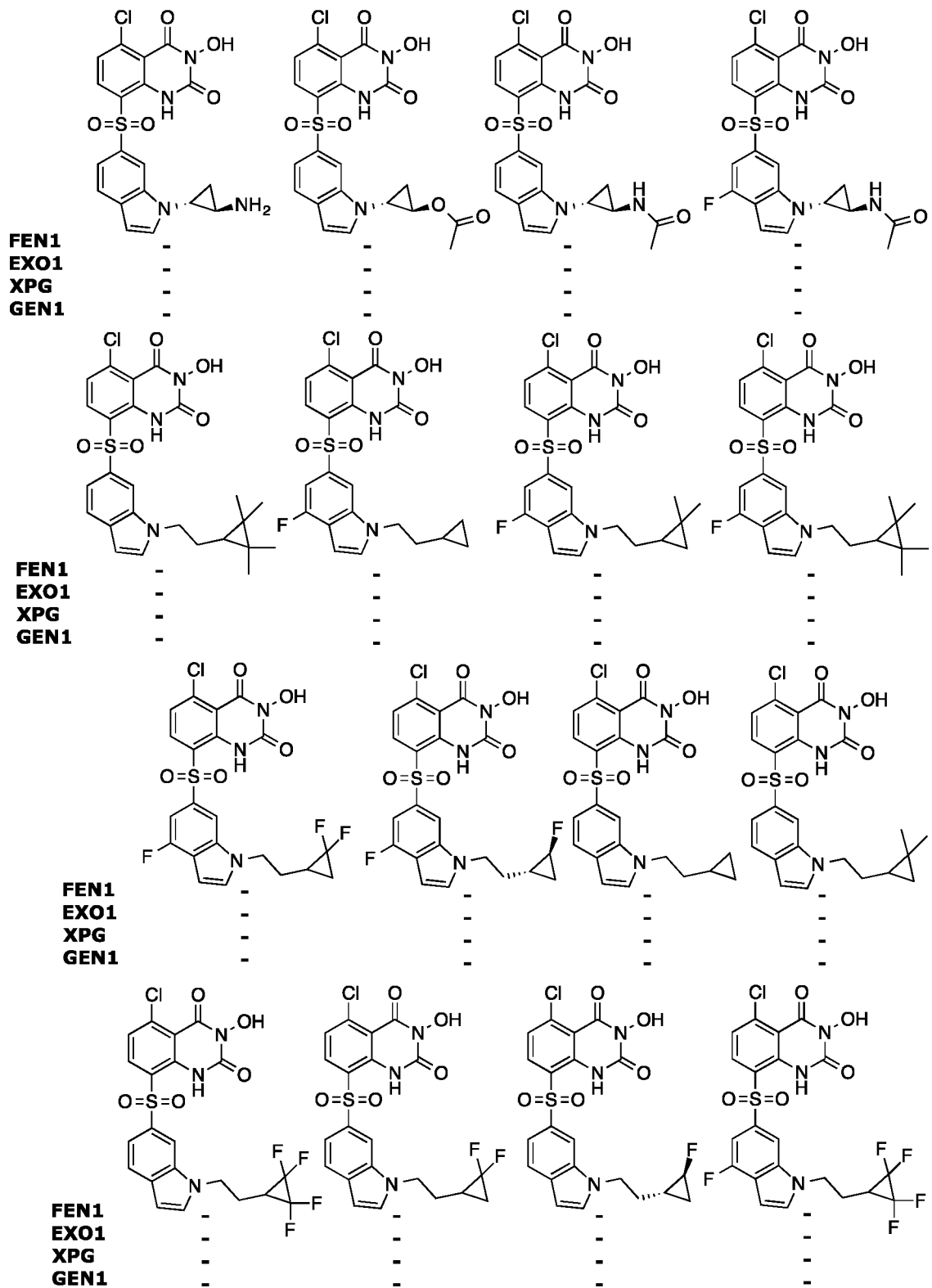

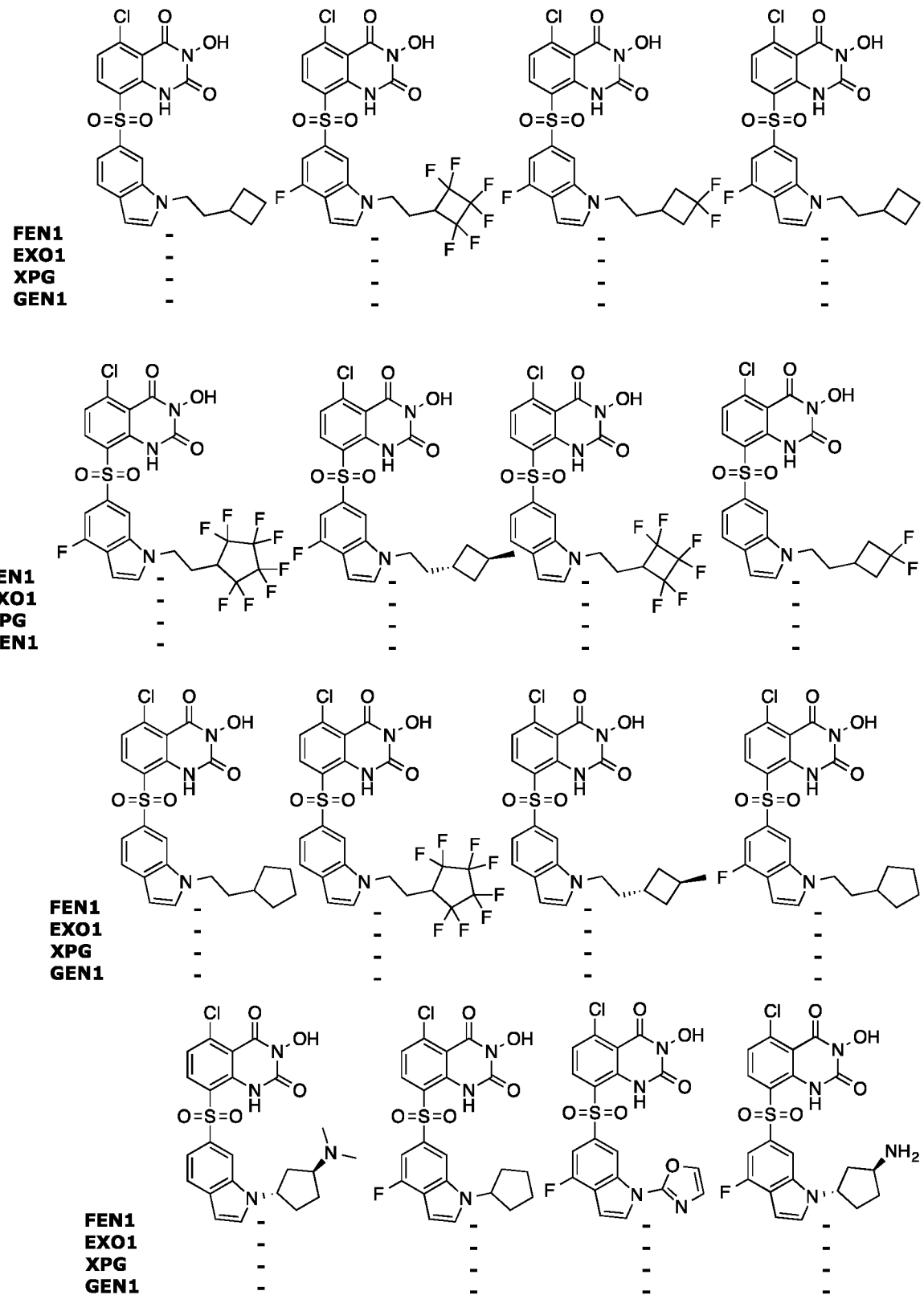

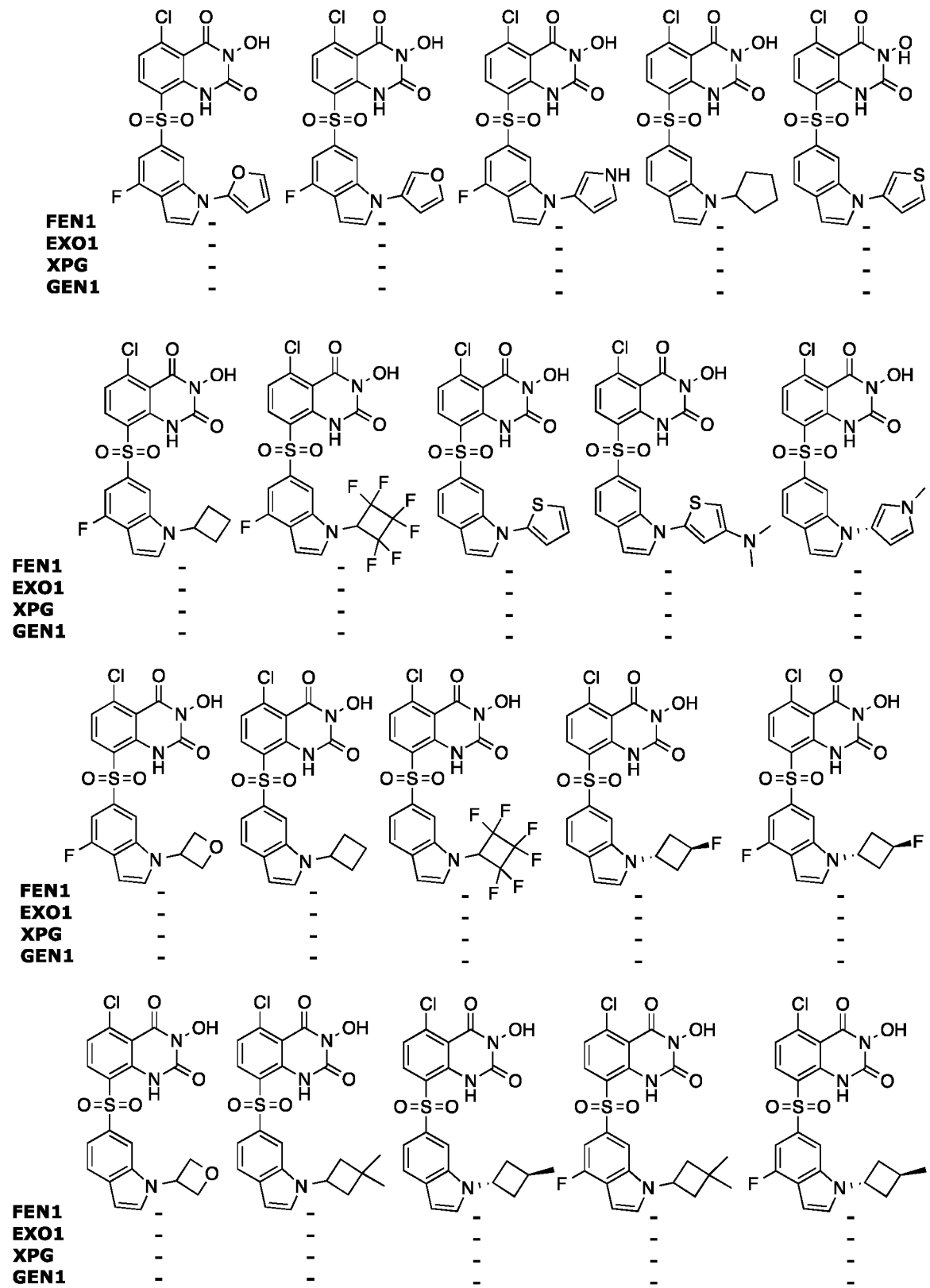

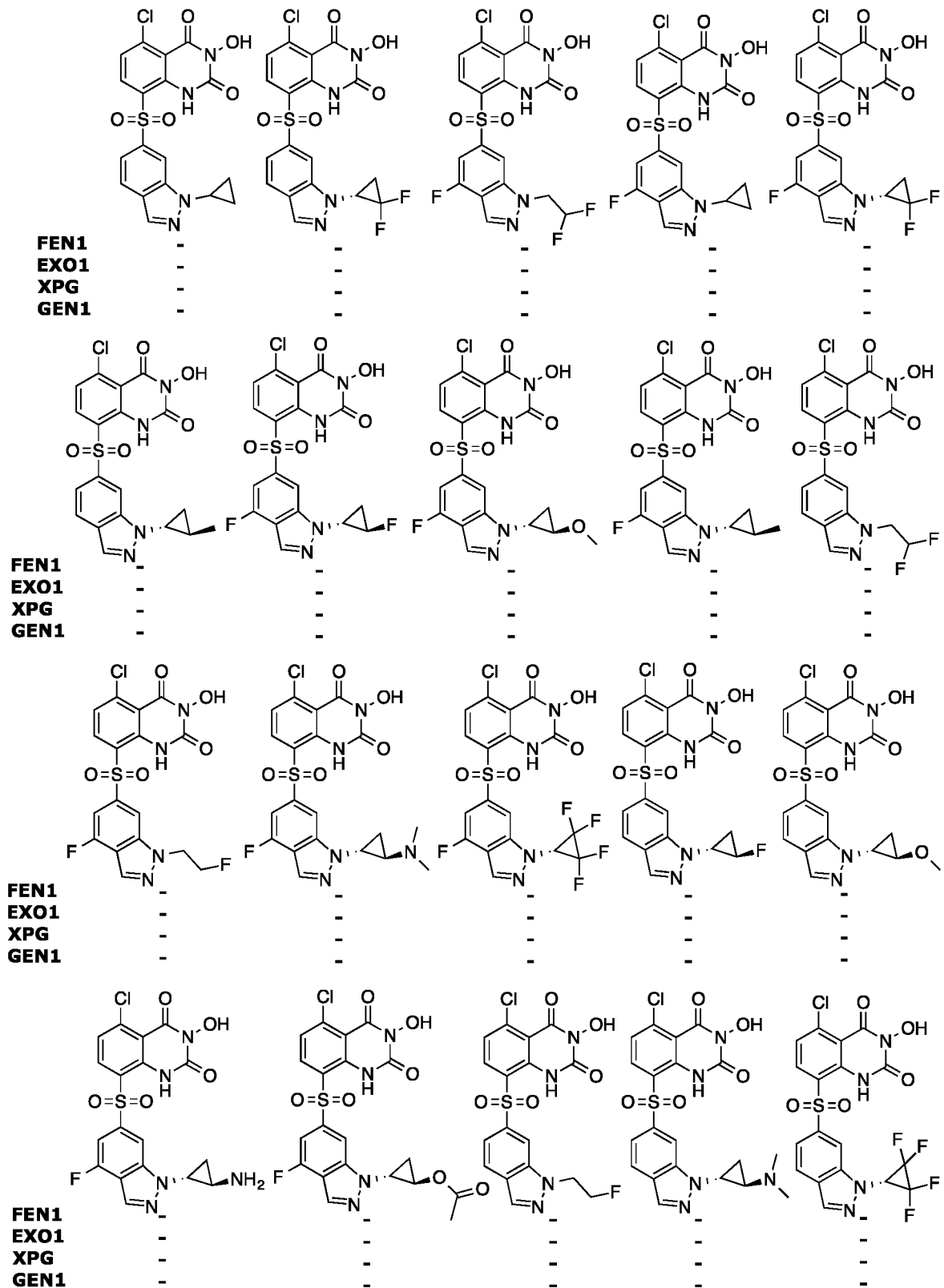

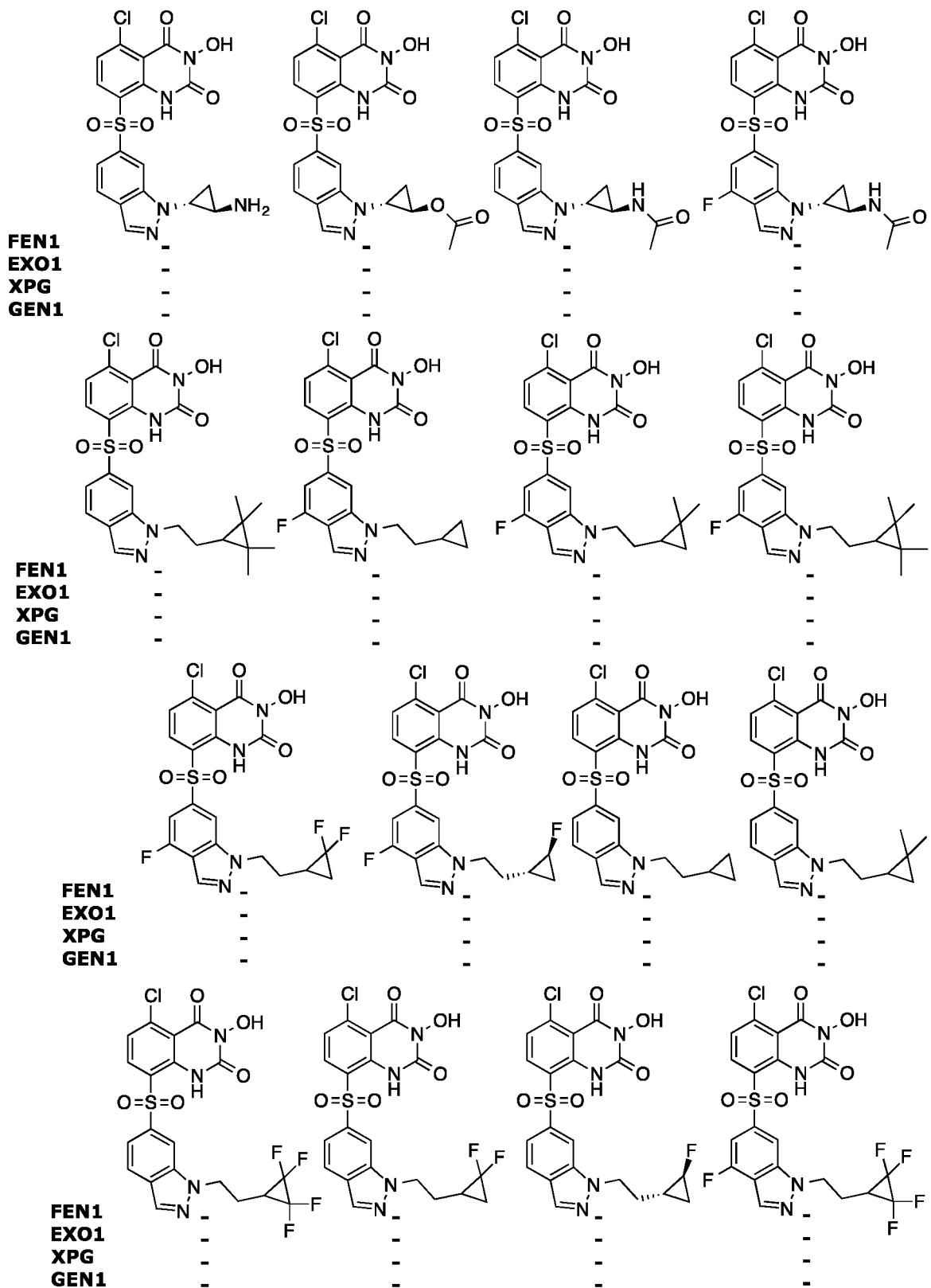

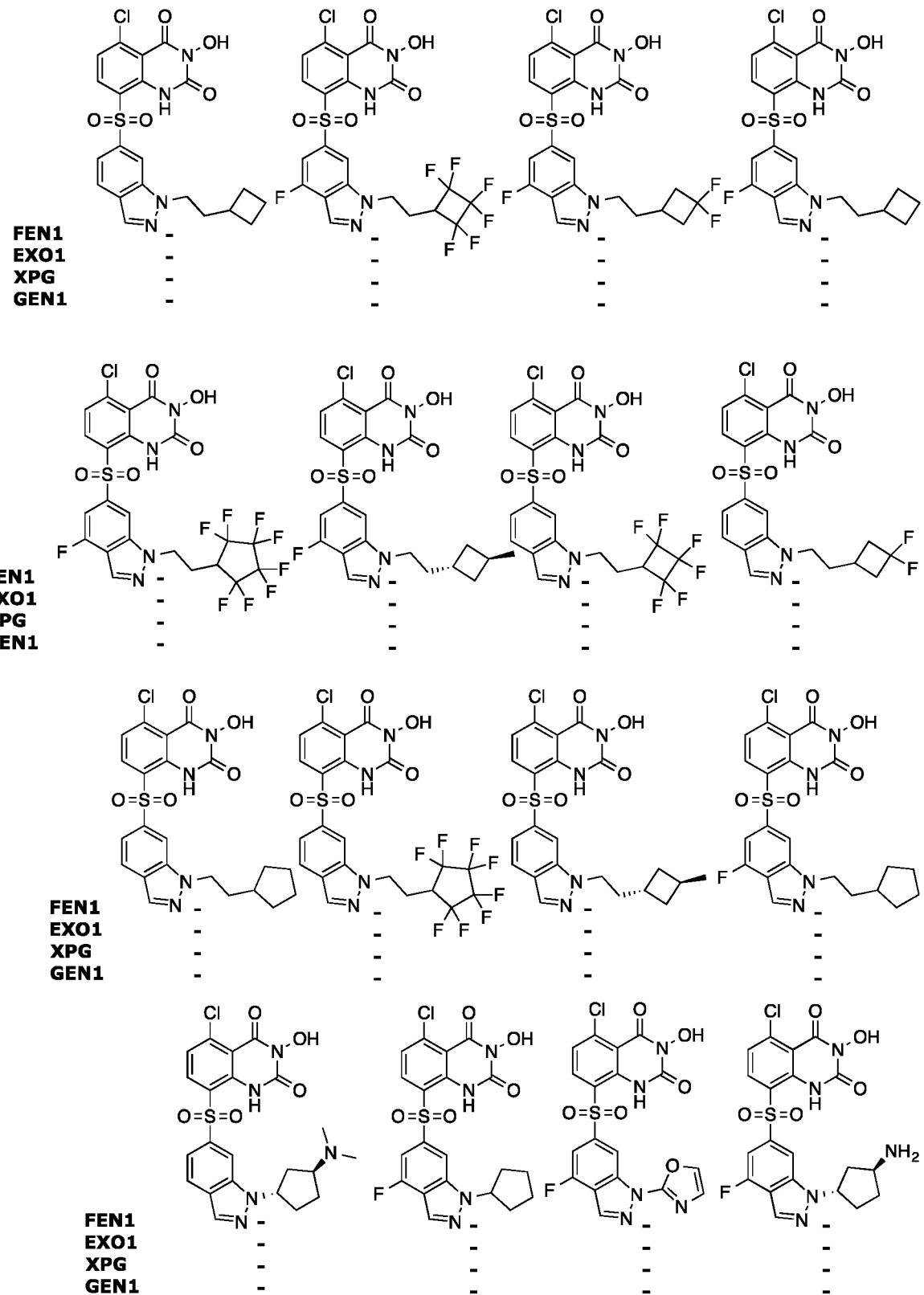

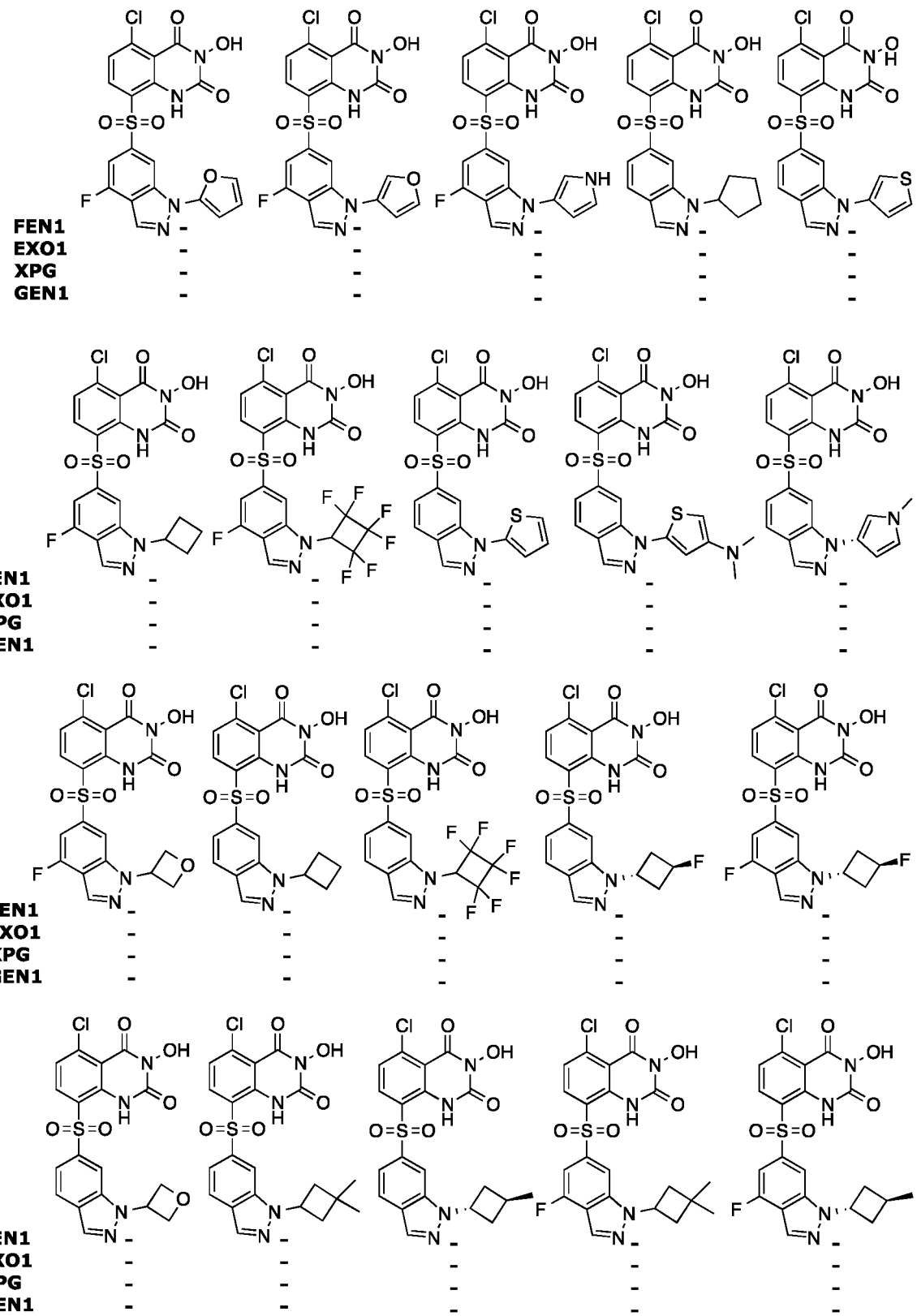

| | | | | |
|---|---|---|---|---|
| FEN1 +++ | +++ | +++ | +++ | +++ |
| EXO1 +++ | +++ | +++ | +++ | +++ |
| XPG +++ | +++ | +++ | +++ | +++ |
| GEN1 − | − | +++ | +++ | +++ |

| | | | | |
|---|---|---|---|---|
| FEN1 +++ | +++ | +++ | +++ | +++ |
| EXO1 +++ | − | − | − | +++ |
| XPG +++ | − | − | − | +++ |
| GEN1 − | − | − | − | − |

| | | | | |
|---|---|---|---|---|
| FEN1 +++ | +++ | +++ | +++ | +++ |
| EXO1 +++ | − | − | − | − |
| XPG +++ | − | − | − | − |
| GEN1 +++ | − | − | − | − |

| | | | | |
|---|---|---|---|---|
| FEN1 +++ | +++ | +++ | +++ | +++ |
| EXO1 − | − | − | − | − |
| XPG − | − | − | − | − |
| GEN1 − | − | − | − | − |

|          | Structure 1 | Structure 2 | Structure 3 | Structure 4 | Structure 5 |
|----------|-------------|-------------|-------------|-------------|-------------|
| FEN1     | +++         | +++         | +++         | +++         | +++         |
| EXO1     | -           | -           | -           | +++         | -           |
| XPG      | -           | -           | -           | -           | -           |
| GEN1     | -           | -           | -           | -           | -           |

|          | Structure 6 | Structure 7 | Structure 8 | Structure 9 | Structure 10 |
|----------|-------------|-------------|-------------|-------------|--------------|
| FEN1     | +++         | +++         | +++         | +++         | +++          |
| EXO1     | +++         | +++         | ++          | +++         | +++          |
| XPG      | +++         | -           | +++         | -           | ++           |
| GEN1     | -           | -           | +++         | -           | ++           |

|          | Structure 11 | Structure 12 | Structure 13 | Structure 14 | Structure 15 |
|----------|--------------|--------------|--------------|--------------|--------------|
| FEN1     | +++          | +++          | +++          | +++          | +++          |
| EXO1     | +++          | +++          | +++          | -            | -            |
| XPG      | +++          | -            | ++           | -            | -            |
| GEN1     | ++           | -            | +++          | -            | -            |

|          | Structure 16 | Structure 17 | Structure 18 | Structure 19 | Structure 20 |
|----------|--------------|--------------|--------------|--------------|--------------|
| FEN1     | +++          | +++          | +++          | +++          | -            |
| EXO1     | -            | -            | -            | -            | -            |
| XPG      | -            | -            | -            | -            | -            |
| GEN1     | -            | -            | -            | -            | -            |

3-HYDROXY-QUINAZOLINE-2,4-DIONE DERIVATIVES AND THEIR USE AS NUCLEASE MODULATORS

CROSS-REFERENCES TO RELATED APPLICATIONS

This application is a national stage application filed under 35 U.S.C. § 371, of International Patent Application No. PCT/IB2016/001473, filed Sep. 26, 2016, which claims the benefit of U.S. Provisional Application No. 62/233,110, filed Sep. 25, 2015, all of which are incorporated herein by reference in their entireties and for all purposes.

BACKGROUND OF THE INVENTION

Mutation in oncogenes controlling the promotion of cell growth or in antioncogene causing the suppression of cell proliferation often leads to cancer. Nucleases may play a role in causing such mutation directly or by causing rearrangement in chromosomes. Cancer may be related to fragile sites in chromosomes possibly caused by transposable elements.

The occurrence of cancer is frequently associated with chromosomal rearrangements and mutations and nucleases are known to participate in events leading to chromosomal rearrangements and mutations. Such chromosomal rearrangements and mutations have been shown to cause dysfunctional genes in humans.

Flap structure-specific endonuclease 1 (FEN1) plays important roles in DNA replication and base excision repair (BER). Further, FEN1 is overexpressed in cancers such as breast cancer, prostate cancer, stomach cancer, pancreatic cancer, lung cancer, and neuroblastomas.

Xeroderma Pigmentosum Complementation Group G (XPG) protein is an endonuclease, which repairs DNA damage caused by ultraviolet light. The XPG protein repairs DNA by a process called nucleotide excision repair. XPG has a direct role in making one of the incisions required to excise a damaged oligonucleotide, by cleaving 3' to DNA damage during nucleotide excision repair. Mutations in the protein commonly cause Xeroderma Pigmentosum, which often lead to skin cancer.

Exonuclease 1 (EXO1) is an exonuclease gene that participates in the human mismatch repair (MMR) system. Genetic disorders in the MMR system result in the absence of DNA MMR function, resulting in an increased frequency of spontaneous mutations, which may give rise to the steady accumulation of oncogenes and tumor suppressors, which eventually contribute to tumorigenesis.

Four-way DNA intermediates, also known as Holliday junctions (HJ), are formed during homologous recombination and DNA repair, and their resolution is essential for chromosome segregation at meiosis and the repair of stalled/collapsed replication forks in mitotic cells. All organisms possess nucleases that promote HJ resolution by the introduction of symmetrically related nicks in two strands at, or close to, the junction point. GEN1, a nuclease and member of the Rad2/XPG nuclease family, promotes HJ resolution.

Provided herein are solutions to these and other problems in the art.

BRIEF SUMMARY OF THE INVENTION

Herein are provided, inter alia, compounds capable of modulating the level of activity of nucleases such as Flap structure-specific endonuclease 1 (FEN1), Xeroderma Pigmentosum Complementation Group G (XPG) protein, Exonuclease 1 (EXO1) and/or GEN1 and methods of using the same.

In an aspect is provided a compound having the formula (I):

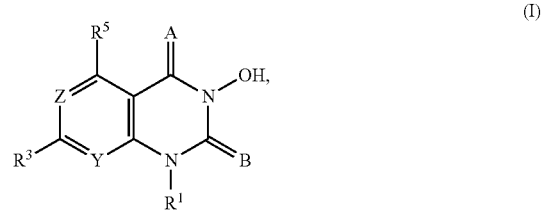

or a pharmaceutically acceptable salt thereof.

A is independently O, S, or $NR^A$. B is independently O, S, or $NR^B$. Y is independently $CR^2$ or N. Z is independently $CR^4$ or N. $R^1$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, $-CX^2_3$, $-CHX^2_2$, $-CH_2X^2$, $-CN$, $-SO_{n2}R^9$, $-SO_{v2}NR^6R^7$, $-NHC(O)NR^6R^7$, $-N(O)_{m2}$, $-NR^6R^7$, $-C(O)R^8$, $-C(O)-OR^8$, $-C(O)NR^6R^7$, $-OR^9$, $-NR^6SO_2R^9$, $-NR^6C(O)R^8$, $-NR^6C(O)OR^8$, $-NR^6OR^8$, $-OCX^2_3$, $-OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, $-CX^3_3$, $-CHX^3_2$, $-CH_2X^3$, $-CN$, $-SO_{n3}R^{13}$, $-SO_{v3}NR^{10}R^{11}$, $-NHC(O)NR^{10}R^{11}$, $-N(O)_{m3}$, $-NR^{10}R^{11}$, $-C(O)R^{12}$, $-C(O)-OR^{12}$, $-OR^{13}$, $-NR^{10}SO_2R^{13}$, $-NR^{10}C(O)R^{12}$, $-NR^{10}C(O)OR^{12}$, $-NR^{10}OR^{12}$, $-OCX^3_3$, $-OCHX^3_2$, substituted or unsubstituted alkyl, substituted or unsubstituted heteroalkyl, substituted or unsubstituted cycloalkyl, substituted or unsubstituted aryl, or substituted or unsubstituted heteroaryl. $R^4$ is independently hydrogen, halogen, $-CX^4_3$, $-CHX^4_2$, $-CH_2X^4$, $-CN$, $-SO_{n4}R^{17}$, $-SO_{v4}NR^{14}R^{15}$, $-NHC(O)NR^{14}R^{15}$, $-N(O)_{m4}$, $-NR^{14}R^{15}$, $-C(O)R^{16}$, $-C(O)-OR^{16}$, $-C(O)NR^{14}R^{15}$, $-OR^{17}$, $-NR^{14}SO_2R^{17}$, $-NR^{14}C(O)R^{16}$, $-NR^{14}C(O)OR^{16}$, $-NR^{14}OR^{16}$, $-OCX^4_3$, $-OCHX^4_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is independently hydrogen, halogen, $-CX^5_3$, $-CHX^5_2$, $-CH_2X^5$, $-CN$, $-SO_{n5}R^{21}$, $-SO_{v5}NR^{18}R^{19}$, $-NHC(O)NR^{18}R^{19}$, $-N(O)_{m5}$, $-NR^{18}R^{19}$, $-C(O)R^{20}$, $-C(O)-OR^{20}$, $-C(O)NR^{18}R^{19}$, $-OR^{21}$, $-NR^{18}S O_2R^{21}$, $-NR^{18}C(O)R^{20}$, $-NR^{18}C(O)OR^{20}$, $-NR^{18}OR^{20}$, $-OCX^5_3$, $-OCHX^5_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^A$, $R^B$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ and $R^7$, $R^{10}$ and $R^{11}$, $R^{14}$ and $R^{15}$, and $R^{18}$ and $R^{19}$ substituents bonded to the same nitrogen atom may optionally be joined to form a substituted or unsubstituted heterocycloalkyl or substituted or unsubstituted heteroaryl. Each X, $X^2$, $X^3$, $X^4$, and $X^5$ is independently —F, —Cl, —Br, or —I. Each m2, m3, m4, and m5 is independently an integer from 1 to 2. Each n2, n3, n4, and n5 is independently an integer from 0 to 3. Each v2, v3, v4, and v5 is independently an integer from 1 to 2.

In an aspect is provided a pharmaceutical composition including a compound described herein, or pharmaceutically acceptable salt thereof, and a pharmaceutically acceptable excipient.

In an aspect is provided a method of treating cancer including administering to a subject in need thereof an effective amount of a compound described herein.

In an aspect is provided a method of treating a disease associated with Flap structure-specific endonuclease 1 (FEN1) activity including administering to a subject in need thereof an effective amount of a compound described herein. In embodiments, the disease is associated with aberrant Flap structure-specific endonuclease 1 (FEN1) activity.

In an aspect is provided a method of treating a disease associated with Xeroderma Pigmentosum Complementation Group G (XPG) activity including administering to a subject in need thereof an effective amount of a compound described herein. In embodiments, the disease is associated with aberrant Xeroderma Pigmentosum Complementation Group G (XPG) activity.

In an aspect is provided a method of treating a disease associated with Exonuclease 1 (EXO1) activity including administering to a subject in need thereof an effective amount of a compound described herein. In embodiments, the disease is associated with aberrant Exonuclease 1 (EXO1) activity.

In an aspect is provided a method of treating a disease associated with GEN1 activity including administering to a subject in need thereof an effective amount of a compound described herein. In embodiments, the disease is associated with aberrant GEN1 activity.

In an aspect is provided a method of inhibiting Flap structure-specific endonuclease 1 (FEN1) activity including contacting the Flap structure-specific endonuclease 1 (FEN1) with a compound described herein. In embodiments, the Flap structure-specific endonuclease 1 (FEN1) is a human Flap structure-specific endonuclease 1 (FEN1).

In an aspect is provided a method of inhibiting Xeroderma Pigmentosum Complementation Group G (XPG) activity including contacting the Xeroderma Pigmentosum Complementation Group G (XPG) with a compound described herein. In embodiments, the Xeroderma Pigmentosum Complementation Group G (XPG) is a human Xeroderma Pigmentosum Complementation Group G (XPG).

In an aspect is provided a method of inhibiting Exonuclease 1 (EXO1) activity including contacting the Exonuclease 1 (EXO1) with a compound described herein. In embodiments, the Exonuclease 1 (EXO1) is a human Exonuclease 1 (EXO1).

In an aspect is provided a method of inhibiting GEN1 activity including contacting the GEN1 with a compound described herein. In embodiments, the GEN1 is a human GEN1.

BRIEF DESCRIPTION OF THE DRAWINGS

The FIGURE shows data for biochemical assays of certain compounds tested against FEN1, XPG, EXO1 and/or GEN1. The symbol "+++" indicates a value for the compound tested of less than 100 nM. The symbol "++" indicates a value for the compound tested of between 100 nm and 1 µM. The symbol "+" indicates a value for the compound tested of greater than 1 µM. The symbol "–" indicates the compound was not tested.

DETAILED DESCRIPTION OF THE INVENTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—, —S(O)—$CH_3$, —$CH_2$—$CH_2$—S(O)$_2$—$CH_3$, —CH=CH—O—$CH_3$, —Si($CH_3$)$_3$, —$CH_2$—

CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to eight optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. A 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⌇" denotes the point of attachment of a chemical moiety to the remainder of a molecule or chemical formula.

The term "oxo," as used herein, means an oxygen that is double bonded to a carbon atom.

The term "thio," as used herein, means a sulfur that is single bonded to carbon or to another sulfur.

The term "alkylarylene" as an arylene moiety covalently bonded to an alkylene moiety (also referred to herein as an alkylene linker). In embodiments, the alkylarylene group has the formula:

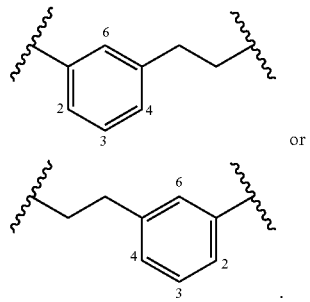

or

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_8$ alkyl or substituted or unsubstituted 2 to 5 membered heteroalkyl). In embodiments, the alkylarylene is unsubstituted.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C (O)NR"R'", —NR"C(O)$_2$R', —NR—C(NR'R"R'")=NR"", —NR—C(NR' R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —NR'SO$_2$R", —NR'C=(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O) CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C (O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C=(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one or more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:
- (A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
- (B) alkyl, heteroalkyl, cycloalkyl, heterocycloalkyl, aryl, and heteroaryl, substituted with at least one substituent selected from:
  - (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  - (ii) alkyl, heteroalkyl, cycloalkyl, heterocycloalkyl, aryl, and heteroaryl, substituted with at least one substituent selected from:
    - (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
    - (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds, generally recognized as stable by those skilled in the art, are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"$S_p$", "$S_t$", or "$S_n$" refers to a sulfide bridge having p, t, or n sulfurs (e.g. $S_2$ is —S—S—, $S_3$ is —S—S—S—, $S_4$ is —S—S—S—S—).

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

"Analog," or "analogue" is used in accordance with its plain and ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts," *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein include those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

An "Flap endonuclease 1 inhibitor" or "FEN1 compound" or "FEN1 inhibitor" refers to a compound (e.g. compounds described herein) that reduces the activity of Flap endonuclease 1 when compared to a control, such as absence of the compound or a compound with known inactivity. In embodiments, a wild type FEN1 protein is identified by NCBI Accession NP_004102. In embodiments, exemplary X-ray crystallographic structures for FEN1 are disclosed in PDB (Protein Data Bank) Nos. 5FV7, 5E0V, 3UVU, 3Q8K, 3Q8L, 3Q8M, and 1UL1.

An "Xeroderma Pigmentosum Complementation Group G inhibitor" or "XPG, "XPG-I" compound," "XPG inhibitor" or "XPG-I inhibitor" refers to a compound (e.g. compounds described herein) that reduces the activity of Xeroderma Pigmentosum Complementation Group G when compared to a control, such as absence of the compound or a compound with known inactivity. In embodiments, the wild type XPG protein is identified by NCBI Accession NP_000114. In embodiments, a wild-type XPG-I domain is identified within NCBI Accession NP_000114. In embodiments, an exemplary X-ray crystallographic structure for XPG is disclosed in PDB No. 5EKF.

An "Exonuclease 1inhibitor" or "EXO1 compound" or "EXO1 inhibitor" refers to a compound (e.g. compounds described herein) that reduces the activity of "Exonuclease 1 when compared to a control, such as absence of the compound or a compound with known inactivity. In embodiments, the wild type EXO1 protein is identified by NCBI Accession AAN39382. In embodiments, exemplary X-ray crystallographic structures for EXO1 are disclosed in PDB Nos. 3QE9, 3QEA and 3QEB.

An "GEN1 inhibitor" or "GEN1 compound" or refers to a compound (e.g. compounds described herein) that reduces the activity of GEN1 when compared to a control, such as absence of the compound or a compound with known inactivity. In embodiments, the wild type GEN1 protein is identified by NCBI Accession NP_001123481. In embodiments, exemplary X-ray crystallographic structures for GEN1 are disclosed in PDB Nos. 5T9J.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As used herein, the phrase "consisting essentially of" when referring to a method or compound means that the method or compound may include additional elements that do not materially affect the characteristics of the method or compound. The phrase "consisting essentially of" when used in the context of a method claim that uses a compound set forth herein means that the recited compound (or pharmaceutically acceptable salts thereof) is administered along with, optionally, pharmaceutically acceptable excipients (e.g. binders, surfactants etc.) but that additional pharmaceutically active compounds (compounds with known biological activity useful for pharmaceutical purposes, such as an anti-cancer compound) are not administered. Non-limiting examples of pharmaceutically acceptable excipients are provided herein.

As defined herein, the term "activation," "activate," "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). A "Flap endonuclease 1 inhibitor" and "FEN1 inhibitor" is a compound that negatively affects (e.g. decreases) the activity or function of Flap endonuclease 1 relative to the activity or function of Flap endonuclease 1 in the absence of the inhibitor (e.g., wherein the FEN1 inhibitor binds FEN1). A "Xeroderma Pigmentosum Complementation Group G protein inhibitor," "Xeroderma Pigmentosum Complementation Group G protein domain inhibitor," "XPG-I inhibitor" and "XPG" inhibitor" is a compound that negatively affects (e.g. decreases) the activity or function of Xeroderma Pigmentosum Complementation Group G protein or protein domain relative to the activity or function of Xeroderma Pigmentosum Complementation Group G protein or protein domain in the absence of the inhibitor (e.g., wherein the XPG inhibitor binds XPG). An "Exonuclease 1 inhibitor" and "EXO1 inhibitor" is a compound that negatively affects (e.g. decreases) the activity or function of Exonuclease 1 relative to the activity or function of Exonuclease 1 in the absence of the inhibitor (e.g., wherein the EXO1 inhibitor binds EXO1). A "GEN1 inhibitor" is a compound that negatively affects (e.g. decreases) the activity or function of GEN1 relative to the activity or function of GEN1 in the absence of the inhibitor (e.g., wherein the GEN1 inhibitor binds GEN1).

The terms "Flap endonuclease 1" and "FEN1" are used in accordance with their customary meaning in the art and refer to a protein (including homologs, isoforms, and functional fragments thereof) with Flap endonuclease 1. The term includes any recombinant or naturally-occurring form of Flap endonuclease 1 or variants thereof that maintain Flap endonuclease 1 (e.g. within at least 30%, 40%, 50%, 60%, 70%, 80%, 90%, 95%, or 100% activity compared to wildtype Flap endonuclease 1). In embodiments, the FEN1 is a human FEN1.

The terms "Xeroderma Pigmentosum Complementation Group G," "Xeroderma Pigmentosum Complementation Group G domain," "XPG-I" and "XPG" are used in accordance with their customary meaning in the art and refer to a protein (including homologs, isoforms, and functional fragments thereof) with Xeroderma Pigmentosum Complementation Group G. The term includes any recombinant or naturally-occurring form of Xeroderma Pigmentosum Complementation Group G or variants thereof that maintain Xeroderma Pigmentosum Complementation Group G (e.g. within at least 30%, 40%, 50%, 60%, 70%, 80%, 90%, 95%, or 100% activity compared to wildtype Xeroderma Pigmentosum Complementation Group G). In embodiments, the XPG is a human XPG.

The terms "Exonuclease 1" and "EXO1" are used in accordance with their customary meaning in the art and refer to a protein (including homologs, isoforms, and functional fragments thereof) with Exonuclease 1. The term includes any recombinant or naturally-occurring form of Exonuclease 1 or variants thereof that maintain Exonuclease 1 (e.g. within at least 30%, 40%, 50%, 60%, 70%, 80%, 90%, 95%, or 100% activity compared to wildtype Exonuclease 1). In embodiments, the EXO1 is a human EXO1.

The term "GEN1" are used in accordance with their customary meaning in the art and refers to a protein (including homologs, isoforms, and functional fragments thereof) with GEN1. The term includes any recombinant or naturally-occurring form of GEN1 or variants thereof that maintain GEN1 (e.g. within at least 30%, 40%, 50%, 60%, 70%, 80%, 90%, 95%, or 100% activity compared to wildtype Exonuclease 1). In embodiments, the GEN1 is a human GEN1.

The terms "disease" or "condition" refer to a state of being or health status of a patient or subject capable of being treated with the compounds or methods provided herein. The disease may be a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

"Cancer model organism," as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein include cell lines from animals (e.g. mice) and from humans.

An "anticancer agent" as used herein refers to a molecule (e.g. compound, peptide, protein, nucleic acid, antibody) used to treat cancer through destruction or inhibition of cancer cells or tissues. Anticancer agents may be selective for certain cancers or certain tissues. In embodiments, anticancer agents herein may include nuclease (e.g., endonuclease, exonuclease and resolvase) inhibitors.

"Selective" or "selectivity" or the like of a compound refers to the compound's ability to discriminate between molecular targets (e.g. a compound having selectivity toward FEN1, EXO1, XPG, XPG-I and/or GEN1).

The terms "treating" or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "therapeutically effective amount" or "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington: *The Science and Practice of Pharmacy*, 20th Edition, 2003, Gennaro, Ed., Lippincott, Williams & Wilkins).

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of *liposomal* formulations, intravenous infusion, transdermal patches, etc.

The term "co-administer" means that a composition described herein is administered at the same time, just prior to, or just after the administration of one or more additional therapies. The compounds of the invention can be administered alone or can be co-administered to the patient. Co-administration is meant to include simultaneous or sequential administration of the compounds individually or in combination (more than one compound). Thus, the preparations can also be combined, when desired, with other active substances (e.g. to reduce metabolic degradation).

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-11107, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule. In some embodiments, a Flap endonuclease 1 (FEN1), Xeroderma Pigmentosum Complementation Group G protein (XPG), Exonuclease 1 (EXO1) and/or GEN1 associated disease modulator is a compound that reduces the severity of one or more symptoms of a disease associated with Flap endonuclease 1 (FEN1), Xeroderma Pigmentosum Complementation Group G (XPG), Exonuclease 1 (EXO1) or GEN1 (e.g. cancer, inflammatory disease). A Flap endonuclease 1 (FEN1), Xeroderma Pigmentosum Complementation Group G protein (XPG), Exonuclease 1 (EXO1) or GEN1 modulator is a compound that increases or decreases the activity or function or level of activity or level of function of Flap endonuclease 1 (FEN1), Xeroderma Pigmentosum Complementation Group G protein (XPG), Exonuclease 1 (EXO1) or GEN1.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a cancer associated with Flap endonuclease 1 (FEN1), Xeroderma Pigmentosum Complementation Group G (XPG), Exonuclease 1 (EXO1) and/or GEN1 activity, Flap endonuclease 1 (FEN1), Xeroderma Pigmentosum Complementation Group G (XPG), Exonuclease 1 (EXO1) and/or GEN1 associated cancer, Flap endonuclease 1 (FEN1), Xeroderma Pigmentosum Complementation Group G (XPG), Exonuclease 1 (EXO1) and/or GEN1 associated disease) means that the disease (e.g. cancer, inflammatory disease) is caused by (in whole or in part), or a symptom of the disease is caused by (in whole or in part) the substance or substance activity or function. For example, a cancer associated with Flap endonuclease 1 (FEN1), Xeroderma Pigmentosum Complementation Group G (XPG), Exonuclease 1 (EXO1) or GEN1 activity or function may be a cancer that results (entirely or partially) from aberrant Flap endonuclease 1 (FEN1), Xeroderma Pigmentosum Complementation Group G (XPG), Exonuclease 1 (EXO1) or GEN1, respectively, function (e.g. enzyme activity, protein-protein interaction, signaling pathway) or a cancer wherein a particular symptom of the disease is caused (entirely or partially) by aberrant Flap endonuclease 1 (FEN1), Xeroderma Pigmentosum Complementation Group G (XPG), Exonuclease 1 (EXO1) or GEN1, respectively, activity or function. As used herein, what is described as being associated with a disease, if a causative agent, could be a target for treatment of the disease. For example, a cancer associated with Flap endonuclease 1 (FEN1), Xeroderma Pigmentosum Complementation Group G (XPG), Exonuclease 1 (EXO1) or GEN1 activity or function or a Flap endonuclease 1 (FEN1), Xeroderma Pigmentosum Complementation Group G (XPG), Exonuclease 1 (EXO1) or GEN1 associated cancer, may be treated with a Flap endonuclease 1 (FEN1), Xeroderma Pigmentosum Complementation Group G (XPG), Exonuclease 1 (EXO1) or GEN1, respectively, modulator or Flap endonuclease 1 (FEN1), Xeroderma Pigmentosum Complementation Group G (XPG), Exonuclease 1 (EXO1) or GEN1, respectively, inhibitor, in the instance where increased Flap endonuclease 1 (FEN1), Xeroderma Pigmentosum Complementation Group G (XPG), Exonuclease 1 (EXO1) or GEN1, respectively, activity or function (e.g. signaling pathway activity) causes the cancer. For example, an inflammatory disease associated with Flap endonuclease 1 (FEN1), Xeroderma Pigmentosum Complementation Group G (XPG), Exonuclease 1 (EXO1) or GEN1 activity or function or a Flap endonuclease 1 (FEN1), Xeroderma Pigmentosum Complementation Group G (XPG), Exonuclease 1 (EXO1) or GEN1 associated inflammatory disease, may be treated with a Flap endonuclease 1 (FEN1), Xeroderma Pigmentosum Complementation Group G (XPG), Exonuclease 1 (EXO1) or GEN1, respectively, modulator or Flap endonuclease 1 (FEN1), Xeroderma Pigmentosum Complementation Group G (XPG), Exonuclease 1 (EXO1) or GEN1, respectively, inhibitor, in the instance where increased Flap endonuclease 1 (FEN1), Xeroderma Pigmentosum Complementation Group G (XPG), Exonuclease 1 (EXO1) or GEN1, respectively, activity or function (e.g. signaling pathway activity) causes the disease.

The term "aberrant" as used herein refers to different from normal. When used to describe enzymatic activity or protein function, aberrant refers to activity or function that is greater or less than a normal control or the average of normal non-diseased control samples, such as the activity or function in a healthy subject. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components. For example, binding of a Flap endonuclease 1 (FEN1), Xeroderma Pigmentosum Complementation Group G (XPG), Exonuclease 1 (EXO1) or GEN1 with a compound as described herein may reduce the level of a product of the Flap endonuclease 1 (FEN1), Xeroderma Pigmentosum Complementation Group G (XPG), Exonuclease 1 (EXO1) or GEN1, respectively, catalyzed reaction or the level of a downstream derivative of the product or binding may reduce the interactions between the Flap endonuclease 1 (FEN1), Xeroderma Pigmentosum Complementation Group G (XPG), Exonuclease 1 (EXO1) or GEN1 enzyme/protein or a Flap endonuclease 1 (FEN1), Xeroderma Pigmentosum Complementation Group G (XPG), Exonuclease 1 (EXO1) or GEN1, respectively, reaction product and downstream effectors or signaling pathway components, resulting in changes in cell growth, proliferation, or survival.

II. Compounds

In an aspect is provided a compound having the formula (I):

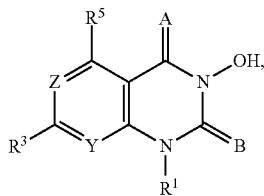

or a pharmaceutically acceptable salt thereof.

A is independently O, S, or $NR^A$. B is independently O, S, or $NR^B$. Y is independently $CR^2$ or N. Z is independently $CR^4$ or N. $R^1$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, $-CX^2_3$, $-CHX^2_2$, $-CH_2X^2$, $-CN$, $-SO_{n2}R^9$, $-SO_{v2}NR^6R^7$, $-NHC(O)NR^6R^7$, $-N(O)_{m2}$, $-NR^6R^7$, $-C(O)R^8$, $-C(O)-OR^8$, $-C(O)NR^6R^7$, $-OR^9$, $-NR^6SO_2R^9$, $-NR^6C(O)R^8$, $-NR^6C(O)OR^8$, $-NR^6OR^8$, $-OCX^2_3$, $-OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, $-CX^3_3$, $-CHX^3_2$, $-CH_2X^3$, $-CN$, $-SO_{n3}R^{13}$, $-SO_{v3}NR^{10}R^{11}$, $-NHC(O)NR^{10}R^{11}$, $-N(O)_{m3}$, $-NR^{10}R^{11}$, $-C(O)R^{12}$, $-C(O)-OR^{12}$, $-OR^{13}$, $-NR^{10}SO_2R^{13}$, $-NR^{10}C(O)R^{12}$, $-NR^{10}C(O)OR^{12}$, $-NR^{10}OR^{12}$, $-OCX^3_3$, $-OCHX^3_2$, substituted or unsubstituted alkyl, substituted or unsubstituted heteroalkyl, substituted or unsubstituted cycloalkyl, substituted or unsubstituted aryl, or substituted or unsubstituted heteroaryl. $R^4$ is independently hydrogen, halogen, $-CX^4_3$, $-CHX^4_2$, $-CH_2X^4$, $-CN$, $-SO_{n4}R^{17}$, $-SO_{v4}NR^{14}R^{15}$, $-NHC(O)NR^{14}R^{15}$, $-N(O)_{m4}$, $-NR^{14}R^{15}$, $-C(O)R^{16}$, $-C(O)-OR^{16}$, $-C(O)NR^{14}R^{15}$, $-OR^{17}$, $-NR^{14}SO_2R^{17}$, $-NR^{14}C(O)R^{16}$, $-NR^{14}C(O)OR^{16}$, $-NR^{14}OR^{16}$, $-OCX^4_3$, $-OCHX^4_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is independently hydrogen, halogen, $-CX^5_3$, $-CHX^5_2$, $-CH_2X^5$, $-CN$, $-SO_{n5}R^{21}$, $-SO_{v5}NR^{18}R^{19}$, $-NHC(O)NR^{18}R^{19}$, $-N(O)_{m5}$, $-NR^{18}R^{19}$, $-C(O)R^{20}$, $-C(O)-OR^{20}$, $-C(O)NR^{18}R^{19}$, $-OR^{21}$, $-NR^{18}SO_2R^{21}$, $-NR^{18}C(O)R^{20}$, $-NR^{18}C(O)OR^{20}$, $-NR^{18}OR^{20}$, $-OCX^5_3$, $-OCHX^5_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^A$, $R^B$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ and $R^7$, $R^{10}$ and $R^{11}$, $R^{14}$ and $R^{15}$, and $R^{18}$ and $R^{19}$ substituents bonded to the same nitrogen atom may optionally be joined to form a substituted or unsubstituted heterocycloalkyl or substituted or unsubstituted heteroaryl. Each X, $X^2$, $X^3$, $X^4$, and $X^5$ is independently $-F$, $-Cl$, $-Br$, or $-I$. Each m2, m3, m4, and m5 is independently an integer from 1 to 2. Each n2, n3, n4, and n5 is independently an integer from 0 to 3. Each v2, v3, v4, and v5 is independently an integer from 1 to 2.

In an aspect is provided a compound of Formula (I), or a pharmaceutically acceptable salt thereof, consisting essentially of:

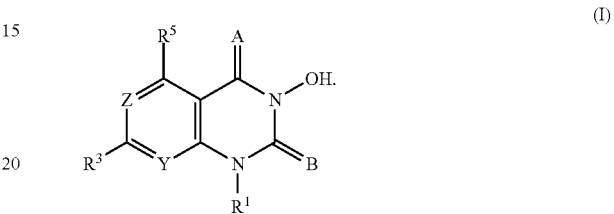

A is independently O, S, or $NR^A$. B is independently O, S, or $NR^B$. Y is independently $CR^2$ or N. Z is independently $CR^4$ or N. $R^1$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, $-CX^2_3$, $-CHX^2_2$, $-CH_2X^2$, $-CN$, $-SO_{n2}R^9$, $-SO_{v2}NR^6R^7$, $-NHC(O)NR^6R^7$, $-N(O)_{m2}$, $-NR^6R^7$, $-C(O)R^8$, $-C(O)-OR^8$, $-C(O)NR^6R^7$, $-OR^9$, $-NR^6SO_2R^9$, $-NR^6C(O)R^8$, $-NR^6C(O)OR^8$, $-NR^6OR^8$, $-OCX^2_3$, $-OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, $-CX^3_3$, $-CHX^3_2$, $-CH_2X^3$, $-CN$, $-SO_{n3}R^{13}$, $-SO_{v3}NR^{10}R^{11}$, $-NHC(O)NR^{10}R^{11}$, $-N(O)_{m3}$, $-NR^{10}R^{11}$, $-C(O)R^{12}$, $-C(O)-OR^{12}$, $-OR^{13}$, $-NR^{10}SO_2R^{13}$, $-NR^{10}C(O)R^{12}$, $-NR^{10}C(O)OR^{12}$, $-NR^{10}OR^{12}$, $-OCX^3_3$, $-OCHX^3_2$, substituted or unsubstituted alkyl, substituted or unsubstituted heteroalkyl, substituted or unsubstituted cycloalkyl, substituted or unsubstituted aryl, or substituted or unsubstituted heteroaryl. $R^4$ is independently hydrogen, halogen, $-CX^4_3$, $-CHX^4_2$, $-CH_2X^4$, $-CN$, $-SO_{n4}R^{17}$, $-SO_{v4}NR^{14}R^{15}$, $-NHC(O)NR^{14}R^{15}$, $-N(O)_{m4}$, $-NR^{14}R^{15}$, $-C(O)R^{16}$, $-C(O)-OR^{16}$, $-C(O)NR^{14}R^{15}$, $-OR^{17}$, $-NR^{14}SO_2R^{17}$, $-NR^{14}C(O)R^{16}$, $-NR^{14}C(O)OR^{16}-NR^{14}OR^{16}$, $-OCX^4_3$, $-OCHX^4_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is independently hydrogen, halogen, $-CX^5_3$, $-CHX^5_2$, $-CH_2X$, $-CN$, $-SO_{n5}R^{21}$, $-SO_{v5}NR^{18}R^{19}$, $-NHC(O)NR^{18}R^{19}$, $-N(O)_{m5}$, $-NR^{18}R^{19}$, $-C(O)R^{20}$, $-C(O)-OR^{20}$, $-C(O)NR^{18}R^{19}$, $-OR^{21}$, $-NR^{18}SO_2R^{21}$, $-NR^{18}C(O)R^{20}$, $-NR^{18}C(O)OR^{20}$, $-NR^{18}OR^{20}$, $-OCX^5_3$, $-OCHX^5_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^A$, $R^B$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ and $R^7$, $R^{10}$ and R", $R^{14}$ and $R^{15}$, and $R^{18}$ and $R^{19}$ substituents bonded to the same nitrogen atom may optionally be joined to form a substituted or unsubstituted heterocycloalkyl or substituted or unsubstituted heteroaryl. Each X, $X^2$, $X^3$, $X^4$, and $X^5$ is independently —F, —Cl, —Br, or —I. Each m2, m3, m4, and m5 is independently an integer from 1 to 2. Each n2, n3, n4, and n5 is independently an integer from 0 to 3. Each v2, v3, v4, and v5 is independently an integer from 1 to 2.

In embodiments, A is independently O. In embodiments, A is independently S. In embodiments, A is independently $NR^A$.

In embodiments, B is independently O. In embodiments, B is independently S. In embodiments, B is independently $NR^B$.

In embodiments, Y is independently $CR^2$. In embodiments, Y is independently N.

In embodiments, Z is independently $CR^4$. In embodiments, Z is independently N.

In embodiments, $R^1$ is independently hydrogen. In embodiments, $R^1$ is independently substituted or unsubstituted alkyl. In embodiments, $R^1$ is independently substituted or unsubstituted heteroalkyl. In embodiments, $R^1$ is independently substituted or unsubstituted cycloalkyl. In embodiments, $R^1$ is independently substituted or unsubstituted heterocycloalkyl. In embodiments, $R^1$ is independently substituted or unsubstituted aryl. In embodiments, $R^1$ is independently substituted or unsubstituted heteroaryl. In embodiments, $R^1$ is independently substituted alkyl. In embodiments, $R^1$ is independently substituted heteroalkyl. In embodiments, $R^1$ is independently substituted cycloalkyl. In embodiments, $R^1$ is independently substituted heterocycloalkyl. In embodiments, $R^1$ is independently substituted aryl. In embodiments, $R^1$ is independently substituted heteroaryl. In embodiments, $R^1$ is independently unsubstituted alkyl. In embodiments, $R^1$ is independently unsubstituted heteroalkyl. In embodiments, $R^1$ is independently unsubstituted cycloalkyl. In embodiments, $R^1$ is independently unsubstituted heterocycloalkyl. In embodiments, $R^1$ is independently unsubstituted aryl. In embodiments, $R^1$ is independently unsubstituted heteroaryl. In embodiments, $R^1$ is independently substituted or unsubstituted $C_1$-$C_6$ alkyl. In embodiments, $R^1$ is independently substituted or unsubstituted 2 to 6 membered heteroalkyl. In embodiments, $R^1$ is independently substituted or unsubstituted $C_3$-$C_8$ cycloalkyl. In embodiments, $R^1$ is independently substituted or unsubstituted 3 to 8 membered heterocycloalkyl. In embodiments, $R^1$ is independently substituted or unsubstituted $C_6$ aryl. In embodiments, $R^1$ is independently substituted or unsubstituted 5 to 6 membered heteroaryl. In embodiments, $R^1$ is independently substituted $C_1$-$C_6$ alkyl. In embodiments, $R^1$ is independently substituted 2 to 6 membered heteroalkyl. In embodiments, $R^1$ is independently substituted $C_3$-$C_8$ cycloalkyl. In embodiments, $R^1$ is independently substituted 3 to 8 membered heterocycloalkyl. In embodiments, $R^1$ is independently substituted $C_6$ aryl. In embodiments, $R^1$ is independently substituted 5 to 6 membered heteroaryl. In embodiments, $R^1$ is independently unsubstituted $C_1$-$C_6$ alkyl. In embodiments, $R^1$ is independently unsubstituted 2 to 6 membered heteroalkyl. In embodiments, $R^1$ is independently unsubstituted $C_3$-$C_8$ cycloalkyl. In embodiments, $R^1$ is independently unsubstituted 3 to 8 membered heterocycloalkyl. In embodiments, $R^1$ is independently unsubstituted $C_6$ aryl. In embodiments, $R^1$ is independently unsubstituted 5 to 6 membered heteroaryl.

In embodiments, $R^2$ is independently hydrogen. In embodiments, $R^2$ is independently halogen. In embodiments, $R^2$ is independently —$CX^2_3$. In embodiments, $R^2$ is independently —$CHX^2_2$. In embodiments, $R^2$ is independently —$CH_2X^2$. In embodiments, $R^2$ is independently —CN. In embodiments, $R^2$ is independently —$SO_{n2}R^9$. In embodiments, $R^2$ is independently —$SO_{v2}NR^6R^7$. In embodiments, $R^2$ is independently —$NHC(O)NR^6R^7$. In embodiments, $R^2$ is independently —$N(O)_{m2}$. In embodiments, $R^2$ is independently —$NR^6R^7$. In embodiments, $R^2$ is independently —$C(O)R^8$. In embodiments, $R^2$ is independently —C(O)—$OR^8$. In embodiments, $R^2$ is independently —$C(O)NR^6R^7$. In embodiments, $R^2$ is independently —$OR^9$. In embodiments, $R^2$ is independently —$NR^6SO_2R^9$. In embodiments, $R^2$ is independently —$NR^6C(O)R^8$. In embodiments, $R^2$ is independently —$NR^6C(O)OR^8$. In embodiments, $R^2$ is independently —$NR^6OR^8$. In embodiments, $R^2$ is independently —$OCX^2_3$. In embodiments, $R^2$ is independently —$OCHX^2_2$. In embodiments, $R^2$ is independently substituted or unsubstituted alkyl. In embodiments, $R^2$ is independently substituted or unsubstituted heteroalkyl. In embodiments, $R^2$ is independently substituted or unsubstituted cycloalkyl. In embodiments, $R^2$ is independently substituted or unsubstituted heterocycloalkyl. In embodiments, $R^2$ is independently substituted or unsubstituted aryl. In embodiments, $R^2$ is independently substituted or unsubstituted heteroaryl. In embodiments, $R^2$ is independently substituted alkyl. In embodiments, $R^2$ is independently substituted heteroalkyl. In embodiments, $R^2$ is independently substituted cycloalkyl. In embodiments, $R^2$ is independently substituted heterocycloalkyl. In embodiments, $R^2$ is independently substituted aryl. In embodiments, $R^2$ is independently substituted heteroaryl. In embodiments, $R^2$ is independently unsubstituted alkyl. In embodiments, $R^2$ is independently unsubstituted heteroalkyl. In embodiments, $R^2$ is independently unsubstituted cycloalkyl. In embodiments, $R^2$ is independently unsubstituted heterocycloalkyl. In embodiments, $R^2$ is independently unsubstituted aryl. In embodiments, $R^2$ is independently unsubstituted heteroaryl. In embodiments, $R^2$ is independently substituted or unsubstituted $C_1$-$C_6$ alkyl. In embodiments, $R^2$ is independently substituted or unsubstituted 2 to 6 membered heteroalkyl. In embodiments, $R^2$ is independently substituted or unsubstituted $C_3$-$C_8$ cycloalkyl. In embodiments, $R^2$ is independently substituted or unsubstituted 3 to 8 membered heterocycloalkyl. In embodiments, $R^2$ is independently substituted or unsubstituted $C_6$ aryl. In embodiments, $R^2$ is independently substituted or unsubstituted 5 to 6 membered heteroaryl. In embodiments, $R^2$ is independently substituted $C_1$-$C_6$ alkyl. In embodiments, $R^2$ is independently substituted 2 to 6 membered heteroalkyl. In embodiments, $R^2$ is independently substituted $C_3$-$C_8$ cycloalkyl. In embodiments, $R^2$ is independently substituted 3 to 8 membered heterocycloalkyl. In embodiments, $R^2$ is independently substituted $C_6$ aryl. In embodiments, $R^2$ is independently substituted 5 to 6 membered heteroaryl. In embodiments, $R^2$ is independently unsubstituted $C_1$-$C_6$ alkyl. In embodiments, $R^2$ is independently unsubstituted 2 to 6 membered heteroalkyl. In embodiments, $R^2$ is independently unsubstituted $C_3$-$C_8$ cycloalkyl. In embodiments, $R^2$ is independently unsubstituted 3 to 8 membered heterocycloalkyl. In embodiments, $R^2$ is independently unsubstituted $C_6$ aryl. In embodiments, $R^2$ is independently unsubstituted 5 to 6 membered heteroaryl.

In embodiments, $R^3$ is independently hydrogen. In embodiments, $R^3$ is independently halogen. In embodiments, $R^3$ is independently —$CX^3{}_3$. In embodiments, $R^3$ is independently —$CHX^3{}_2$. In embodiments, $R^3$ is independently —$CH_2X^3$. In embodiments, $R^3$ is independently —CN. In embodiments, $R^3$ is independently —$SO_{n3}R^{13}$. In embodiments, $R^3$ is independently —$SO_{v3}NR^{10}R^{11}$. In embodiments, $R^3$ is independently —$NHC(O)NR^{10}R^{11}$. In embodiments, $R^3$ is independently —$N(O)_{m3}$. In embodiments, $R^3$ is independently —$NR^{10}R^{11}$. In embodiments, $R^3$ is independently —$C(O)R^{12}$. In embodiments, $R^3$ is independently —$C(O)$—$OR^{12}$. In embodiments, $R^3$ is independently —$OR^{13}$. In embodiments, $R^3$ is independently —$NR^{10}SO_2R^{13}$. In embodiments, $R^3$ is independently —$NR^{10}C(O)R^{12}$. In embodiments, $R^3$ is independently —$NR^{10}C(O)OR^{12}$. In embodiments, $R^3$ is independently —$NR^{10}OR^{12}$. In embodiments, $R^3$ is independently —$OCX^3{}_3$. In embodiments, $R^3$ is independently —$OCHX^3{}_2$. In embodiments, $R^3$ is independently substituted or unsubstituted alkyl. In embodiments, $R^3$ is independently substituted or unsubstituted heteroalkyl. In embodiments, $R^3$ is independently substituted or unsubstituted cycloalkyl. In embodiments, $R^3$ is independently substituted or unsubstituted aryl. In embodiments, $R^3$ is independently substituted or unsubstituted heteroaryl. In embodiments, $R^3$ is independently substituted alkyl. In embodiments, $R^3$ is independently substituted heteroalkyl. In embodiments, $R^3$ is independently substituted cycloalkyl. In embodiments, $R^3$ is independently substituted aryl. In embodiments, $R^3$ is independently substituted heteroaryl. In embodiments, $R^3$ is independently unsubstituted alkyl. In embodiments, $R^3$ is independently unsubstituted heteroalkyl. In embodiments, $R^3$ is independently unsubstituted cycloalkyl. In embodiments, $R^3$ is independently unsubstituted aryl. In embodiments, $R^3$ is independently unsubstituted heteroaryl. In embodiments, $R^3$ is independently substituted or unsubstituted $C_1$-$C_6$ alkyl. In embodiments, $R^3$ is independently substituted or unsubstituted 2 to 6 membered heteroalkyl. In embodiments, $R^3$ is independently substituted or unsubstituted $C_3$-$C_8$ cycloalkyl. In embodiments, $R^3$ is independently substituted or unsubstituted $C_6$ aryl. In embodiments, $R^3$ is independently substituted or unsubstituted 5 to 6 membered heteroaryl. In embodiments, $R^3$ is independently substituted $C_1$-$C_6$ alkyl. In embodiments, $R^3$ is independently substituted 2 to 6 membered heteroalkyl. In embodiments, $R^3$ is independently substituted $C_3$-$C_8$ cycloalkyl. In embodiments, $R^3$ is independently substituted $C_6$ aryl. In embodiments, $R^3$ is independently substituted 5 to 6 membered heteroaryl. In embodiments, $R^3$ is independently unsubstituted $C_1$-$C_6$ alkyl. In embodiments, $R^3$ is independently unsubstituted 2 to 6 membered heteroalkyl. In embodiments, $R^3$ is independently unsubstituted $C_3$-$C_8$ cycloalkyl. In embodiments, $R^3$ is independently unsubstituted $C_6$ aryl. In embodiments, $R^3$ is independently unsubstituted 5 to 6 membered heteroaryl.

In embodiments, $R^4$ is independently hydrogen. In embodiments, $R^4$ is independently halogen. In embodiments, $R^4$ is independently —$CX^4{}_3$. In embodiments, $R^4$ is independently —$CHX^4{}_2$. In embodiments, $R^4$ is independently —$CH_2X^4$. In embodiments, $R^4$ is independently —CN. In embodiments, $R^4$ is independently —$SO_{n4}R^{17}$. In embodiments, $R^4$ is independently —$SO_{v4}NR^{14}R^{15}$. In embodiments, $R^4$ is independently —$NHC(O)NR^{14}R^{15}$. In embodiments, $R^4$ is independently —$N(O)_{m4}$. In embodiments, $R^4$ is independently —$NR^{14}R^{15}$. In embodiments, $R^4$ is independently —$C(O)R^{16}$. In embodiments, $R^4$ is independently —$C(O)$—$OR^{16}$. In embodiments, $R^4$ is independently —$C(O)NR^{14}R^{15}$. In embodiments, $R^4$ is independently —$OR^{17}$. In embodiments, $R^4$ is independently —$NR^{14}SO_2R^{17}$. In embodiments, $R^4$ is independently —$NR^{14}C(O)R^{16}$. In embodiments, $R^4$ is independently —$NR^{14}C(O)OR^{16}$. In embodiments, $R^4$ is independently —$NR^{14}OR^{16}$. In embodiments, $R^4$ is independently —$OCX^4{}_3$. In embodiments, $R^4$ is independently —$OCHX^4{}_2$. In embodiments, $R^4$ is independently substituted or unsubstituted alkyl. In embodiments, $R^4$ is independently substituted or unsubstituted heteroalkyl. In embodiments, $R^4$ is independently substituted or unsubstituted cycloalkyl. In embodiments, $R^4$ is independently substituted or unsubstituted heterocycloalkyl. In embodiments, $R^4$ is independently substituted or unsubstituted aryl. In embodiments, $R^4$ is independently substituted or unsubstituted heteroaryl. In embodiments, $R^4$ is independently substituted alkyl. In embodiments, $R^4$ is independently substituted heteroalkyl. In embodiments, $R^4$ is independently substituted cycloalkyl. In embodiments, $R^4$ is independently substituted heterocycloalkyl. In embodiments, $R^4$ is independently substituted aryl. In embodiments, $R^4$ is independently substituted heteroaryl. In embodiments, $R^4$ is independently unsubstituted alkyl. In embodiments, $R^4$ is independently unsubstituted heteroalkyl. In embodiments, $R^4$ is independently unsubstituted cycloalkyl. In embodiments, $R^4$ is independently unsubstituted heterocycloalkyl. In embodiments, $R^4$ is independently unsubstituted aryl. In embodiments, $R^4$ is independently unsubstituted heteroaryl. In embodiments, $R^4$ is independently substituted or unsubstituted $C_1$-$C_6$ alkyl. In embodiments, $R^4$ is independently substituted or unsubstituted 2 to 6 membered heteroalkyl. In embodiments, $R^4$ is independently substituted or unsubstituted $C_3$-$C_8$ cycloalkyl. In embodiments, $R^4$ is independently substituted or unsubstituted 3 to 8 membered heterocycloalkyl. In embodiments, $R^4$ is independently substituted or unsubstituted $C_6$ aryl. In embodiments, $R^4$ is independently substituted or unsubstituted 5 to 6 membered heteroaryl. In embodiments, $R^4$ is independently substituted $C_1$-$C_6$ alkyl. In embodiments, $R^4$ is independently substituted 2 to 6 membered heteroalkyl. In embodiments, $R^4$ is independently substituted $C_3$-$C_8$ cycloalkyl. In embodiments, $R^4$ is independently substituted 3 to 8 membered heterocycloalkyl. In embodiments, $R^4$ is independently substituted $C_6$ aryl. In embodiments, $R^4$ is independently substituted 5 to 6 membered heteroaryl. In embodiments, $R^4$ is independently unsubstituted $C_1$-$C_6$ alkyl. In embodiments, $R^4$ is independently unsubstituted 2 to 6 membered heteroalkyl. In embodiments, $R^4$ is independently unsubstituted $C_3$-$C_8$ cycloalkyl. In embodiments, $R^4$ is independently unsubstituted 3 to 8 membered heterocycloalkyl. In embodiments, $R^4$ is independently unsubstituted $C_6$ aryl. In embodiments, $R^4$ is independently unsubstituted 5 to 6 membered heteroaryl.

In embodiments, $R^5$ is independently hydrogen. In embodiments, $R^5$ is independently halogen. In embodiments, $R^5$ is independently —$CX^5{}_3$. In embodiments, $R^5$ is independently —$CHX^5{}_2$. In embodiments, $R^5$ is independently —$CH_2X^5$. In embodiments, $R^5$ is independently —CN. In embodiments, $R^5$ is independently —$SO_{n5}R^{21}$. In embodiments, $R^5$ is independently —$SO_{v5}NR^{18}R^{19}$. In embodiments, $R^5$ is independently —$NHC(O)NR^{18}R^{19}$. In embodiments, $R^5$ is independently —$N(O)_{m5}$. In embodiments, $R^5$ is independently —$NR^{18}R^{19}$. In embodiments, $R^5$ is independently —$C(O)R^{20}$. In embodiments, $R^5$ is independently —$C(O)$—$OR^{20}$. In embodiments, $R^5$ is independently —C(O)NR$^{18}$R$^{19}$. In embodiments, R$^5$ is independently —OR$^{21}$. In embodiments, R$^5$ is independently —NR$^{18}$SO$_2$R$^{21}$. In embodiments, R$^5$ is independently —NR$^{18}$C(O)R$^{20}$. In embodiments, R$^5$ is independently —NR$^{18}$C(O)OR$^{20}$. In embodiments, R$^5$ is independently —NR$^{18}$OR$^{20}$. In embodiments, R$^5$ is independently —OCX$^5_3$. In embodiments, R$^5$ is independently —OCHX$^5_2$. In embodiments, R$^5$ is independently substituted or unsubstituted alkyl. In embodiments, R$^5$ is independently substituted or unsubstituted heteroalkyl. In embodiments, R$^5$ is independently substituted or unsubstituted cycloalkyl. In embodiments, R$^5$ is independently substituted or unsubstituted heterocycloalkyl. In embodiments, R$^5$ is independently substituted or unsubstituted aryl. In embodiments, R$^5$ is independently substituted or unsubstituted heteroaryl. In embodiments, R$^5$ is independently substituted alkyl. In embodiments, R$^5$ is independently substituted heteroalkyl. In embodiments, R$^5$ is independently substituted cycloalkyl. In embodiments, R$^5$ is independently substituted heterocycloalkyl. In embodiments, R$^5$ is independently substituted aryl. In embodiments, R$^5$ is independently substituted heteroaryl. In embodiments, R$^5$ is independently unsubstituted alkyl. In embodiments, R$^5$ is independently unsubstituted heteroalkyl. In embodiments, R$^5$ is independently unsubstituted cycloalkyl. In embodiments, R$^5$ is independently unsubstituted heterocycloalkyl. In embodiments, R$^5$ is independently unsubstituted aryl. In embodiments, R$^5$ is independently unsubstituted heteroaryl. In embodiments, R$^5$ is independently substituted or unsubstituted C$_1$-C$_6$ alkyl. In embodiments, R$^5$ is independently substituted or unsubstituted 2 to 6 membered heteroalkyl. In embodiments, R$^5$ is independently substituted or unsubstituted C$_3$-C$_8$ cycloalkyl. In embodiments, R$^5$ is independently substituted or unsubstituted 3 to 8 membered heterocycloalkyl. In embodiments, R$^5$ is independently substituted or unsubstituted C$_6$ aryl. In embodiments, R$^5$ is independently substituted or unsubstituted 5 to 6 membered heteroaryl. In embodiments, R$^5$ is independently substituted C$_1$-C$_6$ alkyl. In embodiments, R$^5$ is independently substituted 2 to 6 membered heteroalkyl. In embodiments, R$^5$ is independently substituted C$_3$-C$_8$ cycloalkyl. In embodiments, R$^5$ is independently substituted 3 to 8 membered heterocycloalkyl. In embodiments, R$^5$ is independently substituted C$_6$ aryl. In embodiments, R$^5$ is independently substituted 5 to 6 membered heteroaryl. In embodiments, R$^5$ is independently unsubstituted C$_1$-C$_6$ alkyl. In embodiments, R$^5$ is independently unsubstituted 2 to 6 membered heteroalkyl. In embodiments, R$^5$ is independently unsubstituted C$_3$-C$_8$ cycloalkyl. In embodiments, R$^5$ is independently unsubstituted 3 to 8 membered heterocycloalkyl. In embodiments, R$^5$ is independently unsubstituted C$_6$ aryl. In embodiments, R$^5$ is independently unsubstituted 5 to 6 membered heteroaryl.

In embodiments, R$^A$ is independently hydrogen. In embodiments, R$^A$ is independently —CX$_3$. In embodiments, R$^A$ is independently —CN. In embodiments, R$^A$ is independently —COOH. In embodiments, R$^A$ is independently —CONH$_2$. In embodiments, R$^A$ is independently —CHX$_2$. In embodiments, R$^A$ is independently —CH$_2$X. In embodiments, R$^A$ is independently substituted or unsubstituted alkyl. In embodiments, R$^A$ is independently substituted or unsubstituted heteroalkyl. In embodiments, R$^A$ is independently substituted or unsubstituted cycloalkyl. In embodiments, R$^A$ is independently substituted or unsubstituted heterocycloalkyl. In embodiments, R$^A$ is independently substituted or unsubstituted aryl. In embodiments, R$^A$ is independently substituted or unsubstituted heteroaryl. In embodiments, R$^A$ is independently substituted alkyl. In embodiments, R$^A$ is independently substituted heteroalkyl. In embodiments, R$^A$ is independently substituted cycloalkyl. In embodiments, R$^A$ is independently substituted heterocycloalkyl. In embodiments, R$^A$ is independently substituted aryl. In embodiments, R$^A$ is independently substituted heteroaryl. In embodiments, R$^A$ is independently unsubstituted alkyl. In embodiments, R$^A$ is independently unsubstituted heteroalkyl. In embodiments, R$^A$ is independently unsubstituted cycloalkyl. In embodiments, R$^A$ is independently unsubstituted heterocycloalkyl. In embodiments, R$^A$ is independently unsubstituted aryl. In embodiments, R$^A$ is independently unsubstituted heteroaryl. In embodiments, R$^A$ is independently substituted or unsubstituted C$_1$-C$_6$ alkyl. In embodiments, R$^A$ is independently substituted or unsubstituted 2 to 6 membered heteroalkyl. In embodiments, R$^A$ is independently substituted or unsubstituted C$_3$-C$_8$ cycloalkyl. In embodiments, R$^A$ is independently substituted or unsubstituted 3 to 8 membered heterocycloalkyl. In embodiments, R$^A$ is independently substituted or unsubstituted C$_6$ aryl. In embodiments, R$^A$ is independently substituted or unsubstituted 5 to 6 membered heteroaryl. In embodiments, R$^A$ is independently substituted C$_1$-C$_6$ alkyl. In embodiments, R$^A$ is independently substituted 2 to 6 membered heteroalkyl. In embodiments, R$^A$ is independently substituted C$_3$-C$_8$ cycloalkyl. In embodiments, R$^A$ is independently substituted 3 to 8 membered heterocycloalkyl. In embodiments, R$^A$ is independently substituted C$_6$ aryl. In embodiments, R$^A$ is independently substituted 5 to 6 membered heteroaryl. In embodiments, R$^A$ is independently unsubstituted C$_1$-C$_6$ alkyl. In embodiments, R$^A$ is independently unsubstituted 2 to 6 membered heteroalkyl. In embodiments, R$^A$ is independently unsubstituted C$_3$-C$_8$ cycloalkyl. In embodiments, R$^A$ is independently unsubstituted 3 to 8 membered heterocycloalkyl. In embodiments, R$^A$ is independently unsubstituted C$_6$ aryl. In embodiments, R$^A$ is independently unsubstituted 5 to 6 membered heteroaryl.

In embodiments, R$^B$ is independently hydrogen. In embodiments, R$^B$ is independently —CX$_3$. In embodiments, R$^B$ is independently —CN. In embodiments, R$^B$ is independently —COOH. In embodiments, R$^B$ is independently —CONH$_2$. In embodiments, R$^B$ is independently —CHX$_2$. In embodiments, R$^B$ is independently —CH$_2$X. In embodiments, R$^B$ is independently substituted or unsubstituted alkyl. In embodiments, R$^B$ is independently substituted or unsubstituted heteroalkyl. In embodiments, R$^B$ is independently substituted or unsubstituted cycloalkyl. In embodiments, R$^B$ is independently substituted or unsubstituted heterocycloalkyl. In embodiments, R$^B$ is independently substituted or unsubstituted aryl. In embodiments, R$^B$ is independently substituted or unsubstituted heteroaryl. In embodiments, R$^B$ is independently substituted alkyl. In embodiments, R$^B$ is independently substituted heteroalkyl. In embodiments, R$^B$ is independently substituted cycloalkyl. In embodiments, R$^B$ is independently substituted heterocycloalkyl. In embodiments, R$^B$ is independently substituted aryl. In embodiments, R$^B$ is independently substituted heteroaryl. In embodiments, R$^B$ is independently unsubstituted alkyl. In embodiments, R$^B$ is independently unsubstituted heteroalkyl. In embodiments, R$^B$ is independently unsubstituted cycloalkyl. In embodiments, R$^B$ is independently unsubstituted heterocycloalkyl. In embodiments, R$^B$ is independently unsubstituted aryl. In embodiments, R$^B$ is independently unsubstituted heteroaryl. In embodiments, R$^B$ is independently substituted or unsubstituted C$_1$-C$_6$ alkyl. In embodiments, R$^B$ is independently substituted or unsubstituted 2 to 6 membered heteroalkyl. In embodiments, R$^B$ is independently substituted or unsubstituted C$_3$-C$_8$ cycloalkyl.

In embodiments, $R^B$ is independently substituted or unsubstituted 3 to 8 membered heterocycloalkyl. In embodiments, $R^B$ is independently substituted or unsubstituted $C_6$ aryl. In embodiments, $R^B$ is independently substituted or unsubstituted 5 to 6 membered heteroaryl. In embodiments, $R^B$ is independently substituted $C_1$-$C_6$ alkyl. In embodiments, $R^B$ is independently substituted 2 to 6 membered heteroalkyl. In embodiments, $R^B$ is independently substituted $C_3$-$C_8$ cycloalkyl. In embodiments, $R^B$ is independently substituted 3 to 8 membered heterocycloalkyl. In embodiments, $R^B$ is independently substituted $C_6$ aryl. In embodiments, $R^B$ is independently substituted 5 to 6 membered heteroaryl. In embodiments, $R^B$ is independently unsubstituted $C_1$-$C_6$ alkyl. In embodiments, $R^B$ is independently unsubstituted 2 to 6 membered heteroalkyl. In embodiments, $R^B$ is independently unsubstituted $C_3$-$C_8$ cycloalkyl. In embodiments, $R^B$ is independently unsubstituted 3 to 8 membered heterocycloalkyl. In embodiments, $R^B$ is independently unsubstituted $C_6$ aryl. In embodiments, $R^B$ is independently unsubstituted 5 to 6 membered heteroaryl.

In embodiments, $R^6$ is independently hydrogen. In embodiments, $R^6$ is independently —$CX_3$. In embodiments, $R^6$ is independently —CN. In embodiments, $R^6$ is independently —COOH. In embodiments, $R^6$ is independently —$CONH_2$. In embodiments, $R^6$ is independently —$CHX_2$. In embodiments, $R^6$ is independently —$CH_2X$. In embodiments, $R^6$ is independently substituted or unsubstituted alkyl. In embodiments, $R^6$ is independently substituted or unsubstituted heteroalkyl. In embodiments, $R^6$ is independently substituted or unsubstituted cycloalkyl. In embodiments, $R^6$ is independently substituted or unsubstituted heterocycloalkyl. In embodiments, $R^6$ is independently substituted or unsubstituted aryl. In embodiments, $R^6$ is independently substituted or unsubstituted heteroaryl. In embodiments, $R^6$ is independently substituted alkyl. In embodiments, $R^6$ is independently substituted heteroalkyl. In embodiments, $R^6$ is independently substituted cycloalkyl. In embodiments, $R^6$ is independently substituted heterocycloalkyl. In embodiments, $R^6$ is independently substituted aryl. In embodiments, $R^6$ is independently substituted heteroaryl. In embodiments, $R^6$ is independently unsubstituted alkyl. In embodiments, $R^6$ is independently unsubstituted heteroalkyl. In embodiments, $R^6$ is independently unsubstituted cycloalkyl. In embodiments, $R^6$ is independently unsubstituted heterocycloalkyl. In embodiments, $R^6$ is independently unsubstituted aryl. In embodiments, $R^6$ is independently unsubstituted heteroaryl. In embodiments, $R^6$ is independently substituted or unsubstituted $C_1$-$C_6$ alkyl. In embodiments, $R^6$ is independently substituted or unsubstituted 2 to 6 membered heteroalkyl. In embodiments, $R^6$ is independently substituted or unsubstituted $C_3$-$C_8$ cycloalkyl. In embodiments, $R^6$ is independently substituted or unsubstituted 3 to 8 membered heterocycloalkyl. In embodiments, $R^6$ is independently substituted or unsubstituted $C_6$ aryl. In embodiments, $R^6$ is independently substituted or unsubstituted 5 to 6 membered heteroaryl. In embodiments, $R^6$ is independently substituted $C_1$-$C_6$ alkyl. In embodiments, $R^6$ is independently substituted 2 to 6 membered heteroalkyl. In embodiments, $R^6$ is independently substituted $C_3$-$C_8$ cycloalkyl. In embodiments, $R^6$ is independently substituted 3 to 8 membered heterocycloalkyl. In embodiments, $R^6$ is independently substituted $C_6$ aryl. In embodiments, $R^6$ is independently substituted 5 to 6 membered heteroaryl. In embodiments, $R^6$ is independently unsubstituted $C_1$-$C_6$ alkyl. In embodiments, $R^6$ is independently unsubstituted 2 to 6 membered heteroalkyl. In embodiments, $R^6$ is independently unsubstituted $C_3$-$C_8$ cycloalkyl. In embodiments, $R^6$ is independently unsubstituted 3 to 8 membered heterocycloalkyl. In embodiments, $R^6$ is independently unsubstituted $C_6$ aryl. In embodiments, $R^6$ is independently unsubstituted 5 to 6 membered heteroaryl.

In embodiments, $R^7$ is independently hydrogen. In embodiments, $R^7$ is independently —$CX_3$. In embodiments, $R^7$ is independently —CN. In embodiments, $R^7$ is independently —COOH. In embodiments, $R^7$ is independently —$CONH_2$. In embodiments, $R^7$ is independently —$CHX_2$. In embodiments, $R^7$ is independently —$CH_2X$. In embodiments, $R^7$ is independently substituted or unsubstituted alkyl. In embodiments, $R^7$ is independently substituted or unsubstituted heteroalkyl. In embodiments, $R^7$ is independently substituted or unsubstituted cycloalkyl. In embodiments, $R^7$ is independently substituted or unsubstituted heterocycloalkyl. In embodiments, $R^7$ is independently substituted or unsubstituted aryl. In embodiments, $R^7$ is independently substituted or unsubstituted heteroaryl. In embodiments, $R^7$ is independently substituted alkyl. In embodiments, $R^7$ is independently substituted heteroalkyl. In embodiments, $R^7$ is independently substituted cycloalkyl. In embodiments, $R^7$ is independently substituted heterocycloalkyl. In embodiments, $R^7$ is independently substituted aryl. In embodiments, $R^7$ is independently substituted heteroaryl. In embodiments, $R^7$ is independently unsubstituted alkyl. In embodiments, $R^7$ is independently unsubstituted heteroalkyl. In embodiments, $R^7$ is independently unsubstituted cycloalkyl. In embodiments, $R^7$ is independently unsubstituted heterocycloalkyl. In embodiments, $R^7$ is independently unsubstituted aryl. In embodiments, $R^7$ is independently unsubstituted heteroaryl. In embodiments, $R^7$ is independently substituted or unsubstituted $C_1$-$C_6$ alkyl. In embodiments, $R^7$ is independently substituted or unsubstituted 2 to 6 membered heteroalkyl. In embodiments, $R^7$ is independently substituted or unsubstituted $C_3$-$C_8$ cycloalkyl. In embodiments, $R^7$ is independently substituted or unsubstituted 3 to 8 membered heterocycloalkyl. In embodiments, $R^7$ is independently substituted or unsubstituted $C_6$ aryl. In embodiments, $R^7$ is independently substituted or unsubstituted 5 to 6 membered heteroaryl. In embodiments, $R^7$ is independently substituted $C_1$-$C_6$ alkyl. In embodiments, $R^7$ is independently substituted 2 to 6 membered heteroalkyl. In embodiments, $R^7$ is independently substituted $C_3$-$C_8$ cycloalkyl. In embodiments, $R^7$ is independently substituted 3 to 8 membered heterocycloalkyl. In embodiments, $R^7$ is independently substituted $C_6$ aryl. In embodiments, $R^7$ is independently substituted 5 to 6 membered heteroaryl. In embodiments, $R^7$ is independently unsubstituted $C_1$-$C_6$ alkyl. In embodiments, $R^7$ is independently unsubstituted 2 to 6 membered heteroalkyl. In embodiments, $R^7$ is independently unsubstituted $C_3$-$C_8$ cycloalkyl. In embodiments, $R^7$ is independently unsubstituted 3 to 8 membered heterocycloalkyl. In embodiments, $R^7$ is independently unsubstituted $C_6$ aryl. In embodiments, $R^7$ is independently unsubstituted 5 to 6 membered heteroaryl.

In embodiments, $R^8$ is independently hydrogen. In embodiments, $R^8$ is independently —$CX_3$. In embodiments, $R^8$ is independently —CN. In embodiments, $R^8$ is independently —COOH. In embodiments, $R^8$ is independently —$CONH_2$. In embodiments, $R^8$ is independently —$CHX_2$. In embodiments, $R^8$ is independently —$CH_2X$. In embodiments, $R^8$ is independently substituted or unsubstituted alkyl. In embodiments, $R^8$ is independently substituted or unsubstituted heteroalkyl. In embodiments, $R^8$ is independently substituted or unsubstituted cycloalkyl. In embodiments, $R^8$ is independently substituted or unsubstituted heterocycloalkyl. In embodiments, $R^8$ is independently substituted or unsubstituted aryl. In embodiments, $R^8$ is independently substituted or unsubstituted heteroaryl. In embodiments, $R^8$ is independently substituted alkyl. In embodiments, $R^8$ is independently substituted heteroalkyl. In embodiments, $R^8$ is independently substituted cycloalkyl. In embodiments, $R^8$ is independently substituted heterocycloalkyl. In embodiments, $R^8$ is independently substituted aryl. In embodiments, $R^8$ is independently substituted heteroaryl. In embodiments, $R^8$ is independently unsubstituted alkyl. In embodiments, $R^8$ is independently unsubstituted heteroalkyl. In embodiments, $R^8$ is independently unsubstituted cycloalkyl. In embodiments, $R^8$ is independently unsubstituted heterocycloalkyl. In embodiments, $R^8$ is independently unsubstituted aryl. In embodiments, $R^8$ is independently unsubstituted heteroaryl. In embodiments, $R^8$ is independently substituted or unsubstituted $C_1$-$C_6$ alkyl. In embodiments, $R^8$ is independently substituted or unsubstituted 2 to 6 membered heteroalkyl. In embodiments, $R^8$ is independently substituted or unsubstituted $C_3$-$C_8$ cycloalkyl. In embodiments, $R^8$ is independently substituted or unsubstituted 3 to 8 membered heterocycloalkyl. In embodiments, $R^8$ is independently substituted or unsubstituted $C_6$ aryl. In embodiments, $R^8$ is independently substituted or unsubstituted 5 to 6 membered heteroaryl. In embodiments, $R^8$ is independently substituted $C_1$-$C_6$ alkyl. In embodiments, $R^8$ is independently substituted 2 to 6 membered heteroalkyl. In embodiments, $R^8$ is independently substituted $C_3$-$C_8$ cycloalkyl. In embodiments, $R^8$ is independently substituted 3 to 8 membered heterocycloalkyl. In embodiments, $R^8$ is independently substituted $C_6$ aryl. In embodiments, $R^8$ is independently substituted 5 to 6 membered heteroaryl. In embodiments, $R^8$ is independently unsubstituted $C_1$-$C_6$ alkyl. In embodiments, $R^8$ is independently unsubstituted 2 to 6 membered heteroalkyl. In embodiments, $R^8$ is independently unsubstituted $C_3$-$C_8$ cycloalkyl. In embodiments, $R^8$ is independently unsubstituted 3 to 8 membered heterocycloalkyl. In embodiments, $R^8$ is independently unsubstituted $C_6$ aryl. In embodiments, $R^8$ is independently unsubstituted 5 to 6 membered heteroaryl.

In embodiments, $R^9$ is independently hydrogen. In embodiments, $R^9$ is independently —$CX_3$. In embodiments, $R^9$ is independently —CN. In embodiments, $R^9$ is independently —COOH. In embodiments, $R^9$ is independently —$CONH_2$. In embodiments, $R^9$ is independently —$CHX_2$. In embodiments, $R^9$ is independently —$CH_2X$. In embodiments, $R^9$ is independently substituted or unsubstituted alkyl. In embodiments, $R^9$ is independently substituted or unsubstituted heteroalkyl. In embodiments, $R^9$ is independently substituted or unsubstituted cycloalkyl. In embodiments, $R^9$ is independently substituted or unsubstituted heterocycloalkyl. In embodiments, $R^9$ is independently substituted or unsubstituted aryl. In embodiments, $R^9$ is independently substituted or unsubstituted heteroaryl. In embodiments, $R^9$ is independently substituted alkyl. In embodiments, $R^9$ is independently substituted heteroalkyl. In embodiments, $R^9$ is independently substituted cycloalkyl. In embodiments, $R^9$ is independently substituted heterocycloalkyl. In embodiments, $R^9$ is independently substituted aryl. In embodiments, $R^9$ is independently substituted heteroaryl. In embodiments, $R^9$ is independently unsubstituted alkyl. In embodiments, $R^9$ is independently unsubstituted heteroalkyl. In embodiments, $R^9$ is independently unsubstituted cycloalkyl. In embodiments, $R^9$ is independently unsubstituted heterocycloalkyl. In embodiments, $R^9$ is independently unsubstituted aryl. In embodiments, $R^9$ is independently unsubstituted heteroaryl. In embodiments, $R^9$ is independently substituted or unsubstituted $C_1$-$C_6$ alkyl. In embodiments, $R^9$ is independently substituted or unsubstituted 2 to 6 membered heteroalkyl. In embodiments, $R^9$ is independently substituted or unsubstituted $C_3$-$C_8$ cycloalkyl. In embodiments, $R^9$ is independently substituted or unsubstituted 3 to 8 membered heterocycloalkyl. In embodiments, $R^9$ is independently substituted or unsubstituted $C_6$ aryl. In embodiments, $R^9$ is independently substituted or unsubstituted 5 to 6 membered heteroaryl. In embodiments, $R^9$ is independently substituted $C_1$-$C_6$ alkyl. In embodiments, $R^9$ is independently substituted 2 to 6 membered heteroalkyl. In embodiments, $R^9$ is independently substituted $C_3$-$C_8$ cycloalkyl. In embodiments, $R^9$ is independently substituted 3 to 8 membered heterocycloalkyl. In embodiments, $R^9$ is independently substituted $C_6$ aryl. In embodiments, $R^9$ is independently substituted 5 to 6 membered heteroaryl. In embodiments, $R^9$ is independently unsubstituted $C_1$-$C_6$ alkyl. In embodiments, $R^9$ is independently unsubstituted 2 to 6 membered heteroalkyl. In embodiments, $R^9$ is independently unsubstituted $C_3$-$C_8$ cycloalkyl. In embodiments, $R^9$ is independently unsubstituted 3 to 8 membered heterocycloalkyl. In embodiments, $R^9$ is independently unsubstituted $C_6$ aryl. In embodiments, $R^9$ is independently unsubstituted 5 to 6 membered heteroaryl.

In embodiments, $R^{10}$ is independently hydrogen. In embodiments, $R^{10}$ is independently —$CX_3$. In embodiments, $R^{10}$ is independently —CN. In embodiments, $R^{10}$ is independently —COOH. In embodiments, $R^{10}$ is independently —$CONH_2$. In embodiments, $R^{10}$ is independently —$CHX_2$. In embodiments, $R^{10}$ is independently —$CH_2X$. In embodiments, $R^{10}$ is independently substituted or unsubstituted alkyl. In embodiments, $R^{10}$ is independently substituted or unsubstituted heteroalkyl. In embodiments, $R^{10}$ is independently substituted or unsubstituted cycloalkyl. In embodiments, $R^{10}$ is independently substituted or unsubstituted heterocycloalkyl. In embodiments, $R^{10}$ is independently substituted or unsubstituted aryl. In embodiments, $R^{10}$ is independently substituted or unsubstituted heteroaryl. In embodiments, $R^{10}$ is independently substituted alkyl. In embodiments, $R^{10}$ is independently substituted heteroalkyl. In embodiments, $R^{10}$ is independently substituted cycloalkyl. In embodiments, $R^{10}$ is independently substituted heterocycloalkyl. In embodiments, $R^{10}$ is independently substituted aryl. In embodiments, $R^{10}$ is independently substituted heteroaryl. In embodiments, $R^{10}$ is independently unsubstituted alkyl. In embodiments, $R^{10}$ is independently unsubstituted heteroalkyl. In embodiments, $R^{10}$ is independently unsubstituted cycloalkyl. In embodiments, $R^{10}$ is independently unsubstituted heterocycloalkyl. In embodiments, $R^{10}$ is independently unsubstituted aryl. In embodiments, $R^{10}$ is independently unsubstituted heteroaryl. In embodiments, $R^{10}$ is independently substituted or unsubstituted $C_1$-$C_6$ alkyl. In embodiments, $R^{10}$ is independently substituted or unsubstituted 2 to 6 membered heteroalkyl. In embodiments, $R^{10}$ is independently substituted or unsubstituted $C_3$-$C_8$ cycloalkyl. In embodiments, $R^{10}$ is independently substituted or unsubstituted 3 to 8 membered heterocycloalkyl. In embodiments, $R^{10}$ is independently substituted or unsubstituted $C_6$ aryl. In embodiments, $R^{10}$ is independently substituted or unsubstituted 5 to 6 membered heteroaryl. In embodiments, $R^{10}$ is independently substituted $C_1$-$C_6$ alkyl. In embodiments, $R^{10}$ is independently substituted 2 to 6 membered heteroalkyl. In embodiments, $R^{10}$ is independently substituted $C_3$-$C_8$ cycloalkyl. In embodiments, $R^{10}$ is independently substituted 3 to 8 membered heterocycloalkyl. In embodiments, $R^{10}$ is independently substituted $C_6$ aryl. In embodiments, $R^{10}$ is independently substituted 5 to 6 membered heteroaryl. In embodiments, $R^{10}$ is independently unsubstituted $C_1$-$C_6$ alkyl. In embodiments, $R^{10}$ is independently unsubstituted 2 to 6 membered heteroalkyl. In embodiments, $R^{10}$ is independently unsubstituted $C_3$-$C_8$ cycloalkyl. In embodiments, $R^{10}$ is independently unsubstituted 3 to 8 membered heterocycloalkyl. In embodiments, $R^{10}$ is independently unsubstituted $C_6$ aryl. In embodiments, $R^{10}$ is independently unsubstituted 5 to 6 membered heteroaryl.

In embodiments, $R^{11}$ is independently hydrogen. In embodiments, $R^{11}$ is independently —$CX_3$. In embodiments, $R^{11}$ is independently —CN. In embodiments, $R^{11}$ is independently —COOH. In embodiments, $R^{11}$ is independently —$CONH_2$. In embodiments, $R^{11}$ is independently —$CHX_2$. In embodiments, $R^{11}$ is independently —$CH_2X$. In embodiments, $R^{11}$ is independently substituted or unsubstituted alkyl. In embodiments, $R^{11}$ is independently substituted or unsubstituted heteroalkyl. In embodiments, $R^{11}$ is independently substituted or unsubstituted cycloalkyl. In embodiments, $R^{11}$ is independently substituted or unsubstituted heterocycloalkyl. In embodiments, $R^{11}$ is independently substituted or unsubstituted aryl. In embodiments, $R^{11}$ is independently substituted or unsubstituted heteroaryl. In embodiments, $R^{11}$ is independently substituted alkyl. In embodiments, $R^{11}$ is independently substituted heteroalkyl. In embodiments, $R^{11}$ is independently substituted cycloalkyl. In embodiments, $R^{11}$ is independently substituted heterocycloalkyl. In embodiments, $R^{11}$ is independently substituted aryl. In embodiments, $R^{11}$ is independently substituted heteroaryl. In embodiments, $R^{11}$ is independently unsubstituted alkyl. In embodiments, $R^{11}$ is independently unsubstituted heteroalkyl. In embodiments, $R^{11}$ is independently unsubstituted cycloalkyl. In embodiments, $R^{11}$ is independently unsubstituted heterocycloalkyl. In embodiments, $R^{11}$ is independently unsubstituted aryl. In embodiments, $R^{11}$ is independently unsubstituted heteroaryl. In embodiments, $R^{11}$ is independently substituted or unsubstituted $C_1$-$C_6$ alkyl. In embodiments, $R^{11}$ is independently substituted or unsubstituted 2 to 6 membered heteroalkyl. In embodiments, $R^{11}$ is independently substituted or unsubstituted $C_3$-$C_8$ cycloalkyl. In embodiments, $R^{11}$ is independently substituted or unsubstituted 3 to 8 membered heterocycloalkyl. In embodiments, $R^{11}$ is independently substituted or unsubstituted $C_6$ aryl. In embodiments, $R^{11}$ is independently substituted or unsubstituted 5 to 6 membered heteroaryl. In embodiments, $R^{11}$ is independently substituted $C_1$-$C_6$ alkyl. In embodiments, $R^{11}$ is independently substituted 2 to 6 membered heteroalkyl. In embodiments, $R^{11}$ is independently substituted $C_3$-$C_8$ cycloalkyl. In embodiments, $R^{11}$ is independently substituted 3 to 8 membered heterocycloalkyl. In embodiments, $R^{11}$ is independently substituted $C_6$ aryl. In embodiments, $R^{11}$ is independently substituted 5 to 6 membered heteroaryl. In embodiments, $R^{11}$ is independently unsubstituted $C_1$-$C_6$ alkyl. In embodiments, $R^{11}$ is independently unsubstituted 2 to 6 membered heteroalkyl. In embodiments, $R^{11}$ is independently unsubstituted $C_3$-$C_8$ cycloalkyl. In embodiments, $R^{11}$ is independently unsubstituted 3 to 8 membered heterocycloalkyl. In embodiments, $R^{11}$ is independently unsubstituted $C_6$ aryl. In embodiments, $R^{11}$ is independently unsubstituted 5 to 6 membered heteroaryl.

In embodiments, $R^{12}$ is independently hydrogen. In embodiments, $R^{12}$ is independently —$CX_3$. In embodiments, $R^{12}$ is independently —CN. In embodiments, $R^{12}$ is independently —COOH. In embodiments, $R^{12}$ is independently —$CONH_2$. In embodiments, $R^{12}$ is independently —$CHX_2$. In embodiments, $R^{12}$ is independently —$CH_2X$. In embodiments, $R^{12}$ is independently substituted or unsubstituted alkyl. In embodiments, $R^{12}$ is independently substituted or unsubstituted heteroalkyl. In embodiments, $R^{12}$ is independently substituted or unsubstituted cycloalkyl. In embodiments, $R^{12}$ is independently substituted or unsubstituted heterocycloalkyl. In embodiments, $R^{12}$ is independently substituted or unsubstituted aryl. In embodiments, $R^{12}$ is independently substituted or unsubstituted heteroaryl. In embodiments, $R^{12}$ is independently substituted alkyl. In embodiments, $R^{12}$ is independently substituted heteroalkyl. In embodiments, $R^{12}$ is independently substituted cycloalkyl. In embodiments, $R^{12}$ is independently substituted heterocycloalkyl. In embodiments, $R^{12}$ is independently substituted aryl. In embodiments, $R^{12}$ is independently substituted heteroaryl. In embodiments, $R^{12}$ is independently unsubstituted alkyl. In embodiments, $R^{12}$ is independently unsubstituted heteroalkyl. In embodiments, $R^{12}$ is independently unsubstituted cycloalkyl. In embodiments, $R^{12}$ is independently unsubstituted heterocycloalkyl. In embodiments, $R^{12}$ is independently unsubstituted aryl. In embodiments, $R^{12}$ is independently unsubstituted heteroaryl. In embodiments, $R^{12}$ is independently substituted or unsubstituted $C_1$-$C_6$ alkyl. In embodiments, $R^{12}$ is independently substituted or unsubstituted 2 to 6 membered heteroalkyl. In embodiments, $R^{12}$ is independently substituted or unsubstituted $C_3$-$C_8$ cycloalkyl. In embodiments, $R^{12}$ is independently substituted or unsubstituted 3 to 8 membered heterocycloalkyl. In embodiments, $R^{12}$ is independently substituted or unsubstituted $C_6$ aryl. In embodiments, $R^{12}$ is independently substituted or unsubstituted 5 to 6 membered heteroaryl. In embodiments, $R^{12}$ is independently substituted $C_1$-$C_6$ alkyl. In embodiments, $R^{12}$ is independently substituted 2 to 6 membered heteroalkyl. In embodiments, $R^{12}$ is independently substituted $C_3$-$C_8$ cycloalkyl. In embodiments, $R^{12}$ is independently substituted 3 to 8 membered heterocycloalkyl. In embodiments, $R^{12}$ is independently substituted $C_6$ aryl. In embodiments, $R^{12}$ is independently substituted 5 to 6 membered heteroaryl. In embodiments, $R^{12}$ is independently unsubstituted $C_1$-$C_6$ alkyl. In embodiments, $R^{12}$ is independently unsubstituted 2 to 6 membered heteroalkyl. In embodiments, $R^{12}$ is independently unsubstituted $C_3$-$C_8$ cycloalkyl. In embodiments, $R^{12}$ is independently unsubstituted 3 to 8 membered heterocycloalkyl. In embodiments, $R^{12}$ is independently unsubstituted $C_6$ aryl. In embodiments, $R^{12}$ is independently unsubstituted 5 to 6 membered heteroaryl.

In embodiments, $R^{13}$ is independently hydrogen. In embodiments, $R^{13}$ is independently —$CX_3$. In embodiments, $R^{13}$ is independently —CN. In embodiments, $R^{13}$ is independently —COOH. In embodiments, $R^{13}$ is independently —$CONH_2$. In embodiments, $R^{13}$ is independently —$CHX_2$. In embodiments, $R^{13}$ is independently —$CH_2X$. In embodiments, $R^{13}$ is independently substituted or unsubstituted alkyl. In embodiments, $R^{13}$ is independently substituted or unsubstituted heteroalkyl. In embodiments, $R^{13}$ is independently substituted or unsubstituted cycloalkyl. In embodiments, $R^{13}$ is independently substituted or unsubstituted heterocycloalkyl. In embodiments, $R^{13}$ is independently substituted or unsubstituted aryl. In embodiments, $R^{13}$ is independently substituted or unsubstituted heteroaryl. In embodiments, $R^{13}$ is independently substituted alkyl. In embodiments, $R^{13}$ is independently substituted heteroalkyl. In embodiments, $R^{13}$ is independently substituted cycloalkyl. In embodiments, $R^{13}$ is independently substituted heterocycloalkyl. In embodiments, $R^{13}$ is independently substituted aryl. In embodiments, $R^{13}$ is independently substituted heteroaryl. In embodiments, $R^{13}$ is independently unsubstituted alkyl. In embodiments, $R^{13}$ is independently unsubstituted heteroalkyl. In embodiments, $R^{13}$ is independently unsubstituted cycloalkyl. In embodiments, $R^{13}$ is independently unsubstituted heterocycloalkyl. In embodiments, $R^{13}$ is independently unsubstituted aryl. In embodiments, $R^{13}$ is independently unsubstituted heteroaryl. In embodiments, $R^{13}$ is independently substituted or unsubstituted $C_1$-$C_6$ alkyl. In embodiments, $R^{13}$ is independently substituted or unsubstituted 2 to 6 membered heteroalkyl. In embodiments, $R^{13}$ is independently substituted or unsubstituted $C_3$-$C_8$ cycloalkyl. In embodiments, $R^{13}$ is independently substituted or unsubstituted 3 to 8 membered heterocycloalkyl. In embodiments, $R^{13}$ is independently substituted or unsubstituted $C_6$ aryl. In embodiments, $R^{13}$ is independently substituted or unsubstituted 5 to 6 membered heteroaryl. In embodiments, $R^{13}$ is independently substituted $C_1$-$C_6$ alkyl. In embodiments, $R^{13}$ is independently substituted 2 to 6 membered heteroalkyl. In embodiments, $R^{13}$ is independently substituted $C_3$-$C_8$ cycloalkyl. In embodiments, $R^{13}$ is independently substituted 3 to 8 membered heterocycloalkyl. In embodiments, $R^{13}$ is independently substituted $C_6$ aryl. In embodiments, $R^{13}$ is independently substituted 5 to 6 membered heteroaryl. In embodiments, $R^{13}$ is independently unsubstituted $C_1$-$C_6$ alkyl. In embodiments, $R^{13}$ is independently unsubstituted 2 to 6 membered heteroalkyl. In embodiments, $R^{13}$ is independently unsubstituted $C_3$-$C_8$ cycloalkyl. In embodiments, $R^{13}$ is independently unsubstituted 3 to 8 membered heterocycloalkyl. In embodiments, $R^{13}$ is independently unsubstituted $C_6$ aryl. In embodiments, $R^{13}$ is independently unsubstituted 5 to 6 membered heteroaryl.

In embodiments, $R^{14}$ is independently hydrogen. In embodiments, $R^{14}$ is independently —$CX_3$. In embodiments, $R^{14}$ is independently —CN. In embodiments, $R^{14}$ is independently —COOH. In embodiments, $R^{14}$ is independently —$CONH_2$. In embodiments, $R^{14}$ is independently —$CHX_2$. In embodiments, $R^{14}$ is independently —$CH_2X$. In embodiments, $R^{14}$ is independently substituted or unsubstituted alkyl. In embodiments, $R^{14}$ is independently substituted or unsubstituted heteroalkyl. In embodiments, $R^{14}$ is independently substituted or unsubstituted cycloalkyl. In embodiments, $R^{14}$ is independently substituted or unsubstituted heterocycloalkyl. In embodiments, $R^{14}$ is independently substituted or unsubstituted aryl. In embodiments, $R^{14}$ is independently substituted or unsubstituted heteroaryl. In embodiments, $R^{14}$ is independently substituted alkyl. In embodiments, $R^{14}$ is independently substituted heteroalkyl. In embodiments, $R^{14}$ is independently substituted cycloalkyl. In embodiments, $R^{14}$ is independently substituted heterocycloalkyl. In embodiments, $R^{14}$ is independently substituted aryl. In embodiments, $R^{14}$ is independently substituted heteroaryl. In embodiments, $R^{14}$ is independently unsubstituted alkyl. In embodiments, $R^{14}$ is independently unsubstituted heteroalkyl. In embodiments, $R^{14}$ is independently unsubstituted cycloalkyl. In embodiments, $R^{14}$ is independently unsubstituted heterocycloalkyl. In embodiments, $R^{14}$ is independently unsubstituted aryl. In embodiments, $R^{14}$ is independently unsubstituted heteroaryl. In embodiments, $R^{14}$ is independently substituted or unsubstituted $C_1$-$C_6$ alkyl. In embodiments, $R^{14}$ is independently substituted or unsubstituted 2 to 6 membered heteroalkyl. In embodiments, $R^{14}$ is independently substituted or unsubstituted $C_3$—C cycloalkyl. In embodiments, $R^{14}$ is independently substituted or unsubstituted 3 to 8 membered heterocycloalkyl. In embodiments, $R^{14}$ is independently substituted or unsubstituted $C_6$ aryl. In embodiments, $R^{14}$ is independently substituted or unsubstituted 5 to 6 membered heteroaryl. In embodiments, $R^{14}$ is independently substituted $C_1$-$C_6$ alkyl. In embodiments, $R^{14}$ is independently substituted 2 to 6 membered heteroalkyl. In embodiments, $R^{14}$ is independently substituted $C_3$—C cycloalkyl. In embodiments, $R^{14}$ is independently substituted 3 to 8 membered heterocycloalkyl. In embodiments, $R^{14}$ is independently substituted $C_6$ aryl. In embodiments, $R^{14}$ is independently substituted 5 to 6 membered heteroaryl. In embodiments, $R^{14}$ is independently unsubstituted $C_1$-$C_6$ alkyl. In embodiments, $R^{14}$ is independently unsubstituted 2 to 6 membered heteroalkyl. In embodiments, $R^{14}$ is independently unsubstituted $C_3$-$C_8$ cycloalkyl. In embodiments, $R^{14}$ is independently unsubstituted 3 to 8 membered heterocycloalkyl. In embodiments, $R^{14}$ is independently unsubstituted $C_6$ aryl. In embodiments, $R^{14}$ is independently unsubstituted 5 to 6 membered heteroaryl.

In embodiments, $R^{15}$ is independently hydrogen. In embodiments, $R^{15}$ is independently —$CX_3$. In embodiments, $R^{15}$ is independently —CN. In embodiments, $R^{15}$ is independently —COOH. In embodiments, $R^{15}$ is independently —$CONH_2$. In embodiments, $R^{15}$ is independently —$CHX_2$. In embodiments, $R^{15}$ is independently —$CH_2X$. In embodiments, $R^{15}$ is independently substituted or unsubstituted alkyl. In embodiments, $R^{15}$ is independently substituted or unsubstituted heteroalkyl. In embodiments, $R^{15}$ is independently substituted or unsubstituted cycloalkyl. In embodiments, $R^{15}$ is independently substituted or unsubstituted heterocycloalkyl. In embodiments, $R^{15}$ is independently substituted or unsubstituted aryl. In embodiments, $R^{15}$ is independently substituted or unsubstituted heteroaryl. In embodiments, $R^{15}$ is independently substituted alkyl. In embodiments, $R^{15}$ is independently substituted heteroalkyl. In embodiments, $R^{15}$ is independently substituted cycloalkyl. In embodiments, $R^{15}$ is independently substituted heterocycloalkyl. In embodiments, $R^{15}$ is independently substituted aryl. In embodiments, $R^{15}$ is independently substituted heteroaryl. In embodiments, $R^{15}$ is independently unsubstituted alkyl. In embodiments, $R^{15}$ is independently unsubstituted heteroalkyl. In embodiments, $R^{15}$ is independently unsubstituted cycloalkyl. In embodiments, $R^{15}$ is independently unsubstituted heterocycloalkyl. In embodiments, $R^{15}$ is independently unsubstituted aryl. In embodiments, $R^{15}$ is independently unsubstituted heteroaryl. In embodiments, $R^{15}$ is independently substituted or unsubstituted $C_1$-$C_6$ alkyl. In embodiments, $R^{15}$ is independently substituted or unsubstituted 2 to 6 membered heteroalkyl. In embodiments, $R^{15}$ is independently substituted or unsubstituted $C_3$-$C_8$ cycloalkyl. In embodiments, $R^{15}$ is independently substituted or unsubstituted 3 to 8 membered heterocycloalkyl. In embodiments, $R^{15}$ is independently substituted or unsubstituted $C_6$ aryl. In embodiments, $R^{15}$ is independently substituted or unsubstituted 5 to 6 membered heteroaryl. In embodiments, $R^{15}$ is independently substituted $C_1$-$C_6$ alkyl. In embodiments, $R^{15}$ is independently substituted 2 to 6 membered heteroalkyl. In embodiments, $R^{15}$ is independently substituted $C_3$-$C_8$ cycloalkyl. In embodiments, $R^{15}$ is independently substituted 3 to 8 membered heterocycloalkyl. In embodiments, $R^{15}$ is independently substituted $C_6$ aryl. In embodiments, $R^{15}$ is independently substituted 5 to 6 membered heteroaryl. In embodiments, $R^{15}$ is independently unsubstituted $C_1$-$C_6$ alkyl. In embodiments, $R^{15}$ is independently unsubstituted 2 to 6 membered heteroalkyl. In embodiments, $R^{15}$ is independently unsubstituted $C_3$-$C_8$ cycloalkyl. In embodiments, $R^{15}$ is independently unsubstituted 3 to 8 membered heterocycloalkyl. In embodiments, $R^{15}$ is independently unsubstituted $C_6$ aryl. In embodiments, $R^{15}$ is independently unsubstituted 5 to 6 membered heteroaryl.

In embodiments, $R^{16}$ is independently hydrogen. In embodiments, $R^{16}$ is independently —$CX_3$. In embodiments, $R^{16}$ is independently —CN. In embodiments, $R^{16}$ is independently —COOH. In embodiments, $R^{16}$ is independently —$CONH_2$. In embodiments, $R^{16}$ is independently —$CHX_2$. In embodiments, $R^{16}$ is independently —$CH_2X$. In embodiments, $R^{16}$ is independently substituted or unsubstituted alkyl. In embodiments, $R^{16}$ is independently substituted or unsubstituted heteroalkyl. In embodiments, $R^{16}$ is independently substituted or unsubstituted cycloalkyl. In embodiments, $R^{16}$ is independently substituted or unsubstituted heterocycloalkyl. In embodiments, $R^{16}$ is independently substituted or unsubstituted aryl. In embodiments, $R^{16}$ is independently substituted or unsubstituted heteroaryl. In embodiments, $R^{16}$ is independently substituted alkyl. In embodiments, $R^{16}$ is independently substituted heteroalkyl. In embodiments, $R^{16}$ is independently substituted cycloalkyl. In embodiments, $R^{16}$ is independently substituted heterocycloalkyl. In embodiments, $R^{16}$ is independently substituted aryl. In embodiments, $R^{16}$ is independently substituted heteroaryl. In embodiments, $R^{16}$ is independently unsubstituted alkyl. In embodiments, $R^{16}$ is independently unsubstituted heteroalkyl. In embodiments, $R^{16}$ is independently unsubstituted cycloalkyl. In embodiments, $R^{16}$ is independently unsubstituted heterocycloalkyl. In embodiments, $R^{16}$ is independently unsubstituted aryl. In embodiments, $R^{16}$ is independently unsubstituted heteroaryl. In embodiments, $R^{16}$ is independently substituted or unsubstituted $C_1$-$C_6$ alkyl. In embodiments, $R^{16}$ is independently substituted or unsubstituted 2 to 6 membered heteroalkyl. In embodiments, $R^{16}$ is independently substituted or unsubstituted $C_3$-$C_8$ cycloalkyl. In embodiments, $R^{16}$ is independently substituted or unsubstituted 3 to 8 membered heterocycloalkyl. In embodiments, $R^{16}$ is independently substituted or unsubstituted $C_6$ aryl. In embodiments, $R^{16}$ is independently substituted or unsubstituted 5 to 6 membered heteroaryl. In embodiments, $R^{16}$ is independently substituted $C_1$-$C_6$ alkyl. In embodiments, $R^{16}$ is independently substituted 2 to 6 membered heteroalkyl. In embodiments, $R^{16}$ is independently substituted $C_3$-$C_8$ cycloalkyl. In embodiments, $R^{16}$ is independently substituted 3 to 8 membered heterocycloalkyl. In embodiments, $R^{16}$ is independently substituted $C_6$ aryl. In embodiments, $R^{16}$ is independently substituted 5 to 6 membered heteroaryl. In embodiments, $R^{16}$ is independently unsubstituted $C_1$-$C_6$ alkyl. In embodiments, $R^{16}$ is independently unsubstituted 2 to 6 membered heteroalkyl. In embodiments, $R^{16}$ is independently unsubstituted $C_3$-$C_8$ cycloalkyl. In embodiments, $R^{16}$ is independently unsubstituted 3 to 8 membered heterocycloalkyl. In embodiments, $R^{16}$ is independently unsubstituted $C_6$ aryl. In embodiments, $R^{16}$ is independently unsubstituted 5 to 6 membered heteroaryl.

In embodiments, $R^{17}$ is independently hydrogen. In embodiments, $R^{17}$ is independently —$CX_3$. In embodiments, $R^{17}$ is independently —CN. In embodiments, $R^{17}$ is independently —COOH. In embodiments, $R^{17}$ is independently —$CONH_2$. In embodiments, $R^{17}$ is independently —$CHX_2$. In embodiments, $R^{17}$ is independently —$CH_2X$. In embodiments, $R^{17}$ is independently substituted or unsubstituted alkyl. In embodiments, $R^{17}$ is independently substituted or unsubstituted heteroalkyl. In embodiments, $R^{17}$ is independently substituted or unsubstituted cycloalkyl. In embodiments, $R^{17}$ is independently substituted or unsubstituted heterocycloalkyl. In embodiments, $R^{17}$ is independently substituted or unsubstituted aryl. In embodiments, $R^{17}$ is independently substituted or unsubstituted heteroaryl. In embodiments, $R^{17}$ is independently substituted alkyl. In embodiments, $R^{17}$ is independently substituted heteroalkyl. In embodiments, $R^{17}$ is independently substituted cycloalkyl. In embodiments, $R^{17}$ is independently substituted heterocycloalkyl. In embodiments, $R^{17}$ is independently substituted aryl. In embodiments, $R^{17}$ is independently substituted heteroaryl. In embodiments, $R^{17}$ is independently unsubstituted alkyl. In embodiments, $R^{17}$ is independently unsubstituted heteroalkyl. In embodiments, $R^{17}$ is independently unsubstituted cycloalkyl. In embodiments, $R^{17}$ is independently unsubstituted heterocycloalkyl. In embodiments, $R^{17}$ is independently unsubstituted aryl. In embodiments, $R^{17}$ is independently unsubstituted heteroaryl. In embodiments, $R^{17}$ is independently substituted or unsubstituted $C_1$-$C_6$ alkyl. In embodiments, $R^{17}$ is independently substituted or unsubstituted 2 to 6 membered heteroalkyl. In embodiments, $R^{17}$ is independently substituted or unsubstituted $C_3$-$C_8$ cycloalkyl. In embodiments, $R^{17}$ is independently substituted or unsubstituted 3 to 8 membered heterocycloalkyl. In embodiments, $R^{17}$ is independently substituted or unsubstituted $C_6$ aryl. In embodiments, $R^{17}$ is independently substituted or unsubstituted 5 to 6 membered heteroaryl. In embodiments, $R^{17}$ is independently substituted $C_1$-$C_6$ alkyl. In embodiments, $R^{17}$ is independently substituted 2 to 6 membered heteroalkyl. In embodiments, $R^{17}$ is independently substituted $C_3$-$C_8$ cycloalkyl. In embodiments, $R^{17}$ is independently substituted 3 to 8 membered heterocycloalkyl. In embodiments, $R^{17}$ is independently substituted $C_6$ aryl. In embodiments, $R^{17}$ is independently substituted 5 to 6 membered heteroaryl. In embodiments, $R^{17}$ is independently unsubstituted $C_1$-$C_6$ alkyl. In embodiments, $R^{17}$ is independently unsubstituted 2 to 6 membered heteroalkyl. In embodiments, $R^{17}$ is independently unsubstituted $C_3$-$C_8$ cycloalkyl. In embodiments, $R^{17}$ is independently unsubstituted 3 to 8 membered heterocycloalkyl. In embodiments, $R^{17}$ is independently unsubstituted $C_6$ aryl. In embodiments, $R^{17}$ is independently unsubstituted 5 to 6 membered heteroaryl.

In embodiments, $R^{18}$ is independently hydrogen. In embodiments, $R^{18}$ is independently —$CX_3$. In embodiments, $R^8$ is independently —CN. In embodiments, $R^8$ is independently —COOH. In embodiments, $R^{18}$ is independently —$CONH_2$. In embodiments, $R^{18}$ is independently —$CHX_2$. In embodiments, $R^{18}$ is independently —$CH_2X$. In embodiments, $R^{18}$ is independently substituted or unsubstituted alkyl. In embodiments, $R^{18}$ is independently substituted or unsubstituted heteroalkyl. In embodiments, $R^{18}$ is independently substituted or unsubstituted cycloalkyl. In embodiments, $R^{18}$ is independently substituted or unsubstituted heterocycloalkyl. In embodiments, $R^{18}$ is independently substituted or unsubstituted aryl. In embodiments, $R^{18}$ is independently substituted or unsubstituted heteroaryl. In embodiments, $R^{18}$ is independently substituted alkyl. In embodiments, $R^{18}$ is independently substituted heteroalkyl. In embodiments, $R^{18}$ is independently substituted cycloalkyl. In embodiments, $R^{18}$ is independently substituted heterocycloalkyl. In embodiments, $R^{18}$ is independently substituted aryl. In embodiments, $R^{18}$ is independently substituted heteroaryl. In embodiments, $R^{18}$ is independently unsubstituted alkyl. In embodiments, $R^{18}$ is independently unsubstituted heteroalkyl. In embodiments, $R^{18}$ is independently unsubstituted cycloalkyl. In embodiments, $R^{18}$ is independently unsubstituted heterocycloalkyl. In embodiments, $R^{18}$ is independently unsubstituted aryl. In embodiments, $R^{18}$ is independently unsubstituted heteroaryl. In embodiments, $R^{18}$ is independently substituted or unsubstituted $C_1$-$C_6$ alkyl. In embodiments, $R^{18}$ is independently substituted or unsubstituted 2 to 6 membered heteroalkyl. In embodiments, $R^8$ is independently substituted or unsubstituted $C_3$-$C_8$ cycloalkyl. In embodiments, $R^{18}$ is independently substituted or unsubstituted 3 to 8 membered heterocycloalkyl. In embodiments, $R^{18}$ is independently substituted or unsubstituted $C_6$ aryl. In embodiments, $R^{18}$ is independently substituted or unsubstituted 5 to 6 membered heteroaryl. In embodiments, $R^{18}$ is independently substituted $C_1$-$C_6$ alkyl. In embodiments, $R^{18}$ is independently substituted 2 to 6 membered heteroalkyl. In embodiments, $R^{18}$ is independently substituted $C_3$-$C_8$ cycloalkyl. In embodiments, $R^{18}$ is independently substituted 3 to 8 membered heterocycloalkyl. In embodiments, $R^{18}$ is independently substituted $C_6$ aryl. In embodiments, $R^{18}$ is independently substituted 5 to 6 membered heteroaryl. In embodiments, $R^{18}$ is independently unsubstituted $C_1$-$C_6$ alkyl. In embodiments, $R^{18}$ is independently unsubstituted 2 to 6 membered heteroalkyl. In embodiments, $R^{18}$ is independently unsubstituted $C_3$-$C_8$ cycloalkyl. In embodiments, $R^8$ is independently unsubstituted 3 to 8 membered heterocycloalkyl. In embodiments, $R^{18}$ is independently unsubstituted $C_6$ aryl. In embodiments, $R^{18}$ is independently unsubstituted 5 to 6 membered heteroaryl.

In embodiments, $R^{19}$ is independently hydrogen. In embodiments, $R^{19}$ is independently —$CX_3$. In embodiments, $R^{19}$ is independently —CN. In embodiments, $R^{19}$ is independently —COOH. In embodiments, $R^{19}$ is independently —$CONH_2$. In embodiments, $R^{19}$ is independently —$CHX_2$. In embodiments, $R^{19}$ is independently —$CH_2X$. In embodiments, $R^{19}$ is independently substituted or unsubstituted alkyl. In embodiments, $R^{19}$ is independently substituted or unsubstituted heteroalkyl. In embodiments, $R^{19}$ is independently substituted or unsubstituted cycloalkyl. In embodiments, $R^{19}$ is independently substituted or unsubstituted heterocycloalkyl. In embodiments, $R^{19}$ is independently substituted or unsubstituted aryl. In embodiments, $R^{19}$ is independently substituted or unsubstituted heteroaryl. In embodiments, $R^{19}$ is independently substituted alkyl. In embodiments, $R^{19}$ is independently substituted heteroalkyl. In embodiments, $R^{19}$ is independently substituted cycloalkyl. In embodiments, $R^{19}$ is independently substituted heterocycloalkyl. In embodiments, $R^{19}$ is independently substituted aryl. In embodiments, $R^{19}$ is independently substituted heteroaryl. In embodiments, $R^{19}$ is independently unsubstituted alkyl. In embodiments, $R^{19}$ is independently unsubstituted heteroalkyl. In embodiments, $R^{19}$ is independently unsubstituted cycloalkyl. In embodiments, $R^{19}$ is independently unsubstituted heterocycloalkyl. In embodiments, $R^{19}$ is independently unsubstituted aryl. In embodiments, $R^{19}$ is independently unsubstituted heteroaryl. In embodiments, $R^{19}$ is independently substituted or unsubstituted $C_1$-$C_6$ alkyl. In embodiments, $R^{19}$ is independently substituted or unsubstituted 2 to 6 membered heteroalkyl. In embodiments, $R^{19}$ is independently substituted or unsubstituted $C_3$-$C_8$ cycloalkyl. In embodiments, $R^{19}$ is independently substituted or unsubstituted 3 to 8 membered heterocycloalkyl. In embodiments, $R^{19}$ is independently substituted or unsubstituted $C_6$ aryl. In embodiments, $R^{19}$ is independently substituted or unsubstituted 5 to 6 membered heteroaryl. In embodiments, $R^{19}$ is independently substituted $C_1$-$C_6$ alkyl. In embodiments, $R^{19}$ is independently substituted 2 to 6 membered heteroalkyl. In embodiments, $R^{19}$ is independently substituted $C_3$-$C_8$ cycloalkyl. In embodiments, $R^{19}$ is independently substituted 3 to 8 membered heterocycloalkyl. In embodiments, $R^{19}$ is independently substituted $C_6$ aryl. In embodiments, $R^{19}$ is independently substituted 5 to 6 membered heteroaryl. In embodiments, $R^{19}$ is independently unsubstituted $C_1$-$C_6$ alkyl. In embodiments, $R^{19}$ is independently unsubstituted 2 to 6 membered heteroalkyl. In embodiments, $R^{19}$ is independently unsubstituted $C_3$-$C_8$ cycloalkyl. In embodiments, $R^{19}$ is independently unsubstituted 3 to 8 membered heterocycloalkyl. In embodiments, $R^{19}$ is independently unsubstituted $C_6$ aryl. In embodiments, $R^{19}$ is independently unsubstituted 5 to 6 membered heteroaryl.

In embodiments, $R^{20}$ is independently hydrogen. In embodiments, $R^{20}$ is independently —$CX_3$. In embodiments, $R^{20}$ is independently —CN. In embodiments, $R^{20}$ is independently —COOH. In embodiments, $R^{20}$ is independently —$CONH_2$. In embodiments, $R^{20}$ is independently —$CHX_2$. In embodiments, $R^{20}$ is independently —$CH_2X$. In embodiments, $R^{20}$ is independently substituted or unsubstituted alkyl. In embodiments, $R^{20}$ is independently substituted or unsubstituted heteroalkyl. In embodiments, $R^{20}$ is independently substituted or unsubstituted cycloalkyl. In embodiments, $R^{20}$ is independently substituted or unsubstituted heterocycloalkyl. In embodiments, $R^{20}$ is independently substituted or unsubstituted aryl. In embodiments, $R^{20}$ is independently substituted or unsubstituted heteroaryl. In embodiments, $R^{20}$ is independently substituted alkyl. In embodiments, $R^{20}$ is independently substituted heteroalkyl. In embodiments, $R^{20}$ is independently substituted cycloalkyl. In embodiments, $R^{20}$ is independently substituted heterocycloalkyl. In embodiments, $R^{20}$ is independently substituted aryl. In embodiments, $R^{20}$ is independently substituted heteroaryl. In embodiments, $R^{20}$ is independently unsubstituted alkyl. In embodiments, $R^{20}$ is independently unsubstituted heteroalkyl. In embodiments, $R^{20}$ is independently unsubstituted cycloalkyl. In embodiments, $R^{20}$ is independently unsubstituted heterocycloalkyl. In embodiments, $R^{20}$ is independently unsubstituted aryl. In embodiments, $R^{20}$ is independently unsubstituted heteroaryl. In embodiments, $R^{20}$ is independently substituted or unsubstituted $C_1$-$C_6$ alkyl. In embodiments, $R^{20}$ is independently substituted or unsubstituted 2 to 6 membered heteroalkyl. In embodiments, $R^{20}$ is independently substituted or unsubstituted $C_3$-$C_8$ cycloalkyl. In embodiments, $R^{20}$ is independently substituted or unsubstituted 3 to 8 membered heterocycloalkyl. In embodiments, $R^{20}$ is independently substituted or unsubstituted $C_6$ aryl. In embodiments, $R^{20}$ is independently substituted or unsubstituted 5 to 6 membered heteroaryl. In embodiments, $R^{20}$ is independently substituted $C_1$-$C_6$ alkyl. In embodiments, $R^{20}$ is independently substituted 2 to 6 membered heteroalkyl. In embodiments, $R^{20}$ is independently substituted $C_3$-$C_8$ cycloalkyl. In embodiments, $R^{20}$ is independently substituted 3 to 8 membered heterocycloalkyl. In embodiments, $R^{20}$ is independently substituted $C_6$ aryl. In embodiments, $R^{20}$ is independently substituted 5 to 6 membered heteroaryl. In embodiments, $R^{20}$ is independently unsubstituted $C_1$-$C_6$ alkyl. In embodiments, $R^{20}$ is independently unsubstituted 2 to 6 membered heteroalkyl. In embodiments, $R^{20}$ is independently unsubstituted $C_3$-$C_8$ cycloalkyl. In embodiments, $R^{20}$ is independently unsubstituted 3 to 8 membered heterocycloalkyl. In embodiments, $R^{20}$ is independently unsubstituted $C_6$ aryl. In embodiments, $R^{20}$ is independently unsubstituted 5 to 6 membered heteroaryl.

In embodiments, $R^{21}$ is independently hydrogen. In embodiments, $R^{21}$ is independently —$CX_3$. In embodiments, $R^{21}$ is independently —CN. In embodiments, $R^{21}$ is independently —COOH. In embodiments, $R^{21}$ is independently —$CONH_2$. In embodiments, $R^{21}$ is independently —$CHX_2$. In embodiments, $R^{21}$ is independently —$CH_2X$. In embodiments, $R^{21}$ is independently substituted or unsubstituted alkyl. In embodiments, $R^{21}$ is independently substituted or unsubstituted heteroalkyl. In embodiments, $R^{21}$ is independently substituted or unsubstituted cycloalkyl. In embodiments, $R^{21}$ is independently substituted or unsubstituted heterocycloalkyl. In embodiments, $R^{21}$ is independently substituted or unsubstituted aryl. In embodiments, $R^{21}$ is independently substituted or unsubstituted heteroaryl. In embodiments, $R^{21}$ is independently substituted alkyl. In embodiments, $R^{21}$ is independently substituted heteroalkyl. In embodiments, $R^{21}$ is independently substituted cycloalkyl. In embodiments, $R^{21}$ is independently substituted heterocycloalkyl. In embodiments, $R^{21}$ is independently substituted aryl. In embodiments, $R^{21}$ is independently substituted heteroaryl. In embodiments, $R^{21}$ is independently unsubstituted alkyl. In embodiments, $R^{21}$ is independently unsubstituted heteroalkyl. In embodiments, $R^{21}$ is independently unsubstituted cycloalkyl. In embodiments, $R^{21}$ is independently unsubstituted heterocycloalkyl. In embodiments, $R^{21}$ is independently unsubstituted aryl. In embodiments, $R^{21}$ is independently unsubstituted heteroaryl. In embodiments, $R^{21}$ is independently substituted or unsubstituted $C_1$-$C_6$ alkyl. In embodiments, $R^{21}$ is independently substituted or unsubstituted 2 to 6 membered heteroalkyl. In embodiments, $R^{21}$ is independently substituted or unsubstituted $C_3$-$C_8$ cycloalkyl. In embodiments, $R^{21}$ is independently substituted or unsubstituted 3 to 8 membered heterocycloalkyl. In embodiments, $R^{21}$ is independently substituted or unsubstituted $C_6$ aryl. In embodiments, $R^{21}$ is independently substituted or unsubstituted 5 to 6 membered heteroaryl. In embodiments, $R^{21}$ is independently substituted $C_1$-$C_6$ alkyl. In embodiments, $R^{21}$ is independently substituted 2 to 6 membered heteroalkyl. In embodiments, $R^{21}$ is independently substituted $C_3$-$C_8$ cycloalkyl. In embodiments, $R^{21}$ is independently substituted 3 to 8 membered heterocycloalkyl. In embodiments, $R^{21}$ is independently substituted $C_6$ aryl. In embodiments, $R^{20}$ is independently substituted 5 to 6 membered heteroaryl. In embodiments, $R^{21}$ is independently unsubstituted $C_1$-$C_6$ alkyl. In embodiments, $R^{21}$ is independently unsubstituted 2 to 6 membered heteroalkyl. In embodiments, $R^{21}$ is independently unsubstituted $C_3$-$C_8$ cycloalkyl. In embodiments, $R^{21}$ is independently unsubstituted 3 to 8 membered heterocycloalkyl. In embodiments, $R^{21}$ is independently unsubstituted $C_6$ aryl. In embodiments, $R^{21}$ is independently unsubstituted 5 to 6 membered heteroaryl.

$R^6$ and $R^7$ substituents bonded to the same nitrogen atom may be joined to form a substituted or unsubstituted heterocycloalkyl. $R^6$ and $R^7$ substituents bonded to the same nitrogen atom may be joined to form a substituted or unsubstituted heteroaryl. $R^6$ and $R^7$ substituents bonded to the same nitrogen atom may be joined to form a substituted heterocycloalkyl. $R^6$ and $R^7$ substituents bonded to the same nitrogen atom may be joined to form a substituted heteroaryl. $R^6$ and $R^7$ substituents bonded to the same nitrogen atom may be joined to form an unsubstituted heterocycloalkyl. $R^6$ and $R^7$ substituents bonded to the same nitrogen atom may be joined to form an unsubstituted heteroaryl. $R^6$ and $R^7$ substituents bonded to the same nitrogen atom may be joined to form a substituted or unsubstituted 3 to 8 membered heterocycloalkyl. $R^6$ and $R^7$ substituents bonded to the same nitrogen atom may be joined to form a substituted or unsubstituted 5 to 6 membered heteroaryl. $R^6$ and $R^7$ substituents bonded to the same nitrogen atom may be joined to form a substituted 3 to 8 membered heterocycloalkyl. $R^6$ and $R^7$ substituents bonded to the same nitrogen atom may be joined to form a substituted 5 to 6 membered heteroaryl. $R^6$ and $R^7$ substituents bonded to the same nitrogen atom may be joined to form an unsubstituted 3 to 8 membered heterocycloalkyl. $R^6$ and $R^7$ substituents bonded to the same nitrogen atom may be joined to form an unsubstituted 5 to 6 membered heteroaryl.

$R^{10}$ and $R^{11}$ substituents bonded to the same nitrogen atom may be joined to form a substituted or unsubstituted heterocycloalkyl. $R^{10}$ and $R^{11}$ substituents bonded to the same nitrogen atom may be joined to form a substituted or unsubstituted heteroaryl. $R^{10}$ and $R^{11}$ substituents bonded to the same nitrogen atom may be joined to form a substituted heterocycloalkyl. $R^{10}$ and $R^{11}$ substituents bonded to the same nitrogen atom may be joined to form a substituted heteroaryl. $R^{10}$ and $R^{11}$ substituents bonded to the same nitrogen atom may be joined to form an unsubstituted heterocycloalkyl. $R^{10}$ and $R^{11}$ substituents bonded to the same nitrogen atom may be joined to form an unsubstituted heteroaryl. $R^{10}$ and $R^{11}$ substituents bonded to the same nitrogen atom may be joined to form a substituted or unsubstituted 3 to 8 membered heterocycloalkyl. $R^{10}$ and $R^{11}$ substituents bonded to the same nitrogen atom may be joined to form a substituted or unsubstituted 5 to 6 membered heteroaryl. $R^{10}$ and $R^{11}$ substituents bonded to the same nitrogen atom may be joined to form a substituted 3 to 8 membered heterocycloalkyl. $R^{10}$ and $R^{11}$ substituents bonded to the same nitrogen atom may be joined to form a substituted 5 to 6 membered heteroaryl. $R^{10}$ and $R^{11}$ substituents bonded to the same nitrogen atom may be joined to form an unsubstituted 3 to 8 membered heterocycloalkyl. $R^{10}$ and $R^{11}$ substituents bonded to the same nitrogen atom may be joined to form an unsubstituted 5 to 6 membered heteroaryl.

$R^{14}$ and $R^{15}$ substituents bonded to the same nitrogen atom may be joined to form a substituted or unsubstituted heterocycloalkyl. $R^{14}$ and $R^{15}$ substituents bonded to the same nitrogen atom may be joined to form a substituted or unsubstituted heteroaryl. $R^{14}$ and $R^{15}$ substituents bonded to the same nitrogen atom may be joined to form a substituted heterocycloalkyl. $R^{14}$ and $R^{15}$ substituents bonded to the same nitrogen atom may be joined to form a substituted heteroaryl. $R^{14}$ and $R^{15}$ substituents bonded to the same nitrogen atom may be joined to form an unsubstituted heterocycloalkyl. $R^{14}$ and $R^{15}$ substituents bonded to the same nitrogen atom may be joined to form an unsubstituted heteroaryl. $R^{14}$ and $R^{15}$ substituents bonded to the same nitrogen atom may be joined to form a substituted or unsubstituted 3 to 8 membered heterocycloalkyl. $R^{14}$ and $R^{15}$ substituents bonded to the same nitrogen atom may be joined to form a substituted or unsubstituted 5 to 6 membered heteroaryl. $R^{14}$ and $R^{15}$ substituents bonded to the same nitrogen atom may be joined to form a substituted 3 to 8 membered heterocycloalkyl. $R^{14}$ and $R^{15}$ substituents bonded to the same nitrogen atom may be joined to form a substituted 5 to 6 membered heteroaryl. $R^{14}$ and $R^{15}$ substituents bonded to the same nitrogen atom may be joined to form an unsubstituted 3 to 8 membered heterocycloalkyl. $R^{14}$ and $R^{15}$ substituents bonded to the same nitrogen atom may be joined to form an unsubstituted 5 to 6 membered heteroaryl.

$R^{18}$ and $R^{19}$ substituents bonded to the same nitrogen atom may be joined to form a substituted or unsubstituted heterocycloalkyl. $R^{18}$ and $R^{19}$ substituents bonded to the same nitrogen atom may be joined to form a substituted or unsubstituted heteroaryl. $R^{18}$ and $R^{19}$ substituents bonded to the same nitrogen atom may be joined to form a substituted heterocycloalkyl. $R^{18}$ and $R^{19}$ substituents bonded to the same nitrogen atom may be joined to form a substituted heteroaryl. $R^{18}$ and $R^{19}$ substituents bonded to the same nitrogen atom may be joined to form an unsubstituted heterocycloalkyl. $R^{18}$ and $R^{19}$ substituents bonded to the same nitrogen atom may be joined to form an unsubstituted heteroaryl. $R^8$ and $R^{19}$ substituents bonded to the same nitrogen atom may be joined to form a substituted or unsubstituted 3 to 8 membered heterocycloalkyl. $R^{18}$ and $R^{19}$ substituents bonded to the same nitrogen atom may be joined to form a substituted or unsubstituted 5 to 6 membered heteroaryl. $R^{18}$ and $R^{19}$ substituents bonded to the same nitrogen atom may be joined to form a substituted 3 to 8 membered heterocycloalkyl. $R^{18}$ and $R^{19}$ substituents bonded to the same nitrogen atom may be joined to form a substituted 5 to 6 membered heteroaryl. $R^{18}$ and $R^{19}$ substituents bonded to the same nitrogen atom may be joined to form an unsubstituted 3 to 8 membered heterocycloalkyl. $R^{18}$ and $R^{19}$ substituents bonded to the same nitrogen atom may be joined to form an unsubstituted 5 to 6 membered heteroaryl.

X is independently —F. X is independently —Cl. X is independently —Br. X is independently —I. $X^2$ is independently —F. $X^2$ is independently —Cl. $X^2$ is independently —Br. $X^2$ is independently —I. $X^3$ is independently —F. $X^3$ is independently —Cl. $X^3$ is independently —Br. $X^3$ is independently —I. $X^4$ is independently —F. $X^4$ is independently —Cl. $X^4$ is independently —Br. $X^4$ is independently —I. $X^5$ is independently —F. $X^5$ is independently —Cl. $X^5$ is independently —Br. $X^5$ is independently —I. m2 is independently 1. m2 is independently 2. m3 is independently 1. m3 is independently 2. m4 is independently 1. m4 is independently 2. m5 is independently 1. m5 is independently 2. n2 is independently 0. n2 is independently 1. n2 is independently 2. n2 is independently 3. n3 is independently 0. n3 is independently 1. n3 is independently 2. n3 is independently 3. n4 is independently 0. n4 is independently 1. n4 is independently 2. n4 is independently 3. n5 is independently 0. n5 is independently 1. n5 is independently 2. n5 is independently 3. v2 is independently 1. v2 is independently 2. v3 is independently 1. v3 is independently 2. v4 is independently 1. v4 is independently 2. v5 is independently 1. v5 is independently 2.

In embodiments, $R^1$ is independently hydrogen, $R^2_2$-substituted or unsubstituted alkyl, $R^2_2$-substituted or unsubstituted heteroalkyl, $R^2_2$-substituted or unsubstituted cycloalkyl, $R^2_2$-substituted or unsubstituted heterocycloalkyl, $R^2_2$-substituted or unsubstituted aryl, or $R^2_2$-substituted or unsubstituted heteroaryl.

$R^{22}$ is independently oxo, halogen, —$CX^{22}_3$, —$CHX^{22}_2$, —$OCH_2X^{22}$, —$OCHX^{22}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{22}_3$, —$OCHX^{22}_2$, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl. $X^{22}$ is halogen. In embodiments, $X^{22}$ is F.

$R^{23}$ is independently oxo, halogen, —$CX^{23}_3$, —$CHX^{23}_2$, —$OCH_2X^{23}$, —$OCHX^{23}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{23}_3$, —$OCHX^{23}_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl. $X^{23}$ is halogen. In embodiments, $X^{23}$ is F.

In embodiments, $R^2$ is independently hydrogen, halogen, —$CX^2_3$, —$CHX^2_2$, —$CH_2X^2$, —CN, —$SO_{n2}R^9$, —$SO_{v2}NR^6R^7$, —NHC(O)$NR^6R^7$, —N(O)$_{m2}$, —$NR^6R^7$, —C(O)$R^8$, —C(O)—$OR^8$, —C(O)$NR^6R^7$, —$OR^9$, —$NR^6SO_2R^9$, —$NR^6C(O)R^8$, —$NR^6C(O)OR^8$, —$NR^6OR^8$, —$OCX^2_3$, —$OCHX^2_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl. $X^2$ is independently —F, —Cl, —Br, or —I. In embodiments, $X^2$ is —F.

$R^{25}$ is independently oxo, halogen, —$CX^{25}_3$, —$CHX^{25}_2$, —$OCH_2X^{25}$, —$OCHX^{25}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{25}_3$, —$OCHX^{25}_2$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl. $X^{25}$ is halogen. In embodiments, $X^{25}$ is F.

$R^{26}$ is independently oxo, halogen, —$CX^{26}_3$, —$CHX^{26}_2$, —$OCH_2X^{26}$, —$OCHX^{26}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{26}_3$, —$OCHX^{26}_2$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl. $X^{26}$ is halogen. In embodiments, $X^{26}$ is F.

In embodiments, $R^3$ is independently hydrogen, halogen, —$CX^3_3$, —$CHX^3_2$, —$CH_2X^3$, —CN, —$SO_{n3}R^{13}$, —$SO_{v3}NR^{10}R^{11}$, —NHC(O)$NR^{10}R^{11}$, —N(O)$_{m3}$, —$NR^{10}R^{11}$, —C(O)$R^{12}$, —C(O)—$OR^{12}$, —$OR^{13}$, —$NR^{10}SO_2R^{13}$, —$NR^{10}C(O)R^{12}$, —$NR^{10}C(O)OR^{12}$, —$NR^{10}OR^{12}$, —$OCX^3_3$, —$OCHX^3_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl. $X^3$ is independently —F, —Cl, —Br, or —I. In embodiments, $X^3$ is —F.

$R^{28}$ is independently oxo, halogen, —$CX^{28}_3$, —$CHX^{28}_2$, —$CH_2X^{28}$, —$OCHX^{28}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{28}_3$, —$OCHX^{28}_2$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. $X^{28}$ is halogen. In embodiments, $X^{28}$ is F.

$R^{29}$ is independently oxo, halogen, —$CX^{29}_3$, —$CHX^{29}_2$, —$CH_2X^{29}$, —$OCHX^{29}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —OCX$^{29}{}_3$, —OCHX$^{29}{}_2$, R$^{30}$-substituted or unsubstituted alkyl, R$^{30}$-substituted or unsubstituted heteroalkyl, R$^{30}$-substituted or unsubstituted cycloalkyl, R$^{30}$-substituted or unsubstituted heterocycloalkyl, R$^{30}$-substituted or unsubstituted aryl, or R$^{30}$-substituted or unsubstituted heteroaryl. X$^{29}$ is halogen. In embodiments, X$^{29}$ is F.

In embodiments, R$^4$ is independently hydrogen, halogen, —CX$^4{}_3$, —CHX$^4{}_2$, —CH$_2$X$^4$, —CN, —SO$_{n4}$R$^{17}$, —SO$_{v4}$NR$^{14}$R$^{15}$, —NHC(O)NR$^{14}$R$^{15}$, —N(O)$_{m4}$, —NR$^{14}$R$^{15}$, —C(O)R$^{16}$, —C(O)—OR$^{16}$, —C(O)NR$^{14}$R$^{15}$, —OR$^{17}$, —NR$^{14}$SO$_2$R$^{17}$, —NR$^{14}$C(O)R$^{16}$, —NR$^{14}$C(O)OR$^{16}$—NR$^{14}$OR$^{16}$, —OCX$^4{}_3$, —OCHX$^4{}_2$, R$^{31}$-substituted or unsubstituted alkyl, R$^{31}$-substituted or unsubstituted heteroalkyl, R$^{31}$-substituted or unsubstituted cycloalkyl, R$^{31}$-substituted or unsubstituted heterocycloalkyl, R$^{31}$-substituted or unsubstituted aryl, or R$^{31}$-substituted or unsubstituted heteroaryl. X$^4$ is independently —F, —Cl, —Br, or —I. In embodiments, X$^4$ is —F.

R$^{31}$ is independently oxo, halogen, —CX$^{31}{}_3$, —CHX$^{31}{}_2$, —CH$_2$X$^{31}$, —OCHX$^{31}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{31}{}_3$, —OCHX$^{31}{}_2$, R$^{32}$-substituted or unsubstituted alkyl, R$^{32}$-substituted or unsubstituted heteroalkyl, R$^{32}$-substituted or unsubstituted cycloalkyl, R$^{32}$-substituted or unsubstituted heterocycloalkyl, R$^{32}$-substituted or unsubstituted aryl, or R$^{32}$-substituted or unsubstituted heteroaryl. X$^{31}$ is halogen. In embodiments, X$^{31}$ is F.

R$^{32}$ is independently oxo, halogen, —CX$^{32}{}_3$, —CHX$^{32}{}_2$, —CH$_2$X$^{32}$, —OCHX$^{32}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{32}{}_3$, —OCHX$^{32}{}_2$, R$^{33}$-substituted or unsubstituted alkyl, R$^{33}$-substituted or unsubstituted heteroalkyl, R$^{33}$-substituted or unsubstituted cycloalkyl, R$^{33}$-substituted or unsubstituted heterocycloalkyl, R$^{33}$-substituted or unsubstituted aryl, or R$^{33}$-substituted or unsubstituted heteroaryl. X$^{32}$ is halogen. In embodiments, X$^{32}$ is F.

In embodiments, R$^5$ is independently hydrogen, halogen, —CX$^5{}_3$, —CHX$^5{}_2$, —CH$_2$X$^5$, —CN, —SO$_{n5}$R$^{21}$, —SO$_{v5}$NR$^{18}$R$^{19}$, —NHC(O)NR$^{18}$R$^{19}$, —N(O)$_{m5}$, —NR$^{18}$R$^{19}$, —C(O)R$^{20}$, —C(O)—OR$^{20}$, —C(O)NR$^{18}$R$^{19}$, —OR$^{21}$, —NR$^{18}$SO$_2$R$^{21}$, —NR$^{18}$C(O)R$^{20}$—NR$^{18}$C(O)OR$^{20}$, —NR$^{18}$R$^{20}$, —OCX$^5{}_3$, —OCHX$^5{}_2$, R$^{34}$-substituted or unsubstituted alkyl, R$^{34}$-substituted or unsubstituted heteroalkyl, R$^{34}$-substituted or unsubstituted cycloalkyl, R$^{34}$-substituted or unsubstituted heterocycloalkyl, R$^{34}$-substituted or unsubstituted aryl, or R$^{34}$-substituted or unsubstituted heteroaryl. X$^5$ is independently —F, —Cl, —Br, or —I. In embodiments, X$^5$ is —F.

R$^{34}$ is independently oxo, halogen, —CX$^{34}{}_3$, —CHX$^{34}{}_2$, —CH$_2$X$^{34}$, —OCHX$^{34}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{34}{}_3$, —OCHX$^{34}{}_2$, R$^{35}$-substituted or unsubstituted alkyl, R$^{35}$-substituted or unsubstituted heteroalkyl, R$^{35}$-substituted or unsubstituted cycloalkyl, R$^{35}$-substituted or unsubstituted heterocycloalkyl, R$^{35}$-substituted or unsubstituted aryl, or R$^{35}$-substituted or unsubstituted heteroaryl. X$^{34}$ is halogen. In embodiments, X$^{34}$ is F.

R$^{35}$ is independently oxo, halogen, —CX$^{35}{}_3$, —CHX$^{35}{}_2$, —CH$_2$X$^{35}$, —OCHX$^{35}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{35}{}_3$, —OCHX$^{35}{}_2$, R$^{36}$-substituted or unsubstituted alkyl, R$^{36}$-substituted or unsubstituted heteroalkyl, R$^{36}$-substituted or unsubstituted cycloalkyl, R$^{36}$-substituted or unsubstituted heterocycloalkyl, R$^{36}$-substituted or unsubstituted aryl, or R$^{36}$-substituted or unsubstituted heteroaryl. X$^{35}$ is halogen. In embodiments, X$^{35}$ is F.

In embodiments, R$^A$ is independently hydrogen, —CX$_3$, —CN, —COOH, —CONH$_2$, —CHX$_2$, —CH$_2$X, R$^{36}$-substituted or unsubstituted alkyl, R$^{36}$-substituted or unsubstituted heteroalkyl, R$^{36}$-substituted or unsubstituted cycloalkyl, R$^{36}$-substituted or unsubstituted heterocycloalkyl, R$^{36}$-substituted or unsubstituted aryl, or R$^{36}$-substituted or unsubstituted heteroaryl. X is independently —F, —Cl, —Br, or —I. In embodiments, X is F.

R$^{36}$ is independently oxo, halogen, —CX$^{36}{}_3$, —CHX$^{36}{}_2$, —CH$_2$X$^{36}$, —OCHX$^{36}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{36}{}_3$, —OCHX$^{36}{}_2$, R$^{37}$-substituted or unsubstituted alkyl, R$^{37}$-substituted or unsubstituted heteroalkyl, R$^{37}$-substituted or unsubstituted cycloalkyl, R$^{37}$-substituted or unsubstituted heterocycloalkyl, R$^{37}$-substituted or unsubstituted aryl, or R$^{37}$-substituted or unsubstituted heteroaryl. X$^{36}$ is halogen. In embodiments, X$^{36}$ is F.

R$^{37}$ is independently oxo, halogen, —CX$^{37}{}_3$, —CHX$^{37}{}_2$, —CH$_2$X$^{37}$, —OCHX$^{37}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{37}{}_3$, —OCHX$^{37}{}_2$, R$^{38}$-substituted or unsubstituted alkyl, R$^{38}$-substituted or unsubstituted heteroalkyl, R$^{38}$-substituted or unsubstituted cycloalkyl, R$^{38}$-substituted or unsubstituted heterocycloalkyl, R$^{38}$-substituted or unsubstituted aryl, or R$^{38}$-substituted or unsubstituted heteroaryl. In embodiments, X$^{37}$ is halogen. In embodiments, X$^{37}$ is F.

In embodiments, R$^B$ is independently hydrogen, —CX$_3$, —CN, —COOH, —CONH$_2$, —CHX$_2$, —CH$_2$X, R$^{39}$-substituted or unsubstituted alkyl, R$^{39}$-substituted or unsubstituted heteroalkyl, R$^{39}$-substituted or unsubstituted cycloalkyl, R$^{39}$-substituted or unsubstituted heterocycloalkyl, R$^{39}$-substituted or unsubstituted aryl, or R$^{39}$-substituted or unsubstituted heteroaryl. X is independently —F, —Cl, —Br, or —I. In embodiments, X is F.

R$^{39}$ is independently oxo, halogen, —CX$^{39}{}_3$, —CHX$^{39}{}_2$, —CH$_2$X$^{39}$, —OCHX$^{39}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{39}{}_3$, —OCHX$^{39}{}_2$, R$^{40}$-substituted or unsubstituted alkyl, R$^{40}$-substituted or unsubstituted heteroalkyl, R$^{40}$-substituted or unsubstituted cycloalkyl, R$^{40}$-substituted or unsubstituted heterocycloalkyl, R$^{40}$-substituted or unsubstituted aryl, or R$^{40}$-substituted or unsubstituted heteroaryl. X$^{39}$ is halogen. In embodiments, X$^{39}$ is F.

R$^{40}$ is independently oxo, halogen, —CX$^{40}{}_3$, —CHX$^{40}{}_2$, —CH$_2$X$^{40}$, —OCHX$^{40}{}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{40}_3$, —OCHX$^{40}_2$, R$^{41}$-substituted or unsubstituted alkyl, R$^{41}$-substituted or unsubstituted heteroalkyl, R$^{41}$-substituted or unsubstituted cycloalkyl, R$^{41}$-substituted or unsubstituted heterocycloalkyl, R$^{41}$-substituted or unsubstituted aryl, or R$^{41}$-substituted or unsubstituted heteroaryl. X$^{40}$ is halogen. In embodiments, X$^{40}$ is F.

In embodiments, R$^6$ is independently hydrogen, —CX$_3$, —CN, —COOH, —CONH$_2$, —CHX$_2$, —CH$_2$X, R$^4_2$-substituted or unsubstituted alkyl, R$^4_2$-substituted or unsubstituted heteroalkyl, R$^4_2$-substituted or unsubstituted cycloalkyl, R$^4_2$-substituted or unsubstituted heterocycloalkyl, R$^4_2$-substituted or unsubstituted aryl, or R$^4_2$-substituted or unsubstituted heteroaryl. X is independently —F, —Cl, —Br, or —I. In embodiments, X is F.

R$^{42}$ is independently oxo, halogen, —CX$^{42}_3$, —CHX$^{42}_2$, —CH$_2$X$^{42}$, —OCHX$^{42}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{42}_3$, —OCHX$^{42}_2$, R$^{43}$-substituted or unsubstituted alkyl, R$^{43}$-substituted or unsubstituted heteroalkyl, R$^{43}$-substituted or unsubstituted cycloalkyl, R$^{43}$-substituted or unsubstituted heterocycloalkyl, R$^{43}$-substituted or unsubstituted aryl, or R$^{43}$-substituted or unsubstituted heteroaryl. X$^{42}$ is halogen. In embodiments, X$^{42}$ is F.

R$^{43}$ is independently oxo, halogen, —CX$^{43}_3$, —CHX$^{43}_2$, —CH$_2$X$^{43}$, —OCHX$^{43}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{43}_3$, —OCHX$^{43}_2$, R$^{44}$-substituted or unsubstituted alkyl, R$^{44}$-substituted or unsubstituted heteroalkyl, R$^{44}$-substituted or unsubstituted cycloalkyl, R$^{44}$-substituted or unsubstituted heterocycloalkyl, R$^{44}$-substituted or unsubstituted aryl, or R$^{44}$-substituted or unsubstituted heteroaryl. X$^{43}$ is halogen. In embodiments, X$^{43}$ is F.

In embodiments, R$^7$ is independently hydrogen, —CX$_3$, —CN, —COOH, —CONH$_2$, —CHX$_2$, —CH$_2$X, R$^{45}$-substituted or unsubstituted alkyl, R$^{45}$-substituted or unsubstituted heteroalkyl, R$^{45}$-substituted or unsubstituted cycloalkyl, R$^{45}$-substituted or unsubstituted heterocycloalkyl, R$^{45}$-substituted or unsubstituted aryl, or R$^{45}$-substituted or unsubstituted heteroaryl. X is independently —F, —Cl, —Br, or —I. In embodiments, X is F.

R$^{45}$ is independently oxo, halogen, —CX$^{45}_3$, —CHX$^{45}_2$, —CH$_2$X$^{45}$, —OCHX$^{45}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{45}_3$, —OCHX$^{45}_2$, R$^{46}$-substituted or unsubstituted alkyl, R$^{46}$-substituted or unsubstituted heteroalkyl, R$^{46}$-substituted or unsubstituted cycloalkyl, R$^{46}$-substituted or unsubstituted heterocycloalkyl, R$^{46}$-substituted or unsubstituted aryl, or R$^{46}$-substituted or unsubstituted heteroaryl. X$^{45}$ is halogen. In embodiments, X$^{45}$ is F.

R$^{46}$ is independently oxo, halogen, —CX$^{46}_3$, —CHX$^{46}_2$, —CH$_2$X$^{46}$, —OCHX$^{46}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{46}_3$, —OCHX$^{46}_2$, R$^{47}$-substituted or unsubstituted alkyl, R$^{47}$-substituted or unsubstituted heteroalkyl, R$^{47}$-substituted or unsubstituted cycloalkyl, R$^{47}$-substituted or unsubstituted heterocycloalkyl, R$^{47}$-substituted or unsubstituted aryl, or R$^{47}$-substituted or unsubstituted heteroaryl. X$^{46}$ is halogen. In embodiments, X$^{46}$ is F.

In embodiments, R$^8$ is independently hydrogen, —CX$_3$, —CN, —COOH, —CONH$_2$, —CHX$_2$, —CH$_2$X, R$^{48}$-substituted or unsubstituted alkyl, R$^{48}$-substituted or unsubstituted heteroalkyl, R$^{48}$-substituted or unsubstituted cycloalkyl, R$^{48}$-substituted or unsubstituted heterocycloalkyl, R$^{48}$-substituted or unsubstituted aryl, or R$^{48}$-substituted or unsubstituted heteroaryl. X is independently —F, —Cl, —Br, or —I. In embodiments, X is F.

R$^{48}$ is independently oxo, halogen, —CX$^{48}_3$, —CHX$^{48}_2$, —CH$_2$X$^{48}$, —OCHX$^{48}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{48}_3$, —OCHX$^{48}_2$, R$^{49}$-substituted or unsubstituted alkyl, R$^{49}$-substituted or unsubstituted heteroalkyl, R$^{49}$-substituted or unsubstituted cycloalkyl, R$^{49}$-substituted or unsubstituted heterocycloalkyl, R$^{49}$-substituted or unsubstituted aryl, or R$^{49}$-substituted or unsubstituted heteroaryl. X$^{48}$ is halogen. In embodiments, X$^{48}$ is F.

R$^{49}$ is independently oxo, halogen, —CX$^{49}_3$, —CHX$^{49}_2$, —CH$_2$X$^{49}$, —OCHX$^{49}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{49}_3$, —OCHX$^{49}_2$, R$^{50}$-substituted or unsubstituted alkyl, R$^{50}$-substituted or unsubstituted heteroalkyl, R$^{50}$-substituted or unsubstituted cycloalkyl, R$^{50}$-substituted or unsubstituted heterocycloalkyl, R$^{50}$-substituted or unsubstituted aryl, or R$^{50}$-substituted or unsubstituted heteroaryl. X$^{49}$ is halogen. In embodiments, X$^{49}$ is F.

In embodiments, R$^9$ is independently hydrogen, —CX$_3$, —CN, —COOH, —CONH$_2$, —CHX$_2$, —CH$_2$X, R$^{51}$-substituted or unsubstituted alkyl, R$^{51}$-substituted or unsubstituted heteroalkyl, R$^{51}$-substituted or unsubstituted cycloalkyl, R$^{51}$-substituted or unsubstituted heterocycloalkyl, R$^{51}$-substituted or unsubstituted aryl, or R$^{51}$-substituted or unsubstituted heteroaryl. X is independently —F, —Cl, —Br, or —I. In embodiments, X is F.

R$^{51}$ is independently oxo, halogen, —CX$^{51}_3$, —CHX$^{51}_2$, —CH$_2$X$^{51}$, —OCHX$^{51}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{51}_3$, —OCHX$^{51}_2$, R$^{52}$-substituted or unsubstituted alkyl, R$^{52}$-substituted or unsubstituted heteroalkyl, R$^{52}$-substituted or unsubstituted cycloalkyl, R$^{52}$-substituted or unsubstituted heterocycloalkyl, R$^{52}$-substituted or unsubstituted aryl, or R$^{52}$-substituted or unsubstituted heteroaryl. X$^{51}$ is halogen. In embodiments, X$^{51}$ is F.

R$^{52}$ is independently oxo, halogen, —CX$^{52}_3$, —CHX$^{52}_2$, —CH$_2$X$^{52}$, —OCHX$^{52}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{52}_3$, —OCHX$^{52}_2$, R$^{53}$-substituted or unsubstituted alkyl, R$^{53}$-substituted or unsubstituted heteroalkyl, R$^{53}$-substituted or unsubstituted cycloalkyl, R$^{53}$-substituted or unsubstituted heterocycloalkyl, R$^{53}$-substituted or unsubstituted aryl, or $R^{53}$-substituted or unsubstituted heteroaryl. $X^{52}$ is halogen. In embodiments, $X^{52}$ is F.

In embodiments, $R^{10}$ is independently hydrogen, $-CX_3$, $-CN$, $-COOH$, $-CONH_2$, $-CHX_2$, $-CH_2X$, $R^{54}$-substituted or unsubstituted alkyl, $R^{54}$-substituted or unsubstituted heteroalkyl, $R^{54}$-substituted or unsubstituted cycloalkyl, $R^{54}$-substituted or unsubstituted heterocycloalkyl, $R^{54}$-substituted or unsubstituted aryl, or $R^{54}$-substituted or unsubstituted heteroaryl. X is independently $-F$, $-Cl$, $-Br$, or $-I$. In embodiments, X is F.

$R^{54}$ is independently oxo, halogen, $-CX^{54}_3$, $-CHX^{54}_2$, $-CH_2X^{54}$, $-OCHX^{54}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{54}_3$, $-OCHX^{54}_2$, $R^{55}$-substituted or unsubstituted alkyl, $R^{55}$-substituted or unsubstituted heteroalkyl, $R^{55}$-substituted or unsubstituted cycloalkyl, $R^{55}$-substituted or unsubstituted heterocycloalkyl, $R^{55}$-substituted or unsubstituted aryl, or $R^{55}$-substituted or unsubstituted heteroaryl. $X^{54}$ is halogen. In embodiments, $X^{54}$ is F.

$R^{55}$ is independently oxo, halogen, $-CX^{55}_3$, $-CHX^{55}_2$, $-CH_2X^{55}$, $-OCHX^{55}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{55}_3$, $-OCHX^{55}_2$, $R^{56}$-substituted or unsubstituted alkyl, $R^{56}$-substituted or unsubstituted heteroalkyl, $R^{56}$-substituted or unsubstituted cycloalkyl, $R^{56}$-substituted or unsubstituted heterocycloalkyl, $R^{56}$-substituted or unsubstituted aryl, or $R^{56}$-substituted or unsubstituted heteroaryl. $X^{55}$ is halogen. In embodiments, $X^{55}$ is F.

In embodiments, R" is independently hydrogen, $-CX_3$, $-CN$, $-COOH$, $-CONH_2$, $-CHX_2$, $-CH_2X$, $R^{57}$-substituted or unsubstituted alkyl, $R^{57}$-substituted or unsubstituted heteroalkyl, $R^{57}$-substituted or unsubstituted cycloalkyl, $R^{57}$-substituted or unsubstituted heterocycloalkyl, $R^{57}$-substituted or unsubstituted aryl, or $R^{57}$-substituted or unsubstituted heteroaryl. X is independently $-F$, $-Cl$, $-Br$, or $-I$. In embodiments, X is F.

$R^{57}$ is independently oxo, halogen, $-CX^{57}_3$, $-CHX^{57}_2$, $-CH_2X^{57}$, $-OCHX^{57}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{57}_3$, $-OCHX^{57}_2$, $R^{110}$-substituted or unsubstituted alkyl, $R^{11}$-substituted or unsubstituted heteroalkyl, $R^{110}$-substituted or unsubstituted cycloalkyl, $R^{110}$-substituted or unsubstituted heterocycloalkyl, $R^{110}$-substituted or unsubstituted aryl, or $R^{110}$-substituted or unsubstituted heteroaryl. $X^{57}$ is halogen. In embodiments, $X^{57}$ is F.

$R^{110}$ is independently oxo, halogen, $-CX^{110}_3$, $-CHX^{110}_2$, $-CH_2X^{110}$, $-OCHX^{110}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{110}_3$, $-OCHX^{110}_2$, $R^{59}$-substituted or unsubstituted alkyl, $R^{59}$-substituted or unsubstituted heteroalkyl, $R^{59}$-substituted or unsubstituted cycloalkyl, $R^{59}$-substituted or unsubstituted heterocycloalkyl, $R^{59}$-substituted or unsubstituted aryl, or $R^{59}$-substituted or unsubstituted heteroaryl. $X^{110}$ is halogen. In embodiments, $X^{110}$ is F.

In embodiments, $R^{12}$ is independently hydrogen, $-CX_3$, $-CN$, $-COOH$, $-CONH_2$, $-CHX_2$, $-CH_2X$, $R^{60}$-substituted or unsubstituted alkyl, $R^{60}$-substituted or unsubstituted heteroalkyl, $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl. X is independently $-F$, $-Cl$, $-Br$, or $-I$. In embodiments, X is F.

$R^{60}$ is independently oxo, halogen, $-CX^{60}_3$, $-CHX^{60}_2$, $-CH_2X^{60}$, $-OCHX^{60}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{60}_3$, $-OCHX^{60}_2$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl. $X^{60}$ is halogen. In embodiments, $X^{60}$ is F.

$R^{61}$ is independently oxo, halogen, $-CX^{61}_3$, $-CHX^{61}_2$, $-CH_2X^{61}$, $-OCHX^{61}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{61}_3$, $-OCHX^{61}_2$, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl. $X^{61}$ is halogen. In embodiments, $X^{61}$ is F.

In embodiments, $R^{13}$ is independently hydrogen, $-CX_3$, $-CN$, $-COOH$, $-CONH_2$, $-CHX_2$, $-CH_2X$, $R^{63}$-substituted or unsubstituted alkyl, $R^{63}$-substituted or unsubstituted heteroalkyl, $R^{63}$-substituted or unsubstituted cycloalkyl, $R^{63}$-substituted or unsubstituted heterocycloalkyl, $R^{63}$-substituted or unsubstituted aryl, or $R^{63}$-substituted or unsubstituted heteroaryl. X is independently $-F$, $-Cl$, $-Br$, or $-I$. In embodiments, X is F.

$R^{63}$ is independently oxo, halogen, $-CX^{63}_3$, $-CHX^{63}_2$, $-CH_2X^{63}$, $-OCHX^{63}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{63}_3$, $-OCHX^{63}_2$, $R^{64}$-substituted or unsubstituted alkyl, $R^{64}$-substituted or unsubstituted heteroalkyl, $R^{64}$-substituted or unsubstituted cycloalkyl, $R^{64}$-substituted or unsubstituted heterocycloalkyl, $R^{64}$-substituted or unsubstituted aryl, or $R^{64}$-substituted or unsubstituted heteroaryl. $X^{63}$ is halogen. In embodiments, $X^{63}$ is F.

$R^{64}$ is independently oxo, halogen, $-CX^{64}_3$, $-CHX^{64}_2$, $-CH_2X^{64}$, $-OCHX^{64}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{64}_3$, $-OCHX^{64}_2$, $R^{65}$-substituted or unsubstituted alkyl, $R^{65}$-substituted or unsubstituted heteroalkyl, $R^{65}$-substituted or unsubstituted cycloalkyl, $R^{65}$-substituted or unsubstituted heterocycloalkyl, $R^{65}$-substituted or unsubstituted aryl, or $R^{65}$-substituted or unsubstituted heteroaryl. $X^{64}$ is halogen. In embodiments, $X^{64}$ is F.

In embodiments, $R^{14}$ is independently hydrogen, $-CX_3$, $-CN$, $-COOH$, $-CONH_2$, $-CHX_2$, $-CH_2X$, $R^{66}$-substituted or unsubstituted alkyl, $R^{66}$-substituted or unsubstituted heteroalkyl, $R^{66}$-substituted or unsubstituted cycloalkyl, $R^{66}$-substituted or unsubstituted heterocycloalkyl, $R^{66}$-substituted or unsubstituted aryl, or $R^{66}$-substituted or unsubstituted heteroaryl. X is independently —F, —Cl, —Br, or —I. In embodiments, X is F.

$R^{66}$ is independently oxo, halogen, —CX$^{66}_3$, —CHX$^{66}_2$, —CH$_2$X$^{66}$, —OCHX$^{66}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{66}_3$, —OCHX$^{66}_2$, $R^{67}$-substituted or unsubstituted alkyl, $R^{67}$-substituted or unsubstituted heteroalkyl, $R^{67}$-substituted or unsubstituted cycloalkyl, $R^{67}$-substituted or unsubstituted heterocycloalkyl, $R^{67}$-substituted or unsubstituted aryl, or $R^{67}$-substituted or unsubstituted heteroaryl. $X^{66}$ is halogen. In embodiments, $X^{66}$ is F.

$R^{67}$ is independently oxo, halogen, —CX$^{67}_3$, —CHX$^{67}_2$, —CH$_2$X$^{67}$, —OCHX$^{67}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{67}_3$, —OCHX$^{67}_2$, $R^{68}$-substituted or unsubstituted alkyl, $R^{68}$-substituted or unsubstituted heteroalkyl, $R^{68}$-substituted or unsubstituted cycloalkyl, $R^{68}$-substituted or unsubstituted heterocycloalkyl, $R^{68}$-substituted or unsubstituted aryl, or $R^{68}$-substituted or unsubstituted heteroaryl. $X^{67}$ is halogen. In embodiments, $X^{67}$ is F.

In embodiments, $R^{15}$ is independently hydrogen, —CX$_3$, —CN, —COOH, —CONH$_2$, —CHX$_2$, —CH$_2$X, $R^{69}$-substituted or unsubstituted alkyl, $R^{69}$-substituted or unsubstituted heteroalkyl, $R^{69}$-substituted or unsubstituted cycloalkyl, $R^{69}$-substituted or unsubstituted heterocycloalkyl, $R^{69}$-substituted or unsubstituted aryl, or $R^{69}$-substituted or unsubstituted heteroaryl. X is independently —F, —Cl, —Br, or —I. In embodiments, X is F.

$R^{69}$ is independently oxo, halogen, —CX$^{69}_3$, —CHX$^{69}_2$, —CH$_2$X$^{69}$, —OCHX$^{69}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{69}_3$, —OCHX$^{69}_2$, $R^{70}$-substituted or unsubstituted alkyl, $R^{70}$-substituted or unsubstituted heteroalkyl, $R^{70}$-substituted or unsubstituted cycloalkyl, $R^{70}$-substituted or unsubstituted heterocycloalkyl, $R^{70}$-substituted or unsubstituted aryl, or $R^{70}$-substituted or unsubstituted heteroaryl. $X^{69}$ is halogen. In embodiments, $X^{69}$ is F.

$R^{70}$ is independently oxo, halogen, —CX$^{70}_3$, —CHX$^{70}_2$, —OCH$_2$X$^{70}$, —OCHX$^{70}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{70}_3$, —OCHX$^{70}_2$, $R^{71}$-substituted or unsubstituted alkyl, $R^{71}$-substituted or unsubstituted heteroalkyl, $R^{71}$-substituted or unsubstituted cycloalkyl, $R^{71}$-substituted or unsubstituted heterocycloalkyl, $R^{71}$-substituted or unsubstituted aryl, or $R^{71}$-substituted or unsubstituted heteroaryl. $X^{70}$ is halogen. In embodiments, $X^{70}$ is F.

In embodiments, $R^{16}$ is independently hydrogen, —CX$_3$, —CN, —COOH, —CONH$_2$, —CHX$_2$, —CH$_2$X, $R^{72}$-substituted or unsubstituted alkyl, $R^{72}$-substituted or unsubstituted heteroalkyl, $R^{72}$-substituted or unsubstituted cycloalkyl, $R^{72}$-substituted or unsubstituted heterocycloalkyl, $R^{72}$-substituted or unsubstituted aryl, or $R^{72}$-substituted or unsubstituted heteroaryl. X is independently —F, —Cl, —Br, or —I. In embodiments, X is F.

$R^{72}$ is independently oxo, halogen, —CX$^{72}_3$, —CHX$^{72}_2$, —CH$_2$X$^{72}$, —OCHX$^{72}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{72}_3$, —OCHX$^{72}_2$, $R^{73}$-substituted or unsubstituted alkyl, $R^{73}$-substituted or unsubstituted heteroalkyl, $R^{73}$-substituted or unsubstituted cycloalkyl, $R^{73}$-substituted or unsubstituted heterocycloalkyl, $R^{73}$-substituted or unsubstituted aryl, or $R^{73}$-substituted or unsubstituted heteroaryl. $X^{72}$ is halogen. In embodiments, $X^{72}$ is F.

$R^{73}$ is independently oxo, halogen, —CX$^{73}_3$, —CHX$^{73}_2$, —CH$_2$X$^{73}$, —OCHX$^{73}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{73}_3$, —OCHX$^{73}_2$, $R^{74}$-substituted or unsubstituted alkyl, $R^{74}$-substituted or unsubstituted heteroalkyl, $R^{74}$-substituted or unsubstituted cycloalkyl, $R^{74}$-substituted or unsubstituted heterocycloalkyl, $R^{74}$-substituted or unsubstituted aryl, or $R^{74}$-substituted or unsubstituted heteroaryl. $X^{73}$ is halogen. In embodiments, $X^{73}$ is F.

In embodiments, $R^{17}$ is independently hydrogen, —CX$_3$, —CN, —COOH, —CONH$_2$, —CHX$_2$, —CH$_2$X, $R^{75}$-substituted or unsubstituted alkyl, $R^{75}$-substituted or unsubstituted heteroalkyl, $R^{75}$-substituted or unsubstituted cycloalkyl, $R^{75}$-substituted or unsubstituted heterocycloalkyl, $R^{75}$-substituted or unsubstituted aryl, or $R^{75}$-substituted or unsubstituted heteroaryl. X is independently —F, —Cl, —Br, or —I. In embodiments, X is F.

$R^{75}$ is independently oxo, halogen, —CX$^{75}_3$, —CHX$^{75}_2$, —CH$_2$X$^{75}$, —OCHX$^{75}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{75}_3$, —OCHX$^{75}_2$, $R^{76}$-substituted or unsubstituted alkyl, $R^{76}$-substituted or unsubstituted heteroalkyl, $R^{76}$-substituted or unsubstituted cycloalkyl, $R^{76}$-substituted or unsubstituted heterocycloalkyl, $R^{76}$-substituted or unsubstituted aryl, or $R^{76}$-substituted or unsubstituted heteroaryl. $X^{75}$ is halogen. In embodiments, $X^{75}$ is F.

$R^{76}$ is independently oxo, halogen, —CX$^{76}_3$, —CHX$^{76}_2$, —CH$_2$X$^{76}$, —OCHX$^{76}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{763}$, —OCHX$^{762}$, $R^{77}$-substituted or unsubstituted alkyl, $R^{77}$-substituted or unsubstituted heteroalkyl, $R^{77}$-substituted or unsubstituted cycloalkyl, $R^{77}$-substituted or unsubstituted heterocycloalkyl, $R^{77}$-substituted or unsubstituted aryl, or $R^{77}$-substituted or unsubstituted heteroaryl. $X^{76}$ is halogen. In embodiments, $X^{76}$ is F.

In embodiments, $R^{18}$ is independently hydrogen, —CX$_3$, —CN, —COOH, —CONH$_2$, —CHX$_2$, —CH$_2$X, $R^{78}$-substituted or unsubstituted alkyl, $R^{78}$-substituted or unsubstituted heteroalkyl, $R^{78}$-substituted or unsubstituted cycloalkyl, $R^{78}$-substituted or unsubstituted heterocycloalkyl, $R^{78}$-substituted or unsubstituted aryl, or $R^{78}$-substituted or unsubstituted heteroaryl. X is independently —F, —Cl, —Br, or —I. In embodiments, X is F.

$R^{78}$ is independently oxo, halogen, —$CX^{78}_3$, —$CHX^{78}_2$, —$CH_2X^{78}$, —$OCHX^{78}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{78}_3$, —$OCHX^{78}_2$, $R^{79}$-substituted or unsubstituted alkyl, $R^{79}$-substituted or unsubstituted heteroalkyl, $R^{79}$-substituted or unsubstituted cycloalkyl, $R^{79}$-substituted or unsubstituted heterocycloalkyl, $R^{79}$-substituted or unsubstituted aryl, or $R^{79}$-substituted or unsubstituted heteroaryl. $X^{78}$ is halogen. In embodiments, $X^{78}$ is F.

$R^{79}$ is independently oxo, halogen, —$CX^{79}_3$, —$CHX^{79}_2$, —$CH_2X^{79}$, —$OCHX^{79}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{79}_3$, —$OCHX^{79}_2$, $R^{80}$-substituted or unsubstituted alkyl, $R^{80}$-substituted or unsubstituted heteroalkyl, $R^{80}$-substituted or unsubstituted cycloalkyl, $R^{80}$-substituted or unsubstituted heterocycloalkyl, $R^{80}$-substituted or unsubstituted aryl, or $R^{80}$-substituted or unsubstituted heteroaryl. $X^{79}$ is halogen. In embodiments, $X^{79}$ is F.

In embodiments, $R^{19}$ is independently hydrogen, —$CX_3$, —CN, —COOH, —$CONH_2$, —$CHX_2$, —$CH_2X$, $R^{81}$-substituted or unsubstituted alkyl, $R^{81}$-substituted or unsubstituted heteroalkyl, $R^{81}$-substituted or unsubstituted cycloalkyl, $R^{81}$-substituted or unsubstituted heterocycloalkyl, $R^{81}$-substituted or unsubstituted aryl, or $R^{81}$-substituted or unsubstituted heteroaryl. X is independently —F, —Cl, —Br, or —I. In embodiments, X is F.

$R^{81}$ is independently oxo, halogen, —$CX^{81}_3$, —$CHX^{81}_2$, —$CH_2X^{81}$, —$OCHX^{81}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{81}_3$, —$OCHX^{81}_2$, $R^{82}$-substituted or unsubstituted alkyl, $R^{82}$-substituted or unsubstituted heteroalkyl, $R^{82}$-substituted or unsubstituted cycloalkyl, $R^{82}$-substituted or unsubstituted heterocycloalkyl, $R^{82}$-substituted or unsubstituted aryl, or $R^{82}$-substituted or unsubstituted heteroaryl. $X^{81}$ is halogen. In embodiments, $X^{81}$ is F.

$R^{82}$ is independently oxo, halogen, —$CX^{82}_3$, —$CHX^{82}_2$, —$CH_2X^{82}$, —$OCHX^{82}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{82}_3$, —$OCHX^{82}_2$, $R^{83}$-substituted or unsubstituted alkyl, $R^{83}$-substituted or unsubstituted heteroalkyl, $R^{83}$-substituted or unsubstituted cycloalkyl, $R^{83}$-substituted or unsubstituted heterocycloalkyl, $R^{83}$-substituted or unsubstituted aryl, or $R^{83}$-substituted or unsubstituted heteroaryl. $X^{82}$ is halogen. In embodiments, $X^{82}$ is F.

In embodiments, $R^{20}$ is independently hydrogen, —$CX_3$, —CN, —COOH, —$CONH_2$, —$CHX_2$, —$CH_2X$, $R^{84}$-substituted or unsubstituted alkyl, $R^{84}$-substituted or unsubstituted heteroalkyl, $R^{84}$-substituted or unsubstituted cycloalkyl, $R^{84}$-substituted or unsubstituted heterocycloalkyl, $R^{84}$-substituted or unsubstituted aryl, or $R^{84}$-substituted or unsubstituted heteroaryl. X is independently —F, —Cl, —Br, or —I. In embodiments, X is F.

$R^{84}$ is independently oxo, halogen, —$CX^{84}_3$, —$CHX^{84}_2$, —$CH_2X^{84}$, —$OCHX^{84}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{84}_3$, —$OCHX^{84}_2$, $R^{85}$-substituted or unsubstituted alkyl, $R^{85}$-substituted or unsubstituted heteroalkyl, $R^{85}$-substituted or unsubstituted cycloalkyl, $R^{85}$-substituted or unsubstituted heterocycloalkyl, $R^{85}$-substituted or unsubstituted aryl, or $R^{85}$-substituted or unsubstituted heteroaryl. $X^{84}$ is halogen. In embodiments, $X^{84}$ is F.

$R^{85}$ is independently oxo, halogen, —$CX^{85}_3$, —$CHX^{85}_2$, —$CH_2X^{85}$, —$OCHX^{85}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{85}_3$, —$OCHX^{85}_2$, $R^{86}$-substituted or unsubstituted alkyl, $R^{86}$-substituted or unsubstituted heteroalkyl, $R^{86}$-substituted or unsubstituted cycloalkyl, $R^{86}$-substituted or unsubstituted heterocycloalkyl, $R^{86}$-substituted or unsubstituted aryl, or $R^{86}$-substituted or unsubstituted heteroaryl. $X^{85}$ is halogen. In embodiments, $X^{85}$ is F.

In embodiments, $R^{21}$ is independently hydrogen, —$CX_3$, —CN, —COOH, —$CONH_2$, —$CHX_2$, —$CH_2X$, $R^{87}$-substituted or unsubstituted alkyl, $R^{87}$-substituted or unsubstituted heteroalkyl, $R^{87}$-substituted or unsubstituted cycloalkyl, $R^{87}$-substituted or unsubstituted heterocycloalkyl, $R^{87}$-substituted or unsubstituted aryl, or $R^{87}$-substituted or unsubstituted heteroaryl. X is independently —F, —Cl, —Br, or —I. In embodiments, X is F.

$R^{87}$ is independently oxo, halogen, —$CX^{87}_3$, —$CHX^{87}_2$, —$CH_2X^{87}$, —$OCHX^{87}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{87}_3$, —$OCHX^{87}_2$, $R^{88}$-substituted or unsubstituted alkyl, $R^{88}$-substituted or unsubstituted heteroalkyl, $R^{88}$-substituted or unsubstituted cycloalkyl, $R^{88}$-substituted or unsubstituted heterocycloalkyl, $R^{88}$-substituted or unsubstituted aryl, or $R^{88}$-substituted or unsubstituted heteroaryl. $X^{87}$ is halogen. In embodiments, $X^{87}$ is F.

$R^{88}$ is independently oxo, halogen, —$CX^{88}_3$, —$CHX_2$, —$CH_2X^{88}$, —$OCHX^{88}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{88}_3$, —$OCHX^{88}_2$, $R^{89}$-substituted or unsubstituted alkyl, $R^{89}$-substituted or unsubstituted heteroalkyl, $R^{89}$-substituted or unsubstituted cycloalkyl, $R^{89}$-substituted or unsubstituted heterocycloalkyl, $R^{89}$-substituted or unsubstituted aryl, or $R^{89}$-substituted or unsubstituted heteroaryl. $X^{88}$ is halogen. In embodiments, $X^{88}$ is F.

In embodiments, $R^6$ and $R^7$ substituents bonded to the same nitrogen atom may be joined to form a $R^{90}$-substituted or unsubstituted heterocycloalkyl or $R^{90}$-substituted or unsubstituted heteroaryl.

$R^{90}$ is independently oxo, halogen, —$CX^{90}_3$, —$CHX^{90}_2$, —$CH_2X^{90}$, —$OCHX^{90}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{90}_3$, —$OCHX^{90}_2$, $R^{91}$-substituted or unsubstituted alkyl, $R^{91}$-substituted or unsubstituted heteroalkyl, $R^{91}$-substituted or unsubstituted cycloalkyl, $R^{91}$-substituted or unsubstituted heterocycloalkyl, $R^{91}$-substituted or unsubstituted aryl, or $R^{91}$-substituted or unsubstituted heteroaryl. $X^{90}$ is halogen. In embodiments, $X^{90}$ is F.

$R^{91}$ is independently oxo, halogen, $-CX^{91}_3$, $-CHX^{91}_2$, $-CH_2X^{91}$, $-OCHX^{91}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{91}_3$, $-OCHX^{91}_2$, $R^{92}$-substituted or unsubstituted alkyl, $R^{92}$-substituted or unsubstituted heteroalkyl, $R^{92}$-substituted or unsubstituted cycloalkyl, $R^{92}$-substituted or unsubstituted heterocycloalkyl, $R^{92}$-substituted or unsubstituted aryl, or $R^{92}$-substituted or unsubstituted heteroaryl. $X^{91}$ is halogen. In embodiments, $X^{91}$ is F.

In embodiments, $R^{10}$ and $R^{11}$ substituents bonded to the same nitrogen atom may be joined to form a $R^{93}$-substituted or unsubstituted heterocycloalkyl or $R^{93}$-substituted or unsubstituted heteroaryl.

$R^{93}$ is independently oxo, halogen, $-CX^{93}_3$, $-CHX^{93}_2$, $-CH_2X^{93}$, $-OCHX^{93}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{93}_3$, $-OCHX^{93}_2$, $R^{94}$-substituted or unsubstituted alkyl, $R^{94}$-substituted or unsubstituted heteroalkyl, $R^{94}$-substituted or unsubstituted cycloalkyl, $R^{94}$-substituted or unsubstituted heterocycloalkyl, $R^{94}$-substituted or unsubstituted aryl, or $R^{94}$-substituted or unsubstituted heteroaryl. $X^{93}$ is halogen. In embodiments, $X^{93}$ is F.

$R^{94}$ is independently oxo, halogen, $-CX^{94}_3$, $-CHX^{94}_2$, $-CH_2X^{94}$, $-OCHX^{94}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{94}_3$, $-OCHX^{94}_2$, $R^{95}$-substituted or unsubstituted alkyl, $R^{95}$-substituted or unsubstituted heteroalkyl, $R^{95}$-substituted or unsubstituted cycloalkyl, $R^{95}$-substituted or unsubstituted heterocycloalkyl, $R^{95}$-substituted or unsubstituted aryl, or $R^{95}$-substituted or unsubstituted heteroaryl. $X^{94}$ is halogen. In embodiments, $X^{94}$ is F.

In embodiments, $R^{14}$ and $R^{15}$ substituents bonded to the same nitrogen atom may be joined to form a $R^{96}$-substituted or unsubstituted heterocycloalkyl or $R^{96}$-substituted or unsubstituted heteroaryl.

$R^{96}$ is independently oxo, halogen, $-CX^{96}_3$, $-CHX^{96}_2$, $-CH_2X^{96}$, $-OCHX^{96}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{96}_3$, $-OCHX^{96}_2$, $R^{97}$-substituted or unsubstituted alkyl, $R^{97}$-substituted or unsubstituted heteroalkyl, $R^{97}$-substituted or unsubstituted cycloalkyl, $R^{97}$-substituted or unsubstituted heterocycloalkyl, $R^{97}$-substituted or unsubstituted aryl, or $R^{97}$-substituted or unsubstituted heteroaryl. $X^{96}$ is halogen. In embodiments, $X^{96}$ is F.

$R^{97}$ is independently oxo, halogen, $-CX^{97}_3$, $-CHX^{97}_2$, $-CH_2X^{97}$, $-OCHX^{97}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{97}_3$, $-OCHX^{97}_2$, $R^{98}$-substituted or unsubstituted alkyl, $R^{98}$-substituted or unsubstituted heteroalkyl, $R^{98}$-substituted or unsubstituted cycloalkyl, $R^{98}$-substituted or unsubstituted heterocycloalkyl, $R^{98}$-substituted or unsubstituted aryl, or $R^{98}$-substituted or unsubstituted heteroaryl. $X^{97}$ is halogen. In embodiments, $X^{97}$ is F.

In embodiments, $R^{18}$ and $R^{19}$ substituents bonded to the same nitrogen atom may be joined to form a $R^{99}$-substituted or unsubstituted heterocycloalkyl or $R^{99}$-substituted or unsubstituted heteroaryl.

$R^{99}$ is independently oxo, halogen, $-CX^{99}_3$, $-CHX^{99}_2$, $-CH_2X^{99}$, $-OCHX^{99}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{99}_3$, $-OCHX^{99}_2$, $R^{100}$-substituted or unsubstituted alkyl, $R^{100}$-substituted or unsubstituted heteroalkyl, $R^{100}$-substituted or unsubstituted cycloalkyl, $R^{100}$-substituted or unsubstituted heterocycloalkyl, $R^{100}$-substituted or unsubstituted aryl, or $R^{100}$-substituted or unsubstituted heteroaryl. $X^{99}$ is halogen. In embodiments, $X^{99}$ is F.

$R^{100}$ is independently oxo, halogen, $-CX^{100}_3$, $-CHX^{100}_2$, $-CH_2X^{100}$, $-OCHX^{100}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{100}_3$, $-OCHX^{100}_2$, $R^{101}$-substituted or unsubstituted alkyl, $R^{101}$-substituted or unsubstituted heteroalkyl, $R^{101}$-substituted or unsubstituted cycloalkyl, $R^{101}$-substituted or unsubstituted heterocycloalkyl, $R^{101}$-substituted or unsubstituted aryl, or $R^{101}$-substituted or unsubstituted heteroaryl. $X^{100}$ is halogen. In embodiments, $X^{100}$ is F.

$R^{24}$, $R^{27}$, $R^{30}$, $R^{33}$, $R^{36}$, $R^{38}$, $R^{41}$, $R^{44}$, $R^{47}$, $R^{50}$, $R^{53}$, $R^{56}$, $R^{59}$, $R^{62}$, $R^{65}$, $R^{68}$, $R^{71}$, $R^{74}$, $R^{77}$, $R^{80}$, $R^{83}$, $R^{86}$, $R^{89}$, $R^{92}$, $R^{95}$, $R^{98}$, and $R^{101}$ are independently hydrogen, oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl.

In aspects provided herein, there are compounds having structural Formula (II):

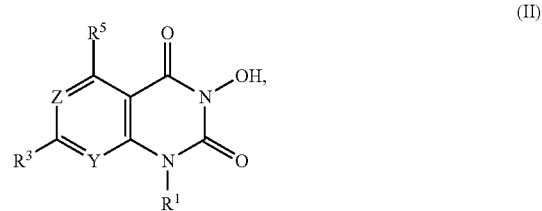

(II)

or a pharmaceutically acceptable salt thereof.

Y, Z, $R^1$, $R^3$ and $R^5$ are as defined herein, including embodiments.

In embodiments, Y is $CR^2$. In embodiments, Y is N. In embodiments, Z is $CR^4$. In embodiments, Z is N. In embodiments, Y is $CR^2$ and Z is N. In embodiments, Y is $CR^2$ and Z is $CR^4$. In embodiments, Y is N and Z is $CR^4$.

In embodiments, Y is $CR^2$, Z is N and $R^1$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, Y is $CR^2$, Z is $CR^4$ and $R^1$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, Y is N, Z is $CR^4$ and $R^1$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, Y is $CR^2$ and $R^2$ is $-SO_2R^9$, substituted or unsubstituted alkyl, substituted or unsubstituted heteroalkyl, substituted or unsubstituted aryl or substituted or unsubstituted heteroaryl.

In embodiments, $R^1$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is hydrogen, substituted or unsubstituted alkyl, substituted or unsubstituted heteroalkyl, substituted or unsubstituted aryl or substituted or unsubstituted heteroaryl.

In embodiments, $R^2$ is $-SO_2R^9$, substituted or unsubstituted alkyl, substituted or unsubstituted heteroalkyl, substituted or unsubstituted aryl or substituted or unsubstituted heteroaryl.

In embodiments, $R^3$ is $SO_2R^{13}$ substituted or unsubstituted alkyl, substituted or unsubstituted heteroalkyl, substituted or unsubstituted aryl or substituted or unsubstituted heteroaryl.

In aspects provided herein, there are compounds having structural Formula (III):

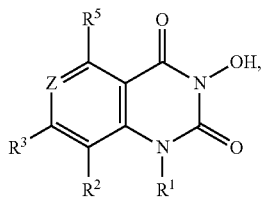

(III)

or a pharmaceutically acceptable salt thereof.

Z, $R^1$, $R^2$, $R^3$ and $R^5$ are as defined herein, including embodiments.

In embodiments, $R^2$ is hydrogen, halogen, $-SO_{n2}R^9$, $-SO_{v2}NR^6R^7$, $-C(O)NR^6R^7$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^3$, $R^4$ and $R^5$ are independently hydrogen, halogen, substituted or unsubstituted alkyl or substituted or unsubstituted heteroalkyl. In embodiments, $R^3$ is hydrogen. In embodiments, and $R^4$ is hydrogen. In embodiments, $R^5$ is hydrogen, halogen, substituted or unsubstituted alkyl or substituted or unsubstituted heteroalkyl. In embodiments, $R^5$ is hydrogen. In embodiments, $R^5$ is halogen. In embodiments, $R^5$ is substituted or unsubstituted alkyl. In embodiments, $R^5$ is substituted or unsubstituted heteroalkyl.

In embodiments, $R^5$ is fluorine. In embodiments, $R^5$ is chlorine. In embodiments, $R^5$ is bromine. In embodiments, $R^5$ is iodine.

In embodiments, $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl In aspects provided herein, there are compounds having structural Formula (IIIa):

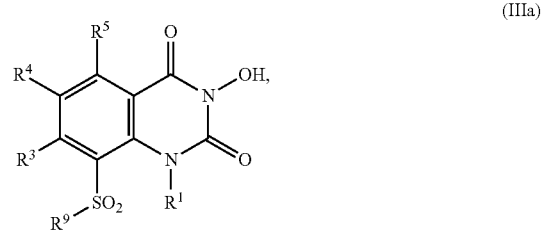

(IIIa)

or a pharmaceutically acceptable salt thereof.

$R^1$, $R^3$, $R^4$, $R^5$ and $R^9$ are as defined herein, including embodiments.

In aspects provided herein, there are compounds having structural Formula (IV):

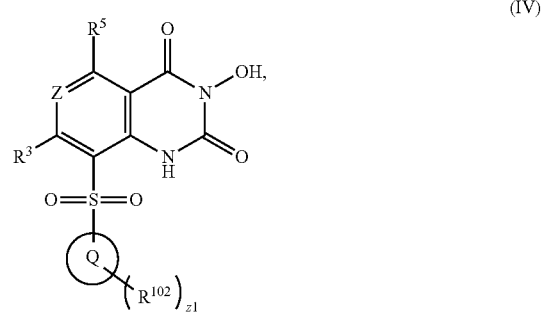

(IV)

or a pharmaceutically acceptable salt thereof. Z is as described herein, including embodiments. Q is substituted or unsubstituted cycloalkyl, substituted or unsubstituted heterocycloalkyl, substituted or unsubstituted aryl or substituted or unsubstituted heteroaryl. $R^{102}$ is hydrogen, halogen, $-CX^{102}_3$, $-CHX^{102}_2$, $-CH_2X^{102}$, $-CN$, $-SO_{n102}R^{102D}$, $-SO_{v102}NR^{102A}R^{102B}$, $-NHC(O)NR^{102A}R^{102B}$, $-N(O)_{m102}$, $-NR^{102A}R^{102B}$, $-C(O)R^{102C}$, $-C(O)OR^{102C}$, $-C(O)NR^{102A}R^{102B}$, $-OR^{102D}$, $-NR^{102A}SO_2R^{102D}$, $-NR^{102A}C(O)R^{102C}$, $-NR^{102A}C(O)OR^{102C}$, $-NR^{102A}OR^{102C}$, $-OCX^{102}_3$, $-OCHX^{102}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102B}$ and $R^{102C}$ substituents bonded to the same nitrogen atom may optionally be joined to form a substituted or unsubstituted heterocycloalkyl or substituted or unsubstituted heteroaryl. $R^{102A}$, $R^{102B}$, $R^{102C}$ and $R^{102D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102B}$ and $R^{102C}$ substituents bonded to the same nitrogen atom may optionally be joined to form a substituted or unsubstituted heterocycloalkyl or substituted or unsubstituted heteroaryl. $X^{102}$ is independently —F, —Cl, —Br, or —I. The symbol z1 is an integer from 0 to 6. The symbol m102 is an integer from 1 to 2. The symbol n102 is an integer from 0 to 3. The symbol v102 is an integer from 1 to 2.

In embodiments, z1 is 0. In embodiments, z1 is 1. In embodiments, z1 is 2. In embodiments, z1 is 3. In embodiments, z1 is 4. In embodiments, z1 is 5. In embodiments, z1 is 6.

In embodiments, m102 is 1. In embodiments, m102 is 2.

In embodiments, n102 is 0. In embodiments, n102 is 1. In embodiments, n102 is 2. In embodiments, n102 is 3.

In embodiments, v102 is 1. In embodiments, v102 is 2.

In embodiments, $R^3$ is hydrogen, halogen, substituted or unsubstituted alkyl or substituted or unsubstituted heteroalkyl. In embodiments, $R^4$ is hydrogen, halogen, substituted or unsubstituted alkyl or substituted or unsubstituted heteroalkyl. In embodiments, $R^5$ is hydrogen, halogen, substituted or unsubstituted alkyl or substituted or unsubstituted heteroalkyl. In embodiments, $R^5$ is halogen, substituted or unsubstituted alkyl or substituted or unsubstituted heteroalky. In embodiments, $R^3$, $R^4$ and $R^5$ are independently hydrogen, halogen, substituted or unsubstituted alkyl or substituted or unsubstituted heteroalkyl.

In embodiments, Q is substituted or unsubstituted cycloalkyl. In embodiments, Q is substituted cycloalkyl. In embodiments, Q is unsubstituted cycloalkyl. In embodiments, Q is substituted or unsubstituted heterocycloalkyl. In embodiments, Q is substituted heterocycloalkyl. In embodiments, Q is unsubstituted heterocycloalkyl. In embodiments, Q is substituted or unsubstituted aryl. In embodiments, Q is substituted aryl. In embodiments, Q is unsubstituted aryl. In embodiments, Q is or substituted or unsubstituted heteroaryl. In embodiments, Q is substituted heteroaryl. In embodiments, Q is unsubstituted heteroaryl.

In embodiments, Q is substituted or unsubstituted thiophenyl, substituted or unsubstituted pyridinyl, substituted or unsubstituted pyrazinyl, substituted or unsubstituted pyrimidinyl, substituted or unsubstituted furanyl, substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted furazanyl, substituted or unsubstituted 1,2,3-oxadiazolyl, substituted or unsubstituted 1,2,4-oxadiazolyl, substituted or unsubstituted 1,2,5-oxadiazolyl, substituted or unsubstituted 1,3,4-oxadiazolyl, substituted or unsubstituted 1,2,3-thiadiazolyl, substituted or unsubstituted 1,2,4-thiadiazolyl, substituted or unsubstituted 1,2,5-thiadiazolyl, substituted or unsubstituted 1,3,4-thiadiazolyl, substituted or unsubstituted benzothiophenyl, substituted or unsubstituted benzofuranyl, substituted or unsubstituted indolyl, substituted or unsubstituted isoindolyl, substituted or unsubstituted indazolyl, substituted or unsubstituted benzimidazolyl, substituted or unsubstituted benzthiazolyl, substituted or unsubstituted benzoisoxazolyl or substituted or unsubstituted benzoimidazolyl.

In embodiments, Q is substituted or unsubstituted cycloalkyl (e.g., $C_3$-$C_8$ cycloalkyl, $C_3$-$C_6$ cycloalkyl, or $C_5$-$C_6$ cycloalkyl). In embodiments, Q is substituted cycloalkyl (e.g., $C_3$-$C_8$ cycloalkyl, $C_3$-$C_6$ cycloalkyl, or $C_5$-$C_6$ cycloalkyl). In embodiments, Q is unsubstituted cycloalkyl (e.g., $C_3$-$C_8$ cycloalkyl, $C_3$-$C_6$ cycloalkyl, or $C_5$-$C_6$ cycloalkyl).

In embodiments, Q is substituted or unsubstituted heterocycloalkyl (e.g., 3 to 8 membered heterocycloalkyl, 3 to 6 membered heterocycloalkyl, or 5 to 6 membered heterocycloalkyl). In embodiments, Q is substituted heterocycloalkyl (e.g., 3 to 8 membered heterocycloalkyl, 3 to 6 membered heterocycloalkyl, or 5 to 6 membered heterocycloalkyl). In embodiments, Q is an unsubstituted heterocycloalkyl (e.g., 3 to 8 membered heterocycloalkyl, 3 to 6 membered heterocycloalkyl, or 5 to 6 membered heterocycloalkyl).

In embodiments, Q is substituted or unsubstituted aryl (e.g., $C_6$-$C_{10}$ aryl, $C_{10}$ aryl, or phenyl). In embodiments, Q is substituted aryl (e.g., $C_6$-$C_{10}$ aryl, $C_{10}$ aryl, or phenyl). In embodiments, Q is is an unsubstituted aryl (e.g., $C_6$-$C_{10}$ aryl, $C_{10}$ aryl, or phenyl).

In embodiments, Q is substituted or unsubstituted heteroaryl (e.g., 5 to 10 membered heteroaryl, 5 to 9 membered heteroaryl, or 5 to 6 membered heteroaryl). In embodiments, Q is substituted heteroaryl (e.g., 5 to 10 membered heteroaryl, 5 to 9 membered heteroaryl, or 5 to 6 membered heteroaryl). In embodiments, Q is an unsubstituted heteroaryl (e.g., 5 to 10 membered heteroaryl, 5 to 9 membered heteroaryl, or 5 to 6 membered heteroaryl).

In embodiments, $R^{102}$ is hydrogen. In embodiments, $R^{102}$ is halogen. In embodiments, $R^{102}$ is —CN. In embodiments, $R^{102}$ is —NHC(O)NR$^{102A}$R$^{102B}$. In embodiments, $R^{102}$ is —NR$^{102A}$R$^{102B}$, —OR$^{102D}$. In embodiments, $R^{102}$ is substituted or unsubstituted alkyl. In embodiments, $R^{102}$ is substituted or unsubstituted heteroalkyl. In embodiments, $R^{102}$ is substituted or unsubstituted cycloalkyl. In embodiments, $R^{102}$ is substituted or unsubstituted heterocycloalkyl. In embodiments, $R^{102}$ is substituted or unsubstituted aryl. In embodiments, $R^{102}$ is substituted or unsubstituted heteroaryl.

In embodiments, $R^{102}$ is hydrogen, halogen, —CX$^{102}_3$, —CHX$^{102}_2$, —CH$_2$X$^{102}$, —CN, —SO$_{n1}$R$^{102A}$, —SO$_{v1}$NR$^{102B}$R$^{102C}$, —NNR$^{102B}$R$^{102C}$, —ONR$^{102B}$R$^{102C}$, —NHC(O)NHNR$^{102B}$R$^{102C}$, —NHC(O)NR$^{102B}$R$^{102C}$, —N(O)$_{m1}$, —NR$^{102B}$R$^{102C}$, —C(O)R$^{102D}$, —C(O)OR$^{102D}$, —C(O)NR$^{102B}$R$^{102C}$, —OR$^{102A}$, —NR$^{102B}$SO$_2$R$^{102A}$, —NR$^{102B}$C(O)R$^{102D}$, —NR$^{102B}$C(O)OR$^{102D}$, —NR$^{102B}$OR$^{102D}$, —OCX$^{102}_3$, —OCHX$^{102}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{102}$ is halogen, —CX$^{102}_3$, —CHX$^{102}_2$, —CH$_2$X$^{102}$, —CN, —SO$_n$R$^{102A}$SO$_{v1}$NR$^{102B}$R$^{102C}$, —NR$^{102B}$R$^{102C}$, —ONR$^{102B}$R$^{102C}$, —NHC(O)NHNR$^{102B}$R$^{102C}$, —NHC(O)NR$^{102B}$R$^{102C}$, —N(O)$_{m1}$, —NR$^{102B}$R$^{102C}$, —C(O)R$^{102D}$, —C(O)OR$^{102D}$, C(O)NR$^{102B}$R$^{102C}$, —OR$^{102A}$, —NR$^{102B}$SO$_2$R$^{102A}$, —NR$^{102B}$C(O)R$^{102D}$, —NR$^{102B}$C(O)OR$^{102D}$, —NR$^{102B}$OR$^{102D}$, —OCX$^{102}_3$, —OCHX$^{102}_2$, $R^{104}$-substituted or unsubstituted alkyl (e.g., $C_1$-$C_8$ alkyl, $C_1$-$C_6$ alkyl, or $C_1$-$C_4$ alkyl), $R^{104}$-substituted or unsubstituted heteroalkyl (e.g., 2 to 8 membered heteroalkyl, 2 to 6 membered heteroalkyl, or 2 to 4 membered heteroalkyl), $R^{104}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104}$-substituted or unsubstituted aryl (e.g., $C_6$-$C_{10}$ aryl, $C_{10}$ aryl, or phenyl), or $R^{104}$ substituted or unsubstituted heteroaryl (e.g., 5 to 10 membered heteroaryl, 5 to 9 membered heteroaryl, or 5 to 6 membered heteroaryl).

In embodiments, $R^{102}$ is $R^{104}$-substituted or unsubstituted alkyl (e.g., $C_1$-$C_8$ alkyl, $C_1$-$C_6$ alkyl, or $C_1$-$C_4$ alkyl). In embodiments, $R^{102}$ is $R^{104}$-substituted alkyl (e.g., $C_1$-$C_8$ alkyl, $C_1$-$C_6$ alkyl, or $C_1$-$C_4$ alkyl). In embodiments, $R^{102}$ is an unsubstituted alkyl (e.g., $C_1$-$C_8$ alkyl, $C_1$-$C_6$ alkyl, or $C_1$-$C_4$ alkyl).

In embodiments, $R^{102}$ is $R^{104}$-substituted or unsubstituted heteroalkyl (e.g., 2 to 8 membered heteroalkyl, 2 to 6 membered heteroalkyl, or 2 to 4 membered heteroalkyl). In embodiments, $R^{102}$ is $R^{104}$-substituted heteroalkyl (e.g., 2 to 8 membered heteroalkyl, 2 to 6 membered heteroalkyl, or 2 to 4 membered heteroalkyl). In embodiments, $R^{102}$ is an unsubstituted heteroalkyl (e.g., 2 to 8 membered heteroalkyl, 2 to 6 membered heteroalkyl, or 2 to 4 membered heteroalkyl).

In embodiments, $R^{102}$ is $R^{104}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{102}$ is $R^{104}$-substituted cycloalkyl (e.g., $C_3$-$C_8$ cycloalkyl, $C_3$-$C_6$ cycloalkyl, or $C_5$-$C_6$ cycloalkyl). In embodiments, $R^{102}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{102}$ is $R^{104}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{102}$ is $R^{104}$-substituted heterocycloalkyl (e.g., 3 to 8 membered heterocycloalkyl, 3 to 6 membered heterocycloalkyl, or 5 to 6 membered heterocycloalkyl). In embodiments, $R^{102}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{102}$ is $R^{104}$-substituted or unsubstituted aryl (e.g., $C_6$-$C_{10}$ aryl, $C_{10}$ aryl, or phenyl). In embodiments, $R^{102}$ is $R^{104}$-substituted aryl (e.g., $C_6$-$C_{10}$ aryl, $C_{10}$ aryl, or phenyl). In embodiments, $R^{102}$ is an unsubstituted aryl (e.g., $C_6$-$C_{10}$ aryl, $C_{10}$ aryl, or phenyl).

In embodiments, $R^{102}$ is $R^{104}$-substituted or unsubstituted heteroaryl (e.g., 5 to 10 membered heteroaryl, 5 to 9 membered heteroaryl, or 5 to 6 membered heteroaryl). In embodiments, $R^{102}$ is $R^{104}$-substituted heteroaryl (e.g., 5 to 10 membered heteroaryl, 5 to 9 membered heteroaryl, or 5 to 6 membered heteroaryl). In embodiments, $R^{102}$ is an unsubstituted heteroaryl (e.g., 5 to 10 membered heteroaryl, 5 to 9 membered heteroaryl, or 5 to 6 membered heteroaryl).

In embodiments, $R^{102A}$, $R^{102B}$, $R^{102C}$ and $R^{102D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{102B}$ and $R^{102C}$ substituents bonded to the same nitrogen atom may optionally be joined to form a substituted or unsubstituted heterocycloalkyl or substituted or unsubstituted heteroaryl.

In embodiments, $R^{102A}$ is hydrogen, halogen, —$CF_3$, —$CCl_3$, —$CBr_3$, —$CI_3$, —COOH, —$CONH_2$, $R^{104A}$-substituted or unsubstituted alkyl (e.g., $C_1$-$C_8$ alkyl, $C_1$-$C_6$ alkyl, or $C_1$-$C_4$ alkyl), $R^{104A}$-substituted or unsubstituted heteroalkyl (e.g., 2 to 8 membered heteroalkyl, 2 to 6 membered heteroalkyl, or 2 to 4 membered heteroalkyl), $R^{104A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104A}$-substituted or unsubstituted aryl (e.g., $C_6$-$C_{10}$ aryl, $C_{10}$ aryl, or phenyl), or $R^{104A}$-substituted or unsubstituted heteroaryl (e.g., 5 to 10 membered heteroaryl, 5 to 9 membered heteroaryl, or 5 to 6 membered heteroaryl).

In embodiments, $R^{102B}$ is hydrogen, halogen, —$CF_3$, —$CCl_3$, —$CBr_3$, —$CI_3$, —COOH, —$CONH_2$, $R^{104B}$-substituted or unsubstituted alkyl (e.g., $C_1$-$C_8$ alkyl, $C_1$-$C_6$ alkyl, or $C_1$-$C_4$ alkyl), $R^{104B}$-substituted or unsubstituted heteroalkyl (e.g., 2 to 8 membered heteroalkyl, 2 to 6 membered heteroalkyl, or 2 to 4 membered heteroalkyl), $R^{104B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104B}$-substituted or unsubstituted aryl (e.g., $C_6$-$C_{10}$ aryl, $C_{10}$ aryl, or phenyl), or $R^{104B}$-substituted or unsubstituted heteroaryl (e.g., 5 to 10 membered heteroaryl, 5 to 9 membered heteroaryl, or 5 to 6 membered heteroaryl). In embodiments, $R^{102B}$ and $R^{102C}$ substituents bonded to the same nitrogen atom may optionally be joined to form a $R^{104B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{104B}$-substituted or unsubstituted heteroaryl (e.g., 5 to 10 membered heteroaryl, 5 to 9 membered heteroaryl, or 5 to 6 membered heteroaryl).

In embodiments, $R^{102C}$ is hydrogen, halogen, —$CF_3$, —$CCl_3$, —$CBr_3$, —$CI_3$, —COOH, —$CONH_2$, $R^{104C}$-substituted or unsubstituted alkyl (e.g., $C_1$-$C_8$ alkyl, $C_1$-$C_6$ alkyl, or $C_1$-$C_4$ alkyl), $R^{104C}$-substituted or unsubstituted heteroalkyl (e.g., 2 to 8 membered heteroalkyl, 2 to 6 membered heteroalkyl, or 2 to 4 membered heteroalkyl), $R^{104C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104C}$-substituted or unsubstituted aryl (e.g., $C_6$-$C_{10}$ aryl, $C_{10}$ aryl, or phenyl), or $R^{104C}$-substituted or unsubstituted heteroaryl (e.g., 5 to 10 membered heteroaryl, 5 to 9 membered heteroaryl, or 5 to 6 membered heteroaryl). In embodiments, $R^{102B}$ and $R^{102C}$ substituents bonded to the same nitrogen atom may optionally be joined to form a $R^{104C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{104C}$-substituted or unsubstituted heteroaryl (e.g., 5 to 10 membered heteroaryl, 5 to 9 membered heteroaryl, or 5 to 6 membered heteroaryl).

In embodiments, $R^{102D}$ is hydrogen, halogen, —$CF_3$, —$CCl_3$, —$CBr_3$, —$CI_3$, —COOH, —$CONH_2$, $R^{104D}$-substituted or unsubstituted alkyl (e.g., $C_1$-$C_8$ alkyl, $C_1$-$C_6$ alkyl, or $C_1$-$C_4$ alkyl), $R^{104D}$-substituted or unsubstituted heteroalkyl (e.g., 2 to 8 membered heteroalkyl, 2 to 6 membered heteroalkyl, or 2 to 4 membered heteroalkyl), $R^{104D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104D}$-substituted or unsubstituted aryl (e.g., $C_6$-$C_{10}$ aryl, $C_{10}$ aryl, or phenyl), or $R^{104D}$-substituted or unsubstituted heteroaryl (e.g., 5 to 10 membered heteroaryl, 5 to 9 membered heteroaryl, or 5 to 6 membered heteroaryl).

$R^{104}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —OCHBr$_2$, —OCHI$_2$, —OCHF$_2$, R$^{105}$-substituted or unsubstituted alkyl (e.g., C$_1$-C$_8$ alkyl, C$_1$-C$_6$ alkyl, or C$_1$-C$_4$ alkyl), R$^{105}$ substituted or unsubstituted heteroalkyl (e.g., 2 to 8 membered heteroalkyl, 2 to 6 membered heteroalkyl, or 2 to 4 membered heteroalkyl), R$^{105}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{105}$-substituted or unsubstituted heterocycloalkyl (e.g., 3 to 8 membered heterocycloalkyl, 3 to 6 membered heterocycloalkyl, or 5 to 6 membered heterocycloalkyl), R$^{105}$-substituted or unsubstituted aryl (e.g., C$_6$-C$_{10}$ aryl, C$_{10}$ aryl, or phenyl), or R$^{105}$-substituted or unsubstituted heteroaryl (e.g., 5 to 10 membered heteroaryl, 5 to 9 membered heteroaryl, or 5 to 6 membered heteroaryl).

In embodiments, R$^{104}$ is R$^{105}$-substituted or unsubstituted alkyl (e.g., C$_1$-C$_8$ alkyl, C$_1$-C$_6$ alkyl, or C$_1$-C$_4$ alkyl). In embodiments, R$^{104}$ is R$^{105}$-substituted alkyl (e.g., C$_1$-C$_8$ alkyl, C$_1$-C$_6$ alkyl, or C$_1$-C$_4$ alkyl). In embodiments, R$^{104}$ is an unsubstituted alkyl (e.g., C$_1$-C$_8$ alkyl, C$_1$-C$_6$ alkyl, or C$_1$-C$_4$ alkyl).

In embodiments, R$^{104}$ is R$^{105}$-substituted or unsubstituted heteroalkyl (e.g., 2 to 8 membered heteroalkyl, 2 to 6 membered heteroalkyl, or 2 to 4 membered heteroalkyl). In embodiments, R$^{104}$ is R$^{105}$-substituted heteroalkyl (e.g., 2 to 8 membered heteroalkyl, 2 to 6 membered heteroalkyl, or 2 to 4 membered heteroalkyl). In embodiments, R$^{104}$ is an unsubstituted heteroalkyl (e.g., 2 to 8 membered heteroalkyl, 2 to 6 membered heteroalkyl, or 2 to 4 membered heteroalkyl).

In embodiments, R$^{104}$ is R$^{105}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{104}$ is R$^{105}$-substituted cycloalkyl (e.g., C$_3$-C$_8$ cycloalkyl, C$_3$-C$_6$ cycloalkyl, or C$_5$-C$_6$ cycloalkyl). In embodiments, R$^{104}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^{104}$ is R$^{105}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{104}$ is R$^{105}$-substituted heterocycloalkyl (e.g., 3 to 8 membered heterocycloalkyl, 3 to 6 membered heterocycloalkyl, or 5 to 6 membered heterocycloalkyl). In embodiments, R$^{104}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^{104}$ is R$^{105}$-substituted or unsubstituted aryl (e.g., C$_6$-C$_{10}$ aryl, C$_{10}$ aryl, or phenyl). In embodiments, R$^{104}$ is R$^{105}$-substituted aryl (e.g., C$_6$-C$_{10}$ aryl, C$_{10}$ aryl, or phenyl). In embodiments, R$^{104}$ is an unsubstituted aryl (e.g., C$_6$-C$_{10}$ aryl, C$_{10}$ aryl, or phenyl).

In embodiments, R$^{104}$ is R$^{105}$-substituted or unsubstituted heteroaryl (e.g., 5 to 10 membered heteroaryl, 5 to 9 membered heteroaryl, or 5 to 6 membered heteroaryl). In embodiments, R$^{104}$ is R$^{105}$-substituted heteroaryl (e.g., 5 to 10 membered heteroaryl, 5 to 9 membered heteroaryl, or 5 to 6 membered heteroaryl). In embodiments, R$^{104}$ is an unsubstituted heteroaryl (e.g., 5 to 10 membered heteroaryl, 5 to 9 membered heteroaryl, or 5 to 6 membered heteroaryl).

R$^{105}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, R$^{106}$-substituted or unsubstituted alkyl (e.g., C$_1$-C$_8$ alkyl, C$_1$-C$_6$ alkyl, or C$_1$-C$_4$ alkyl), R$^{106}$-substituted or unsubstituted heteroalkyl (e.g., 2 to 8 membered heteroalkyl, 2 to 6 membered heteroalkyl, or 2 to 4 membered heteroalkyl), R$^{106}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{106}$-substituted or unsubstituted heterocycloalkyl (e.g., 3 to 8 membered heterocycloalkyl, 3 to 6 membered heterocycloalkyl, or 5 to 6 membered heterocycloalkyl), R$^{106}$-substituted or unsubstituted aryl (e.g., C$_6$-C$_{10}$ aryl, C$_{10}$ aryl, or phenyl), or R$^{106}$-substituted or unsubstituted heteroaryl (e.g., 5 to 10 membered heteroaryl, 5 to 9 membered heteroaryl, or 5 to 6 membered heteroaryl).

In embodiments, R$^{105}$ is R$^{106}$-substituted or unsubstituted alkyl (e.g., C$_1$-C$_8$ alkyl, C$_1$-C$_6$ alkyl, or C$_1$-C$_4$ alkyl). In embodiments, R$^{105}$ is R$^{106}$-substituted alkyl (e.g., C$_1$-C$_8$ alkyl, C$_1$-C$_6$ alkyl, or C$_1$-C$_4$ alkyl). In embodiments, R$^{105}$ is an unsubstituted alkyl (e.g., C$_1$-C$_8$ alkyl, C$_1$-C$_6$ alkyl, or C$_1$-C$_4$ alkyl).

In embodiments, R$^{105}$ is R$^{106}$-substituted or unsubstituted heteroalkyl (e.g., 2 to 8 membered heteroalkyl, 2 to 6 membered heteroalkyl, or 2 to 4 membered heteroalkyl). In embodiments, R$^{105}$ is R$^{106}$-substituted heteroalkyl (e.g., 2 to 8 membered heteroalkyl, 2 to 6 membered heteroalkyl, or 2 to 4 membered heteroalkyl). In embodiments, R$^{105}$ is an unsubstituted heteroalkyl (e.g., 2 to 8 membered heteroalkyl, 2 to 6 membered heteroalkyl, or 2 to 4 membered heteroalkyl).

In embodiments, R$^{105}$ is R$^{106}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{105}$ is R$^{106}$-substituted cycloalkyl (e.g., C$_3$-C$_8$ cycloalkyl, C$_3$-C$_6$ cycloalkyl, or C$_5$-C$_6$ cycloalkyl). In embodiments, R$^{105}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^{105}$ is R$^{106}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{105}$ is R$^{106}$-substituted heterocycloalkyl (e.g., 3 to 8 membered heterocycloalkyl, 3 to 6 membered heterocycloalkyl, or 5 to 6 membered heterocycloalkyl). In embodiments, R$^{105}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^{105}$ is R$^{106}$-substituted or unsubstituted aryl (e.g., C$_6$-C$_{10}$ aryl, C$_{10}$ aryl, or phenyl). In embodiments, R$^{105}$ is R$^{106}$-substituted aryl (e.g., C$_6$-C$_{10}$ aryl, C$_{10}$ aryl, or phenyl). In embodiments, R$^{105}$ is an unsubstituted aryl (e.g., C$_6$-C$_{10}$ aryl, C$_{10}$ aryl, or phenyl).

In embodiments, R$^{105}$ is R$^{106}$-substituted or unsubstituted heteroaryl (e.g., 5 to 10 membered heteroaryl, 5 to 9 membered heteroaryl, or 5 to 6 membered heteroaryl). In embodiments, R$^{105}$ is R$^{106}$-substituted heteroaryl (e.g., 5 to 10 membered heteroaryl, 5 to 9 membered heteroaryl, or 5 to 6 membered heteroaryl). In embodiments, R$^{105}$ is an unsubstituted heteroaryl (e.g., 5 to 10 membered heteroaryl, 5 to 9 membered heteroaryl, or 5 to 6 membered heteroaryl).

In aspects provided herein, there are compounds having structural Formula (V):

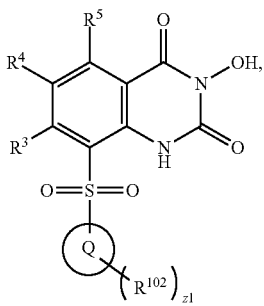

(V)

or a pharmaceutically acceptable salt thereof.

z1, Q, $R^3$, $R^4$, $R^5$ and $R^{102}$ are as defined herein, including embodiments.

In aspects provided herein, there are compounds having structural Formula (VI):

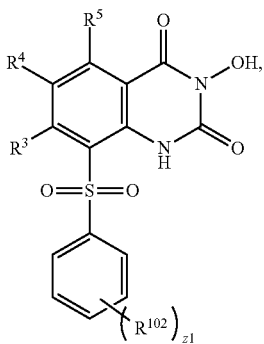

(VI)

or a pharmaceutically acceptable salt thereof.

z1, $R^3$, $R^4$, $R^5$ and $R^{102}$ are as defined herein, including embodiments.

In aspects provided herein, there are compounds having structural Formula (VIa):

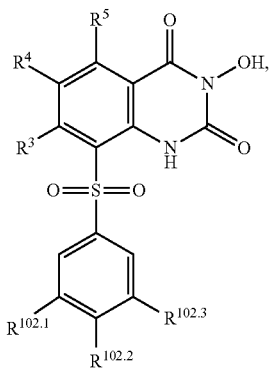

(VIa)

or a pharmaceutically acceptable salt thereof. $R^3$, $R^4$ and $R^5$ are as defined herein, including embodiments. $R^{102.1}$ is hydrogen, halogen, $-CX^{102.1}_3$, $-CHX^{102.1}_2$, $-CH_2X^{102.1}$, $-CN$, $-SO_{n102.1}R^{102.1D}$, $-SO_{v102.1}NR^{102.1A}R^{102.1B}$, $-NHC(O)NR^{102.1A}R^{102.1B}$, $-N(O)_{m102.1}$, $-NR^{102.1A}R^{102.1B}$, $-C(O)R^{102.1C}$, $-C(O)-OR^{102.1C}$, $-C(O)NR^{102.1A}R^{102.1B}$, $-OR^{102.1D}$, $-NR^{102.1A}SO_2R^{102.1D}$, $-NR^{102.1A}C(O)R^{102.1C}$, $-NR^{102.1A}C(O)OR^{102.1C}$, $-NR^{102.1A}OR^{102.1C}$, $-OCX^{102.1}_3$, $-OCHX^{102.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.1B}$ and $R^{102.1C}$ substituents bonded to the same nitrogen atom may optionally be joined to form a substituted or unsubstituted heterocycloalkyl or substituted or unsubstituted heteroaryl. $R^{102.2}$ is hydrogen, halogen, $-CX^{102.2}_3$, $-CHX^{102.2}_2$, $-CH_2X^{102.2}$, $-CN$, $-SO_{n102.2}R^{102.2D}$, $-SO_{v102.2}NR^{102.2A}R^{102.2B}$, $-NHC(O)NR^{102.2A}R^{102.2B}$, $-N(O)_{m102.2}$, $-NR^{102.2A}R^{102.2B}$, $-C(O)R^{102.2C}$, $-C(O)-OR^{102.2C}$, $-C(O)NR^{102.2A}R^{102.2B}$, $-OR^{102.2D}$, $-NR^{102.2A}SO_2R^{102.2D}$, $-NR^{102.2A}C(O)R^{102.2C}$, $-NR^{102.2A}C(O)OR^{102.2C}$, $-NR^{102.2A}OR^{102.2C}$, $-OCX^{102.2}_3$, $-OCHX^{102.2}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.2B}$ and $R^{102.2C}$ substituents bonded to the same nitrogen atom may optionally be joined to form a substituted or unsubstituted heterocycloalkyl or substituted or unsubstituted heteroaryl. $R^{102.3}$ is hydrogen, halogen, $-CX^{102.3}_3$, $-CHX^{102.3}_2$, $-CH_2X^{102.3}$, $-CN$, $-SO_{n102.3}R^{102.3D}$, $-SO_{v102.3}NR^{102.3A}R^{102.3B}$, $-NHC(O)NR^{102.3A}R^{102.3B}$, $-N(O)_{m102.3}$, $-NR^{102.3A}R^{102.3B}$, $-C(O)R^{102.3C}$, $-C(O)-OR^{102.3C}$, $-C(O)NR^{102.3A}R^{102.3B}$, $-OR^{102.3D}$, $-NR^{102.3A}SO_2R^{102.3D}$, $-NR^{102.3A}C(O)R^{102.3C}$, $-NR^{102.3A}C(O)OR^{102.3C}$, $-NR^{102.3A}OR^{102.3C}$, $-OCX^{102.3}_3$, $-OCHX^{102.3}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.3B}$ and $R^{102.3C}$ substituents bonded to the same nitrogen atom may optionally be joined to form a substituted or unsubstituted heterocycloalkyl or substituted or unsubstituted heteroaryl; $R^{102.1}$ and $R^{102.2}$ or $R^{102.2}$ and $R^{102.3}$ may optionally be joined to form a substituted or unsubstituted cycloalkyl, substituted or unsubstituted heterocycloalkyl, substituted or unsubstituted aryl or substituted or unsubstituted heteroaryl. $R^{102.1A}$, $R^{102.1B}$, $R^{102.1C}$, $R^{102.1D}$, $R^{102.2A}$, $R^{102.2B}$, $R^{102.2C}$, $R^{102.2D}$ $R^{102.3A}$, $R^{102.3B}$, $R^{102.3C}$ and $R^{102.3D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.1B}$ and $R^{102.1C}$ and $R^{102.2B}$ and $R^{102.2C}$ and $R^{102.3B}$ and $R^{102.3C}$ substituents bonded to the same nitrogen atom may optionally be joined to form a substituted or unsubstituted heterocycloalkyl or substituted or unsubstituted heteroaryl. $X^{102.1}$, $X^{102.2}$ and $X^{102.3}$ are independently $-F$, $-Cl$, $-Br$, or $-I$. The symbols m102.1, m102.2 and m102.3 are independently an integer from 1 to 2. The symbols n102.1, n102.2 and n102.3 are independently an integer from 0 to 3. The symbols v102.1, v102.2 and v102.3 are independently an integer from 1 to 2.

In embodiments, $R^{102.1}$ is hydrogen. In embodiments, $R^{102.1}$ is halogen. In embodiments, $R^{102.1}$ is $-CN$. In embodiments, $R^{102.1}$ is $-NHC(O)NR^{102.1A}R^{102.1B}$. In embodiments, $R^{102.1}$ is $-NR^{102.1A}R^{102.1B}$. In embodiments, $R^{102.1}$ is $-OR^{102.1D}$. In embodiments, $R^{102.1}$ is substituted or unsubstituted alkyl. In embodiments, $R^{102.1}$ is substituted or unsubstituted heteroalkyl. In embodiments, $R^{102.1}$ is substituted or unsubstituted aryl. In embodiments, $R^{102.1}$ is substituted or unsubstituted heteroaryl.

In embodiments, $R^{102.2}$ is hydrogen. In embodiments, $R^{102.2}$ is halogen. In embodiments, $R^{102.2}$ is —CN. In embodiments, $R^{102.2}$ is —NHC(O)NR$^{102.2A}$R$^{102.2B}$. In embodiments, $R^{102.2}$ is —NR$^{102.2A}$R$^{102.2B}$. In embodiments, $R^{102.2}$ is —OR$^{102.2D}$. In embodiments, $R^{102.2}$ is substituted or unsubstituted alkyl. In embodiments, $R^{102.2}$ is substituted or unsubstituted heteroalkyl. In embodiments, $R^{102.2}$ is substituted or unsubstituted aryl. In embodiments, $R^{102.2}$ is substituted or unsubstituted heteroaryl.

In embodiments, $R^{102.3}$ is hydrogen. In embodiments, $R^{102.3}$ is halogen. In embodiments, $R^{102.3}$ is —CN. In embodiments, $R^{102.3}$ is —NHC(O)NR$^{102.3A}$R$^{102.3B}$. In embodiments, $R^{102.3}$ is —NR$^{102.3A}$R$^{102.3B}$. In embodiments, $R^{102.3}$ is —OR$^{102.3D}$. In embodiments, $R^{102.3}$ is substituted or unsubstituted alkyl. In embodiments, $R^{102.3}$ is substituted or unsubstituted heteroalkyl. In embodiments, $R^{102.3}$ is substituted or unsubstituted aryl. In embodiments, $R^{102.3}$ is substituted or unsubstituted heteroaryl.

In embodiments, m102.1 is 1. In embodiments, m102.1 is 2. In embodiments, m102.2 is 1. In embodiments, m102.2 is 2. In embodiments, m102.3 is 1. In embodiments, m102.3 is 2.

In embodiments, n102.1 is 0. In embodiments, n102.1 is 1. In embodiments, n102.1 is 2. In embodiments, n102.1 is 3. In embodiments, n102.2 is 0. In embodiments, n102.2 is 1. In embodiments, n102.2 is 2. In embodiments, n102.2 is 3. In embodiments, n102.3 is 0. In embodiments, n102.3 is 1. In embodiments, n102.3 is 2. In embodiments, n102.2 is 3.

In embodiments, v102.1 is 1. In embodiments, v102.1 is 2. In embodiments, v102.2 is 1. In embodiments, v102.2 is 2. In embodiments, v102.3 is 1. In embodiments, v102.3 is 2.

In embodiments, $R^{102.1}$ is hydrogen, halogen, —CX$^{102.1}_3$, —CHX$^{102.1}_2$, —CH$_2$X$^{102.1}$, —CN, —SO$_{n1}$R$^{102.1A}$, —SO$_{v1}$NR$^{102.1B}$R$^{102.1C}$, —NR$^{102.1B}$R$^{102.1C}$, —ONR$^{102.1B}$R$^{102.1C}$, —NHC(O)NHNR$^{102.1B}$R$^{102.1C}$, —NHC(O)NR$^{102.1B}$R$^{102.1C}$, —N(O)$_{m1}$, —NR$^{102.1B}$R$^{102.1C}$, —C(O)R$^{102.1D}$, —C(O)OR$^{102.1D}$, —C(O)NR$^{102.1B}$R$^{102.1C}$, —OR$^{102.1A}$, —NR$^{102.1B}$SO$_2$R$^{102.1A}$, —NR$^{102.1B}$C(O)R$^{102.1D}$, —NR$^{102.1B}$C(O)OR$^{102.1D}$, —NR$^{102.1B}$OR$^{102.1D}$, —OCX$^{102.1}_3$, —OCHX$^{102.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{102.1}$ is halogen, —CX$^{102.1}_3$, —CHX$^{102.1}_2$, —CH$_2$X$^{102.1}$, —CN, —SO$_{n1}$R$^{102.1A}$, —SO$_{v1}$NR$^{102.1B}$R$^{102.1C}$, —NHNR$^{102.1B}$R$^{102.1C}$, —ONR$^{102.1B}$R$^{102.1C}$, —NHC(O)NHNR$^{102.1B}$R$^{102.1C}$, —NHC(O)NR$^{102.1B}$R$^{102.1C}$, —N(O)$_{M1}$, —NR$^{102.1B}$R$^{102.1C}$, —C(O)R$^{102.1D}$, —C(O)OR$^{102.1D}$, —C(O)NR$^{102.1B}$R$^{102.1C}$, —OR$^{102.1A}$, —NR$^{102.1B}$SO$_2$R$^{102.1A}$, —NR$^{102.1B}$C(O)R$^{102.1D}$, —NR$^{102.1B}$C(O)OR$^{102.1D}$, —NR$^{102.1B}$OR$^{102.1D}$, —OCX$^{102.1}_3$, —OCHX$^{102.1}_2$, R$^{104.1}$-substituted or unsubstituted alkyl (e.g., $C_1$-$C_8$ alkyl, $C_1$-$C_6$ alkyl, or $C_1$-$C_4$ alkyl), R$^{104.1}$-substituted or unsubstituted heteroalkyl (e.g., 2 to 8 membered heteroalkyl, 2 to 6 membered heteroalkyl, or 2 to 4 membered heteroalkyl), R$^{104.1}$-substituted or unsubstituted cycloalkyl (e.g., $C_3$-$C_8$ cycloalkyl, $C_3$-$C_6$ cycloalkyl, or $C_5$-$C_6$ cycloalkyl), R$^{104.1}$-substituted or unsubstituted heterocycloalkyl (e.g., 3 to 8 membered heterocycloalkyl, 3 to 6 membered heterocycloalkyl, or 5 to 6 membered heterocycloalkyl), R$^{104.1}$-substituted or unsubstituted aryl (e.g., $C_6$-$C_{10}$ aryl, $C_{10}$ aryl, or phenyl), or R$^{104.1}$-substituted or unsubstituted heteroaryl (e.g., 5 to 10 membered heteroaryl, 5 to 9 membered heteroaryl, or 5 to 6 membered heteroaryl).

In embodiments, $R^{102.1}$ is R$^{104.1}$-substituted or unsubstituted alkyl (e.g., $C_1$-$C_8$ alkyl, $C_1$-$C_6$ alkyl, or $C_1$-$C_4$ alkyl). In embodiments, $R^{102.1}$ is R$^{104.1}$-substituted alkyl (e.g., $C_1$-$C_8$ alkyl, $C_1$-$C_6$ alkyl, or $C_1$-$C_4$ alkyl). In embodiments, $R^{102.1}$ is an unsubstituted alkyl (e.g., $C_1$-$C_8$ alkyl, $C_1$-$C_6$ alkyl, or $C_1$-$C_4$ alkyl).

In embodiments, $R^{102.1}$ is R$^{104.1}$-substituted or unsubstituted heteroalkyl (e.g., 2 to 8 membered heteroalkyl, 2 to 6 membered heteroalkyl, or 2 to 4 membered heteroalkyl). In embodiments, $R^{102.1}$ is R$^{104.1}$-substituted heteroalkyl (e.g., 2 to 8 membered heteroalkyl, 2 to 6 membered heteroalkyl, or 2 to 4 membered heteroalkyl). In embodiments, $R^{102.1}$ is an unsubstituted heteroalkyl (e.g., 2 to 8 membered heteroalkyl, 2 to 6 membered heteroalkyl, or 2 to 4 membered heteroalkyl).

In embodiments, $R^{102.1}$ is R$^{104.1}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{102.1}$ is R$^{104.1}$-substituted cycloalkyl (e.g., $C_3$-$C_8$ cycloalkyl, $C_3$-$C_6$ cycloalkyl, or $C_5$-$C_6$ cycloalkyl). In embodiments, $R^{102.1}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{102.1}$ is R$^{104.1}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{102.1}$ is R$^{104.1}$-substituted heterocycloalkyl (e.g., 3 to 8 membered heterocycloalkyl, 3 to 6 membered heterocycloalkyl, or 5 to 6 membered heterocycloalkyl). In embodiments, $R^{102.1}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{102.1}$ is R$^{104.1}$-substituted or unsubstituted aryl (e.g., $C_6$-$C_{10}$ aryl, $C_{10}$ aryl, or phenyl). In embodiments, $R^{102.1}$ is R$^{104.1}$-substituted aryl (e.g., $C_6$-$C_{10}$ aryl, $C_{10}$ aryl, or phenyl). In embodiments, $R^{102.1}$ is an unsubstituted aryl (e.g., $C_6$-$C_{10}$ aryl, $C_{10}$ aryl, or phenyl).

In embodiments, $R^{102.1}$ is R$^{104.1}$-substituted or unsubstituted heteroaryl (e.g., 5 to 10 membered heteroaryl, 5 to 9 membered heteroaryl, or 5 to 6 membered heteroaryl). In embodiments, $R^{102.1}$ is R$^{104.1}$-substituted heteroaryl (e.g., 5 to 10 membered heteroaryl, 5 to 9 membered heteroaryl, or 5 to 6 membered heteroaryl). In embodiments, $R^{102.1}$ is an unsubstituted heteroaryl (e.g., 5 to 10 membered heteroaryl, 5 to 9 membered heteroaryl, or 5 to 6 membered heteroaryl).

In embodiments, $R^{102.1A}$, $R^{102.1B}$, $R^{102.1C}$ and $R^{102.1D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{102.1B}$ and $R^{102.1C}$ substituents bonded to the same nitrogen atom may optionally be joined to form a substituted or unsubstituted heterocycloalkyl or substituted or unsubstituted heteroaryl.

In embodiments, $R^{102.1A}$ is hydrogen, halogen, —CF$_3$, —CCl$_3$, —CBr$_3$, —CI$_3$, —COOH, —CONH$_2$, R$^{104.1A}$-substituted or unsubstituted alkyl (e.g., $C_1$-$C_8$ alkyl, $C_1$-$C_6$ alkyl, or $C_1$-$C_4$ alkyl), R$^{104.1A}$-substituted or unsubstituted heteroalkyl (e.g., 2 to 8 membered heteroalkyl, 2 to 6 membered heteroalkyl, or 2 to 4 membered heteroalkyl), $R^{104.1A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.1A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.1A}$-substituted or unsubstituted aryl (e.g., $C_6$-$C_{10}$ aryl, $C_{10}$ aryl, or phenyl), or $R^{104.1A}$-substituted or unsubstituted heteroaryl (e.g., 5 to 10 membered heteroaryl, 5 to 9 membered heteroaryl, or 5 to 6 membered heteroaryl).

In embodiments, $R^{102.1B}$ is hydrogen, halogen, —$CF_3$, —$CCl_3$, —$CBr_3$, —$CI_3$, —COOH, —$CONH_2$, $R^{104.1B}$-substituted or unsubstituted alkyl (e.g., $C_1$-$C_8$ alkyl, $C_1$-$C_6$ alkyl, or $C_1$-$C_4$ alkyl), $R^{104.1B}$-substituted or unsubstituted heteroalkyl (e.g., 2 to 8 membered heteroalkyl, 2 to 6 membered heteroalkyl, or 2 to 4 membered heteroalkyl), $R^{104.1B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.1B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.1B}$-substituted or unsubstituted aryl (e.g., $C_6$-$C_{10}$ aryl, $C_{10}$ aryl, or phenyl), or $R^{104.1B}$-substituted or unsubstituted heteroaryl (e.g., 5 to 10 membered heteroaryl, 5 to 9 membered heteroaryl, or 5 to 6 membered heteroaryl). In embodiments, $R^{102.1B}$ and $R^{102.1C}$ substituents bonded to the same nitrogen atom may optionally be joined to form a $R^{104.1B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{104.1B}$-substituted or unsubstituted heteroaryl (e.g., 5 to 10 membered heteroaryl, 5 to 9 membered heteroaryl, or 5 to 6 membered heteroaryl).

In embodiments, $R^{102.1C}$ is hydrogen, halogen, —$CF_3$, —$CCl_3$, —$CBr_3$, —$CI_3$, —COOH, —$CONH_2$, $R^{104.1C}$-substituted or unsubstituted alkyl (e.g., $C_1$-$C_8$ alkyl, $C_1$-$C_6$ alkyl, or $C_1$-$C_4$ alkyl), $R^{104.1C}$-substituted or unsubstituted heteroalkyl (e.g., 2 to 8 membered heteroalkyl, 2 to 6 membered heteroalkyl, or 2 to 4 membered heteroalkyl), $R^{104.1C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.1C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.1C}$-substituted or unsubstituted aryl (e.g., $C_6$-$C_{10}$ aryl, $C_{10}$ aryl, or phenyl), or $R^{104.1C}$-substituted or unsubstituted heteroaryl (e.g., 5 to 10 membered heteroaryl, 5 to 9 membered heteroaryl, or 5 to 6 membered heteroaryl). In embodiments, $R^{102.1B}$ and $R^{102.1C}$ substituents bonded to the same nitrogen atom may optionally be joined to form a $R^{104.1C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{104.1C}$-substituted or unsubstituted heteroaryl (e.g., 5 to 10 membered heteroaryl, 5 to 9 membered heteroaryl, or 5 to 6 membered heteroaryl).

In embodiments, $R^{102.1D}$ is hydrogen, halogen, —$CF_3$, —$CCl_3$, —$CBr_3$, —$CI_3$, —COOH, —$CONH_2$, $R^{104.1D}$-substituted or unsubstituted alkyl (e.g., $C_1$-$C_8$ alkyl, $C_1$-$C_6$ alkyl, or $C_1$-$C_4$ alkyl), $R^{104.1D}$-substituted or unsubstituted heteroalkyl (e.g., 2 to 8 membered heteroalkyl, 2 to 6 membered heteroalkyl, or 2 to 4 membered heteroalkyl), $R^{104.1D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.1D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.1D}$-substituted or unsubstituted aryl (e.g., $C_6$-$C_{10}$ aryl, $C_{10}$ aryl, or phenyl), or $R^{104.1D}$-substituted or unsubstituted heteroaryl (e.g., 5 to 10 membered heteroaryl, 5 to 9 membered heteroaryl, or 5 to 6 membered heteroaryl).

$R^{104.1}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —OCHF 2, $R^{105.1}$-substituted or unsubstituted alkyl (e.g., $C_1$-$C_8$ alkyl, $C_1$-$C_6$ alkyl, or $C_1$-$C_4$ alkyl), $R^{105.1}$-substituted or unsubstituted heteroalkyl (e.g., 2 to 8 membered heteroalkyl, 2 to 6 membered heteroalkyl, or 2 to 4 membered heteroalkyl), $R^{105.1}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{105.1}$-substituted or unsubstituted heterocycloalkyl (e.g., 3 to 8 membered heterocycloalkyl, 3 to 6 membered heterocycloalkyl, or 5 to 6 membered heterocycloalkyl), $R^{105.1}$-substituted or unsubstituted aryl (e.g., $C_6$-$C_{10}$ aryl, $C_{10}$ aryl, or phenyl), or $R^{105.1}$-substituted or unsubstituted heteroaryl (e.g., 5 to 10 membered heteroaryl, 5 to 9 membered heteroaryl, or 5 to 6 membered heteroaryl).

In embodiments, $R^{104.1}$ is $R^{105.1}$-substituted or unsubstituted alkyl (e.g., $C_1$-$C_8$ alkyl, $C_1$-$C_6$ alkyl, or $C_1$-$C_4$ alkyl). In embodiments, $R^{104.1}$ is $R^{105.1}$-substituted alkyl (e.g., $C_1$-$C_8$ alkyl, $C_1$-$C_6$ alkyl, or $C_1$-$C_4$ alkyl). In embodiments, $R^{104.1}$ is an unsubstituted alkyl (e.g., $C_1$-$C_8$ alkyl, $C_1$-$C_6$ alkyl, or $C_1$-$C_4$ alkyl).

In embodiments, $R^{104.1}$ is $R^{105.1}$-substituted or unsubstituted heteroalkyl (e.g., 2 to 8 membered heteroalkyl, 2 to 6 membered heteroalkyl, or 2 to 4 membered heteroalkyl). In embodiments, $R^{104.1}$ is $R^{105.1}$-substituted heteroalkyl (e.g., 2 to 8 membered heteroalkyl, 2 to 6 membered heteroalkyl, or 2 to 4 membered heteroalkyl). In embodiments, $R^{104.1}$ is an unsubstituted heteroalkyl (e.g., 2 to 8 membered heteroalkyl, 2 to 6 membered heteroalkyl, or 2 to 4 membered heteroalkyl).

In embodiments, $R^{104.1}$ is $R^{105.1}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{104.1}$ is $R^{105.1}$-substituted cycloalkyl (e.g., $C_3$-$C_8$ cycloalkyl, $C_3$-$C_6$ cycloalkyl, or $C_5$-$C_6$ cycloalkyl). In embodiments, $R^{104.1}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{104.1}$ is $R^{105.1}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{104.1}$ is $R^{105.1}$-substituted heterocycloalkyl (e.g., 3 to 8 membered heterocycloalkyl, 3 to 6 membered heterocycloalkyl, or 5 to 6 membered heterocycloalkyl). In embodiments, $R^{104.1}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{104.1}$ is $R^{105.1}$-substituted or unsubstituted aryl (e.g., $C_6$-$C_{10}$ aryl, $C_{10}$ aryl, or phenyl). In embodiments, $R^{104.1}$ is $R^{105.1}$-substituted aryl (e.g., $C_6$-$C_{10}$ aryl, $C_{10}$ aryl, or phenyl). In embodiments, $R^{104.1}$ is an unsubstituted aryl (e.g., $C_6$-$C_{10}$ aryl, $C_{10}$ aryl, or phenyl).

In embodiments, $R^{104.1}$ is $R^{105.1}$-substituted or unsubstituted heteroaryl (e.g., 5 to 10 membered heteroaryl, 5 to 9 membered heteroaryl, or 5 to 6 membered heteroaryl). In embodiments, $R^{104.1}$ is $R^{150.1}$-substituted heteroaryl (e.g., 5 to 10 membered heteroaryl, 5 to 9 membered heteroaryl, or 5 to 6 membered heteroaryl). In embodiments, $R^{104.1}$ is an unsubstituted heteroaryl (e.g., 5 to 10 membered heteroaryl, 5 to 9 membered heteroaryl, or 5 to 6 membered heteroaryl).

$R^{105.1}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $R^{106.1}$-substituted or unsubstituted alkyl (e.g., $C_1$-$C_8$ alkyl, $C_1$-$C_6$ alkyl, or $C_1$-$C_4$ alkyl), $R^{106.1}$-substituted or unsubstituted heteroalkyl (e.g., 2 to 8 membered heteroalkyl, 2 to 6 membered heteroalkyl, or 2 to 4 membered heteroalkyl), $R^{106.1}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{106.1}$-substituted or unsubstituted heterocycloalkyl (e.g., 3 to 8 membered heterocycloalkyl, 3 to 6 membered heterocycloalkyl, or 5 to 6 membered heterocycloalkyl), $R^{106.1}$-substituted or unsubstituted aryl (e.g., $C_6$-$C_{10}$ aryl, $C_{10}$ aryl, or phenyl), or $R^{106.1}$-substituted or unsubstituted heteroaryl (e.g., 5 to 10 membered heteroaryl, 5 to 9 membered heteroaryl, or 5 to 6 membered heteroaryl).

In embodiments, $R^{105.1}$ is $R^{106.1}$-substituted or unsubstituted alkyl (e.g., $C_1$-$C_8$ alkyl, $C_1$-$C_6$ alkyl, or $C_1$-$C_4$ alkyl). In embodiments, $R^{105.1}$ is $R^{106.1}$-substituted alkyl (e.g., $C_1$-$C_8$ alkyl, $C_1$-$C_6$ alkyl, or $C_1$-$C_4$ alkyl). In embodiments, $R^{105.1}$ is an unsubstituted alkyl (e.g., $C_1$-$C_8$ alkyl, $C_1$-$C_6$ alkyl, or $C_1$-$C_4$ alkyl).

In embodiments, $R^{105.1}$ is $R^{106.1}$-substituted or unsubstituted heteroalkyl (e.g., 2 to 8 membered heteroalkyl, 2 to 6 membered heteroalkyl, or 2 to 4 membered heteroalkyl). In embodiments, $R^{105.1}$ is $R^{106.1}$-substituted heteroalkyl (e.g., 2 to 8 membered heteroalkyl, 2 to 6 membered heteroalkyl, or 2 to 4 membered heteroalkyl). In embodiments, $R^{105.1}$ is an unsubstituted heteroalkyl (e.g., 2 to 8 membered heteroalkyl, 2 to 6 membered heteroalkyl, or 2 to 4 membered heteroalkyl).

In embodiments, $R^{105.1}$ is $R^{106.1}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{105.1}$ is $R^{106.1}$-substituted cycloalkyl (e.g., $C_3$-$C_8$ cycloalkyl, $C_3$-$C_6$ cycloalkyl, or $C_5$-$C_6$ cycloalkyl). In embodiments, $R^{105.1}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{105.1}$ is $R^{106.1}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{105.1}$ is $R^{106.1}$-substituted heterocycloalkyl (e.g., 3 to 8 membered heterocycloalkyl, 3 to 6 membered heterocycloalkyl, or 5 to 6 membered heterocycloalkyl). In embodiments, $R^{105.1}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{105.1}$ is $R^{106.1}$-substituted or unsubstituted aryl (e.g., $C_6$-$C_{10}$ aryl, $C_{10}$ aryl, or phenyl). In embodiments, $R^{105.1}$ is $R^{106.1}$-substituted aryl (e.g., $C_6$-$C_{10}$ aryl, $C_{10}$ aryl, or phenyl). In embodiments, $R^{105.1}$ is an unsubstituted aryl (e.g., $C_6$-$C_{10}$ aryl, $C_{10}$ aryl, or phenyl).

In embodiments, $R^{105.1}$ is $R^{106.1}$-substituted or unsubstituted heteroaryl (e.g., 5 to 10 membered heteroaryl, 5 to 9 membered heteroaryl, or 5 to 6 membered heteroaryl). In embodiments, $R^{105.1}$ is $R^{106.1}$-substituted heteroaryl (e.g., 5 to 10 membered heteroaryl, 5 to 9 membered heteroaryl, or 5 to 6 membered heteroaryl). In embodiments, $R^{105.1}$ is an unsubstituted heteroaryl (e.g., 5 to 10 membered heteroaryl, 5 to 9 membered heteroaryl, or 5 to 6 membered heteroaryl).

In embodiments, $R^{102.2}$ is hydrogen, halogen, $-CX^{102.2}_3$, $-CHX^{102.2}_2$, $-CH_2X^{102.2}$, $-CN$, $-SO_{n1}R^{102.2A}$, $-SO_{v1}NR^{102.2B}R^{102.2C}$, $-NHNR^{102.2B}R^{102.2C}$, $-ONR^{102.2B}R^{102.2C}$, $-NHC(O)NHNR^{102.2B}R^{102.2C}$, $-NHC(O)NR^{102.2B}R^{102.2C}$, $-N(O)_{m1}$, $-NR^{102.2B}R^{102.2C}$, $-C(O)R^{102.2D}$, $-C(O)OR^{102.2D}$, $-C(O)NR^{102.2B}R^{102.2C}$, $-OR^{102.2A}$, $-NR^{102.2B}SO_2R^{102.2A}$, $-NR^{102.2B}C(O)R^{102.2D}$, $-^{102.2B}C(O)OR^{102.2D}$, $-^{102.2B}OR^{102.2D}$, $-OCX^{102.2}_3$, $-OCHX^{102.2}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{102.2}$ is halogen, $-CX^{102.2}_3$, $-CHX^{102.2}_2$, $-CH_2X^{102.2}$, $-CN$, $-SO_{n1}R^{102.2A}$, $-SO_{v1}NR^{102.2B}R^{102.2C}$, $-NHNR^{102.2B}R^{102.2C}$, $-ONR^{102.2B}R^{102.2C}$, $-NHC(O)NHNR^{102.2B}R^{102.2C}$, $-NHC(O)NR^{102.2B}R^{102.2C}$, $-N(O)_{m1}$, $-NR^{102.2B}R^{102.2C}$, $-C(O)R^{102.2D}$, $-C(O)OR^{102.2D}$, $-C(O)NR^{102.2B}R^{102.2C}$, $-OR^{102.2A}$, $-NR^{102.2B}SO_2R^{102.2A}$, $-NR^{102.2B}C(O)R^{102.2D}$, $-^{102.2B}C(O)OR^{102.2D}$, $-^{102.2B}OR^{102.2D}$, $-OCX^{102.2}_3$, $-OCHX^{102.2}_2$, $R^{104.2}$-substituted or unsubstituted alkyl (e.g., $C_1$-$C_8$ alkyl, $C_1$-$C_6$ alkyl, or $C_1$-$C_4$ alkyl), $R^{104.2}$-substituted or unsubstituted heteroalkyl (e.g., 2 to 8 membered heteroalkyl, 2 to 6 membered heteroalkyl, or 2 to 4 membered heteroalkyl), $R^{104.2}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.2}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.2}$-substituted or unsubstituted aryl (e.g., $C_6$-$C_{10}$ aryl, $C_{10}$ aryl, or phenyl), or $R^{104.2}$-substituted or unsubstituted heteroaryl (e.g., 5 to 10 membered heteroaryl, 5 to 9 membered heteroaryl, or 5 to 6 membered heteroaryl).

In embodiments, $R^{102.2}$ is $R^{104.2}$-substituted or unsubstituted alkyl (e.g., $C_1$-$C_8$ alkyl, $C_1$-$C_6$ alkyl, or $C_1$-$C_4$ alkyl). In embodiments, $R^{102.2}$ is $R^{104.2}$-substituted alkyl (e.g., $C_1$-$C_8$ alkyl, $C_1$-$C_6$ alkyl, or $C_1$-$C_4$ alkyl). In embodiments, $R^{102.2}$ is an unsubstituted alkyl (e.g., $C_1$-$C_8$ alkyl, $C_1$-$C_6$ alkyl, or $C_1$-$C_4$ alkyl).

In embodiments, $R^{102.2}$ is $R^{104.2}$-substituted or unsubstituted heteroalkyl (e.g., 2 to 8 membered heteroalkyl, 2 to 6 membered heteroalkyl, or 2 to 4 membered heteroalkyl). In embodiments, $R^{102.2}$ is $R^{104.2}$-substituted heteroalkyl (e.g., 2 to 8 membered heteroalkyl, 2 to 6 membered heteroalkyl, or 2 to 4 membered heteroalkyl). In embodiments, $R^{102.2}$ is an unsubstituted heteroalkyl (e.g., 2 to 8 membered heteroalkyl, 2 to 6 membered heteroalkyl, or 2 to 4 membered heteroalkyl).

In embodiments, $R^{102.2}$ is $R^{104.2}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{102.2}$ is $R^{104.2}$-substituted cycloalkyl (e.g., $C_3$-$C_8$ cycloalkyl, $C_3$-$C_6$ cycloalkyl, or $C_5$-$C_6$ cycloalkyl). In embodiments, $R^{102.2}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{102.2}$ is $R^{104.2}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{102.2}$ is $R^{104.2}$-substituted heterocycloalkyl (e.g., 3 to 8 membered heterocycloalkyl, 3 to 6 membered heterocycloalkyl, or 5 to 6 membered heterocycloalkyl). In embodiments, $R^{102.2}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{102.2}$ is $R^{104.2}$-substituted or unsubstituted aryl (e.g., $C_6$-$C_{10}$ aryl, $C_{10}$ aryl, or phenyl). In embodiments, $R^{102.2}$ is $R^{104.2}$-substituted aryl (e.g., $C_6$-$C_{10}$ aryl, $C_{10}$ aryl, or phenyl). In embodiments, $R^{102.2}$ is an unsubstituted aryl (e.g., $C_6$-$C_{10}$ aryl, $C_{10}$ aryl, or phenyl).

In embodiments, $R^{102.2}$ is $R^{104.2}$-substituted or unsubstituted heteroaryl (e.g., 5 to 10 membered heteroaryl, 5 to 9 membered heteroaryl, or 5 to 6 membered heteroaryl). In embodiments, $R^{102.2}$ is $R^{104.2}$-substituted heteroaryl (e.g., 5 to 10 membered heteroaryl, 5 to 9 membered heteroaryl, or 5 to 6 membered heteroaryl). In embodiments, $R^{102.2}$ is an unsubstituted heteroaryl (e.g., 5 to 10 membered heteroaryl, 5 to 9 membered heteroaryl, or 5 to 6 membered heteroaryl).

In embodiments, $R^{102.2A}$, $R^{102.2B}$, $R^{102.2C}$ and $R^{102.2D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{102.2B}$ and $R^{102.2C}$ substituents bonded to the same nitrogen atom may optionally be joined to form a substituted or unsubstituted heterocycloalkyl or substituted or unsubstituted heteroaryl.

In embodiments, $R^{102.2A}$ is hydrogen, halogen, —$CF_3$, —$CCl_3$, —$CBr_3$, —$CI_3$, —COOH, —$CONH_2$, $R^{104.2A}$-substituted or unsubstituted alkyl (e.g., $C_1$-$C_8$ alkyl, $C_1$-$C_6$ alkyl, or $C_1$-$C_4$ alkyl), $R^{104.2A}$-substituted or unsubstituted heteroalkyl (e.g., 2 to 8 membered heteroalkyl, 2 to 6 membered heteroalkyl, or 2 to 4 membered heteroalkyl), $R^{104.2A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.2A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.2A}$-substituted or unsubstituted aryl (e.g., $C_6$-$C_{10}$ aryl, $C_{10}$ aryl, or phenyl), or $R^{104.2A}$-substituted or unsubstituted heteroaryl (e.g., 5 to 10 membered heteroaryl, 5 to 9 membered heteroaryl, or 5 to 6 membered heteroaryl).

In embodiments, $R^{102.2B}$ is hydrogen, halogen, —$CF_3$, —$CCl_3$, —$CBr_3$, —$CI_3$, —COOH, —$CONH_2$, $R^{104.2B}$-substituted or unsubstituted alkyl (e.g., $C_1$-$C_8$ alkyl, $C_1$-$C_6$ alkyl, or $C_1$-$C_4$ alkyl), $R^{104.2B}$-substituted or unsubstituted heteroalkyl (e.g., 2 to 8 membered heteroalkyl, 2 to 6 membered heteroalkyl, or 2 to 4 membered heteroalkyl), $R^{104.2B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.2B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.2B}$-substituted or unsubstituted aryl (e.g., $C_6$-$C_{10}$ aryl, $C_{10}$ aryl, or phenyl), or $R^{104.2B}$-substituted or unsubstituted heteroaryl (e.g., 5 to 10 membered heteroaryl, 5 to 9 membered heteroaryl, or 5 to 6 membered heteroaryl). In embodiments, $R^{102.2B}$ and $R^{102.2C}$ substituents bonded to the same nitrogen atom may optionally be joined to form a $R^{104.2B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{104.2B}$-substituted or unsubstituted heteroaryl (e.g., 5 to 10 membered heteroaryl, 5 to 9 membered heteroaryl, or 5 to 6 membered heteroaryl).

In embodiments, $R^{102.2C}$ is hydrogen, halogen, —$CF_3$, —$CCl_3$, —$CBr_3$, —$CI_3$, —COOH, —$CONH_2$, $R^{104.2C}$-substituted or unsubstituted alkyl (e.g., $C_1$-$C_8$ alkyl, $C_1$-$C_6$ alkyl, or $C_1$-$C_4$ alkyl), $R^{104.2C}$-substituted or unsubstituted heteroalkyl (e.g., 2 to 8 membered heteroalkyl, 2 to 6 membered heteroalkyl, or 2 to 4 membered heteroalkyl), $R^{104.2C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.2C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.2C}$-substituted or unsubstituted aryl (e.g., $C_6$-$C_{10}$ aryl, $C_{10}$ aryl, or phenyl), or $R^{104.2C}$-substituted or unsubstituted heteroaryl (e.g., 5 to 10 membered heteroaryl, 5 to 9 membered heteroaryl, or 5 to 6 membered heteroaryl). In embodiments, $R^{102.2B}$ and $R^{102.2C}$ substituents bonded to the same nitrogen atom may optionally be joined to form a $R^{104.2C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{104.2C}$-substituted or unsubstituted heteroaryl (e.g., 5 to 10 membered heteroaryl, 5 to 9 membered heteroaryl, or 5 to 6 membered heteroaryl).

In embodiments, $R^{102.2D}$ is hydrogen, halogen, —$CF_3$, —$CCl_3$, —$CBr_3$, —$CI_3$, —COOH, —$CONH_2$, $R^{104.2D}$-substituted or unsubstituted alkyl (e.g., $C_1$-$C_8$ alkyl, $C_1$-$C_6$ alkyl, or $C_1$-$C_4$ alkyl), $R^{104.2D}$-substituted or unsubstituted heteroalkyl (e.g., 2 to 8 membered heteroalkyl, 2 to 6 membered heteroalkyl, or 2 to 4 membered heteroalkyl), $R^{104.2D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.2D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.2D}$-substituted or unsubstituted aryl (e.g., $C_6$-$C_{10}$ aryl, $C_{10}$ aryl, or phenyl), or $R^{104.2D}$-substituted or unsubstituted heteroaryl (e.g., 5 to 10 membered heteroaryl, 5 to 9 membered heteroaryl, or 5 to 6 membered heteroaryl).

$R^{104.2}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{105.2}$-substituted or unsubstituted alkyl (e.g., $C_1$-$C_8$ alkyl, $C_1$-$C_6$ alkyl, or $C_1$-$C_4$ alkyl), $R^{105.2}$-substituted or unsubstituted heteroalkyl (e.g., 2 to 8 membered heteroalkyl, 2 to 6 membered heteroalkyl, or 2 to 4 membered heteroalkyl), $R^{105.2}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{105.2}$-substituted or unsubstituted heterocycloalkyl (e.g., 3 to 8 membered heterocycloalkyl, 3 to 6 membered heterocycloalkyl, or 5 to 6 membered heterocycloalkyl), $R^{105.2}$-substituted or unsubstituted aryl (e.g., $C_6$-$C_{10}$ aryl, $C_{10}$ aryl, or phenyl), or $R^{105.2}$-substituted or unsubstituted heteroaryl (e.g., 5 to 10 membered heteroaryl, 5 to 9 membered heteroaryl, or 5 to 6 membered heteroaryl).

In embodiments, $R^{104.2}$ is $R^{105.2}$-substituted or unsubstituted alkyl (e.g., $C_1$-$C_8$ alkyl, $C_1$-$C_6$ alkyl, or $C_1$-$C_4$ alkyl). In embodiments, $R^{104.2}$ is $R^{105.2}$-substituted alkyl (e.g., $C_1$-$C_8$ alkyl, $C_1$-$C_6$ alkyl, or $C_1$-$C_4$ alkyl). In embodiments, $R^{104.2}$ is an unsubstituted alkyl (e.g., $C_1$-$C_8$ alkyl, $C_1$-$C_6$ alkyl, or $C_1$-$C_4$ alkyl).

In embodiments, $R^{104.2}$ is $R^{105.2}$-substituted or unsubstituted heteroalkyl (e.g., 2 to 8 membered heteroalkyl, 2 to 6 membered heteroalkyl, or 2 to 4 membered heteroalkyl). In embodiments, $R^{104.2}$ is $R^{105.2}$-substituted heteroalkyl (e.g., 2 to 8 membered heteroalkyl, 2 to 6 membered heteroalkyl, or 2 to 4 membered heteroalkyl). In embodiments, $R^{104.2}$ is an unsubstituted heteroalkyl (e.g., 2 to 8 membered heteroalkyl, 2 to 6 membered heteroalkyl, or 2 to 4 membered heteroalkyl).

In embodiments, $R^{104.2}$ is $R^{105.2}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{104.2}$ is $R^{105.2}$- substituted cycloalkyl (e.g., $C_3$-$C_8$ cycloalkyl, $C_3$-$C_6$ cycloalkyl, or $C_5$-$C_6$ cycloalkyl). In embodiments, $R^{104.2}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{104.2}$ is $R^{105.2}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{104.2}$ is $R^{105.2}$-substituted heterocycloalkyl (e.g., 3 to 8 membered heterocycloalkyl, 3 to 6 membered heterocycloalkyl, or 5 to 6 membered heterocycloalkyl). In embodiments, $R^{104.2}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{104.2}$ is $R^{105.2}$-substituted or unsubstituted aryl (e.g., $C_6$-$C_{10}$ aryl, $C_{10}$ aryl, or phenyl). In embodiments, $R^{104.2}$ is $R^{105.2}$-substituted aryl (e.g., $C_6$-$C_{10}$ aryl, $C_{10}$ aryl, or phenyl). In embodiments, $R^{104.2}$ is an unsubstituted aryl (e.g., $C_6$-$C_{10}$ aryl, $C_{10}$ aryl, or phenyl).

In embodiments, $R^{104.2}$ is $R^{105.2}$-substituted or unsubstituted heteroaryl (e.g., 5 to 10 membered heteroaryl, 5 to 9 membered heteroaryl, or 5 to 6 membered heteroaryl). In embodiments, $R^{104.2}$ is $R^{105.2}$-substituted heteroaryl (e.g., 5 to 10 membered heteroaryl, 5 to 9 membered heteroaryl, or 5 to 6 membered heteroaryl). In embodiments, $R^{104.2}$ is an unsubstituted heteroaryl (e.g., 5 to 10 membered heteroaryl, 5 to 9 membered heteroaryl, or 5 to 6 membered heteroaryl).

$R^{105.2}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{106.2}$-substituted or unsubstituted alkyl (e.g., $C_1$-$C_8$ alkyl, $C_1$-$C_6$ alkyl, or $C_1$-$C_4$ alkyl), $R^{106.2}$-substituted or unsubstituted heteroalkyl (e.g., 2 to 8 membered heteroalkyl, 2 to 6 membered heteroalkyl, or 2 to 4 membered heteroalkyl), $R^{106.2}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{106.2}$-substituted or unsubstituted heterocycloalkyl (e.g., 3 to 8 membered heterocycloalkyl, 3 to 6 membered heterocycloalkyl, or 5 to 6 membered heterocycloalkyl), $R^{106.2}$-substituted or unsubstituted aryl (e.g., $C_6$-$C_{10}$ aryl, $C_{10}$ aryl, or phenyl), or $R^{106.2}$-substituted or unsubstituted heteroaryl (e.g., 5 to 10 membered heteroaryl, 5 to 9 membered heteroaryl, or 5 to 6 membered heteroaryl).

In embodiments, $R^{105.2}$ is $R^{106.2}$-substituted or unsubstituted alkyl (e.g., $C_1$-$C_8$ alkyl, $C_1$-$C_6$ alkyl, or $C_1$-$C_4$ alkyl). In embodiments, $R^{105.2}$ is $R^{106.2}$-Substituted alkyl (e.g., $C_1$-$C_8$ alkyl, $C_1$-$C_6$ alkyl, or $C_1$-$C_4$ alkyl). In embodiments, $R^{105.2}$ is an unsubstituted alkyl (e.g., $C_1$-$C_5$ alkyl, $C_1$-$C_6$ alkyl, or $C_1$-$C_4$ alkyl).

In embodiments, $R^{105.2}$ is $R^{106.2}$-substituted or unsubstituted heteroalkyl (e.g., 2 to 8 membered heteroalkyl, 2 to 6 membered heteroalkyl, or 2 to 4 membered heteroalkyl). In embodiments, $R^{105.2}$ is $R^{106.2}$-substituted heteroalkyl (e.g., 2 to 8 membered heteroalkyl, 2 to 6 membered heteroalkyl, or 2 to 4 membered heteroalkyl). In embodiments, $R^{105.2}$ is an unsubstituted heteroalkyl (e.g., 2 to 8 membered heteroalkyl, 2 to 6 membered heteroalkyl, or 2 to 4 membered heteroalkyl).

In embodiments, $R^{105.2}$ is $R^{106.2}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{105.2}$ is $R^{106.2}$-substituted cycloalkyl (e.g., $C_3$-$C_8$ cycloalkyl, $C_3$-$C_6$ cycloalkyl, or $C_5$-$C_6$ cycloalkyl). In embodiments, $R^{105.2}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{105.2}$ is $R^{106.2}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{105.2}$ is $R^{106.2}$-substituted heterocycloalkyl (e.g., 3 to 8 membered heterocycloalkyl, 3 to 6 membered heterocycloalkyl, or 5 to 6 membered heterocycloalkyl). In embodiments, $R^{105.2}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{105.2}$ is $R^{106.2}$-substituted or unsubstituted aryl (e.g., $C_6$-$C_{10}$ aryl, $C_{10}$ aryl, or phenyl). In embodiments, $R^{105.2}$ is $R^{106.2}$-substituted aryl (e.g., $C_6$-$C_{10}$ aryl, $C_{10}$ aryl, or phenyl). In embodiments, $R^{105.2}$ is an unsubstituted aryl (e.g., $C_6$-$C_{10}$ aryl, $C_{10}$ aryl, or phenyl).

In embodiments, $R^{105.2}$ is $R^{106.2}$-substituted or unsubstituted heteroaryl (e.g., 5 to 10 membered heteroaryl, 5 to 9 membered heteroaryl, or 5 to 6 membered heteroaryl). In embodiments, $R^{105.2}$ is $R^{106.2}$-substituted heteroaryl (e.g., 5 to 10 membered heteroaryl, 5 to 9 membered heteroaryl, or 5 to 6 membered heteroaryl). In embodiments, $R^{105.2}$ is an unsubstituted heteroaryl (e.g., 5 to 10 membered heteroaryl, 5 to 9 membered heteroaryl, or 5 to 6 membered heteroaryl).

In embodiments, $R^{102.3}$ is hydrogen, halogen, —$CX^{102.3}_3$, —$CHX^{102.3}_2$, —$CH_2X^{102.3}$, —CN, —$SO_{n1}R^{102.3A}$, —$SO_{v1}NR^{102.3B}R^{102.3C}$, —$NHNR^{102.3B}R^{102.3C}$, —$ONR^{102.3B}R^{102.3C}$, —$NHC(O)NHNR^{102.3B}R^{102.3C}$, —$NHC(O)NR^{102.3B}R^{102.3C}$, —$N(O)_{m1}$, —$NR^{102.3B}R^{102.3C}$, —$C(O)R^{102.3D}$, —$C(O)OR^{102.3D}$, —$C(O)NR^{102.3B}R^{102.3C}$, —$OR^{102.3A}$, —$NR^{102.3B}SO_2R^{102.3A}$, —$NR^{102.3B}C(O)R^{102.3D}$, —$NR^{102.3B}C(O)OR^{102.3D}$, —$NR^{102.3B}OR^{102.3D}$, —$OCX^{102.3}_3$, —$OCHX^{102.3}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{102.3}$ is halogen, —$CX^{102.3}_3$, —$CHX^{102.3}_2$, —$CH_2X^{102.3}$, —CN, —$SO_{n1}R^{102.3A}$, —$SO_{v1}NR^{102.3B}R^{102.3C}$, —$NHNR^{102.3B}R^{102.3C}$, —$ONR^{102.3B}R^{102.3C}$, —$NHC(O)NHNR^{102.3B}R^{102.3C}$, —$NHC(O)NR^{102.3B}R^{102.3C}$, —$N(O)_{m1}$, —$NR^{102.3B}R^{102.3C}$, —$C(O)R^{102.3D}$, —$C(O)OR^{102.3D}$, —$C(O)NR^{102.3B}R^{102.3C}$, —$OR^{102.3A}$, —$NR^{102.3B}SO_2R^{102.3A}$, —$NR^{102.3B}C(O)R^{102.3D}$, —$NR^{102.3B}C(O)OR^{102.3D}$, —$NR^{102.3B}OR^{102.3D}$, —$OCX^{102.3}_3$, —$OCHX^{102.3}_2$, $R^{104.3}$-substituted alkyl (e.g., $C_1$-$C_8$ alkyl, $C_1$-$C_6$ alkyl, or $C_1$-$C_4$ alkyl), $R^{104.3}$-substituted or unsubstituted heteroalkyl (e.g., 2 to 8 membered heteroalkyl, 2 to 6 membered heteroalkyl, or 2 to 4 membered heteroalkyl), $R^{104.3}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.3}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.3}$-substituted or unsubstituted aryl (e.g., $C_6$-$C_{10}$ aryl, $C_{10}$ aryl, or phenyl), or $R^{104.3}$-substituted or unsubstituted heteroaryl (e.g., 5 to 10 membered heteroaryl, 5 to 9 membered heteroaryl, or 5 to 6 membered heteroaryl).

In embodiments, $R^{102.3}$ is $R^{104.3}$-substituted or unsubstituted alkyl (e.g., $C_1$-$C_8$ alkyl, $C_1$-$C_6$ alkyl, or $C_1$-$C_4$ alkyl). In embodiments, $R^{102.3}$ is $R^{104.3}$-substituted alkyl (e.g., $C_1$-$C_8$ alkyl, $C_1$-$C_6$ alkyl, or $C_1$-$C_4$ alkyl). In embodiments, $R^{102.3}$ is an unsubstituted alkyl (e.g., $C_1$-$C_8$ alkyl, $C_1$-$C_6$ alkyl, or $C_1$-$C_4$ alkyl).

In embodiments, $R^{102.3}$ is $R^{104.3}$-substituted or unsubstituted heteroalkyl (e.g., 2 to 8 membered heteroalkyl, 2 to 6 membered heteroalkyl, or 2 to 4 membered heteroalkyl). In embodiments, $R^{102.3}$ is $R^{104.3}$-substituted heteroalkyl (e.g., 2 to 8 membered heteroalkyl, 2 to 6 membered heteroalkyl, or 2 to 4 membered heteroalkyl). In embodiments, $R^{102.3}$ is an unsubstituted heteroalkyl (e.g., 2 to 8 membered heteroalkyl, 2 to 6 membered heteroalkyl, or 2 to 4 membered heteroalkyl).

In embodiments, $R^{102.3}$ is $R^{104.3}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{102.3}$ is $R^{104.3}$-substituted cycloalkyl (e.g., $C_3$-$C_8$ cycloalkyl, $C_3$-$C_6$ cycloalkyl, or $C_5$-$C_6$ cycloalkyl). In embodiments, $R^{102.3}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{102.3}$ is $R^{104.3}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{102.3}$ is $R^{104.3}$-substituted heterocycloalkyl (e.g., 3 to 8 membered heterocycloalkyl, 3 to 6 membered heterocycloalkyl, or 5 to 6 membered heterocycloalkyl). In embodiments, $R^{102.3}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{102.3}$ is $R^{104.3}$-substituted or unsubstituted aryl (e.g., $C_6$-$C_{10}$ aryl, $C_{10}$ aryl, or phenyl). In embodiments, $R^{102.3}$ is $R^{104.3}$-substituted aryl (e.g., $C_6$-$C_{10}$ aryl, $C_{10}$ aryl, or phenyl). In embodiments, $R^{102.3}$ is an unsubstituted aryl (e.g., $C_6$-$C_{10}$ aryl, $C_{10}$ aryl, or phenyl).

In embodiments, $R^{102.3}$ is $R^{104.3}$-substituted or unsubstituted heteroaryl (e.g., 5 to 10 membered heteroaryl, 5 to 9 membered heteroaryl, or 5 to 6 membered heteroaryl). In embodiments, $R^{102.3}$ is $R^{104.3}$-substituted heteroaryl (e.g., 5 to 10 membered heteroaryl, 5 to 9 membered heteroaryl, or 5 to 6 membered heteroaryl). In embodiments, $R^{102.3}$ is an unsubstituted heteroaryl (e.g., 5 to 10 membered heteroaryl, 5 to 9 membered heteroaryl, or 5 to 6 membered heteroaryl).

In embodiments, $R^{102.3A}$, $R^{102.3B}$, $R^{102.3C}$ and $R^{102.3D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{102.3B}$ and $R^{102.3C}$ substituents bonded to the same nitrogen atom may optionally be joined to form a substituted or unsubstituted heterocycloalkyl or substituted or unsubstituted heteroaryl.

In embodiments, $R^{102.3A}$ is hydrogen, halogen, —$CF_3$, —$CCl_3$, —$CBr_3$, —$CI_3$, —COOH, —$CONH_2$, $R^{104.3A}$-substituted or unsubstituted alkyl (e.g., $C_1$-$C_8$ alkyl, $C_1$-$C_6$ alkyl, or $C_1$-$C_4$ alkyl), $R^{104.3A}$-substituted or unsubstituted heteroalkyl (e.g., 2 to 8 membered heteroalkyl, 2 to 6 membered heteroalkyl, or 2 to 4 membered heteroalkyl), $R^{104.3A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.3A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.3A}$-substituted or unsubstituted aryl (e.g., $C_6$-$C_{10}$ aryl, $C_{10}$ aryl, or phenyl), or $R^{104.3A}$-substituted or unsubstituted heteroaryl (e.g., 5 to 10 membered heteroaryl, 5 to 9 membered heteroaryl, or 5 to 6 membered heteroaryl).

In embodiments, $R^{102.3B}$ is hydrogen, halogen, —$CF_3$, —$CCl_3$, —$CBr_3$, —$CI_3$, —COOH, —$CONH_2$, $R^{104.3B}$-substituted or unsubstituted alkyl (e.g., $C_1$-$C_8$ alkyl, $C_1$-$C_6$ alkyl, or $C_1$-$C_4$ alkyl), $R^{104.3B}$-substituted or unsubstituted heteroalkyl (e.g., 2 to 8 membered heteroalkyl, 2 to 6 membered heteroalkyl, or 2 to 4 membered heteroalkyl), $R^{104.3B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.3B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.3B}$-substituted or unsubstituted aryl (e.g., $C_6$-$C_{10}$ aryl, $C_{10}$ aryl, or phenyl), or $R^{104.3B}$-substituted or unsubstituted heteroaryl (e.g., 5 to 10 membered heteroaryl, 5 to 9 membered heteroaryl, or 5 to 6 membered heteroaryl). In embodiments, $R^{102.3B}$ and $R^{102.3C}$ substituents bonded to the same nitrogen atom may optionally be joined to form a $R^{104.3B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{104.3B}$-substituted or unsubstituted heteroaryl (e.g., 5 to 10 membered heteroaryl, 5 to 9 membered heteroaryl, or 5 to 6 membered heteroaryl).

In embodiments, $R^{102.3C}$ is hydrogen, halogen, —$CF_3$, —$CCl_3$, —$CBr_3$, —$CI_3$, —COOH, —$CONH_2$, $R^{104.3C}$-substituted or unsubstituted alkyl (e.g., $C_1$-$C_8$ alkyl, $C_1$-$C_6$ alkyl, or $C_1$-$C_4$ alkyl), $R^{104.3C}$-substituted or unsubstituted heteroalkyl (e.g., 2 to 8 membered heteroalkyl, 2 to 6 membered heteroalkyl, or 2 to 4 membered heteroalkyl), $R^{104.3C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.3C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.3C}$-substituted or unsubstituted aryl (e.g., $C_6$-$C_{10}$ aryl, $C_{10}$ aryl, or phenyl), or $R^{104.3C}$-substituted or unsubstituted heteroaryl (e.g., 5 to 10 membered heteroaryl, 5 to 9 membered heteroaryl, or 5 to 6 membered heteroaryl). In embodiments, $R^{102.3B}$ and $R^{102.3C}$ substituents bonded to the same nitrogen atom may optionally be joined to form a $R^{104.3C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{104.3C}$-substituted or unsubstituted heteroaryl (e.g., 5 to 10 membered heteroaryl, 5 to 9 membered heteroaryl, or 5 to 6 membered heteroaryl).

In embodiments, $R^{102.3D}$ is hydrogen, halogen, —$CF_3$, —$CCl_3$, —$CBr_3$, —$CI_3$, —COOH, —$CONH_2$, $R^{104.3D}$-substituted or unsubstituted alkyl (e.g., $C_1$-$C_8$ alkyl, $C_1$-$C_6$ alkyl, or $C_1$-$C_4$ alkyl), $R^{104.3D}$-substituted or unsubstituted heteroalkyl (e.g., 2 to 8 membered heteroalkyl, 2 to 6 membered heteroalkyl, or 2 to 4 membered heteroalkyl), $R^{104.3D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.3D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.3D}$-substituted or unsubstituted aryl (e.g., $C_6$-$C_{10}$ aryl, $C_{10}$ aryl, or phenyl), or $R^{104.3D}$-substituted or unsubstituted heteroaryl (e.g., 5 to 10 membered heteroaryl, 5 to 9 membered heteroaryl, or 5 to 6 membered heteroaryl).

$R^{104.3}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —OCHF 2, $R^{105.3}$-substituted or unsubstituted alkyl (e.g., $C_1$-$C_8$ alkyl, $C_1$-$C_6$ alkyl, or $C_1$-$C_4$ alkyl), $R^{105.3}$-substituted or unsubstituted heteroalkyl (e.g., 2 to 8 membered heteroalkyl, 2 to 6 membered heteroalkyl, or 2 to 4 membered heteroalkyl), $R^{105.3}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{105.3}$-substituted or unsubstituted heterocycloalkyl (e.g., 3 to 8 membered heterocycloalkyl, 3 to 6 membered heterocycloalkyl, or 5 to 6 membered heterocycloalkyl), $R^{105.3}$-substituted or unsubstituted aryl (e.g., $C_6$-$C_{10}$ aryl, $C_{10}$ aryl, or phenyl), or $R^{105.3}$-substituted or unsubstituted heteroaryl (e.g., 5 to 10 membered heteroaryl, 5 to 9 membered heteroaryl, or 5 to 6 membered heteroaryl).

In embodiments, $R^{104.3}$ is $R^{105.3}$-substituted or unsubstituted alkyl (e.g., $C_1$-$C_8$ alkyl, $C_1$-$C_6$ alkyl, or $C_1$-$C_4$ alkyl). In embodiments, $R^{104.3}$ is $R^{105.3}$-substituted alkyl (e.g., $C_1$-$C_8$ alkyl, $C_1$-$C_6$ alkyl, or $C_1$-$C_4$ alkyl). In embodiments, $R^{104.3}$ is an unsubstituted alkyl (e.g., $C_1$-$C_8$ alkyl, $C_1$-$C_6$ alkyl, or $C_1$-$C_4$ alkyl).

In embodiments, $R^{104.3}$ is $R^{105.3}$-substituted or unsubstituted heteroalkyl (e.g., 2 to 8 membered heteroalkyl, 2 to 6 membered heteroalkyl, or 2 to 4 membered heteroalkyl). In embodiments, $R^{104.3}$ is $R^{105.3}$-substituted heteroalkyl (e.g., 2 to 8 membered heteroalkyl, 2 to 6 membered heteroalkyl, or 2 to 4 membered heteroalkyl). In embodiments, $R^{104.3}$ is an unsubstituted heteroalkyl (e.g., 2 to 8 membered heteroalkyl, 2 to 6 membered heteroalkyl, or 2 to 4 membered heteroalkyl).

In embodiments, $R^{104.3}$ is $R^{105.3}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{104.3}$ is $R^{105.3}$ substituted cycloalkyl (e.g., $C_3$-$C_8$ cycloalkyl, $C_3$-$C_6$ cycloalkyl, or $C_5$-$C_6$ cycloalkyl). In embodiments, $R^{104.3}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{104.3}$ is $R^{105.3}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{104.3}$ is $R^{105.3}$-substituted heterocycloalkyl (e.g., 3 to 8 membered heterocycloalkyl, 3 to 6 membered heterocycloalkyl, or 5 to 6 membered heterocycloalkyl). In embodiments, $R^{104.3}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{104.3}$ is $R^{105.3}$-substituted or unsubstituted aryl (e.g., $C_6$-$C_{10}$ aryl, $C_{10}$ aryl, or phenyl). In embodiments, $R^{104.3}$ is $R^{105.3}$-substituted aryl (e.g., $C_6$-$C_{10}$ aryl, $C_{10}$ aryl, or phenyl). In embodiments, $R^{104.3}$ is an unsubstituted aryl (e.g., $C_{6-10}$ aryl, C aryl, or phenyl).

In embodiments, $R^{104.3}$ is $R^{105.3}$-substituted or unsubstituted heteroaryl (e.g., 5 to 10 membered heteroaryl, 5 to 9 membered heteroaryl, or 5 to 6 membered heteroaryl). In embodiments, $R^{104.3}$ is $R^{105.3}$-substituted heteroaryl (e.g., 5 to 10 membered heteroaryl, 5 to 9 membered heteroaryl, or 5 to 6 membered heteroaryl). In embodiments, $R^{104.3}$ is an unsubstituted heteroaryl (e.g., 5 to 10 membered heteroaryl, 5 to 9 membered heteroaryl, or 5 to 6 membered heteroaryl).

$R^{105.3}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —OCHF 2, $R^{106.3}$-substituted or unsubstituted alkyl (e.g., $C_1$-$C_8$ alkyl, $C_1$-$C_6$ alkyl, or $C_1$-$C_4$ alkyl), $R^{106.3}$-substituted or unsubstituted heteroalkyl (e.g., 2 to 8 membered heteroalkyl, 2 to 6 membered heteroalkyl, or 2 to 4 membered heteroalkyl), $R^{106.3}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{106.3}$-substituted or unsubstituted heterocycloalkyl (e.g., 3 to 8 membered heterocycloalkyl, 3 to 6 membered heterocycloalkyl, or 5 to 6 membered heterocycloalkyl), $R^{106.3}$-substituted or unsubstituted aryl (e.g., $C_6$-$C_{10}$ aryl, $C_{10}$ aryl, or phenyl), or $R^{106.3}$-substituted or unsubstituted heteroaryl (e.g., 5 to 10 membered heteroaryl, 5 to 9 membered heteroaryl, or 5 to 6 membered heteroaryl).

In embodiments, $R^{105.3}$ is $R^{106.3}$-substituted or unsubstituted alkyl (e.g., $C_1$-$C_8$ alkyl, $C_1$-$C_6$ alkyl, or $C_1$-$C_4$ alkyl). In embodiments, $R^{105.3}$ is $R^{106.3}$-Substituted alkyl (e.g., $C_1$-$C_8$ alkyl, $C_1$-$C_6$ alkyl, or $C_1$-$C_4$ alkyl). In embodiments, $R^{105.3}$ is an unsubstituted alkyl (e.g., $C_1$-$C_8$ alkyl, $C_1$-$C_6$ alkyl, or $C_1$-$C_4$ alkyl).

In embodiments, $R^{105.3}$ is $R^{106.3}$-substituted or unsubstituted heteroalkyl (e.g., 2 to 8 membered heteroalkyl, 2 to 6 membered heteroalkyl, or 2 to 4 membered heteroalkyl). In embodiments, $R^{105.3}$ is $R^{106.3}$-substituted heteroalkyl (e.g., 2 to 8 membered heteroalkyl, 2 to 6 membered heteroalkyl, or 2 to 4 membered heteroalkyl). In embodiments, $R^{105.3}$ is an unsubstituted heteroalkyl (e.g., 2 to 8 membered heteroalkyl, 2 to 6 membered heteroalkyl, or 2 to 4 membered heteroalkyl).

In embodiments, $R^{105.3}$ is $R^{106.3}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{105.3}$ is $R^{106.3}$-substituted cycloalkyl (e.g., $C_3$-$C_8$ cycloalkyl, $C_3$-$C_6$ cycloalkyl, or $C_5$-$C_6$ cycloalkyl). In embodiments, $R^{105.3}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{105.3}$ is $R^{106.3}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{105.3}$ is $R^{106.3}$-substituted heterocycloalkyl (e.g., 3 to 8 membered heterocycloalkyl, 3 to 6 membered heterocycloalkyl, or 5 to 6 membered heterocycloalkyl). In embodiments, $R^{105.3}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{105.3}$ is $R^{106.3}$-substituted or unsubstituted aryl (e.g., $C_6$-$C_{10}$ aryl, $C_{10}$ aryl, or phenyl). In embodiments, $R^{105.3}$ is $R^{106.3}$-substituted aryl (e.g., $C_6$-$C_{10}$ aryl, $C_{10}$ aryl, or phenyl). In embodiments, $R^{105.3}$ is an unsubstituted aryl (e.g., $C_6$-$C_{10}$ aryl, $C_{10}$ aryl, or phenyl).

In embodiments, $R^{105.3}$ is $R^{106.3}$-substituted or unsubstituted heteroaryl (e.g., 5 to 10 membered heteroaryl, 5 to 9 membered heteroaryl, or 5 to 6 membered heteroaryl). In embodiments, $R^{105.3}$ is $R^{106.3}$-substituted heteroaryl (e.g., 5 to 10 membered heteroaryl, 5 to 9 membered heteroaryl, or 5 to 6 membered heteroaryl). In embodiments, $R^{105.3}$ is an unsubstituted heteroaryl (e.g., 5 to 10 membered heteroaryl, 5 to 9 membered heteroaryl, or 5 to 6 membered heteroaryl).

In aspects provided herein, there are compounds having structural Formula (VII):

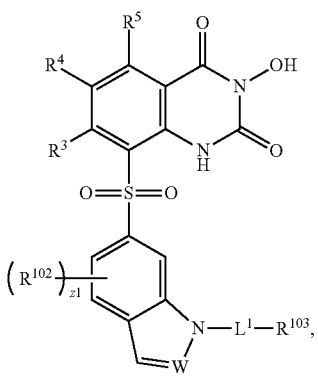

(VII)

or a pharmaceutically acceptable salt thereof. z1, $R^3$, $R^4$ and $R^{102}$ are as defined herein, including embodiments. W is independently $CR^{102.4}$ or N. $L^1$ is a bond, substituted or unsubstituted alkylene or substituted or unsubstituted heteroalkylene, substituted or unsubstituted cycloalkylene or substituted or unsubstituted heterocycloalkylene, substituted or unsubstituted arylene or substituted or unsubstituted heteroarylene. $R^{102}$ is hydrogen, halogen, $-CX^{102}_3$, $-CHX^{102}_2$, $-CH_2X^{102}$, $-CN$, $-SO_{n102}R^{102B}$, $-SO_{v102}NR^{102A}R^{102B}$, $-NHC(O)NR^{102A}R^{102B}$, $-N(O)_{m102}$, $-NR^{102A}R^{102B}$, $-C(O)R^{102C}$, $-C(O)-OR^{102C}$, $-C(O)NR^{102A}R^{102B}$, $-OR^{102D}$, $-NR^{102A}SO_2R^{102D}$, $-NR^{102A}C(O)R^{102C}$, $-NR^{102A}C(O)OR^{102C}$, $-NR^{102A}OR^{102C}$, $-OCX^{102}_3$, $-OCHX^{102}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102B}$ and $R^{102C}$ substituents bonded to the same nitrogen atom may optionally be joined to form a substituted or unsubstituted heterocycloalkyl or substituted or unsubstituted heteroaryl. $R^{102.4}$ is hydrogen, halogen, $-CX^{102.4}_3$, $-CHX^{102.4}_2$, $-CH_2X^{102.4}$, $-CN$, $-SO_{n102.4}R^{102.4D}$, $-SO_{v102.4}NR^{102.4A}R^{102.4B}$, $-NHC(O)NR^{102.4A}R^{102.4B}$, $-N(O)_{m102.4}$, $-NR^{102.4A}R^{102.4B}$, $-C(O)R^{102.4C}$, $-C(O)OR^{102.4C}$, $-C(O)NR^{102.4A}R^{102.4B}$, $-OR^{102.4D}$, $-NR^{102.4A}SO_2R^{102.4D}$, $-NR^{102.4A}C(O)R^{102.4C}$, $-NR^{102.4A}C(O)OR^{102.4C}$, $-NR^{102.4A}OR^{102.4C}$, $-OCX^{102.4}_3$, $-OCHX^{102.4}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.4B}$ and $R^{102.4C}$ substituents bonded to the same nitrogen atom may optionally be joined to form a substituted or unsubstituted heterocycloalkyl or substituted or unsubstituted heteroaryl. $R^{103}$ is hydrogen, halogen, $-CX^{103}_3$, $-CHX^{103}_2$, $-CH_2X^{103}$, $-CN$, $-SO_{n103}R^{103D}$, $-SO_{v103}NR^{103A}R^{103B}$, $-NHC(O)NR^{103A}R^{103B}$, $-N(O)_{m103}$, $-NR^{103A}R^{103B}$, $-C(O)R^{103C}$, $-C(O)-OR^{103C}$, $-C(O)NR^{103A}R^{103B}$, $-OR^{103D}$, $-NR^{103A}SO_2R^{103D}$, $-NR^{103A}C(O)R^{103C}$, $-NR^{103A}C(O)OR^{103C}$, $-NR^{103A}OR^{103C}$, $-OCX^{103}_3$, $-OCHX^{103}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{103B}$ and $R^{103C}$ substituents bonded to the same nitrogen atom may optionally be joined to form a substituted or unsubstituted heterocycloalkyl or substituted or unsubstituted heteroaryl. $R^{102A}$, $R^{102B}$, $R^{102C}$, $R^{102D}$, $R^{102.4A}$, $R^{102.4B}$, $R^{102.4C}$, $R^{102.4D}$, $-R^{103A}$, $R^{103B}$, $R^{103C}$ and $R^{103D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102B}$ and $R^{102C}$, $R^{102.4B}$ and $R^{102.4C}$ and $R^{103B}$ and $R^{103C}$ and substituents bonded to the same nitrogen atom may optionally be joined to form a substituted or unsubstituted heterocycloalkyl or substituted or unsubstituted heteroaryl. $X^{102.4}$, $X^{102.4}$ and $X^{103}$ are independently $-F$, $-Cl$, $-Br$, or $-I$. The symbols m102.4 and m103 are independently an integer from 1 to 2. The symbols n102.4 and n103 are independently an integer from 0 to 3. The symbols v102.4 and v103 are independently an integer from 1 to 2.

In embodiments, m102.4 is 1. In embodiments, m102.4 is 2. In embodiments, m103 is 1. In embodiments, m103 is 2. In embodiments, n102.4 is 0. In embodiments, n102.4 is 1. In embodiments, n102.4 is 2. In embodiments, n102.4 is 3. In embodiments, n103 is 0. In embodiments, n103 is 1. In embodiments, n103 is 2. In embodiments, n103 is 3. In embodiments, v102.4 is 1. In embodiments, v102.4 is 2. In embodiments, v103 is 1. In embodiments, v103 is 2. In embodiments, W is N. In embodiments, W is CH.

In embodiments, $L^1$ is substituted or unsubstituted alkylene. In embodiments, $L^1$ is substituted or unsubstituted heteroalkylene. In embodiments, $L^1$ is a bond. $L^1$ is substituted or unsubstituted cycloalkylene. In embodiments, $L^1$ is substituted or unsubstituted heterocycloalkylene. $L^1$ is substituted or unsubstituted arylene. In embodiments, $L^1$ is substituted or unsubstituted heteroarylene.

In embodiments, $L^1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^1$ is a bond, substituted or unsubstituted alkylene (e.g., $C_1$-$C_8$ alkylene, $C_1$-$C_6$ alkylene, or $C_1$-$C_4$ alkylene), substituted or unsubstituted heteroalkylene (e.g., 2 to 8 membered heteroalkylene, 2 to 6 membered heteroalkylene, or 2 to 4 membered heteroalkylene), substituted or unsubstituted cycloalkylene (e.g., $C_3$-$C_8$ cycloalkylene, $C_3$-$C_6$ cycloalkylene, or $C_5$-$C_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., $C_6$-$C_{10}$ arylene, $C_{10}$ arylene, or phenylene), or substituted or unsubstituted heteroarylene (e.g., 5 to 10 membered heteroarylene, 5 to 9 membered heteroarylene, or 5 to 6 membered heteroarylene).

In embodiments, $L^1$ is a bond, $R^{114}$-substituted or unsubstituted alkylene (e.g., $C_1$-$C_8$ alkylene, $C_1$-$C_6$ alkylene, or $C_1$-$C_4$ alkylene), $R^{114}$-substituted or unsubstituted heteroalkylene (e.g., 2 to 8 membered heteroalkylene, 2 to 6 membered heteroalkylene, or 2 to 4 membered heteroalkylene), $R^{114}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{114}$-substituted or unsubstituted heterocycloalkylene (e.g., 3 to 8 membered heterocycloalkylene, 3 to 6 membered heterocycloalkylene, or 5 to 6 membered heterocycloalkylene), $R^{114}$-substituted or unsubstituted arylene (e.g., $C_6$-$C_{10}$ arylene, $C_{10}$ arylene, or phenylene), or $R^{114}$-substituted or unsubstituted heteroarylene (e.g., 5 to 10 membered heteroarylene, 5 to 9 membered heteroarylene, or 5 to 6 membered heteroarylene).

In embodiments, $L^1$ is $R^{114}$-substituted or unsubstituted alkylene (e.g., $C_1$-$C_8$ alkylene, $C_1$-$C_6$ alkylene, or $C_1$-$C_4$ alkylene). In embodiments, $L^1$ is $R^{114}$-substituted alkylene (e.g., $C_1$-$C_8$ alkylene, $C_1$-$C_6$ alkylene, or $C_1$-$C_4$ alkylene). In embodiments, $L^1$ is an unsubstituted alkylene (e.g., $C_1$-$C_8$ alkylene, $C_1$-$C_6$ alkylene, or $C_1$-$C_4$ alkylene).

In embodiments, $L^1$ is $R^{114}$-substituted or unsubstituted heteroalkylene (e.g., 2 to 8 membered heteroalkylene, 2 to 6 membered heteroalkylene, or 2 to 4 membered heteroalkylene).

In embodiments, $L^1$ is $R^{114}$-substituted heteroalkylene (e.g., 2 to 8 membered heteroalkylene, 2 to 6 membered heteroalkylene, or 2 to 4 membered heteroalkylene). In embodiments, $L^1$ is an unsubstituted heteroalkylene (e.g., 2 to 8 membered heteroalkylene, 2 to 6 membered heteroalkylene, or 2 to 4 membered heteroalkylene).

In embodiments, $L^1$ is $R^{114}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^1$ is $R^{114}$-substituted cycloalkylene (e.g., $C_3$-$C_8$ cycloalkylene, $C_3$-$C_6$ cycloalkylene, or $C_5$-$C_6$ cycloalkylene). In embodiments, $L^1$ is an unsubstituted cycloalkylene (e.g., $C_3$-$C_8$ cycloalkylene, $C_3$-$C_6$ cycloalkylene, or $C_5$-$C_6$ cycloalkylene).

In embodiments, $L^1$ is $R^{114}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, L is $R^{114}$-substituted heterocycloalkylene (e.g., 3 to 8 membered heterocycloalkylene, 3 to 6 membered heterocycloalkylene, or 5 to 6 membered heterocycloalkylene). In embodiments, $L^1$ is an unsubstituted heterocycloalkylene (e.g., 3 to 8 membered heterocycloalkylene, 3 to 6 membered heterocycloalkylene, or 5 to 6 membered heterocycloalkylene).

In embodiments, $L^1$ is $R^{114}$-substituted or unsubstituted arylene (e.g., $C_6$-$C_{10}$ arylene, $C_{10}$ arylene, or phenylene). In embodiments, $L^1$ is $R^{114}$-substituted arylene (e.g., $C_6$-$C_{10}$ arylene, $C_{10}$ arylene, or phenylene). In embodiments, $L^1$ is an unsubstituted arylene (e.g., $C_6$-$C_{10}$ arylene, $C_{10}$ arylene, or phenylene).

In embodiments, $L^1$ is $R^{114}$-substituted or unsubstituted heteroarylene (e.g., 5 to 10 membered heteroarylene, 5 to 9 membered heteroarylene, or 5 to 6 membered heteroarylene). In embodiments, $L^1$ is $R^{114}$-substituted heteroarylene (e.g., 5 to 10 membered heteroarylene, 5 to 9 membered heteroarylene, or 5 to 6 membered heteroarylene). In embodiments, L is an unsubstituted heteroarylene (e.g., 5 to 10 membered heteroarylene, 5 to 9 membered heteroarylene, or 5 to 6 membered heteroarylene).

In embodiments, $R^{102.4}$ is hydrogen, halogen, —$CX^{102.4}_3$, —$CHX^{102.4}_2$, —$CH_2X^{102.4}$, —CN, —$SO_{n1}R^{102.4A}$, —$SO_{v1}NR^{102.4B}R^{102.4C}$, —$NHNR^{102.4B}R^{102.4C}$, —$ONR^{102.4B}R^{102.4C}$, —$NHC(O)NHNR^{102.4B}R^{102.4C}$, —$NHC(O)NR^{102.4B}R^{102.4C}$, —$N(O)_{m1}$, —$NR^{102.4B}R^{102.4C}$, —$C(O)R^{102.4D}$, —$C(O)OR^{102.4D}$, —$C(O)NR^{102.4B}R^{102.4C}$, —$OR^{102.4A}$, —$NR^{102.4B}SO_2R^{102.4A}$, —$NR^{102.4B}C(O)R^{102.4D}$, —$NR^{102.4B}C(O)OR^{102.4D}$, —$NR^{102.4B}OR^{102.4D}$, —$OCX^{102.4}_3$, —$OCHX^{102.4}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{102.4}$ is halogen, —$CX^{102.4}_3$, —$CHX^{102.4}_2$, —$CH_2X^{102.4}$, —CN, —$SO_{n1}R^{102.4A}$, —$SO_{v1}NR^{02.4B}R^{102.4C}$, —$NHNR^{102.4B}R^{102.4C}$, —$ONR^{102.4B}R^{102.4C}$, —$NHC(O)NHNR^{102.4B}R^{102.4C}$, —$NHC(O)NR^{102.4B}R^{102.4C}$, —$N(O)_{m1}$, —$NR^{102.4B}R^{102.4C}$, —$C(O)R^{102.4D}$, —$C(O)OR^{102.4D}$, —$C(O)NR^{102.4B}R^{102.4C}$, —$OR^{102.4A}$, —$NR^{102.4B}SO_2R^{102.4A}$, —$NR^{102.4B}C(O)R^{102.4D}$, —$NR^{102.4B}C(O)OR^{102.4D}$, —$NR^{102.4B}OR^{102.4D}$, —$OCX^{102.4}_3$, —$OCHX^{102.4}_2$, $R^{104.4}$-substituted or unsubstituted alkyl (e.g., $C_1$-$C_8$ alkyl, $C_1$-$C_6$ alkyl, or $C_1$-$C_4$ alkyl), $R^{104.4}$-substituted or unsubstituted heteroalkyl (e.g., 2 to 8 membered heteroalkyl, 2 to 6 membered heteroalkyl, or 2 to 4 membered heteroalkyl), $R^{104.4}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.4}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.4}$-substituted or unsubstituted aryl (e.g., $C_6$-$C_{10}$ aryl, $C_{10}$ aryl, or phenyl), or $R^{104.4}$-substituted or unsubstituted heteroaryl (e.g., 5 to 10 membered heteroaryl, 5 to 9 membered heteroaryl, or 5 to 6 membered heteroaryl).

In embodiments, $R^{102.4}$ is $R^{104.4}$-substituted or unsubstituted alkyl (e.g., $C_1$-$C_8$ alkyl, $C_1$-$C_6$ alkyl, or $C_1$-$C_4$ alkyl). In embodiments, $R^{102.4}$ is $R^{104.4}$-substituted alkyl (e.g., $C_1$-$C_8$ alkyl, $C_1$-$C_6$ alkyl, or $C_1$-$C_4$ alkyl). In embodiments, $R^{102.4}$ is an unsubstituted alkyl (e.g., $C_1$-$C_5$ alkyl, $C_1$-$C_6$ alkyl, or $C_1$-$C_4$ alkyl).

In embodiments, $R^{102.4}$ is $R^{104.4}$-substituted or unsubstituted heteroalkyl (e.g., 2 to 8 membered heteroalkyl, 2 to 6 membered heteroalkyl, or 2 to 4 membered heteroalkyl). In embodiments, $R^{102.4}$ is $R^{104.4}$-substituted heteroalkyl (e.g., 2 to 8 membered heteroalkyl, 2 to 6 membered heteroalkyl, or 2 to 4 membered heteroalkyl). In embodiments, $R^{102.4}$ is an unsubstituted heteroalkyl (e.g., 2 to 8 membered heteroalkyl, 2 to 6 membered heteroalkyl, or 2 to 4 membered heteroalkyl).

In embodiments, $R^{102.4}$ is $R^{104.4}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{102.4}$ is $R^{104.4}$-substituted cycloalkyl (e.g., $C_3$-$C_8$ cycloalkyl, $C_3$-$C_6$ cycloalkyl, or $C_5$-$C_6$ cycloalkyl). In embodiments, $R^{102.4}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{102.4}$ is $R^{104.4}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{102.4}$ is $R^{104.4}$-substituted heterocycloalkyl (e.g., 3 to 8 membered heterocycloalkyl, 3 to 6 membered heterocycloalkyl, or 5 to 6 membered heterocycloalkyl). In embodiments, $R^{102.4}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{102.4}$ is $R^{104.4}$-substituted or unsubstituted aryl (e.g., $C_6$-$C_{10}$ aryl, $C_{10}$ aryl, or phenyl). In embodiments, $R^{102.4}$ is $R^{104.4}$-substituted aryl (e.g., $C_6$-$C_{10}$ aryl, $C_{10}$ aryl, or phenyl). In embodiments, $R^{102.4}$ is an unsubstituted aryl (e.g., $C_6$-$C_{10}$ aryl, $C_{10}$ aryl, or phenyl).

In embodiments, $R^{102.4}$ is $R^{104.4}$-substituted or unsubstituted heteroaryl (e.g., 5 to 10 membered heteroaryl, 5 to 9 membered heteroaryl, or 5 to 6 membered heteroaryl). In embodiments, $R^{102.4}$ is $R^{104.4}$-substituted heteroaryl (e.g., 5 to 10 membered heteroaryl, 5 to 9 membered heteroaryl, or 5 to 6 membered heteroaryl). In embodiments, $R^{102.4}$ is an unsubstituted heteroaryl (e.g., 5 to 10 membered heteroaryl, 5 to 9 membered heteroaryl, or 5 to 6 membered heteroaryl).

In embodiments, $R^{102.4A}$, $R^{102.4B}$, $R^{102.4C}$ and $R^{102.4D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{102.4B}$ and $R^{102.4C}$ substituents bonded to the same nitrogen atom may optionally be joined to form a substituted or unsubstituted heterocycloalkyl or substituted or unsubstituted heteroaryl.

In embodiments, $R^{102.4A}$ is hydrogen, halogen, —$CF_3$, —$CCl_3$, —$CBr_3$, —$CI_3$, —COOH, —$CONH_2$, $R^{104.4A}$-substituted or unsubstituted alkyl (e.g., $C_1$-$C_8$ alkyl, $C_1$-$C_6$ alkyl, or $C_1$-$C_4$ alkyl), $R^{104.4A}$-substituted or unsubstituted heteroalkyl (e.g., 2 to 8 membered heteroalkyl, 2 to 6 membered heteroalkyl, or 2 to 4 membered heteroalkyl), $R^{104.4A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.4A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.4A}$-substituted or unsubstituted aryl (e.g., $C_6$-$C_{10}$ aryl, $C_{10}$ aryl, or phenyl), or $R^{104.4A}$-substituted or unsubstituted heteroaryl (e.g., 5 to 10 membered heteroaryl, 5 to 9 membered heteroaryl, or 5 to 6 membered heteroaryl).

In embodiments, $R^{102.4B}$ is hydrogen, halogen, —$CF_3$, —$CCl_3$, —$CBr_3$, —$CI_3$, —COOH, —$CONH_2$, $R^{104.4B}$-substituted or unsubstituted alkyl (e.g., $C_1$-$C_8$ alkyl, $C_1$-$C_6$ alkyl, or $C_1$-$C_4$ alkyl), $R^{104.4B}$-substituted or unsubstituted heteroalkyl (e.g., 2 to 8 membered heteroalkyl, 2 to 6 membered heteroalkyl, or 2 to 4 membered heteroalkyl), $R^{104.4B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.4B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.4B}$-substituted or unsubstituted aryl (e.g., $C_6$-$C_{10}$ aryl, $C_{10}$ aryl, or phenyl), or $R^{104.4B}$-substituted or unsubstituted heteroaryl (e.g., 5 to 10 membered heteroaryl, 5 to 9 membered heteroaryl, or 5 to 6 membered heteroaryl). In embodiments, $R^{102.4B}$ and $R^{102.4C}$ substituents bonded to the same nitrogen atom may optionally be joined to form a $R^{104.4B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{104.4B}$-substituted or unsubstituted heteroaryl (e.g., 5 to 10 membered heteroaryl, 5 to 9 membered heteroaryl, or 5 to 6 membered heteroaryl).

In embodiments, $R^{102.4C}$ is hydrogen, halogen, —$CF_3$, —$CCl_3$, —$CBr_3$, —$CI_3$, —COOH, —$CONH_2$, $R^{104.4C}$-substituted or unsubstituted alkyl (e.g., $C_1$-$C_8$ alkyl, $C_1$-$C_6$ alkyl, or $C_1$-$C_4$ alkyl), $R^{104.4C}$-substituted or unsubstituted heteroalkyl (e.g., 2 to 8 membered heteroalkyl, 2 to 6 membered heteroalkyl, or 2 to 4 membered heteroalkyl), $R^{104.4C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.4C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.4C}$-substituted or unsubstituted aryl (e.g., $C_6$-$C_{10}$ aryl, $C_{10}$ aryl, or phenyl), or $R^{104.4C}$-substituted or unsubstituted heteroaryl (e.g., 5 to 10 membered heteroaryl, 5 to 9 membered heteroaryl, or 5 to 6 membered heteroaryl). In embodiments, $R^{102.4B}$ and $R^{102.4C}$ substituents bonded to the same nitrogen atom may optionally be joined to form a $R^{104.4C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{104.4C}$-substituted or unsubstituted heteroaryl (e.g., 5 to 10 membered heteroaryl, 5 to 9 membered heteroaryl, or 5 to 6 membered heteroaryl).

In embodiments, $R^{102.4D}$ is hydrogen, halogen, —$CF_3$, —$CCl_3$, —$CBr_3$, —$CI_3$, —COOH, —$CONH_2$, $R^{104.4D}$-substituted or unsubstituted alkyl (e.g., $C_1$-$C_8$ alkyl, $C_1$-$C_6$ alkyl, or $C_1$-$C_4$ alkyl), $R^{104.4D}$-substituted or unsubstituted heteroalkyl (e.g., 2 to 8 membered heteroalkyl, 2 to 6 membered heteroalkyl, or 2 to 4 membered heteroalkyl), $R^{104.4D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{104.4D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{104.4D}$-substituted or unsubstituted aryl (e.g., $C_6$-$C_{10}$ aryl, $C_{10}$ aryl, or phenyl), or $R^{104.4D}$-substituted or unsubstituted heteroaryl (e.g., 5 to 10 membered heteroaryl, 5 to 9 membered heteroaryl, or 5 to 6 membered heteroaryl).

$R^{104.4}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{105.4}$-substituted or unsubstituted alkyl (e.g., $C_1$-$C_8$ alkyl, $C_1$-$C_6$ alkyl, or $C_1$-$C_4$ alkyl), $R^{105.4}$-substituted or unsubstituted heteroalkyl (e.g., 2 to 8 membered heteroalkyl, 2 to 6 membered heteroalkyl, or 2 to 4 membered heteroalkyl), $R^{105.4}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{105.4}$-substituted or unsubstituted heterocycloalkyl (e.g., 3 to 8 membered heterocycloalkyl, 3 to 6 membered heterocycloalkyl, or 5 to 6 membered heterocycloalkyl), $R^{105.4}$-substituted or unsubstituted aryl (e.g., $C_6$-$C_{10}$ aryl, $C_{10}$ aryl, or phenyl), or $R^{105.4}$-substituted or unsubstituted heteroaryl (e.g., 5 to 10 membered heteroaryl, 5 to 9 membered heteroaryl, or 5 to 6 membered heteroaryl).

In embodiments, $R^{104.4}$ is $R^{105.4}$-substituted or unsubstituted alkyl (e.g., $C_1$-$C_8$ alkyl, $C_1$-$C_6$ alkyl, or $C_1$-$C_4$ alkyl). In embodiments, $R^{104.4}$ is $R^{105.4}$-substituted alkyl (e.g., $C_1$-$C_8$ alkyl, $C_1$-$C_6$ alkyl, or $C_1$-$C_4$ alkyl). In embodiments, $R^{104.4}$ is an unsubstituted alkyl (e.g., $C_1$-$C_5$ alkyl, $C_1$-$C_6$ alkyl, or $C_1$-$C_4$ alkyl).

In embodiments, $R^{104.4}$ is $R^{104.4}$-substituted or unsubstituted heteroalkyl (e.g., 2 to 8 membered heteroalkyl, 2 to 6 membered heteroalkyl, or 2 to 4 membered heteroalkyl). In embodiments, $R^{104.4}$ is $R^{105.4}$-substituted heteroalkyl (e.g., 2 to 8 membered heteroalkyl, 2 to 6 membered heteroalkyl, or 2 to 4 membered heteroalkyl). In embodiments, $R^{104.4}$ is an unsubstituted heteroalkyl (e.g., 2 to 8 membered heteroalkyl, 2 to 6 membered heteroalkyl, or 2 to 4 membered heteroalkyl).

In embodiments, $R^{104.4}$ is $R^{105.4}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{104.4}$ is $R^{105.4}$-substituted cycloalkyl (e.g., $C_3$-$C_8$ cycloalkyl, $C_3$-$C_6$ cycloalkyl, or $C_5$-$C_6$ cycloalkyl). In embodiments, $R^{104.4}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{104.4}$ is $R^{105.4}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{104.4}$ is $R^{105.4}$-substituted heterocycloalkyl (e.g., 3 to 8 membered heterocycloalkyl, 3 to 6 membered heterocycloalkyl, or 5 to 6 membered heterocycloalkyl). In embodiments, $R^{104.4}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{104.4}$ is $R^{105.4}$-substituted or unsubstituted aryl (e.g., $C_6$-$C_{10}$ aryl, $C_{10}$ aryl, or phenyl). In embodiments, $R^{104.4}$ is $R^{105.4}$-substituted aryl (e.g., $C_6$-$C_{10}$ aryl, $C_{10}$ aryl, or phenyl). In embodiments, $R^{104.4}$ is an unsubstituted aryl (e.g., $C_6$-$C_{10}$ aryl, $C_{10}$ aryl, or phenyl).

In embodiments, $R^{104.4}$ is $R^{105.4}$-substituted or unsubstituted heteroaryl (e.g., 5 to 10 membered heteroaryl, 5 to 9 membered heteroaryl, or 5 to 6 membered heteroaryl). In embodiments, $R^{104.4}$ is $R^{105.4}$-substituted heteroaryl (e.g., 5 to 10 membered heteroaryl, 5 to 9 membered heteroaryl, or 5 to 6 membered heteroaryl). In embodiments, $R^{104.4}$ is an unsubstituted heteroaryl (e.g., 5 to 10 membered heteroaryl, 5 to 9 membered heteroaryl, or 5 to 6 membered heteroaryl).

$R^{105.4}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{106.4}$-substituted or unsubstituted alkyl (e.g., $C_1$-$C_8$ alkyl, $C_1$-$C_6$ alkyl, or $C_1$-$C_4$ alkyl), $R^{106.4}$-substituted or unsubstituted heteroalkyl (e.g., 2 to 8 membered heteroalkyl, 2 to 6 membered heteroalkyl, or 2 to 4 membered heteroalkyl), $R^{106.4}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{106.4}$-substituted or unsubstituted heterocycloalkyl (e.g., 3 to 8 membered heterocycloalkyl, 3 to 6 membered heterocycloalkyl, or 5 to 6 membered heterocycloalkyl), $R^{106.4}$-substituted or unsubstituted aryl (e.g., $C_6$-$C_{10}$ aryl, $C_{10}$ aryl, or phenyl), or $R^{106.4}$-substituted or unsubstituted heteroaryl (e.g., 5 to 10 membered heteroaryl, 5 to 9 membered heteroaryl, or 5 to 6 membered heteroaryl).

In embodiments, $R^{105.4}$ is $R^{106.4}$-substituted or unsubstituted alkyl (e.g., $C_1$-$C_8$ alkyl, $C_1$-$C_6$ alkyl, or $C_1$-$C_4$ alkyl). In embodiments, $R^{105.4}$ is $R^{106.4}$-Substituted alkyl (e.g., $C_1$-$C_8$ alkyl, $C_1$-$C_6$ alkyl, or $C_1$-$C_4$ alkyl). In embodiments, $R^{105.4}$ is an unsubstituted alkyl (e.g., $C_1$-$C_8$ alkyl, $C_1$-$C_6$ alkyl, or $C_1$-$C_4$ alkyl).

In embodiments, $R^{105.4}$ is $R^{106.4}$-substituted or unsubstituted heteroalkyl (e.g., 2 to 8 membered heteroalkyl, 2 to 6 membered heteroalkyl, or 2 to 4 membered heteroalkyl). In embodiments, $R^{105.4}$ is $R^{106.4}$-substituted heteroalkyl (e.g., 2 to 8 membered heteroalkyl, 2 to 6 membered heteroalkyl, or 2 to 4 membered heteroalkyl). In embodiments, $R^{105.4}$ is an unsubstituted heteroalkyl (e.g., 2 to 8 membered heteroalkyl, 2 to 6 membered heteroalkyl, or 2 to 4 membered heteroalkyl).

In embodiments, $R^{105.4}$ is $R^{106.4}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{105.4}$ is $R^{106.4}$-substituted cycloalkyl (e.g., $C_3$-$C_8$ cycloalkyl, $C_3$-$C_6$ cycloalkyl, or $C_5$-$C_6$ cycloalkyl). In embodiments, $R^{105.4}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{105.4}$ is $R^{106.4}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{105.4}$ is $R^{106.4}$-substituted heterocycloalkyl (e.g., 3 to 8 membered heterocycloalkyl, 3 to 6 membered heterocycloalkyl, or 5 to 6 membered heterocycloalkyl). In embodiments, $R^{105.4}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{105.4}$ is $R^{106.4}$-substituted or unsubstituted aryl (e.g., $C_6$-$C_{10}$ aryl, $C_{10}$ aryl, or phenyl). In embodiments, $R^{105.4}$ is $R^{106.4}$-substituted aryl (e.g., $C_6$-$C_{10}$ aryl, $C_{10}$ aryl, or phenyl). In embodiments, $R^{105.4}$ is an unsubstituted aryl (e.g., $C_6$-$C_{10}$ aryl, $C_{10}$ aryl, or phenyl).

In embodiments, $R^{105.4}$ is $R^{106.4}$-substituted or unsubstituted heteroaryl (e.g., 5 to 10 membered heteroaryl, 5 to 9 membered heteroaryl, or 5 to 6 membered heteroaryl). In embodiments, $R^{105.4}$ is $R^{106.4}$-substituted heteroaryl (e.g., 5 to 10 membered heteroaryl, 5 to 9 membered heteroaryl, or 5 to 6 membered heteroaryl). In embodiments, $R^{105.4}$ is an unsubstituted heteroaryl (e.g., 5 to 10 membered heteroaryl, 5 to 9 membered heteroaryl, or 5 to 6 membered heteroaryl).

In embodiments, $R^{103}$ is substituted or unsubstituted cycloalkyl. In embodiments, $R^{103}$ is substituted or unsubstituted heterocycloalkyl. In embodiments, $R^{103}$ is substituted or unsubstituted aryl. In embodiments, $R^{103}$ is substituted or unsubstituted heteroaryl.

In embodiments, $R^{103}$ is hydrogen, halogen, —$CX^{103}_3$, —$CHX^{103}_2$, —$CH_2X^{103}$, —CN, —$SO_{n1}R^{103A}$, —$SO_{v1}NR^{103B}R^{103C}$, —$NNR^{103B}R^{103C}$, —$ONR^{103B}R^{103C}$, —$NHC(O)NHNR^{103B}R^{103C}$, —$NHC(O)NR^{103B}R^{103C}$, —$N(O)_{m1}$, —$NR^{103B}R^{103C}$, —$C(O)R^{103D}$, —$C(O)OR^{103D}$, —$C(O)NR^{103B}R^{103C}$, —$OR^{103A}$, —$NR^{103B}SO_2R^{103A}$, —$NR^{03B}C(O)R^{103D}$, —$NR^{103B}C(O)OR^{103D}$, —$NR^{103B}OR^{103D}$, —$OCX^{103}_3$, —$OCHX^{103}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{103}$ is halogen, —$CX^{103}_3$, —$CHX^{103}_2$, —$CH_2X^{103}$, —CN, —$SO_nR^{103A}$, —$SO_{v1}NR^{103B}R^{103C}$, —$NHNR^{103B}R^{103C}$, —$ONR^{103B}R^{103C}$, —NHC(O)$NHNR^{103B}R^{103C}$, —$NHC(O)NR^{103B}R^{103C}$, —$N(O)_{m1}$, —$NR^{103B}R^{103C}$, —$C(O)R^{103D}$, —$C(O)OR^{103D}$, —$C(O)NR^{103B}R^{103C}$, —$OR^{103A}$, —$NR^{103B}SO_2R^{103A}$, —$NR^{03B}C(O)R^{103D}$, —$NR^{103B}C(O)OR^{103D}$, —$NR^{103B}OR^{103D}$, —$OCX^{103}_3$, —$OCHX^{103}_2$, $R^{107}$-substituted or unsubstituted alkyl (e.g., $C_1$-$C_8$ alkyl, $C_1$-$C_6$ alkyl, or $C_1$-$C_4$ alkyl), $R^{107}$-substituted or unsubstituted heteroalkyl (e.g., 2 to 8 membered heteroalkyl, 2 to 6 membered heteroalkyl, or 2 to 4 membered heteroalkyl), $R^{107}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{107}$-substituted or unsubstituted heterocycloalkyl (e.g., 3 to 8 membered heterocycloalkyl, 3 to 6 membered heterocycloalkyl, or 5 to 6 membered heterocycloalkyl), $R^{107}$-substituted or unsubstituted aryl (e.g., $C_6$-$C_{10}$ aryl, $C_{10}$ aryl, or phenyl), or $R^{107}$-substituted or unsubstituted heteroaryl (e.g., 5 to 10 membered heteroaryl, 5 to 9 membered heteroaryl, or 5 to 6 membered heteroaryl).

In embodiments, $R^{103}$ is $R^{107}$-substituted or unsubstituted alkyl (e.g., $C_1$-$C_8$ alkyl, $C_1$-$C_6$ alkyl, or $C_1$-$C_4$ alkyl). In embodiments, $R^{103}$ is $R^{107}$-substituted alkyl (e.g., $C_1$-$C_8$ alkyl, $C_1$-$C_6$ alkyl, or $C_1$-$C_4$ alkyl). In embodiments, $R^{103}$ is an unsubstituted alkyl (e.g., $C_1$-$C_8$ alkyl, $C_1$-$C_6$ alkyl, or $C_1$-$C_4$ alkyl).

In embodiments, $R^{103}$ is $R^{107}$-substituted or unsubstituted heteroalkyl (e.g., 2 to 8 membered heteroalkyl, 2 to 6 membered heteroalkyl, or 2 to 4 membered heteroalkyl). In embodiments, $R^{103}$ is $R^{107}$-substituted heteroalkyl (e.g., 2 to 8 membered heteroalkyl, 2 to 6 membered heteroalkyl, or 2 to 4 membered heteroalkyl). In embodiments, $R^{103}$ is an unsubstituted heteroalkyl (e.g., 2 to 8 membered heteroalkyl, 2 to 6 membered heteroalkyl, or 2 to 4 membered heteroalkyl).

In embodiments, $R^{103}$ is $R^{107}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{103}$ is $R^{107}$-substituted cycloalkyl (e.g., $C_3$-$C_8$ cycloalkyl, $C_3$-$C_6$ cycloalkyl, or $C_5$-$C_6$ cycloalkyl). In embodiments, $R^{103}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{103}$ is $R^{107}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{103}$ is $R^{107}$-substituted heterocycloalkyl (e.g., 3 to 8 membered heterocycloalkyl, 3 to 6 membered heterocycloalkyl, or 5 to 6 membered heterocycloalkyl). In embodiments, $R^{103}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{103}$ is $R^{107}$-substituted or unsubstituted aryl (e.g., $C_6$-$C_{10}$ aryl, $C_{10}$ aryl, or phenyl). In embodiments, $R^{103}$ is $R^{107}$-substituted aryl (e.g., $C_6$-$C_{10}$ aryl, $C_{10}$ aryl, or phenyl). In embodiments, $R^{103}$ is an unsubstituted aryl (e.g., $C_6$-$C_{10}$ aryl, $C_{10}$ aryl, or phenyl).

In embodiments, $R^{103}$ is $R^{107}$-substituted or unsubstituted heteroaryl (e.g., 5 to 10 membered heteroaryl, 5 to 9 membered heteroaryl, or 5 to 6 membered heteroaryl). In embodiments, $R^{103}$ is $R^{107}$-substituted heteroaryl (e.g., 5 to 10 membered heteroaryl, 5 to 9 membered heteroaryl, or 5 to 6 membered heteroaryl). In embodiments, $R^{103}$ is an unsubstituted heteroaryl (e.g., 5 to 10 membered heteroaryl, 5 to 9 membered heteroaryl, or 5 to 6 membered heteroaryl).

In embodiments, $R^{103A}$, $R^{103B}$, $R^{103C}$ and $R^{103D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{103B}$ and $R^{103C}$ substituents bonded to the same nitrogen atom may optionally be joined to form a substituted or unsubstituted heterocycloalkyl or substituted or unsubstituted heteroaryl.

In embodiments, $R^{103A}$ is hydrogen, halogen, —$CF_3$, —$CCl_3$, —$CBr_3$, —$CI_3$, —COOH, —$CONH_2$, $R^{107A}$-substituted or unsubstituted alkyl (e.g., $C_1$-$C_8$ alkyl, $C_1$-$C_6$ alkyl, or $C_1$-$C_4$ alkyl), $R^{107A}$-substituted or unsubstituted heteroalkyl (e.g., 2 to 8 membered heteroalkyl, 2 to 6 membered heteroalkyl, or 2 to 4 membered heteroalkyl), $R^{107A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{107A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{107A}$-substituted or unsubstituted aryl (e.g., $C_6$-$C_{10}$ aryl, $C_{10}$ aryl, or phenyl), or $R^{107A}$-substituted or unsubstituted heteroaryl (e.g., 5 to 10 membered heteroaryl, 5 to 9 membered heteroaryl, or 5 to 6 membered heteroaryl).

In embodiments, $R^{103B}$ is hydrogen, halogen, —$CF_3$, —$CCl_3$, —$CBr_3$, —$CI_3$, —COOH, —$CONH_2$, $R^{107B}$-substituted or unsubstituted alkyl (e.g., $C_1$-$C_8$ alkyl, $C_1$-$C_6$ alkyl, or $C_1$-$C_4$ alkyl), $R^{107B}$-substituted or unsubstituted heteroalkyl (e.g., 2 to 8 membered heteroalkyl, 2 to 6 membered heteroalkyl, or 2 to 4 membered heteroalkyl), $R^{107B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{107B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{107B}$-substituted or unsubstituted aryl (e.g., $C_6$-$C_{10}$ aryl, $C_{10}$ aryl, or phenyl), or $R^{107B}$-substituted or unsubstituted heteroaryl (e.g., 5 to 10 membered heteroaryl, 5 to 9 membered heteroaryl, or 5 to 6 membered heteroaryl). In embodiments, $R^{103B}$ and $R^{103C}$ substituents bonded to the same nitrogen atom may optionally be joined to form a $R^{107B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{107B}$-substituted or unsubstituted heteroaryl (e.g., 5 to 10 membered heteroaryl, 5 to 9 membered heteroaryl, or 5 to 6 membered heteroaryl).

In embodiments, $R^{103C}$ is hydrogen, halogen, —$CF_3$, —$CCl_3$, —$CBr_3$, —$CI_3$, —COOH, —$CONH_2$, $R^{107C}$-substituted or unsubstituted alkyl (e.g., $C_1$-$C_8$ alkyl, $C_1$-$C_6$ alkyl, or $C_1$-$C_4$ alkyl), $R^{107C}$-substituted or unsubstituted heteroalkyl (e.g., 2 to 8 membered heteroalkyl, 2 to 6 membered heteroalkyl, or 2 to 4 membered heteroalkyl), $R^{107C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{107C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{107C}$-substituted or unsubstituted aryl (e.g., $C_6$-$C_{10}$ aryl, $C_{10}$ aryl, or phenyl), or $R^{107C}$-substituted or unsubstituted heteroaryl (e.g., 5 to 10 membered heteroaryl, 5 to 9 membered heteroaryl, or 5 to 6 membered heteroaryl). In embodiments, $R^{103B}$ and $R^{103C}$ substituents bonded to the same nitrogen atom may optionally be joined to form a $R^{107C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{107C}$-substituted or unsubstituted heteroaryl (e.g., 5 to 10 membered heteroaryl, 5 to 9 membered heteroaryl, or 5 to 6 membered heteroaryl).

In embodiments, $R^{103D}$ is hydrogen, halogen, —$CF_3$, —$CCl_3$, —$CBr_3$, —$CI_3$, —COOH, —$CONH_2$, $R^{107D}$-substituted or unsubstituted alkyl (e.g., $C_1$-$C_8$ alkyl, $C_1$-$C_6$ alkyl, or $C_1$-$C_4$ alkyl), $R^{107D}$-substituted or unsubstituted heteroalkyl (e.g., 2 to 8 membered heteroalkyl, 2 to 6 membered heteroalkyl, or 2 to 4 membered heteroalkyl), $R^{107D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{107D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{107D}$-substituted or unsubstituted aryl (e.g., $C_6$-$C_{10}$ aryl, $C_{10}$ aryl, or phenyl), or $R^{107D}$-substituted or unsubstituted heteroaryl (e.g., 5 to 10 membered heteroaryl, 5 to 9 membered heteroaryl, or 5 to 6 membered heteroaryl).

$R^{107}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{108}$-substituted or unsubstituted alkyl (e.g., $C_1$-$C_8$ alkyl, $C_1$-$C_6$ alkyl, or $C_1$-$C_4$ alkyl), $R^{108}$-substituted or unsubstituted heteroalkyl (e.g., 2 to 8 membered heteroalkyl, 2 to 6 membered heteroalkyl, or 2 to 4 membered heteroalkyl), $R^{108}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{108}$-substituted or unsubstituted heterocycloalkyl (e.g., 3 to 8 membered heterocycloalkyl, 3 to 6 membered heterocycloalkyl, or 5 to 6 membered heterocycloalkyl), $R^{108}$-substituted or unsubstituted aryl (e.g., $C_6$-$C_{10}$ aryl, $C_{10}$ aryl, or phenyl), or $R^{108}$-substituted or unsubstituted heteroaryl (e.g., 5 to 10 membered heteroaryl, 5 to 9 membered heteroaryl, or 5 to 6 membered heteroaryl).

In embodiments, $R^{107}$ is $R^{108}$-substituted or unsubstituted alkyl (e.g., $C_1$-$C_8$ alkyl, $C_1$-$C_6$ alkyl, or $C_1$-$C_4$ alkyl). In embodiments, $R^{107}$ is $R^{108}$-substituted alkyl (e.g., $C_1$-$C_8$ alkyl, $C_1$-$C_6$ alkyl, or $C_1$-$C_4$ alkyl). In embodiments, $R^{107}$ is an unsubstituted alkyl (e.g., $C_1$-$C_8$ alkyl, $C_1$-$C_6$ alkyl, or $C_1$-$C_4$ alkyl).

In embodiments, $R^{107}$ is $R^{108}$-substituted or unsubstituted heteroalkyl (e.g., 2 to 8 membered heteroalkyl, 2 to 6 membered heteroalkyl, or 2 to 4 membered heteroalkyl). In embodiments, $R^{107}$ is $R^{108}$-substituted heteroalkyl (e.g., 2 to 8 membered heteroalkyl, 2 to 6 membered heteroalkyl, or 2 to 4 membered heteroalkyl). In embodiments, $R^{107}$ is an unsubstituted heteroalkyl (e.g., 2 to 8 membered heteroalkyl, 2 to 6 membered heteroalkyl, or 2 to 4 membered heteroalkyl).

In embodiments, $R^{107}$ is $R^{108}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{107}$ is $R^{108}$-substituted cycloalkyl (e.g., $C_3$-$C_8$ cycloalkyl, $C_3$-$C_6$ cycloalkyl, or $C_5$-$C_6$ cycloalkyl). In embodiments, $R^{107}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{107}$ is $R^{108}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{107}$ is $R^{108}$-substituted heterocycloalkyl (e.g., 3 to 8 membered heterocycloalkyl, 3 to 6 membered heterocycloalkyl, or 5 to 6 membered heterocycloalkyl). In embodiments, $R^{107}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{107}$ is $R^{108}$-substituted or unsubstituted aryl (e.g., $C_6$-$C_{10}$ aryl, $C_{10}$ aryl, or phenyl). In embodiments, $R^{107}$ is $R^{108}$-substituted aryl (e.g., $C_6$-$C_{10}$ aryl, $C_{10}$ aryl, or phenyl). In embodiments, $R^{107}$ is an unsubstituted aryl (e.g., $C_6$-$C_{10}$ aryl, $C_{10}$ aryl, or phenyl).

In embodiments, $R^{107}$ is $R^{108}$-substituted or unsubstituted heteroaryl (e.g., 5 to 10 membered heteroaryl, 5 to 9 membered heteroaryl, or 5 to 6 membered heteroaryl). In embodiments, $R^{107}$ is $R^{108}$-substituted heteroaryl (e.g., 5 to 10 membered heteroaryl, 5 to 9 membered heteroaryl, or 5 to 6 membered heteroaryl). In embodiments, $R^{107}$ is an unsubstituted heteroaryl (e.g., 5 to 10 membered heteroaryl, 5 to 9 membered heteroaryl, or 5 to 6 membered heteroaryl).

$R^{108}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{109}$-substituted or unsubstituted alkyl (e.g., $C_1$-$C_8$ alkyl, $C_1$-$C_6$ alkyl, or $C_1$-$C_4$ alkyl), $R^{109}$-substituted or unsubstituted heteroalkyl (e.g., 2 to 8 membered heteroalkyl, 2 to 6 membered heteroalkyl, or 2 to 4 membered heteroalkyl), $R^{109}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{109}$-substituted or unsubstituted heterocycloalkyl (e.g., 3 to 8 membered heterocycloalkyl, 3 to 6 membered heterocycloalkyl, or 5 to 6 membered heterocycloalkyl), $R^{109}$-substituted or unsubstituted aryl (e.g., $C_6$-$C_{10}$ aryl, $C_{10}$ aryl, or phenyl), or $R^{109}$-substituted or unsubstituted heteroaryl (e.g., 5 to 10 membered heteroaryl, 5 to 9 membered heteroaryl, or 5 to 6 membered heteroaryl).

In embodiments, $R^{108}$ is $R^{109}$-substituted or unsubstituted alkyl (e.g., $C_1$-$C_8$ alkyl, $C_1$-$C_6$ alkyl, or $C_1$-$C_4$ alkyl). In embodiments, $R^{108}$ is $R^{109}$-substituted alkyl (e.g., $C_1$-$C_8$ alkyl, $C_1$-$C_6$ alkyl, or $C_1$-$C_4$ alkyl). In embodiments, $R^{108}$ is an unsubstituted alkyl (e.g., $C_1$-$C_8$ alkyl, $C_1$-$C_6$ alkyl, or $C_1$-$C_4$ alkyl).

In embodiments, $R^{108}$ is $R^{109}$-substituted or unsubstituted heteroalkyl (e.g., 2 to 8 membered heteroalkyl, 2 to 6 membered heteroalkyl, or 2 to 4 membered heteroalkyl). In embodiments, $R^{108}$ is $R^{109}$-substituted heteroalkyl (e.g., 2 to 8 membered heteroalkyl, 2 to 6 membered heteroalkyl, or 2 to 4 membered heteroalkyl). In embodiments, $R^{108}$ is an unsubstituted heteroalkyl (e.g., 2 to 8 membered heteroalkyl, 2 to 6 membered heteroalkyl, or 2 to 4 membered heteroalkyl).

In embodiments, $R^{108}$ is $R^{109}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{108}$ is $R^{109}$-substituted cycloalkyl (e.g., $C_3$-$C_8$ cycloalkyl, $C_3$-$C_6$ cycloalkyl, or $C_5$-$C_6$ cycloalkyl). In embodiments, $R^{108}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{108}$ is $R^{109}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{108}$ is $R^{109}$-substituted heterocycloalkyl (e.g., 3 to 8 membered heterocycloalkyl, 3 to 6 membered heterocycloalkyl, or 5 to 6 membered heterocycloalkyl). In embodiments, $R^{108}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{108}$ is $R^{109}$-substituted or unsubstituted aryl (e.g., $C_6$-$C_{10}$ aryl, $C_{10}$ aryl, or phenyl). In embodiments, $R^{108}$ is $R^{109}$-substituted aryl (e.g., $C_6$-$C_{10}$ aryl, $C_{10}$ aryl, or phenyl). In embodiments, $R^{108}$ is an unsubstituted aryl (e.g., $C_6$-$C_{10}$ aryl, $C_{10}$ aryl, or phenyl).

In embodiments, $R^{108}$ is $R^{109}$-substituted or unsubstituted heteroaryl (e.g., 5 to 10 membered heteroaryl, 5 to 9 membered heteroaryl, or 5 to 6 membered heteroaryl). In embodiments, $R^{108}$ is $R^{109}$-substituted heteroaryl (e.g., 5 to 10 membered heteroaryl, 5 to 9 membered heteroaryl, or 5 to 6 membered heteroaryl). In embodiments, $R^{108}$ is an unsubstituted heteroaryl (e.g., 5 to 10 membered heteroaryl, 5 to 9 membered heteroaryl, or 5 to 6 membered heteroaryl).

In aspects provided herein, there are compounds having structural Formula (VIII):

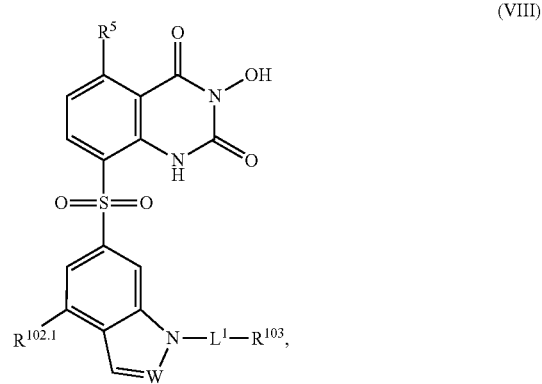

(VIII)

or a pharmaceutically acceptable salt thereof. $L^1$, W, $R^5$, $R^{102.1}$ and $R^{103}$ are as described herein, including embodiments.

$R^{104.1A}$, $R^{104.1B}$, $R^{104.1C}$, $R^{104.1D}$, —$R^{104.2A}$, $R^{104.2B}$, $R^{104.2C}$, $R^{104.2D}$, —$R^{104.3A}$, $R^{104.3B}$, $R^{104.3C}$, $R^{104.3D}$, —$R^{104.4A}$, $R^{104.4B}$, $R^{104.4C}$, $R^{104.4D}$, —$R^{106}$, $R^{106.1}$, $R^{106.2}$, $R^{106.3}$, $R^{106.4}$, $R^{107A}$, $R^{107B}$, $R^{107C}$, $R^{107D}$ $R^{109}$ and $R^{114}$ are independently hydrogen, oxo, halogen, —$CCl_3$, —$CBr_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $X^{102}$ is —Cl. In embodiments, $X^{102}$ is —F. In embodiments, $X^{102}$ is —Br. In embodiments, $X^{102}$ is —I. In embodiments, $X^{102.1}$ is —Cl. In embodiments, $X^{102.1}$ is —F. In embodiments, $X^{102.1}$ is —Br. In embodiments, $X^{102.1}$ is —I. In embodiments, $X^{102.2}$ is —Cl. In embodiments, $X^{102.2}$ is —F. In embodiments, $X^{102.2}$ is —Br. In embodiments, $X^{102.2}$ is —I. In embodiments, $X^{102.3}$ is —Cl. In embodiments, $X^{102.3}$ is —F. In embodiments, $X^{102.3}$ is —Br. In embodiments, $X^{102.3}$ is —I. In embodiments, $X^{102.4}$ is —Cl. In embodiments, $X^{102.4}$ is —F. In embodiments, $X^{102.4}$ is —Br. In embodiments, $X^{102.4}$ is —I. In embodiments, $X^{103}$ is —C$_1$. In embodiments, $X^{103}$ is —F. In embodiments, $X^{103}$ is —Br. In embodiments, $X^{103}$ is —I.

In certain embodiments, are provided a compound selected from:

3-hydroxy-1-methylpyrido[2,3-d]pyrimidine-2,4(1H,3H)-dione
3-hydroxy-1-phenylpyrido[2,3-d]pyrimidine-2,4(1H,3H)-dione
3-hydroxy-7-(phenylsulfonyl)pyrido[2,3-d]pyrimidine-2,4(1H,3H)-dione
3-hydroxy-7-(phenylsulfonyl)quinazoline-2,4(1H,3H)-dione
3-hydroxy-7-phenylpyrido[2,3-d]pyrimidine-2,4(1H,3H)-dione
3-hydroxy-7-phenylquinazoline-2,4(1H,3H)-dione
3-hydroxy-8-(phenylsulfonyl)quinazoline-2,4(1H,3H)-dione
3-hydroxy-8-phenylquinazoline-2,4(1H,3H)-dione
3-hydroxy-8-tosylquinazoline-2,4(1H,3H)-dione
3-hydroxypyrido[2,3-d]pyrimidine-2,4(1H,3H)-dione
3-hydroxypyrido[4,3-d]pyrimidine-2,4(1H,3H)-dione
3-hydroxyquinazoline-2,4(1H,3H)-dione
5-chloro-3-hydroxy-8-phenylquinazoline-2,4(1H,3H)-dione
7-(benzyl sulfonyl)-3-hydroxypyrido[3,2-d]pyrimidine-2,4(1H,3H)-dione
7-(benzylsulfonyl)-3-hydroxyquinazoline-2,4(1H,3H)-dione
7-benzyl-3-hydroxypyrido[2,3-d]pyrimidine-2,4(1H,3H)-dione
7-benzyl-3-hydroxyquinazoline-2,4(1H,3H)-dione
8-(benzylsulfonyl)-3-hydroxyquinazoline-2,4(1H,3H)-dione
8-benzyl-3-hydroxyquinazoline-2,4(1H,3H)-dione
8-benzyl-5-chloro-3-hydroxyquinazoline-2,4(1H,3H)-dione
3-hydroxy-8-((3-(trifluoromethyl)phenyl)sulfonyl)quinazoline-2,4(1H,3H)-dione
3-hydroxy-8-((3-hydroxyphenyl)sulfonyl)quinazoline-2,4(1H,3H)-dione
3-hydroxy-8-((3-methoxyphenyl)sulfonyl)quinazoline-2,4(1H,3H)-dione
3-hydroxy-8-(m-tolylsulfonyl)quinazoline-2,4(1H,3H)-dione
5-bromo-3-hydroxyquinazoline-2,4(1H,3H)-dione
5-chloro-3-hydroxy-8-(m-tolylsulfonyl)quinazoline-2,4(1H,3H)-dione
5-chloro-3-hydroxy-8-(phenylsulfonyl)quinazoline-2,4(1H,3H)-dione
5-fluoro-3-hydroxyquinazoline-2,4(1H,3H)-dione
6-chloro-3-hydroxy-8-(m-tolylsulfonyl)quinazoline-2,4(1H,3H)-dione
6-fluoro-3-hydroxy-8-(phenyl sulfonyl)quinazoline-2,4(1H,3H)-dione
6-fluoro-3-hydroxyquinazoline-2,4(1H,3H)-dione
7-fluoro-3-hydroxy-8-(m-tolylsulfonyl)quinazoline-2,4(1H,3H)-dione
7-fluoro-3-hydroxyquinazoline-2,4(1H,3H)-dione
8-((3,5-dimethylphenyl)sulfonyl)-3-hydroxyquinazoline-2,4(1H,3H)-dione
8-((3-aminophenyl)sulfonyl)-3-hydroxyquinazoline-2,4(1H,3H)-dione
8-((3-bromophenyl)sulfonyl)-3-hydroxyquinazoline-2,4(1H,3H)-dione
8-((3-chlorophenyl)sulfonyl)-3-hydroxyquinazoline-2,4(1H,3H)-dione
8-((4-bromophenyl)sulfonyl)-3-hydroxyquinazoline-2,4(1H,3H)-dione
8-((4-chlorophenyl)sulfonyl)-3-hydroxyquinazoline-2,4(1H,3H)-dione
8-fluoro-3-hydroxyquinazoline-2,4(1H,3H)-dione
methyl (3-((3-hydroxy-2,4-dioxo-1,2,3,4-tetrahydroquinazolin-8-yl)sulfonyl)phenyl)carbamate
N-(3-((3-hydroxy-2,4-dioxo-1,2,3,4-tetrahydroquinazolin-8-yl)sulfonyl)phenyl)acetamide
1-(3-((3-hydroxy-2,4-dioxo-1,2,3,4-tetrahydroquinazolin-8-yl)sulfonyl)phenyl)-3-methylurea
1-(3-((3-hydroxy-2,4-dioxo-1,2,3,4-tetrahydroquinazolin-8-yl)sulfonyl)phenyl)urea
3-((3-hydroxy-2,4-dioxo-1,2,3,4-tetrahydroquinazolin-8-yl)sulfonyl)benzonitrile
3-hydroxy-8-((3-(pyridin-2-ylamino)phenyl)sulfonyl)quinazoline-2,4(1H,3H)-dione
3-hydroxy-8-((3-(pyrimidin-2-ylamino)phenyl)sulfonyl)quinazoline-2,4(1H,3H)-dione
5-chloro-8-((3,5-difluorophenyl)sulfonyl)-3-hydroxyquinazoline-2,4(1H,3H)-dione
5-chloro-8-((3-fluorophenyl)sulfonyl)-3-hydroxyquinazoline-2,4(1H,3H)-dione
5-fluoro-3-hydroxy-8-(m-tolyl sulfonyl)quinazoline-2,4(1H,3H)-dione
6-fluoro-3-hydroxy-8-(m-tolyl sulfonyl)quinazoline-2,4(1H,3H)-dione
7-chloro-3-hydroxy-8-(m-tolyl sulfonyl)quinazoline-2,4(1H,3H)-dione
7-fluoro-3-hydroxy-8-(phenyl sulfonyl)quinazoline-2,4(1H,3H)-dione
8-((3,5-dibromophenyl)sulfonyl)-3-hydroxyquinazoline-2,4(1H,3H)-dione
8-((3,5-dichlorophenyl)sulfonyl)-3-hydroxyquinazoline-2,4(1H,3H)-dione
8-((3,5-difluorophenyl)sulfonyl)-3-hydroxyquinazoline-2,4(1H,3H)-dione
8-((3,5-dihydroxyphenyl)sulfonyl)-3-hydroxyquinazoline-2,4(1H,3H)-dione
8-((3,5-dimethoxyphenyl)sulfonyl)-3-hydroxyquinazoline-2,4(1H,3H)-dione 8-((3-(dimethylamino)phenyl)sulfonyl)-3-hydroxyquinazoline-2,4(1H,3H)-dione
8-((3-fluorophenyl)sulfonyl)-3-hydroxyquinazoline-2,4(1H,3H)-dione
N,N-(5-((3-hydroxy-2,4-dioxo-1,2,3,4-tetrahydroquinazolin-8-yl)sulfonyl)-1,3-phenylene)diacetamide
3-hydroxy-5-methoxy-8-(m-tolylsulfonyl)quinazoline-2,4(1H,3H)-dione
3-hydroxy-5-methoxy-8-(phenylsulfonyl)quinazoline-2,4(1H,3H)-dione
3-hydroxy-8-(thiophen-2-ylsulfonyl)quinazoline-2,4(1H,3H)-dione
5-chloro-3-hydroxy-8-(thiophen-2-ylsulfonyl)quinazoline-2,4(1H,3H)-dione
5-chloro-8-((3-chloro-5-methylphenyl)sulfonyl)-3-hydroxyquinazoline-2,4(1H,3H)-dione
5-chloro-8-((3-fluoro-5-methylphenyl)sulfonyl)-3-hydroxyquinazoline-2,4(1H,3H)-dione
8-((1H-benzo[d]imidazol-5-yl)sulfonyl)-3-hydroxyquinazoline-2,4(1H,3H)-dione
8-((3,5-bis(dimethylamino)phenyl)sulfonyl)-3-hydroxyquinazoline-2,4(1H,3H)-dione
8-((3,5-diaminophenyl)sulfonyl)-3-hydroxyquinazoline-2,4(1H,3H)-dione
(1R,2R)-2-(6-((5-chloro-3-hydroxy-2,4-dioxo-1,2,3,4-tetrahydroquinazolin-8-yl)sulfonyl)-4-fluoro-1H-indol-1-yl)cyclopropyl acetate
(R)-5-chloro-8-((1-(2,2-difluorocyclopropyl)-1H-indol-6-yl)sulfonyl)-3-hydroxyquinazoline-2,4(1H,3H)-dione
(R)-5-chloro-8-((1-(2,2-difluorocyclopropyl)-4-fluoro-1H-indol-6-yl)sulfonyl)-3-hydroxyquinazoline-2,4(1H,3H)-dione
5-chloro-3-hydroxy-8-((1-(((1R,2R)-2-methoxycyclopropyl)-1H-indol-6-yl)sulfonyl)quinazoline-2,4(1H,3H)-dione
5-chloro-3-hydroxy-8-((1-(((1R,2R)-2-methylcyclopropyl)-1H-indol-6-yl)sulfonyl)quinazoline-2,4(1H,3H)-dione
5-chloro-3-hydroxy-8-((1-(2,2,3,3-tetrafluorocyclopropyl)-1H-indol-6-yl)sulfonyl)quinazoline-2,4(1H,3H)-dione
5-chloro-8-((1-(((1R,2R)-2-(dimethylamino)cyclopropyl)-1H-indol-6-yl)sulfonyl)-3-hydroxyquinazoline-2,4(1H,3H)-dione
5-chloro-8-((1-(((1R,2R)-2-(dimethylamino)cyclopropyl)-4-fluoro-1H-indol-6-yl)sulfonyl)-3-hydroxyquinazoline-2,4(1H,3H)-dione
5-chloro-8-((1-((1R,2R)-2-fluorocyclopropyl)-1H-indol-6-yl)sulfonyl)-3-hydroxyquinazoline-2,4(1H,3H)-dione
5-chloro-8-((1-(2,2-difluoroethyl)-1H-indol-6-yl)sulfonyl)-3-hydroxyquinazoline-2,4(1H,3H)-dione
5-chloro-8-((1-(2,2-difluoroethyl)-4-fluoro-1H-indol-6-yl)sulfonyl)-3-hydroxyquinazoline-2,4(1H,3H)-dione
5-chloro-8-((1-(2-fluoroethyl)-1H-indol-6-yl)sulfonyl)-3-hydroxyquinazoline-2,4(1H,3H)-dione
5-chloro-8-((1-cyclopropyl-1H-indol-6-yl)sulfonyl)-3-hydroxyquinazoline-2,4(1H,3H)-dione
5-chloro-8-((1-cyclopropyl-4-fluoro-1H-indol-6-yl)sulfonyl)-3-hydroxyquinazoline-2,4(1H,3H)-dione
5-chloro-8-((4-fluoro-1-((1R,2R)-2-fluorocyclopropyl)-1H-indol-6-yl)sulfonyl)-3-hydroxyquinazoline-2,4(1H,3H)-dione
5-chloro-8-((4-fluoro-1-((1R,2R)-2-methoxycyclopropyl)-1H-indol-6-yl)sulfonyl)-3-hydroxyquinazoline-2,4(1H,3H)-dione
5-chloro-8-((4-fluoro-1-((1R,2R)-2-methylcyclopropyl)-1H-indol-6-yl)sulfonyl)-3-hydroxyquinazoline-2,4(1H,3H)-dione
5-chloro-8-((4-fluoro-1-(2,2,3,3-tetrafluorocyclopropyl)-1H-indol-6-yl)sulfonyl)-3-hydroxyquinazoline-2,4(1H,3H)-dione
5-chloro-8-((4-fluoro-1-(2-fluoroethyl)-1H-indol-6-yl)sulfonyl)-3-hydroxyquinazoline-2,4(1H,3H)-dione
8-((1-((1R,2R)-2-aminocyclopropyl)-4-fluoro-1H-indol-6-yl)sulfonyl)-5-chloro-3-hydroxyquinazoline-2,4(1H,3H)-dione
(1R,2R)-2-(6-((5-chloro-3-hydroxy-2,4-dioxo-1,2,3,4-tetrahydroquinazolin-8-yl)sulfonyl)-1H-indol-1-yl)cyclopropyl acetate
N-((1R,2R)-2-(6-((5-chloro-3-hydroxy-2,4-dioxo-1,2,3,4-tetrahydroquinazolin-8-yl)sulfonyl)-1H-indol-1-yl)cyclopropyl)acetamide
N-((1R,2R)-2-(6-((5-chloro-3-hydroxy-2,4-dioxo-1,2,3,4-tetrahydroquinazolin-8-yl)sulfonyl)-4-fluoro-1H-indol-1-yl)cyclopropyl)acetamide
5-chloro-3-hydroxy-8-((1-(2-(2,2,3,3-tetrafluorocyclopropyl)ethyl)-1H-indol-6-yl)sulfonyl)quinazoline-2,4(1H,3H)-dione
5-chloro-3-hydroxy-8-((1-(2-(2,2,3,3-tetramethylcyclopropyl)ethyl)-1H-indol-6-yl)sulfonyl)quinazoline-2,4(1H,3H)-dione
5-chloro-8-((1-(2-((1S,2S)-2-fluorocyclopropyl)ethyl)-1H-indol-6-yl)sulfonyl)-3-hydroxyquinazoline-2,4(1H,3H)-dione
5-chloro-8-((1-(2-(2,2-difluorocyclopropyl)ethyl)-1H-indol-6-yl)sulfonyl)-3-hydroxyquinazoline-2,4(1H,3H)-dione
5-chloro-8-((1-(2-(2,2-difluorocyclopropyl)ethyl)-4-fluoro-1H-indol-6-yl)sulfonyl)-3-hydroxyquinazoline-2,4(1H,3H)-dione
5-chloro-8-((1-(2-(2,2-dimethylcyclopropyl)ethyl)-1H-indol-6-yl)sulfonyl)-3-hydroxyquinazoline-2,4(1H,3H)-dione
5-chloro-8-((1-(2-(2,2-dimethylcyclopropyl)ethyl)-4-fluoro-1H-indol-6-yl)sulfonyl)-3-hydroxyquinazoline-2,4(1H,3H)-dione
5-chloro-8-((1-(2-cyclopropylethyl)-1H-indol-6-yl)sulfonyl)-3-hydroxyquinazoline-2,4(1H,3H)-dione
5-chloro-8-((1-(2-cyclopropylethyl)-4-fluoro-1H-indol-6-yl)sulfonyl)-3-hydroxyquinazoline-2,4(1H,3H)-dione
5-chloro-8-((4-fluoro-1-(2-((1S,2S)-2-fluorocyclopropyl)ethyl)-1H-indol-6-yl)sulfonyl)-3-hydroxyquinazoline-2,4(1H,3H)-dione
5-chloro-8-((4-fluoro-1-(2-(2,2,3,3-tetrafluorocyclopropyl)ethyl)-1H-indol-6-yl)sulfonyl)-3-hydroxyquinazoline-2,4(1H,3H)-dione
5-chloro-8-((4-fluoro-1-(2-(2,2,3,3-tetramethylcyclopropyl)ethyl)-1H-indol-6-yl)sulfonyl)-3-hydroxyquinazoline-2,4(1H,3H)-dione
8-((1-((1R,2R)-2-aminocyclopropyl)-1H-indol-6-yl)sulfonyl)-5-chloro-3-hydroxyquinazoline-2,4(1H,3H)-dione
5-chloro-8-((1-(2-(3,3-difluorocyclobutyl)ethyl)-4-fluoro-1H-indol-6-yl)sulfonyl)-3-hydroxyquinazoline-2,4(1H,3H)-dione
5-chloro-8-((1-(2-cyclobutylethyl)-1H-indol-6-yl)sulfonyl)-3-hydroxyquinazoline-2,4(1H,3H)-dione
5-chloro-8-((1-(2-cyclobutylethyl)-4-fluoro-1H-indol-6-yl)sulfonyl)-3-hydroxyquinazoline-2,4(1H,3H)-dione
5-chloro-8-((4-fluoro-1-(2-(2,2,3,3,4,4-hexafluorocyclobutyl)ethyl)-1H-indol-6-yl)sulfonyl)-3-hydroxyquinazoline-2,4(1H,3H)-dione
5-chloro-8-((1-(2-(2,2,3,3,4,4-hexafluorocyclobutyl)ethyl)-1H-indol-6-yl)sulfonyl)-3-hydroxyquinazoline-2,4(1H,3H)-dione 5-chloro-8-((1-(2-(3,3-difluorocyclobutyl)ethyl)-1H-indol-6-yl)sulfonyl)-3-hydroxyquinazoline-2,4(1H,3H)-dione
5-chloro-8-((4-fluoro-1-(2-(2,2,3,3,4,4,5,5-octafluorocyclopentyl)ethyl)-1H-indol-6-yl)sulfonyl)-3-hydroxyquinazoline-2,4(1H,3H)-dione
5-chloro-8-((4-fluoro-1-(2-(3-methylcyclobutyl)ethyl)-1H-indol-6-yl)sulfonyl)-3-hydroxyquinazoline-2,4(1H,3H)-dione
5-chloro-3-hydroxy-8-((1-(2-(2,2,3,3,4,4,5,5-octafluorocyclopentyl)ethyl)-1H-indol-6-yl)sulfonyl)quinazoline-2,4(1H,3H)-dione
5-chloro-3-hydroxy-8-((1-(2-(3-methylcyclobutyl)ethyl)-1H-indol-6-yl)sulfonyl)quinazoline-2,4(1H,3H)-dione
5-chloro-8-((1-(2-cyclopentylethyl)-1H-indol-6-yl)sulfonyl)-3-hydroxyquinazoline-2,4(1H,3H)-dione
5-chloro-8-((1-(2-cyclopentylethyl)-4-fluoro-1H-indol-6-yl)sulfonyl)-3-hydroxyquinazoline-2,4(1H,3H)-dione
5-chloro-8-((1-((1S,3S)-3-(dimethylamino)cyclopentyl)-1H-indol-6-yl)sulfonyl)-3-hydroxyquinazoline-2,4(1H,3H)-dione
5-chloro-8-((1-cyclopentyl-4-fluoro-1H-indol-6-yl)sulfonyl)-3-hydroxyquinazoline-2,4(1H,3H)-dione
5-chloro-8-((4-fluoro-1-(oxazol-2-yl)-1H-indol-6-yl)sulfonyl)-3-hydroxyquinazoline-2,4(1H,3H)-dione
8-((1-((1S,3S)-3-aminocyclopentyl)-4-fluoro-1H-indol-6-yl)sulfonyl)-5-chloro-3-hydroxyquinazoline-2,4(1H,3H)-dione
5-chloro-3-hydroxy-8-((1-((1r,3r)-3-methylcyclobutyl)-1H-indol-6-yl)sulfonyl)quinazoline-2,4(1H,3H)-dione
5-chloro-3-hydroxy-8-((1-(1-methyl-1H-pyrrol-3-yl)-1H-indol-6-yl)sulfonyl)quinazoline-2,4(1H,3H)-dione
5-chloro-3-hydroxy-8-((1-(oxetan-3-yl)-1H-indol-6-yl)sulfonyl)quinazoline-2,4(1H,3H)-dione
5-chloro-3-hydroxy-8-((1-(thiophen-2-yl)-1H-indol-6-yl)sulfonyl)quinazoline-2,4(1H,3H)-dione
5-chloro-3-hydroxy-8-((1-(thiophen-3-yl)-1H-indol-6-yl)sulfonyl)quinazoline-2,4(1H,3H)-dione
5-chloro-8-((1-((1r,3r)-3-fluorocyclobutyl)-1H-indol-6-yl)sulfonyl)-3-hydroxyquinazoline-2,4(1H,3H)-dione
5-chloro-8-((1-(2,2,3,3,4,4-hexafluorocyclobutyl)-1H-indol-6-yl)sulfonyl)-3-hydroxyquinazoline-2,4(1H,3H)-dione
5-chloro-8-((1-(3,3-dimethylcyclobutyl)-1H-indol-6-yl)sulfonyl)-3-hydroxyquinazoline-2,4(1H,3H)-dione
5-chloro-8-((1-(3,3-dimethylcyclobutyl)-4-fluoro-1H-indol-6-yl)sulfonyl)-3-hydroxyquinazoline-2,4(1H,3H)-dione
5-chloro-8-((1-(4-(dimethylamino)thiophen-2-yl)-1H-indol-6-yl)sulfonyl)-3-hydroxyquinazoline-2,4(1H,3H)-dione
5-chloro-8-((1-cyclobutyl-1H-indol-6-yl)sulfonyl)-3-hydroxyquinazoline-2,4(1H,3H)-dione
5-chloro-8-((1-cyclobutyl-4-fluoro-1H-indol-6-yl)sulfonyl)-3-hydroxyquinazoline-2,4(1H,3H)-dione
5-chloro-8-((1-cyclopentyl-1H-indol-6-yl)sulfonyl)-3-hydroxyquinazoline-2,4(1H,3H)-dione
5-chloro-8-((4-fluoro-1-((1r,3r)-3-fluorocyclobutyl)-1H-indol-6-yl)sulfonyl)-3-hydroxyquinazoline-2,4(1H,3H)-dione
5-chloro-8-((4-fluoro-1-((1r,3r)-3-methylcyclobutyl)-1H-indol-6-yl)sulfonyl)-3-hydroxyquinazoline-2,4(1H,3H)-dione
5-chloro-8-((4-fluoro-1-(1H-pyrrol-3-yl)-1H-indol-6-yl)sulfonyl)-3-hydroxyquinazoline-2,4(1H,3H)-dione
5-chloro-8-((4-fluoro-1-(2,2,3,3,4,4-hexafluorocyclobutyl)-1H-indol-6-yl)sulfonyl)-3-hydroxyquinazoline-2,4(1H,3H)-dione
5-chloro-8-((4-fluoro-1-(furan-2-yl)-1H-indol-6-yl)sulfonyl)-3-hydroxyquinazoline-2,4(1H,3H)-dione
5-chloro-8-((4-fluoro-1-(furan-3-yl)-1H-indol-6-yl)sulfonyl)-3-hydroxyquinazoline-2,4(1H,3H)-dione
5-chloro-8-((4-fluoro-1-(oxetan-3-yl)-1H-indol-6-yl)sulfonyl)-3-hydroxyquinazoline-2,4(1H,3H)-dione
(1R,2R)-2-(6-((5-chloro-3-hydroxy-2,4-dioxo-1,2,3,4-tetrahydroquinazolin-8-yl)sulfonyl)-4-fluoro-1H-indazol-1-yl)cyclopropyl acetate
(R)-5-chloro-8-((1-(2,2-difluorocyclopropyl)-1H-indazol-6-yl)sulfonyl)-3-hydroxyquinazoline-2,4(1H,3H)-dione
(R)-5-chloro-8-((1-(2,2-difluorocyclopropyl)-4-fluoro-1H-indazol-6-yl)sulfonyl)-3-hydroxyquinazoline-2,4(1H,3H)-dione
5-chloro-3-hydroxy-8-((1-((1R,2R)-2-methoxycyclopropyl)-1H-indazol-6-yl)sulfonyl)quinazoline-2,4(1H,3H)-dione
5-chloro-3-hydroxy-8-((1-((1R,2R)-2-methylcyclopropyl)-1H-indazol-6-yl)sulfonyl)quinazoline-2,4(1H,3H)-dione
5-chloro-3-hydroxy-8-((1-(2,2,3,3-tetrafluorocyclopropyl)-1H-indazol-6-yl)sulfonyl)quinazoline-2,4(1H,3H)-dione
5-chloro-8-((1-((1R,2R)-2-(dimethylamino)cyclopropyl)-1H-indazol-6-yl)sulfonyl)-3-hydroxyquinazoline-2,4(1H,3H)-dione
5-chloro-8-((1-((1R,2R)-2-(dimethylamino)cyclopropyl)-4-fluoro-1H-indazol-6-yl)sulfonyl)-3-hydroxyquinazoline-2,4(1H,3H)-dione
5-chloro-8-((1-((1R,2R)-2-fluorocyclopropyl)-1H-indazol-6-yl)sulfonyl)-3-hydroxyquinazoline-2,4(1H,3H)-dione
5-chloro-8-((1-(2,2-difluoroethyl)-1H-indazol-6-yl)sulfonyl)-3-hydroxyquinazoline-2,4(1H,3H)-dione
5-chloro-8-((1-(2,2-difluoroethyl)-4-fluoro-1H-indazol-6-yl)sulfonyl)-3-hydroxyquinazoline-2,4(1H,3H)-dione
5-chloro-8-((1-(2-fluoroethyl)-1H-indazol-6-yl)sulfonyl)-3-hydroxyquinazoline-2,4(1H,3H)-dione
5-chloro-8-((1-cyclopropyl-1H-indazol-6-yl)sulfonyl)-3-hydroxyquinazoline-2,4(1H,3H)-dione
5-chloro-8-((1-cyclopropyl-4-fluoro-1H-indazol-6-yl)sulfonyl)-3-hydroxyquinazoline-2,4(1H,3H)-dione
5-chloro-8-((4-fluoro-1-((1R,2R)-2-fluorocyclopropyl)-1H-indazol-6-yl)sulfonyl)-3-hydroxyquinazoline-2,4(1H,3H)-dione
5-chloro-8-((4-fluoro-1-((1R,2R)-2-methoxycyclopropyl)-1H-indazol-6-yl)sulfonyl)-3-hydroxyquinazoline-2,4(1H,3H)-dione
5-chloro-8-((4-fluoro-1-((1R,2R)-2-methyl cyclopropyl)-1H-indazol-6-yl)sulfonyl)-3-hydroxyquinazoline-2,4(1H,3H)-dione
5-chloro-8-((4-fluoro-1-(2,2,3,3-tetrafluorocyclopropyl)-1H-indazol-6-yl)sulfonyl)-3-hydroxyquinazoline-2,4(1H,3H)-dione
5-chloro-8-((4-fluoro-1-(2-fluoroethyl)-1H-indazol-6-yl)sulfonyl)-3-hydroxyquinazoline-2,4(1H,3H)-dione
8-((1-((1R,2R)-2-aminocyclopropyl)-4-fluoro-1H-indazol-6-yl)sulfonyl)-5-chloro-3-hydroxyquinazoline-2,4(1H,3H)-dione
(1R,2R)-2-(6-((5-chloro-3-hydroxy-2,4-dioxo-1,2,3,4-tetrahydroquinazolin-8-yl)sulfonyl)-1H-indazol-1-yl)cyclopropyl acetate
N-((1R,2R)-2-(6-((5-chloro-3-hydroxy-2,4-dioxo-1,2,3,4-tetrahydroquinazolin-8-yl)sulfonyl)-1H-indazol-1-yl)cyclopropyl)acetamide
N-((1R,2R)-2-(6-((5-chloro-3-hydroxy-2,4-dioxo-1,2,3,4-tetrahydroquinazolin-8-yl)sulfonyl)-4-fluoro-1H-indazol-1-yl)cyclopropyl)acetamide
5-chloro-3-hydroxy-8-((1-(2-(2,2,3,3-tetrafluorocyclopropyl)ethyl)-1H-indazol-6-yl)sulfonyl)quinazoline-2,4(1H,3H)-dione 5-chloro-3-hydroxy-8-((1-(2-(2,2,3,3-tetramethylcyclopropyl)ethyl)-1H-indazol-6-yl)sulfonyl)quinazoline-2,4(1H,3H)-dione 5-chloro-8-((1-(2-((1S,2S)-2-fluorocyclopropyl)ethyl)-1H-indazol-6-yl)sulfonyl)-3-hydroxyquinazoline-2,4(1H,3H)-dione 5-chloro-8-((1-(2-(2,2-difluorocyclopropyl)ethyl)-1H-indazol-6-yl)sulfonyl)-3-hydroxyquinazoline-2,4(1H,3H)-dione 5-chloro-8-((1-(2-(2,2-difluorocyclopropyl)ethyl)-4-fluoro-1H-indazol-6-yl)sulfonyl)-3-hydroxyquinazoline-2,4(1H,3H)-dione 5-chloro-8-((1-(2-(2,2-dimethylcyclopropyl)ethyl)-1H-indazol-6-yl)sulfonyl)-3-hydroxyquinazoline-2,4(1H,3H)-dione 5-chloro-8-((1-(2-(2,2-dimethylcyclopropyl)ethyl)-4-fluoro-1H-indazol-6-yl)sulfonyl)-3-hydroxyquinazoline-2,4(1H,3H)-dione 5-chloro-8-((1-(2-cyclopropylethyl)-1H-indazol-6-yl)sulfonyl)-3-hydroxyquinazoline-2,4(1H,3H)-dione 5-chloro-8-((1-(2-cyclopropylethyl)-4-fluoro-1H-indazol-6-yl)sulfonyl)-3-hydroxyquinazoline-2,4(1H,3H)-dione 5-chloro-8-((4-fluoro-1-(2-((1S,2S)-2-fluorocyclopropyl)ethyl)-1H-indazol-6-yl)sulfonyl)-3-hydroxyquinazoline-2,4(1H,3H)-dione 5-chloro-8-((4-fluoro-1-(2-(2,2,3,3-tetrafluorocyclopropyl)ethyl)-1H-indazol-6-yl)sulfonyl)-3-hydroxyquinazoline-2,4(1H,3H)-dione 5-chloro-8-((4-fluoro-1-(2-(2,2,3,3-tetramethylcyclopropyl)ethyl)-1H-indazol-6-yl)sulfonyl)-3-hydroxyquinazoline-2,4(1H,3H)-dione 8-((1-((1R,2R)-2-aminocyclopropyl)-1H-indazol-6-yl)sulfonyl)-5-chloro-3-hydroxyquinazoline-2,4(1H,3H)-dione 5-chloro-3-hydroxy-8-((1-(2-((1r,3r)-3-methylcyclobutyl)ethyl)-1H-indazol-6-yl)sulfonyl)quinazoline-2,4(1H,3H)-dione 5-chloro-3-hydroxy-8-((1-(2-(2,2,3,3,4,4,5,5-octafluorocyclopentyl)ethyl)-1H-indazol-6-yl)sulfonyl)quinazoline-2,4(1H,3H)-dione 5-chloro-8-((1-((1S,3S)-3-(dimethylamino)cyclopentyl)-1H-indazol-6-yl)sulfonyl)-3-hydroxyquinazoline-2,4(1H,3H)-dione 5-chloro-8-((1-(2-(2,2,3,3,4,4-hexafluorocyclobutyl)ethyl)-1H-indazol-6-yl)sulfonyl)-3-hydroxyquinazoline-2,4(1H,3H)-dione 5-chloro-8-((1-(2-(3,3-difluorocyclobutyl)ethyl)-1H-indazol-6-yl)sulfonyl)-3-hydroxyquinazoline-2,4(1H,3H)-dione 5-chloro-8-((1-(2-(3,3-difluorocyclobutyl)ethyl)-4-fluoro-1H-indazol-6-yl)sulfonyl)-3-hydroxyquinazoline-2,4(1H,3H)-dione 5-chloro-8-((1-(2-cyclobutylethyl)-1H-indazol-6-yl)sulfonyl)-3-hydroxyquinazoline-2,4(1H,3H)-dione 5-chloro-8-((1-(2-cyclobutylethyl)-4-fluoro-1H-indazol-6-yl)sulfonyl)-3-hydroxyquinazoline-2,4(1H,3H)-dione 5-chloro-8-((1-(2-cyclopentylethyl)-1H-indazol-6-yl)sulfonyl)-3-hydroxyquinazoline-2,4(1H,3H)-dione 5-chloro-8-((1-(2-cyclopentylethyl)-4-fluoro-1H-indazol-6-yl)sulfonyl)-3-hydroxyquinazoline-2,4(1H,3H)-dione 5-chloro-8-((1-cyclopentyl-4-fluoro-1H-indazol-6-yl)sulfonyl)-3-hydroxyquinazoline-2,4(1H,3H)-dione 5-chloro-8-((4-fluoro-1-(2-((1r,3r)-3-methylcyclobutyl)ethyl)-1H-indazol-6-yl)sulfonyl)-3-hydroxyquinazoline-2,4(1H,3H)-dione 5-chloro-8-((4-fluoro-1-(2-(2,2,3,3,4,4,5,5-octafluorocyclopentyl)ethyl)-1H-indazol-6-yl)sulfonyl)-3-hydroxyquinazoline-2,4(1H,3H)-dione 5-chloro-8-((4-fluoro-1-(2-(2,2,3,3,4,4-hexafluorocyclobutyl)ethyl)-1H-indazol-6-yl)sulfonyl)-3-hydroxyquinazoline-2,4(1H,3H)-dione 5-chloro-8-((4-fluoro-1-(oxazol-2-yl)-1H-indazol-6-yl)sulfonyl)-3-hydroxyquinazoline-2,4(1H,3H)-dione 8-((1-((1S,3S)-3-aminocyclopentyl)-4-fluoro-1H-indazol-6-yl)sulfonyl)-5-chloro-3-hydroxyquinazoline-2,4(1H,3H)-dione 5-chloro-3-hydroxy-8-((1-((1r,3r)-3-methylcyclobutyl)-1H-indazol-6-yl)sulfonyl)quinazoline-2,4(1H,3H)-dione 5-chloro-3-hydroxy-8-((1-(1-methyl-1H-pyrrol-3-yl)-1H-indazol-6-yl)sulfonyl)quinazoline-2,4(1H,3H)-dione 5-chloro-3-hydroxy-8-((1-(oxetan-3-yl)-1H-indazol-6-yl)sulfonyl)quinazoline-2,4(1H,3H)-dione 5-chloro-3-hydroxy-8-((1-(thiophen-2-yl)-1H-indazol-6-yl)sulfonyl)quinazoline-2,4(1H,3H)-dione 5-chloro-3-hydroxy-8-((1-(thiophen-3-yl)-1H-indazol-6-yl)sulfonyl)quinazoline-2,4(1H,3H)-dione 5-chloro-8-((1-((1r,3r)-3-fluorocyclobutyl)-1H-indazol-6-yl)sulfonyl)-3-hydroxyquinazoline-2,4(1H,3H)-dione 5-chloro-8-((1-(2,2,3,3,4,4-hexafluorocyclobutyl)-1H-indazol-6-yl)sulfonyl)-3-hydroxyquinazoline-2,4(1H,3H)-dione 5-chloro-8-((1-(3,3-dimethylcyclobutyl)-1H-indazol-6-yl)sulfonyl)-3-hydroxyquinazoline-2,4(1H,3H)-dione 5-chloro-8-((1-(3,3-dimethylcyclobutyl)-4-fluoro-1H-indazol-6-yl)sulfonyl)-3-hydroxyquinazoline-2,4(1H,3H)-dione 5-chloro-8-((1-(4-(dimethylamino)thiophen-2-yl)-1H-indazol-6-yl)sulfonyl)-3-hydroxyquinazoline-2,4(1H,3H)-dione 5-chloro-8-((1-cyclobutyl-1H-indazol-6-yl)sulfonyl)-3-hydroxyquinazoline-2,4(1H,3H)-dione 5-chloro-8-((1-cyclobutyl-4-fluoro-1H-indazol-6-yl)sulfonyl)-3-hydroxyquinazoline-2,4(1H,3H)-dione 5-chloro-8-((1-cyclopentyl-1H-indazol-6-yl)sulfonyl)-3-hydroxyquinazoline-2,4(1H,3H)-dione 5-chloro-8-((4-fluoro-1-((1r,3r)-3-fluorocyclobutyl)-1H-indazol-6-yl)sulfonyl)-3-hydroxyquinazoline-2,4(1H,3H)-dione 5-chloro-8-((4-fluoro-1-((1r,3r)-3-methylcyclobutyl)-1H-indazol-6-yl)sulfonyl)-3-hydroxyquinazoline-2,4(1H,3H)-dione 5-chloro-8-((4-fluoro-1-(1H-pyrrol-3-yl)-1H-indazol-6-yl)sulfonyl)-3-hydroxyquinazoline-2,4(1H,3H)-dione 5-chloro-8-((4-fluoro-1-(2,2,3,3,4,4-hexafluorocyclobutyl)-1H-indazol-6-yl)sulfonyl)-3-hydroxyquinazoline-2,4(1H,3H)-dione 5-chloro-8-((4-fluoro-1-(furan-2-yl)-1H-indazol-6-yl)sulfonyl)-3-hydroxyquinazoline-2,4(1H,3H)-dione 5-chloro-8-((4-fluoro-1-(furan-3-yl)-1H-indazol-6-yl)sulfonyl)-3-hydroxyquinazoline-2,4(1H,3H)-dione 5-chloro-8-((4-fluoro-1-(oxetan-3-yl)-1H-indazol-6-yl)sulfonyl)-3-hydroxyquinazoline-2,4(1H,3H)-dione 3-hydroxy-5-(methylamino)-8-(m-tolylsulfonyl)quinazoline-2,4(1H,3H)-dione 3-hydroxy-5-methoxy-8-(m-tolylsulfonyl)pyrido[4,3-d]pyrimidine-2,4(1H,3H)-dione 3-hydroxy-5-methoxy-8-(phenylsulfonyl)pyrido[4,3-d]pyrimidine-2,4(1H,3H)-dione 3-hydroxy-8-(thiophen-3-ylsulfonyl)quinazoline-2,4(1H,3H)-dione 5-(dimethylamino)-3-hydroxy-8-(m-tolylsulfonyl)quinazoline-2,4(1H,3H)-dione 5-chloro-3-hydroxy-8-((1-methyl-1H-indazol-5-yl)sulfonyl)quinazoline-2,4(1H,3H)-dione
5-chloro-3-hydroxy-8-((1-methyl-1H-indazol-6-yl)sulfonyl)quinazoline-2,4(1H,3H)-dione
5-chloro-3-hydroxy-8-((1-methyl-1H-indol-5-yl)sulfonyl)quinazoline-2,4(1H,3H)-dione
5-chloro-3-hydroxy-8-((1-methyl-1H-indol-6-yl)sulfonyl)quinazoline-2,4(1H,3H)-dione
5-chloro-3-hydroxy-8-(quinolin-6-ylsulfonyl)quinazoline-2,4(1H,3H)-dione
5-chloro-3-hydroxy-8-(quinolin-7-ylsulfonyl)quinazoline-2,4(1H,3H)-dione
5-chloro-3-hydroxy-8-(quinoxalin-6-ylsulfonyl)quinazoline-2,4(1H,3H)-dione
5-chloro-8-((2-fluoro-3-methylphenyl)sulfonyl)-3-hydroxyquinazoline-2,4(1H,3H)-dione
5-chloro-8-((2-fluoro-5-methylphenyl)sulfonyl)-3-hydroxyquinazoline-2,4(1H,3H)-dione
5-chloro-8-((3,4-dichlorophenyl)sulfonyl)-3-hydroxyquinazoline-2,4(1H,3H)-dione
5-chloro-8-((3-fluoro-5-(trifluoromethyl)phenyl)sulfonyl)-3-hydroxyquinazoline-2,4(1H,3H)-dione
5-chloro-8-((3-fluoro-5-methylphenyl)sulfonyl)-3-hydroxyquinazoline-2,4(1H,3H)-dione
5-chloro-8-((4-fluoro-3-methylphenyl)sulfonyl)-3-hydroxyquinazoline-2,4(1H,3H)-dione
8-(benzo[d]thiazol-5-ylsulfonyl)-5-chloro-3-hydroxyquinazoline-2,4(1H,3H)-dione
8-(benzo[d]thiazol-6-ylsulfonyl)-5-chloro-3-hydroxyquinazoline-2,4(1H,3H)-dione
2-(6-((5-chloro-3-hydroxy-2,4-dioxo-1,2,3,4-tetrahydroquinazolin-8-yl)sulfonyl)-4-fluoro-1H-indol-1-yl)-N-methylacetamide
5-chloro-3-hydroxy-8-((1-methyl-1H-benzo[d]imidazol-5-yl)sulfonyl)quinazoline-2,4(1H,3H)-dione
5-chloro-3-hydroxy-8-((1-methyl-1H-benzo[d]imidazol-6-yl)sulfonyl)quinazoline-2,4(1H,3H)-dione
5-chloro-3-hydroxy-8-((1-methyl-1H-indol-6-yl)sulfonyl)quinazoline-2,4(1H,3H)-dione
5-chloro-3-hydroxy-8-((1-propyl-1H-indol-6-yl)sulfonyl)quinazoline-2,4(1H,3H)-dione
5-chloro-3-hydroxy-8-(thiophen-3-ylsulfonyl)quinazoline-2,4(1H,3H)-dione
5-chloro-8-((1-ethyl-4-fluoro-1H-indol-6-yl)sulfonyl)-3-hydroxyquinazoline-2,4(1H,3H)-dione
5-chloro-8-((4-fluoro-1-(2,2,2-trifluoroethyl)-1H-indol-6-yl)sulfonyl)-3-hydroxyquinazoline-2,4(1H,3H)-dione
5-chloro-8-((4-fluoro-1-propyl-1H-indol-6-yl)sulfonyl)-3-hydroxyquinazoline-2,4(1H,3H)-dione
5-chloro-8-((4-fluoro-3-methylphenyl)sulfonyl)-3-hydroxyquinazoline-2,4(1H,3H)-dione
5-chloro-8-((4-fluorobenzo[b]thiophen-6-yl)sulfonyl)-3-hydroxyquinazoline-2,4(1H,3H)-dione
8-((1-benzyl-1H-indol-6-yl)sulfonyl)-5-chloro-3-hydroxyquinazoline-2,4(1H,3H)-dione
8-((1H-indazol-6-yl)sulfonyl)-5-chloro-3-hydroxyquinazoline-2,4(1H,3H)-dione
8-((1H-indol-5-yl)sulfonyl)-5-chloro-3-hydroxyquinazoline-2,4(1H,3H)-dione
8-((1H-indol-6-yl)sulfonyl)-5-chloro-3-hydroxyquinazoline-2,4(1H,3H)-dione
8-((3-benzyl-5-methylphenyl)sulfonyl)-5-chloro-3-hydroxyquinazoline-2,4(1H,3H)-dione
8-(benzo[b]thiophen-5-yl sulfonyl)-5-chloro-3-hydroxyquinazoline-2,4(1H,3H)-dione
8-(benzo[b]thiophen-6-yl sulfonyl)-5-chloro-3-hydroxyquinazoline-2,4(1H,3H)-dione
8-(benzo[d]isoxazol-5-ylsulfonyl)-5-chloro-3-hydroxyquinazoline-2,4(1H,3H)-dione
5-chloro-3-hydroxy-8-((1-(2,2,2-trifluoroethyl)-1H-indol-6-yl)sulfonyl)quinazoline-2,4(1H,3H)-dione
5-chloro-3-hydroxy-8-((1-(2-(methylamino)ethyl)-1H-indol-6-yl)sulfonyl)quinazoline-2,4(1H,3H)-dione
5-chloro-3-hydroxy-8-((1-(2-hydroxyethyl)-1H-indol-6-yl)sulfonyl)quinazoline-2,4(1H,3H)-dione
5-chloro-3-hydroxy-8-((1-(2-methoxyethyl)-1H-indol-6-yl)sulfonyl)quinazoline-2,4(1H,3H)-dione
5-chloro-3-hydroxy-8-((1-(2-morpholinoethyl)-1H-indol-6-yl)sulfonyl)quinazoline-2,4(1H,3H)-dione
5-chloro-3-hydroxy-8-((1-(3-hydroxypropyl)-1H-indol-6-yl)sulfonyl)quinazoline-2,4(1H,3H)-dione
5-chloro-3-hydroxy-8-((1-(3-methoxypropyl)-1H-indazol-6-yl)sulfonyl)quinazoline-2,4(1H,3H)-dione
5-chloro-3-hydroxy-8-((1-(3-methoxypropyl)-1H-indol-6-yl)sulfonyl)quinazoline-2,4(1H,3H)-dione
5-chloro-3-hydroxy-8-((1-isobutyl-1H-indol-6-yl)sulfonyl)quinazoline-2,4(1H,3H)-dione
5-chloro-3-hydroxy-8-((1-isopropyl-1H-indazol-6-yl)sulfonyl)quinazoline-2,4(1H,3H)-dione
5-chloro-3-hydroxy-8-((1-isopropyl-1H-indol-6-yl)sulfonyl)quinazoline-2,4(1H,3H)-dione
5-chloro-3-hydroxy-8-((1-propyl-1H-indazol-6-yl)sulfonyl)quinazoline-2,4(1H,3H)-dione
5-chloro-8-((1-(cyclohexylmethyl)-1H-indol-6-yl)sulfonyl)-3-hydroxyquinazoline-2,4(1H,3H)-dione
5-chloro-8-((4-chlorobenzo[b]thiophen-6-yl)sulfonyl)-3-hydroxyquinazoline-2,4(1H,3H)-dione
5-chloro-8-((4-fluoro-1-isobutyl-1H-indol-6-yl)sulfonyl)-3-hydroxyquinazoline-2,4(1H,3H)-dione
8-((1-(2-aminoethyl)-1H-indol-6-yl)sulfonyl)-5-chloro-3-hydroxyquinazoline-2,4(1H,3H)-dione
8-((1-butyl-1H-indazol-6-yl)sulfonyl)-5-chloro-3-hydroxyquinazoline-2,4(1H,3H)-dione
8-((1-butyl-1H-indol-6-yl)sulfonyl)-5-chloro-3-hydroxyquinazoline-2,4(1H,3H)-dione
8-(benzofuran-5-ylsulfonyl)-5-chloro-3-hydroxyquinazoline-2,4(1H,3H)-dione
8-(benzofuran-6-ylsulfonyl)-5-chloro-3-hydroxyquinazoline-2,4(1H,3H)-dione
3-hydroxy-5-methoxy-8-((1-(2,2,2-trifluoroethyl)-1H-indol-6-yl)sulfonyl)quinazoline-2,4(1H,3H)-dione
3-hydroxy-5-methyl-8-((1-(2,2,2-trifluoroethyl)-1H-indol-6-yl)sulfonyl)quinazoline-2,4(1H,3H)-dione
3-hydroxy-8-((1-(2,2,2-trifluoroethyl)-1H-indol-6-yl)sulfonyl)quinazoline-2,4(1H,3H)-dione
5-bromo-3-hydroxy-8-((1-(2,2,2-trifluoroethyl)-1H-indol-6-yl)sulfonyl)quinazoline-2,4(1H,3H)-dione
5-bromo-8-((4-fluoro-1-(2,2,2-trifluoroethyl)-1H-indol-6-yl)sulfonyl)-3-hydroxyquinazoline-2,4(1H,3H)-dione
5-chloro-3-hydroxy-8-((1-(2,2,2-trifluoroethyl)-1H-indazol-6-yl)sulfonyl)quinazoline-2,4(1H,3H)-dione
5-chloro-3-hydroxy-8-((1-(2-methoxyethyl)-1H-indol-6-yl)sulfonyl)quinazoline-2,4(1H,3H)-dione
5-chloro-3-hydroxy-8-((1-(3,3,3-trifluoropropyl)-1H-indazol-6-yl)sulfonyl)quinazoline-2,4(1H,3H)-dione
5-chloro-3-hydroxy-8-((1-isobutyl-1H-indazol-6-yl)sulfonyl)quinazoline-2,4(1H,3H)-dione
5-chloro-3-hydroxy-8-((1-methyl-1H-pyrrolo[3,2-b]pyridin-6-yl)sulfonyl)quinazoline-2,4(1H,3H)-dione
5-chloro-8-((1-(2-(dimethylamino)ethyl)-1H-indol-6-yl)sulfonyl)-3-hydroxyquinazoline-2,4(1H,3H)-dione
5-fluoro-3-hydroxy-8-((1-(2,2,2-trifluoroethyl)-1H-indol-6-yl)sulfonyl)quinazoline-2,4(1H,3H)-dione 5-fluoro-8-((4-fluoro-1-(2,2,2-trifluoroethyl)-1H-indol-6-yl)sulfonyl)-3-hydroxyquinazoline-2,4(1H,3H)-dione 5-fluoro-8-((4-fluoro-1-methyl-1H-indol-6-yl)sulfonyl)-3-hydroxyquinazoline-2,4(1H,3H)-dione 8-((1-benzyl-1H-indazol-6-yl)sulfonyl)-5-chloro-3-hydroxyquinazoline-2,4(1H,3H)-dione 8-((4-fluoro-1-(2,2,2-trifluoroethyl)-1H-indol-6-yl)sulfonyl)-3-hydroxyquinazoline-2,4(1H,3H)-dione 5-bromo-3-hydroxy-8-((5-methyl-5H-pyrrolo[2,3-b]pyrazin-3-yl)sulfonyl)quinazoline-2,4(1H,3H)-dione (S)-5-chloro-3-hydroxy-8-((1-(1-methylpyrrolidin-3-yl)-1H-indazol-6-yl)sulfonyl)quinazoline-2,4(1H,3H)-dione In some embodiments, a compound as described herein may include multiple instances of X and/or other variables. For example, where each X is different, they may be referred to as, for example, $X^a$, $X^b$, $X^c$, $X^d$, $X^e$, $X^f$, $X^g$, $X^h$, $X^i$, $X^j$, $X^k$, $X^l$, $X^m$, $X^n$, $X^o$, $X^p$, $X^q$, $X^r$, $X^s$, $X^t$, $X^u$, $X^v$, $X^w$, $X^x$, $X^y$, $X^z$, $X^{aa}$, $X^{bb}$, $X^{cc}$, $X^{dd}$, $X^{ee}$, $X^{ff}$, $X^{gg}$, $X^{hh}$, $X^{ii}$, $X^{jj}$, $X^{kk}$, $X^{ll}$, $X^{mm}$, $X^{nn}$, $X^{oo}$, $X^{pp}$, $X^{qq}$, $X^{rr}$, $X^{ss}$, $X^{tt}$, $X^{uu}$, $X^{vv}$, $X^{ww}$, $X^{xx}$, and $X^{yy}$, where the definition of X is assumed for each of $X^a$, $X^b$, $X^c$, $X^d$, $X^e$, $X^f$, $X^g$, $X^h$, $X^i$, $X^j$, $X^k$, $X^l$, $X^m$, $X^n$, $X^o$, $X^p$, $X^q$, $X^r$, $X^s$, $X^t$, $X^u$, $X^v$, $X^w$, $X^x$, $X^y$, $X^z$, $X^{aa}$, $X^{bb}$, $X^{cc}$, $X^{dd}$, $X^{ee}$, $X^{ff}$, $X^{gg}$, $X^{hh}$, $X^{ii}$, $X^{jj}$, $X^{kk}$, $X^{ll}$, $X^{mm}$, $X^{nn}$, $X^{oo}$, $X^{pp}$, $X^{qq}$, $X^{rr}$, $X^{ss}$, $X^{tt}$, $X^{uu}$, $X^{vv}$, $X^{ww}$, $X^{xx}$, and $X^{yy}$. The variables used within a definition of X and/or other variables that appear at multiple instances and are different may similarly be appropriately labeled to distinguish each group for greater clarity.

In some embodiments, the compound is a compound described herein (e.g., in an aspect, embodiment, example, claim, table, scheme, drawing, or figure).

In embodiments, unless otherwise indicated, a compound described herein is a racemic mixture of all stereoisomers. In embodiments, unless otherwise indicated, a compound described herein is a racemic mixture of all enantiomers. In embodiments, unless otherwise indicated, a compound described herein is a racemic mixture of two opposite stereoisomers. In embodiments, unless otherwise indicated, a compound described herein is a racemic mixture of two opposite enantiomers. In embodiments, unless otherwise indicated, a compound described herein is a single stereoisomer. In embodiments, unless otherwise indicated, a compound described herein is a single enantiomer. In embodiments, the compound is a compound described herein (e.g., in an aspect, embodiment, example, figure, table, scheme, or claim).

III. Pharmaceutical Compositions

In an aspect is provided a pharmaceutical composition including a compound described herein, or pharmaceutically acceptable salt thereof, including embodiments, or the structural Formula (I), (II), (III), (IIIa), (IV), (V), (VI), (VIa), (VII) and (VIII), and a pharmaceutically acceptable excipient.

In embodiments of the pharmaceutical compositions, the compound, or pharmaceutically acceptable salt thereof, is included in a therapeutically effective amount.

In an aspect is provided a pharmaceutical composition including a compound described herein, or pharmaceutically acceptable salt thereof, including embodiments, or the structural Formula (I), (II), (III), (IIIa), (IV), (V), (VI), (VIa), (VII) and (VIII), an additional anticancer agent (e.g., immunotherapeutic anticancer agent) and a pharmaceutically acceptable excipient The pharmaceutical compositions of the present disclosure can be formulated to be compatible with the intended method or route of administration; exemplary routes of administration are set forth herein.

The compounds (e.g., nuclease modulator) of the present disclosure may be in the form of compositions suitable for administration to a subject. In general, such compositions are "pharmaceutical compositions" comprising a compound (e.g., nuclease modulator) and one or more pharmaceutically acceptable or physiologically acceptable diluents, carriers or excipients. In certain embodiments, the compound (e.g., nuclease modulator) are present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein.

The pharmaceutical compositions containing the active ingredient (e.g., an inhibitor of nuclease function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture thereof. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethyl cellulose, methylcellulose, hydroxy-propylmethyl cellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxyc-etanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation.

Dispersible powders and granules suitable for preparation of an aqueous suspension by the addition of water provide the active ingredient in admixture with a dispersing or wetting agent, and optionally one or more suspending agents and/or preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a nuclease modulator (e.g., inhibitor) contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate-buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer; N-(2-Hydroxyethyl)piperazine-N'-(2-ethanesulfonic acid) (HEPES); 2-(N-Morpholino)ethanesulfonic acid (MES); 2-(N-Morpholino)ethanesulfonic acid sodium salt (MES); 3-(N-Morpholino)propanesulfonic acid (MOPS); and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time-delay material such as glyceryl monostearate or glyceryl stearate alone, or in combination with a wax, may be employed. Any drug delivery apparatus may be used to deliver a nuclease modulator (e.g., inhibitor), including implants (e.g., implantable pumps) and catheter systems, slow injection pumps and devices, all of which are well known to the skilled artisan.

Depot injections, which are generally administered subcutaneously or intramuscularly, may also be utilized to release the compound (e.g., nuclease modulator) disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor® EL (BASF, Parsippany, N.J.) or phosphate buffered saline (PBS), ethanol, polyol (e.g., glycerol, propylene glycol, and liquid polyethylene glycol), and suitable mixtures thereof. In addition, sterile fixed oils are conventionally employed as a solvent or suspending medium; for this purpose, any bland fixed oil may be employed, including synthetic mono- or diglycerides. Moreover, fatty acids, such as oleic acid, find use in the preparation of injectables. Prolonged absorption of particular injectable formulations can be achieved by including an agent that delays absorption (e.g., aluminum monostearate or gelatin).

The present disclosure contemplates the administration of the compound (e.g., nuclease modulator) in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The compound (e.g., nuclease modulator) contemplated by the present disclosure may be in the form of any other suitable pharmaceutical composition (e.g., sprays for nasal or inhalation use) currently known or developed in the future.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer. In embodiments, the second agent is an anti-cancer agent. In embodiments, the second agent is a chemotherapeutic.

IV. Methods of Treatment

In an aspect is provided a method of treating cancer including administering to a subject in need thereof an effective amount of a compound described herein.

In an aspect is provided a method of treating a disease associated with Flap endonuclease 1 (FEN1) activity including administering to a subject in need thereof an effective amount of a compound described herein. In embodiments, the disease is associated with aberrant Flap endonuclease 1 (FEN1) activity.

In an aspect is provided a method of treating a disease associated with Xeroderma Pigmentosum Complementation Group G protein (XPG) activity including administering to a subject in need thereof an effective amount of a compound described herein. In embodiments, the disease is associated with aberrant Xeroderma Pigmentosum Complementation Group G protein (XPG) activity.

In an aspect is provided a method of treating a disease associated with Exonuclease 1 (EXO1) activity including administering to a subject in need thereof an effective amount of a compound described herein. In embodiments, the disease is associated with aberrant Exonuclease 1 (EXO1) activity.

In an aspect is provided a method of treating a disease associated with GEN1 activity including administering to a subject in need thereof an effective amount of a compound described herein. In embodiments, the disease is associated with aberrant GEN1 activity.

In embodiments, the method includes administering a second agent (e.g. therapeutic agent). In embodiments, the method includes administering a second agent (e.g. therapeutic agent) in a therapeutically effective amount. In embodiments, the second agent is an agent for treating cancer. In embodiments, the second agent is an anti-cancer agent. In embodiments, the second agent is a chemotherapeutic.

In an aspect, there is provided a method of treating cancer, the method including administering to a subject in need thereof a therapeutically effective amount of a compound as described herein, including embodiments, or the Formula (I), (II), (III), (IIIa), (IV), (V), (VI), (VIa), (VII) and (VIII) or a pharmaceutically acceptable salt thereof.

In an aspect, there is provided a method of treating cancer, the method including administering to a subject in need thereof a therapeutically effective amount of a compound as described herein, including embodiments, or the Formula (I), (II), (III), (IIIa), (IV), (V), (VI), (VIa), (VII) and (VIII) or a pharmaceutically acceptable salt thereof and an additional anticancer agent.

V. Methods of Inhibition

In an aspect is provided a method of inhibiting Flap endonuclease 1 (FEN1) activity including contacting the Flap endonuclease 1 (FEN1) with a compound described herein. In embodiments, the Flap endonuclease 1 (FEN1) is a human Flap endonuclease 1 (FEN1).

In an aspect is provided a method of inhibiting Xeroderma Pigmentosum Complementation Group G protein (XPG) activity including contacting the Xeroderma Pigmentosum Complementation Group G protein (XPG) with a compound described herein. In embodiments, the Xeroderma Pigmentosum Complementation Group G protein (XPG) is a human Xeroderma Pigmentosum Complementation Group G protein (XPG).

In an aspect is provided a method of inhibiting Exonuclease 1 (EXO1) activity including contacting the Exonuclease 1 (EXO1) with a compound described herein. In embodiments, the Exonuclease 1 (EXO1) is a human Exonuclease 1 (EXO1).

In an aspect is provided a method of inhibiting GEN1 activity including contacting the GEN1 with a compound described herein. In embodiments, the GEN1is a human GEN1.

In embodiments, the inhibition is competitive inhibition. In embodiments, the inhibition is irreversible. In embodiments, the inhibition is reversible.

In another aspect, there is provided a method of inhibiting nuclease activity, the method including contacting the nuclease with a compound as described herein, including embodiments, or the structural Formula (I), (II), (III), (IIIa), (IV), (V), (VI), (VIa), (VII) and (VIII) or a pharmaceutically acceptable salt thereof.

In embodiments, the nuclease is an endonuclease. In embodiments, the nuclease is an exoonuclease. In embodiments, the nuclease is a resolvase.

In embodiments, the nuclease is Flap structure-specific endonuclease 1(FEN-1). In embodiments, the nuclease is GEN1. In embodiments, the nuclease is Exonuclease 1 (EXO1). In embodiments, the nuclease is Xeroderma Pigmentosum Complementation Group G protein (XPG).

EMBODIMENTS

Embodiments includes embodiment P1 to P25 following.

Embodiment P1

A compound having the formula:

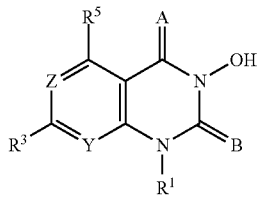

or a pharmaceutically acceptable salt thereof wherein,
$A$ is independently O, S, or $NR^4$
$B$ is independently O, S, or $NR^B$;
$Y$ is independently $CR^2$ or N;
$Z$ is independently $CR^4$ or N;
$R^1$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is independently hydrogen, halogen, $-CX^2_3$, $-CHX^2_2$, $-CH_2X^2$, $-CN$, $-SO_{n2}R^9$, $-SO_{v2}NR^6R^7$, $-NHC(O)NR^6R^7$, $-N(O)_{m2}$, $-NR^6R^7$, $-C(O)R^8$, $-C(O)-OR^8$, $-C(O)NR^6R^7$, $-OR^9$, $-NR^6SO_2R^9$, $-NR^6C(O)R^8$, $-NR^6C(O)OR^8$, $-NR^6OR^8$, $-OCX^2_3$, $-OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is independently hydrogen, halogen, $-CX^3_3$, $-CHX^3_2$, $-CH_2X^3$, $-CN$, $-SO_{n3}R^{13}$, $-SO_{v3}NR^{10}R^{11}$, $-NHC(O)NR^{10}R^{11}$, $-N(O)_{m3}$, $-NR^{10}R^{11}$, $-C(O)R^{12}$, $-C(O)-OR^{12}$, $-OR^{13}$, $-NR^{10}SO_2R^{13}$, $-NR^{10}C(O)R^{12}$, $-NR^{10}C(O)OR^{12}$, $-NR^{10}OR^{12}$, $-OCX^3_3$, $-OCHX^3_2$, substituted or unsubstituted alkyl, substituted or unsubstituted heteroalkyl, substituted or unsubstituted cycloalkyl, substituted or unsubstituted aryl, or substituted or unsubstituted heteroaryl;
$R^4$ is independently hydrogen, halogen, $-CX^4_3$, $-CHX^4_2$, $-CH_2X^4$, $-CN$, $-SO_{n4}R^{17}$, $-SO_{v4}NR^{14}R^{15}$, $-NHC(O)NR^{14}R^{15}$, $-N(O)_{m4}$, $-NR^{14}R^{15}$, $-C(O)R^{16}$, $-C(O)-OR^{16}$, $-C(O)NR^{14}R^{15}$, $-OR^{17}$, $-NR^{14}SO_2R^{17}$, $-NR^{14}C(O)R^{16}$, $-NR^{14}C(O)OR^{16}$, $-NR^{14}OR^{16}$, $-OCX^4_3$, $-OCHX^4_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is independently hydrogen, halogen, $-CX^5_3$, $-CHX^5_2$, $-CH_2X^5$, $-CN$, $-SO_{n5}R^{21}$, $-SO_{v5}NR^{18}R^{19}$, $-NHC(O)NR^{18}R^{19}$, $-N(O)_{m5}$, $-NR^{18}R^{19}$, $-C(O)R^{20}$, $-C(O)-OR^{20}$, $-C(O)NR^{18}R^{19}$, $-OR^{21}$, $-NR^{18}SO_2R^{21}$, $-NR^{18}C(O)R^{20}$, $-NR^{18}C(O)OR^{20}$, $-NR^{18}OR^{20}$, $-OCX^5_3$, $-OCHX^5_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
each $R^A$, $R^B$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ and $R^7$, $R^{10}$ and $R^{11}$, $R^{14}$ and $R^{15}$, and $R^{18}$ and $R^{19}$ substituents bonded to the same nitrogen atom may optionally be joined to form a substituted or unsubstituted heterocycloalkyl or substituted or unsubstituted heteroaryl;
each X, $X^2$, $X^3$, $X^4$, and $X^5$ is independently $-F$, $-Cl$, $-Br$, or $-I$;
each m2, m3, m4, and m5 is independently an integer from 1 to 2;
each n2, n3, n4, and n5 is independently an integer from 0 to 3; and
each v2, v3, v4, and v5 is independently an integer from 1 to 2.

Embodiment P2

The compound of embodiment P1, wherein $R^1$ is hydrogen.

Embodiment P3

The compound of embodiment P1 or P2, wherein Y is N.

Embodiment P4

The compound of embodiment P1 or P2, wherein:
Y is $CR^2$; and
$R^2$ is halogen, $-SO_2R^9$, substituted or unsubstituted alkyl, or substituted or unsubstituted aryl.

Embodiment P5

The compound of embodiment P4, wherein:
$R^2$ is $-SO_{n2}R^9$;
n2 is 2; and
$R^9$ is substituted or unsubstituted alkyl, substituted or unsubstituted aryl, or substituted or unsubstituted heteroaryl.

Embodiment P6

The compound of embodiment P5, wherein $R^9$ is substituted or unsubstituted aryl.

Embodiment P7

The compound of any one of embodiments P1 to P6, wherein $R^3$ is hydrogen or halogen.

Embodiment P8

The compound of embodiment P7, wherein $R^3$ is hydrogen.

Embodiment P9

The compound of any one of embodiments P1 to P8, wherein Z is N.

Embodiment P10

The compound of any one of embodiments P1 to P8, wherein Z is $CR^4$.

Embodiment P11

The compound of embodiment P10, wherein $R^4$ is hydrogen.

Embodiment P12

The compound of any one of embodiments P1 to P11, wherein $R^5$ is hydrogen, halogen, or $-OR^{21}$.

Embodiment P13

The compound of embodiment P12, wherein $R^5$ is halogen.

Embodiment P14

The compound of any one of embodiments 1 to 13, wherein:
A is independently O or S; and
B is independently O or S.

Embodiment P15

The compound of any one of embodiments P1 to P13, wherein:
A is independently O or $NR^A$; and
B is independently O or $NR^B$;
$R^A$ and $R^B$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P16

The compound of any one of embodiments P1 to P13, wherein
A is O; and
B is O.

Embodiment P17

The compound of embodiment P1, wherein:
$R^1$ is hydrogen;
Y is $CR^2$; and
$R^2$ is $-SO_{n2}R^9$.

Embodiment P18

The compound of embodiment P17, wherein n2 is 2.

Embodiment P19

The compound of embodiment P17 or P18, wherein:
$R^3$ is hydrogen; and
Z is $CR^4$.

Embodiment P20

The compound of embodiment P19, wherein $R^4$ is hydrogen.

Embodiment P21

The compound of any one of embodiments P17 to P20, wherein $R^5$ is halogen.

Embodiment P22

The compound of any one of embodiments P17 to P21, wherein
A is O; and
B is O.

Embodiment P23

A pharmaceutical composition comprising the compound of any one of embodiments P1 to P22, or a pharmaceutically acceptable salt thereof, and a pharmaceutically acceptable excipient.

Embodiment P24

A method of inhibiting Flap structure-specific endonuclease 1(FEN-1) activity, said method comprising: contacting the FEN-1 with an effective amount of the compound of any one of embodiments P1 to P22, or a pharmaceutically acceptable salt thereof.

Embodiment P25

A method of treating cancer, said method comprising administering to a subject in need thereof an effective amount of a compound of any one of embodiments P1 to P22, or a pharmaceutically acceptable salt thereof.

Further embodiments include embodiments 26 to 78 following.

Embodiment 26

The compound of embodiment 1, or a pharmaceutically acceptable salt thereof, wherein the compound has structural Formula (II):

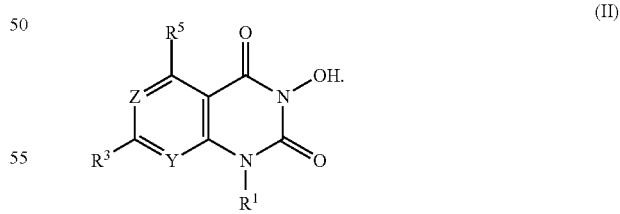

(II)

Embodiment 27

The compound of embodiment 26, wherein:
Y is $CR^2$;
Z is $CR^4$; and
$R^1$ is independently hydrogen, substituted or unsubstituted alkyl, substituted or unsubstituted heteroalkyl, substituted or unsubstituted cycloalkyl, substituted or

Embodiment 28

The compound of embodiment 26, wherein:
Y is $CR^2$;
Z is N; and
$R^1$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 29

The compound of embodiment 26, wherein:
Y is N;
Z is $CR^4$; and
$R^1$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 30

The compound of embodiment 26, wherein:
Y is $CR^2$; and
$R^2$ is —$SO_2R^9$, substituted or unsubstituted alkyl, substituted or unsubstituted heteroalkyl, substituted or unsubstituted aryl or substituted or unsubstituted heteroaryl.

Embodiment 31

The compound of embodiment 26, wherein $R^3$ is $SO_2R^{13}$ substituted or unsubstituted alkyl, substituted or unsubstituted heteroalkyl, substituted or unsubstituted aryl or substituted or unsubstituted heteroaryl.

Embodiment 32

The compound of embodiment 1, or a pharmaceutically acceptable salt thereof, wherein the compound has structural Formula (III):

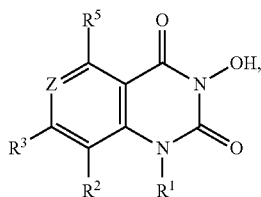

(III)

wherein $R^2$ is hydrogen, halogen, —$SO_{n2}R^9$, —$SO_{v2}NR^6R^7$, —$C(O)NR^6R$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 33

The compound of embodiment 32, wherein:
$R^1$ is hydrogen, substituted or unsubstituted alkyl, substituted or unsubstituted heteroalkyl, substituted or unsubstituted aryl or substituted or unsubstituted heteroaryl.

Embodiment 34

The compound of embodiment 33, or a pharmaceutically acceptable salt thereof, wherein the compound has structural Formula (IIIa):

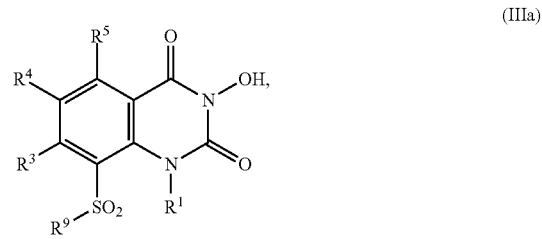

(IIIa)

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 35

The compound of embodiment 1, or a pharmaceutically acceptable salt thereof, wherein the compound has structural Formula (IV):

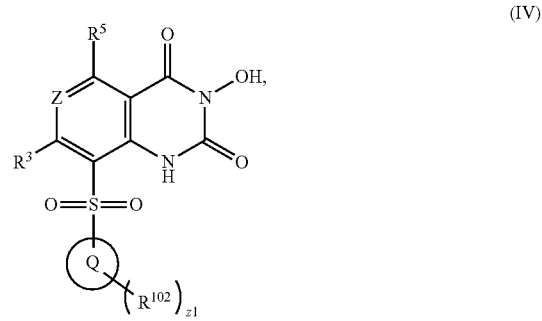

(IV)

wherein:
Q is substituted or unsubstituted cycloalkyl, substituted or unsubstituted heterocycloalkyl, substituted or unsubstituted aryl or substituted or unsubstituted heteroaryl;
z1 is an integer from 0 to 6;
m102 is an integer from 1 to 2;
n102 is an integer from 0 to 3;
v102 is an integer from 1 to 2;
$R^{102}$ is hydrogen, halogen, —$CX^{102}_3$, —$CHX^{102}_2$, —$CH_2X^{102}$, —CN, —$SO_{n102}R^{102B}$, —$SO_{v102}NR^{102A}R^{102B}$, —$NHC(O)NR^{102A}R^{102B}$, —$N(O)_{m102}$, —$NR^{102A}R^{102B}$, —$C(O)R^{102C}$, —$C(O)OR^{102C}$, —$C(O)NR^{102A}R^{102B}$, —$OR^{102D}$, —$NR^{102A}SO_2R^{102D}$, —$R^{102A}C(O)R^{102C}$, —$NR^{102A}C(O)OR^{102C}$, —$NR^{102A}OR^{102C}$, —$OCX^{102}_3$, —$OCHX^{102}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102B}$ and $R^{102C}$ substituents bonded to the same nitrogen atom may optionally be joined to form a substituted or unsubstituted heterocycloalkyl or substituted or unsubstituted heteroaryl;

$R^{102A}$, $R^{102B}$, $R^{102C}$ and $R^{102D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102B}$ and $R^{102C}$ substituents bonded to the same nitrogen atom may optionally be joined to form a substituted or unsubstituted heterocycloalkyl or substituted or unsubstituted heteroaryl; and $X^{102}$ is independently —F, —Cl, —Br, or —I.

Embodiment 36

The compound of embodiment 35, wherein Z is N.

Embodiment 37

The compound of embodiment 35, or a pharmaceutically acceptable salt thereof, wherein the compound has structural Formula (V):

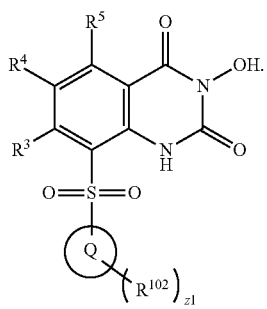

(V)

Embodiment 38

The compound of embodiment 37, wherein $R^3$, $R^4$ and $R^5$ are independently hydrogen, halogen, substituted or unsubstituted alkyl or substituted or unsubstituted heteroalkyl.

Embodiment 39

The compound of embodiment 37, wherein $R^5$ is halogen, substituted or unsubstituted alkyl or substituted or unsubstituted heteroalkyl.

Embodiment 40

The compound of embodiment 37, wherein Q is substituted or unsubstituted aryl or substituted or unsubstituted heteroaryl.

Embodiment 41

The compound of embodiment 37, wherein Q is substituted or unsubstituted heteroaryl.

Embodiment 42

The compound of embodiment 37, wherein Q is substituted or unsubstituted thiophenyl, substituted or unsubstituted pyridinyl, substituted or unsubstituted pyrazinyl, substituted or unsubstituted pyrimidinyl, substituted or unsubstituted furanyl, substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted furazanyl, substituted or unsubstituted 1,2,3-oxadiazolyl, substituted or unsubstituted 1,2,4-oxadiazolyl, substituted or unsubstituted 1,2,5-oxadiazolyl, substituted or unsubstituted 1,3,4-oxadiazolyl, substituted or unsubstituted 1,2,3-thiadiazolyl, substituted or unsubstituted 1,2,4-thiadiazolyl, substituted or unsubstituted 1,2,5-thiadiazolyl, substituted or unsubstituted 1,3,4-thiadiazolyl, substituted or unsubstituted benzothiophenyl, substituted or unsubstituted benzofuranyl, substituted or unsubstituted indolyl, substituted or unsubstituted isoindolyl, substituted or unsubstituted indazolyl, substituted or unsubstituted benzimidazolyl, substituted or unsubstituted benzthiazolyl, substituted or unsubstituted benzoisoxazolyl or substituted or unsubstituted benzoimidazolyl.

Embodiment 43

The compound of embodiment 37, or a pharmaceutically acceptable salt thereof, wherein the compound has structural Formula (VI):

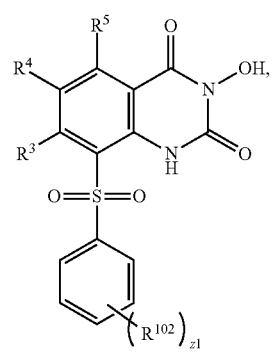

(VI)

wherein z1 is an integer from 0 to 5.

Embodiment 44

The compound of embodiment 43, wherein $R^{102}$ is hydrogen, halogen, —CN, —NHC(O)$NR^{102A}R^{102B}$, —$NR^{102B}$, —$OR^{102D}$, substituted or unsubstituted alkyl, substituted or unsubstituted heteroalkyl, substituted or unsubstituted aryl or substituted or unsubstituted heteroaryl Embodiment 45

The compound of embodiment 43, or a pharmaceutically acceptable salt thereof, wherein the compound has structural Formula (VIa):

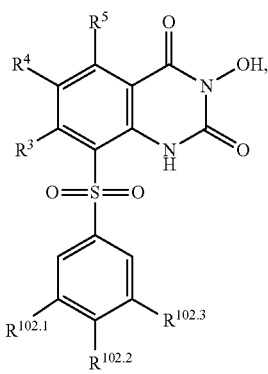

(VIa)

wherein:
m102.1, m102.2 and m102.3 are independently an integer from 1 to 2;
n102.1, n102.2 and n102.3 are independently an integer from 0 to 3;
v102.1, v102.2 and v102.3 are independently an integer from 1 to 2;
$R^{102.1}$ is hydrogen, halogen, $-CX^{102.1}_3$, $-CHX^{102.1}_2$, $-CH_2X^{102.1}$, $-CN$, $-SO_{n102.1}R^{102.1B}$, $-SO_{v102.1}NR^{102.1A}R^{102.1B}$, $-NHC(O)NR^{102.1A}R^{102.1B}$, $-N(O)_{m102.1}$, $-NR^{102.1A}R^{102.1B}$, $-C(O)R^{102.1C}$, $-C(O)-OR^{102.1C}$, $-C(O)NR^{102.1A}R^{102.1B}$, $-OR^{102.1D}$, $-NR^{102.1A}SO_2R^{102.1D}$, $-NR^{102.1A}C(O)R^{102.1C}$, $-NRC^{102.1A}(O)OR^{102.1C}$, $-NR^{102.1A}OR^{102.1C}$, $-OCX^{102.1}_3$, $-OCHX^{102.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.1B}$ and $R^{102.1C}$ substituents bonded to the same nitrogen atom may optionally be joined to form a substituted or unsubstituted heterocycloalkyl or substituted or unsubstituted heteroaryl;

$R^{102.2}$ is hydrogen, halogen, $-CX^{102.2}_3$, $-CHX^{102.2}_2$, $-CH_2X^{102.2}$, $-CN$, $-SO_{n102.2}R^{102.2B}$, $-SO_{v102.2}NR^{102.2A}R^{102.2B}$, $-NHC(O)NR^{102.2A}R^{102.2B}$, $-N(O)_{m102.2}$, $-NR^{102.2A}R^{102.2B}$, $-C(O)R^{102.2C}$, $-C(O)-OR^{102.2C}$, $-C(O)NR^{102.2A}R^{102.2B}$, $-OR^{102.2D}$, $-NR^{102.2A}SO_2R^{102.2D}$, $-NR^{102.2A}C(O)R^{102.2C}$, $-NR^{102.2A}C(O)OR^{102.2C}$, $-NR^{102.2A}OR^{102.2C}$, $-OCX^{102.2}_3$, $-OCHX^{102.2}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.2B}$ and $R^{102.2C}$ substituents bonded to the same nitrogen atom may optionally be joined to form a substituted or unsubstituted heterocycloalkyl or substituted or unsubstituted heteroaryl;

$R^{102.3}$ is hydrogen, halogen, $-CX^{102.3}_3$, $-CHX^{102.3}_2$, $-CH_2X^{102.3}$, $-CN$, $-SO_{n102.3}R^{102.3B}$, $-SO_{v102.3}NR^{102.3A}R^{102.3B}$, $-NHC(O)NR^{102.3A}R^{102.3B}$, $-N(O)_{m102.3}$, $-NR^{102.3A}R^{102.3B}$, $-C(O)R^{102.3C}$, $-C(O)-OR^{102.3C}$, $-C(O)NR^{102.3A}R^{102.3B}$, $-OR^{102.3D}$, $-NR^{102.3A}SO_2R^{102.3D}$, $-NR^{102.3A}C(O)R^{102.3C}$, $-NR^{102.3A}C(O)OR^{102.3C}$, $-NR^{102.3A}OR^{102.3C}$, $-OCX^{102.3}_3$, $-OCHX^{102.3}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.3B}$ and $R^{102.3C}$ substituents bonded to the same nitrogen atom may optionally be joined to form a substituted or unsubstituted heterocycloalkyl or substituted or unsubstituted heteroaryl; $R^{102.1}$ and $R^{102.2}$ or $R^{102.2}$ and $R^{102.3}$ may optionally be joined to form a substituted or unsubstituted cycloalkyl, substituted or unsubstituted heterocycloalkyl, substituted or unsubstituted aryl or substituted or unsubstituted heteroaryl;

$R^{102.1A}$, $R^{102.1B}$, $R^{102.1C}$, $R^{102.1D}$, $R^{102.2A}$, $R^{102.2B}$, $R^{102.2C}$, $R^{102.2D}$, $-R^{102.3A}$, $R^{102.3B}$, $R^{102.3C}$ and $R^{102.3D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.1B}$ and $R^{102.1C}$ and $R^{102.2B}$ and $R^{102.2C}$ and $R^{102.3B}$ and $R^{102.3C}$ substituents bonded to the same nitrogen atom may optionally be joined to form a substituted or unsubstituted heterocycloalkyl or substituted or unsubstituted heteroaryl; and $X^{102.1}$, $X^{102.2}$ and $X^{102.3}$ are independently $-F$, $-Cl$, $-Br$, or $-I$.

Embodiment 46

The compound of embodiment 45, wherein:
$R^{102.1}$ is hydrogen, halogen, $-CN$, $-NHC(O)NR^{102.1A}R^{102.1B}$, $-NR^{102.1A}R^{102.1B}$, $-OR^{102.1D}$, substituted or unsubstituted alkyl, substituted or unsubstituted heteroalkyl, substituted or unsubstituted aryl or substituted or unsubstituted heteroaryl;
$R^{102.2}$ is hydrogen, halogen, $-CN$, $-NHC(O)NR^{102.2A}R^{102.2B}$, $-NR^{102.2A}R^{102.2B}$, $-OR^{102.2D}$, substituted or unsubstituted alkyl, substituted or unsubstituted heteroalkyl, substituted or unsubstituted aryl or substituted or unsubstituted heteroaryl; and
$R^{102.3}$ is hydrogen, halogen, $-CN$, $-NHC(O)NR^{102.3A}R^{102.3B}$, $-NR^{102.3A}R^{102.3B}$, $-OR^{102.3D}$, substituted or unsubstituted alkyl, substituted or unsubstituted heteroalkyl, substituted or unsubstituted aryl or substituted or unsubstituted heteroaryl.

Embodiment 47

The compound of embodiment 1, or a pharmaceutically acceptable salt thereof, wherein the compound has structural Formula (VII):

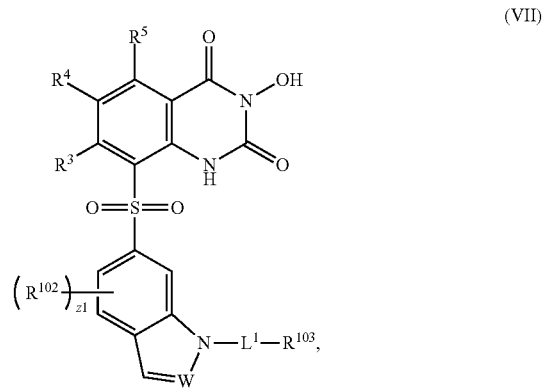

(VII)

wherein:

W is independently $CR^{102.4}$ or N;

$L^1$ is a bond, substituted or unsubstituted alkylene or substituted or unsubstituted heteroalkylene, substituted or unsubstituted cycloalkylene or substituted or unsubstituted heterocycloalkylene, substituted or unsubstituted arylene or substituted or unsubstituted heteroarylene;

z1 is an integer from 0 to 3;

m102, m102.4 and m103 are independently an integer from 1 to 2;

n102, n102.4 and n103 are independently an integer from 0 to 3;

v102, v102.4 and v103 are independently an integer from 1 to 2;

$R^{102}$ is hydrogen, halogen, $-CX^{102}_3$, $-CHX^{102}_2$, $-CH_2X^{102}$, $-CN$, $-SO_{n102}R^{102B}$, $-SO_{v102}NR^{102A}R^{102B}$, $-NHC(O)NR^{102A}R^{102B}$, $-N(O)_{m102}$, $-NR^{102A}R^{102B}$, $-C(O)R^{102C}$, $-C(O)OR^{102C}$, $-C(O)NR^{102A}R^{102B}$, $-OR^{102D}$, $-NR^{102A}SO_2R^{102D}$, $-NR^{102A}(O)R^{102C}$, $-NR^{102A}C(O)OR^{102C}$, $-NR^{102A}OR^{102C}$, $-OCX^{102}_3$, $-OCHX^{102}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102B}$ and $R^{102C}$ substituents bonded to the same nitrogen atom may optionally be joined to form a substituted or unsubstituted heterocycloalkyl or substituted or unsubstituted heteroaryl;

$R^{102.4}$ is hydrogen, halogen, $-CX^{102.4}_3$, $-CHX^{102.4}_2$, $-CH_2X^{102.4}$, $-CN$, $-SO_{n102.4}R^{102.4B}$, $-SO_{v102.4}NR^{102.4A}NR^{102.4B}$, $-NHC(O)NR^{102.4A}R^{102.4B}$, $-N(O)_{m102.4}$, $-NR^{102.4A}R^{102.4B}$, $-C(O)R^{102.4C}$, $-C(O)-OR^{102.4C}$, $-C(O)NR^{102.4A}R^{102.4B}$, $-OR^{102.4D}$, $-NR^{102.4A}SO_2R^{102.4D}$, $-NR^{102.4A}C(O)R^{102.4C}$, $-NR^{102.4A}C(O)OR^{102.4C}$, $-NR^{102.4A}OR^{102.4C}$, $-OCX^{102.43}$, $-OCHX^{102.4}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or unsubstituted heteroaryl; $R^{102.4B}$ and $R^{102.4C}$ substituents bonded to the same nitrogen atom may optionally be joined to form a substituted or unsubstituted heterocycloalkyl or substituted or unsubstituted heteroaryl;

$R^{103}$ is hydrogen, halogen, $-CX^{103}_3$, $-CHX^{103}_2$, $-CH_2X^{103}$, $-CN$, $-SO_{n103}R^{103B}$, $-SO_{v103}NR^{103A}R^{103B}$, $-NHC(O)NR^{103A}R^{103B}$, $-N(O)_{m103}$, $-NR^{103A}$, $R^{103B}$, $-C(O)R^{103C}$, $-C(O)-OR^{103C}$, $-C(O)NR^{103A}R^{103B}$, $-OR^{103D}$, $-NR^{103A}SO_2R^{103D}$, $-NR^{103A}(O)R^{103C}$, $-NR^{103A}C(O)OR^{3C}$, $-NR^{103A}OR^{3C}$, $-OCX^{103}_3$, $-OCHX^{103}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{103B}$ and $R^{103C}$ substituents bonded to the same nitrogen atom may optionally be joined to form a substituted or unsubstituted heterocycloalkyl or substituted or unsubstituted heteroaryl;

$R^{102A}$, $R^{102B}$, $R^{102C}$, $R^{102D}$, $R^{102.4A}$, $R^{102.4B}$, $R^{102.4C}$, $R^{102.4D}$, $-R^{103A}$, $R^{103B}$, $R^{103C}$ and $R^{103D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102B}$ and $R^{102C}$, $R^{102.4B}$ and $R^{102.4C}$ and $R^{103B}$ and $R^{103C}$ and substituents bonded to the same nitrogen atom may optionally be joined to form a substituted or unsubstituted heterocycloalkyl or substituted or unsubstituted heteroaryl; and $X^{102.4}$, $X^{102.4}$ and $X^{103}$ are independently $-F$, $-Cl$, $-Br$, or $-I$.

Embodiment 48

The compound of embodiment 47, wherein $R^3$, $R^4$ and $R^5$ are independently hydrogen, halogen, substituted or unsubstituted alkyl or substituted or unsubstituted heteroalkyl.

Embodiment 49

The compound of embodiment 47, wherein $R^5$ is halogen, substituted or unsubstituted alkyl or substituted or unsubstituted heteroalkyl.

Embodiment 50

The compound of embodiment 47, wherein $R^3$ and $R^4$ are independently hydrogen.

Embodiment 51

The compound of embodiment 47, wherein z1 is 1.

Embodiment 52

The compound of embodiment 1, or a pharmaceutically acceptable salt thereof, wherein the compound has structural Formula (VIII):

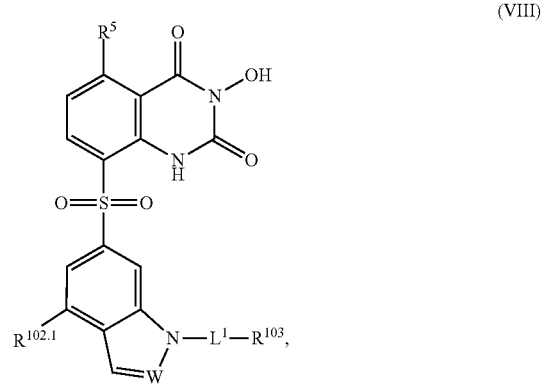

(VIII)

wherein:

W is independently $CR^{102.4}$ or N;

$L^1$ is a bond, substituted or unsubstituted alkylene or substituted or unsubstituted heteroalkylene, substituted or unsubstituted cycloalkylene or substituted or unsubstituted heterocycloalkylene, substituted or unsubstituted arylene or substituted or unsubstituted heteroarylene;

m102.1, m102.4 and m103 are independently an integer from 1 to 2;

n102.1, n102.4 and n103 are independently an integer from 0 to 3;

v102.1, v102.4 and v103 are independently an integer from 1 to 2;

$R^{102.1}$ is hydrogen, halogen, —$CX^{102.1}_3$, —$CHX^{102.1}_2$, —$CH_2X^{102.1}$, —CN, —$SO_{n102.1}R^{102.1D}$, —$SO_{v102.1}NR^{102.1A}R^{102.1B}$, —NHC(O)NR^{102.1A}R^{102.1B}$, —$N(O)_{m102.1}$, —$N^{102.1A}R^{102.1B}$, —$C(O)R^{102.1C}$, —$C(O)$—$OR^{102.1C}$, —$C(O)NR^{102.1A}R^{102.1B}$, —$OR^{102.1D}$, —$NR^{102.1A}SO_2R^{102.1D}$ —$NR^{102.1A}(O)R^{102.1C}$, —$NR^{102.1A}C(O)OR^{102.1C}$, —$NR^{102.1A}OR^{102.1C}$, —$OCX^{102.1}_3$, —$OCHX^{102.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.1B}$ and $R^{102.1C}$ substituents bonded to the same nitrogen atom may optionally be joined to form a substituted or unsubstituted heterocycloalkyl or substituted or unsubstituted heteroaryl; $R^{102.1}$ and $R^{102.2}$ or $R^{102.2}$ and $R^{102.1}$ may optionally be joined to form a substituted or unsubstituted cycloalkyl, substituted or unsubstituted heterocycloalkyl, substituted or unsubstituted aryl or substituted or unsubstituted heteroaryl;

$R^{102.4}$ is hydrogen, halogen, —$CX^{102.4}_3$, —$CHX^{102.4}_2$, —$CH_2X^{102.4}$, —CN, —$SO_{n102.4}R^{102.4D}$, —$SO_{v102.4}NR^{102.4A}R^{102.4B}$, —NHC(O)NR^{102.4A}R^{102.4B}$, —$N(O)_{m102.4}$, —$NR^{102.4A}R^{102.4B}$, —C(O) $R^{102.4C}$, —$C(O)$—$OR^{102.4C}$, —$C(O)NR^{102.4A}R^{102.4B}$, —$OR^{102.4D}$, —$NR^{102.4A}SO_2R^{102.4D}$, —$NR^{102.4A}C(O)R^{102.4C}$, —$NR^{102.4A}C(O)OR^{102.4C}$, —$NR^{102.4A}OR^{102.4C}$, —$OCX^{102.4}_3$, —$OCHX^{102.4}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.4B}$ and $R^{102.4C}$ substituents bonded to the same nitrogen atom may optionally be joined to form a substituted or unsubstituted heterocycloalkyl or substituted or unsubstituted heteroaryl;

$R^{103}$ is hydrogen, halogen, —$CX^{103}_3$, —$CHX^{103}_2$, —$CH_2X^{103}$, —CN, —$SO_{n103}R^{103D}$, —$SO_{v103}NR^{103A}R^{103B}$, —NHC(O)NR^{103A}R^{103B}$, —$N(O)_{m103}$, —$NR^{103A}R^{103B}$, —$C(O)R^{103C}$, —C(O)—$OR^{103C}$, —$C(O)NR^{103A}R^{103B}$, —$OR^{103D}$, —$NR^{103A}SO_2R^{103D}$, —$NR^{103A}C(O)R^{103C}$, —$NR^{103A}C(O)OR^{103C}$, —$NR^{103A}OR^{103C}$, —$OCX^{103}_3$, —$OCHX^{103}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{103B}$ and $R^{103C}$ substituents bonded to the same nitrogen atom may optionally be joined to form a substituted or unsubstituted heterocycloalkyl or substituted or unsubstituted heteroaryl;

$R^{102.1A}$, $R^{102.1B}$, $R^{102.1C}$, $R^{102.1D}$, $R^{102.4A}$, $R^{102.4B}$, $R^{102.4C}$, $R^{102.4D}$, —$R^{103A}$, $R^{103B}$, $R^{103C}$ and $R^{103D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.1B}$ and $R^{102.1C}$ and $R^{102.4B}$ and $R^{102.4C}$ and $R^{103B}$ and $R^{103C}$ substituents bonded to the same nitrogen atom may optionally be joined to form a substituted or unsubstituted heterocycloalkyl or substituted or unsubstituted heteroaryl; and $X^{102.1}$, $X^{102.4}$ and $X^{103}$ are independently —F, —Cl, —Br, or —I.

Embodiment 53

The compound of embodiment 52, wherein $R^{103}$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 54

The compound of embodiment 52, wherein $R^5$ is halogen, substituted or unsubstituted alkyl or substituted or unsubstituted heteroalkyl.

Embodiment 55

The compound of embodiment 52, wherein $R^5$ is halogen.

Embodiment 56

The compound of embodiment 52, wherein $R^5$ is chlorine.

Embodiment 57

The compound of embodiment 52, wherein $R^{102.1}$ is hydrogen or halogen.

Embodiment 58

The compound of embodiment 52, wherein $L^1$ is substituted or unsubstituted alkylene or substituted or unsubstituted heteroalkylene.

Embodiment 59

The compound of embodiment 58, wherein $R^{103}$ is substituted or unsubstituted cycloalkyl, substituted or unsubstituted heterocycloalkyl, substituted or unsubstituted heteroaryl, substituted or unsubstituted aryl or substituted or unsubstituted heteroaryl.

Embodiment 60

The compound of embodiment 59, wherein W is N.

Embodiment 61

The compound of embodiment 59, wherein W is CH.

Embodiment 62

The compound of embodiment 52, wherein $L^1$ is substituted or unsubstituted cycloalkylene, substituted or unsubstituted heterocycloalkylene, substituted or unsubstituted arylene or substituted or unsubstituted heteroarylene.

Embodiment 63

The compound of embodiment 62, wherein W is N.

Embodiment 64

The compound of embodiment 62, wherein W is CH.

Embodiment 65

The compound of embodiment 52, wherein $R^{103}$ is substituted or unsubstituted cycloalkyl, substituted or unsubstituted heterocycloalkyl, substituted or unsubstituted heteroaryl, substituted or unsubstituted aryl or substituted or unsubstituted heteroaryl.

Embodiment 66

The compound of embodiment 65, wherein $L^1$ is a bond.

Embodiment 67

The compound of embodiment 66, wherein W is N.

Embodiment 68

The compound of embodiment 66, wherein W is CH.

Embodiment 69

A pharmaceutical composition comprising the compound of any one of embodiments 26 to 68, or a pharmaceutically acceptable salt thereof, and a pharmaceutically acceptable excipient.

Embodiment 70

A method of inhibiting nuclease activity, comprising: contacting the nuclease with an effective amount of the compound of any one of embodiments 1 to 22 or 26 to 68, or a pharmaceutically acceptable salt thereof.

Embodiment 71

The method of embodiment 70, wherein the nuclease is an endonuclease.

Embodiment 72

The method of embodiment 70, wherein the nuclease is an exonuclease.

Embodiment 73

The method of embodiment 70, wherein the nuclease is a resolvase.

Embodiment 74

The method of embodiment 70, wherein the nuclease is Flap structure-specific endonuclease 1(FEN-1), GEN1, Exonuclease 1 (EXO1) or Xeroderma Pigmentosum Complementation Group G protein (XPG).

Embodiment 75

A method of treating cancer, comprising administering to a subject in need thereof a therapeutically effective amount of a compound, or pharmaceutically acceptable salt thereof, of any one of embodiments 26 to 68.

Embodiment 76

The method of embodiment 72, comprising administering at least one additional anticancer agent in combination with a compound, or pharmaceutically acceptable salt thereof, of any one of embodiments 1 to 22 or 26 to 68.

Embodiment 77

The method of embodiment 76, wherein the anticancer agent is an immunotherapeutic anticancer agent.

Embodiment 78

A pharmaceutical composition, comprising a combination of a compound of any one of embodiments 1 to 22 or 26 to 68 and at least one an additional anticancer agent.

VI. Examples

Synthesis of 5-chloro-3-hydroxy-8-(m-tolylsulfonyl)quinazoline-2,4(1H,3H)-dione (48)

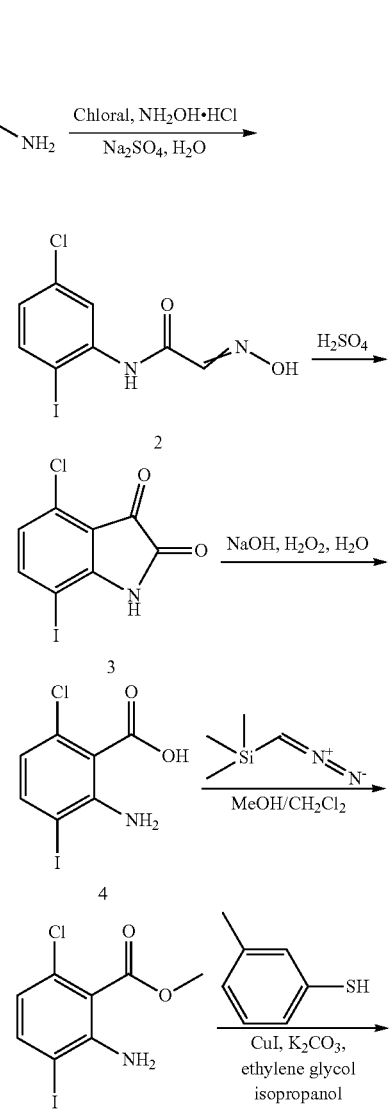

Scheme 1

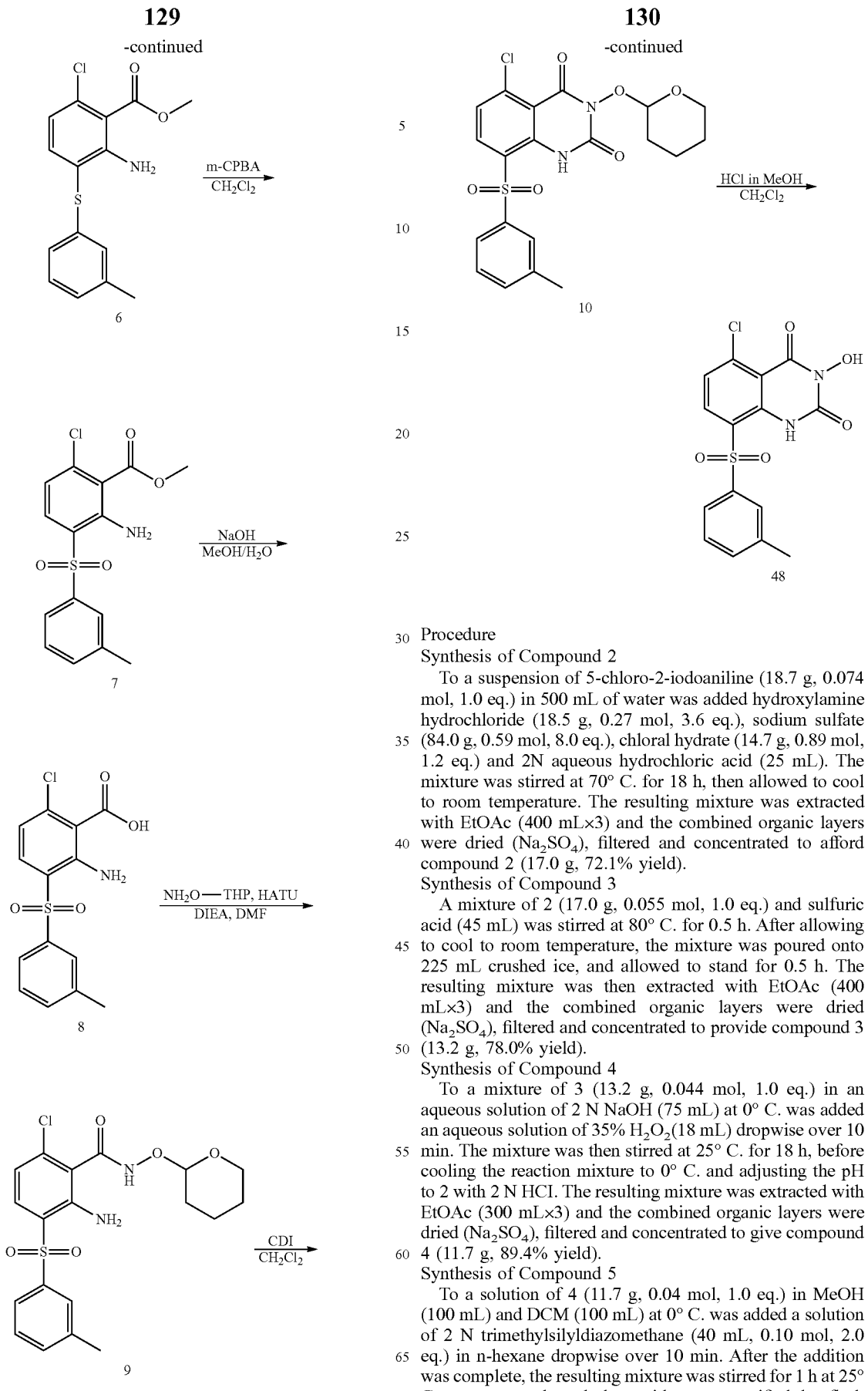

Procedure

Synthesis of Compound 2

To a suspension of 5-chloro-2-iodoaniline (18.7 g, 0.074 mol, 1.0 eq.) in 500 mL of water was added hydroxylamine hydrochloride (18.5 g, 0.27 mol, 3.6 eq.), sodium sulfate (84.0 g, 0.59 mol, 8.0 eq.), chloral hydrate (14.7 g, 0.89 mol, 1.2 eq.) and 2N aqueous hydrochloric acid (25 mL). The mixture was stirred at 70° C. for 18 h, then allowed to cool to room temperature. The resulting mixture was extracted with EtOAc (400 mL×3) and the combined organic layers were dried ($Na_2SO_4$), filtered and concentrated to afford compound 2 (17.0 g, 72.1% yield).

Synthesis of Compound 3

A mixture of 2 (17.0 g, 0.055 mol, 1.0 eq.) and sulfuric acid (45 mL) was stirred at 80° C. for 0.5 h. After allowing to cool to room temperature, the mixture was poured onto 225 mL crushed ice, and allowed to stand for 0.5 h. The resulting mixture was then extracted with EtOAc (400 mL×3) and the combined organic layers were dried ($Na_2SO_4$), filtered and concentrated to provide compound 3 (13.2 g, 78.0% yield).

Synthesis of Compound 4

To a mixture of 3 (13.2 g, 0.044 mol, 1.0 eq.) in an aqueous solution of 2 N NaOH (75 mL) at 0° C. was added an aqueous solution of 35% $H_2O_2$ (18 mL) dropwise over 10 min. The mixture was then stirred at 25° C. for 18 h, before cooling the reaction mixture to 0° C. and adjusting the pH to 2 with 2 N HCl. The resulting mixture was extracted with EtOAc (300 mL×3) and the combined organic layers were dried ($Na_2SO_4$), filtered and concentrated to give compound 4 (11.7 g, 89.4% yield).

Synthesis of Compound 5

To a solution of 4 (11.7 g, 0.04 mol, 1.0 eq.) in MeOH (100 mL) and DCM (100 mL) at 0° C. was added a solution of 2 N trimethylsilyldiazomethane (40 mL, 0.10 mol, 2.0 eq.) in n-hexane dropwise over 10 min. After the addition was complete, the resulting mixture was stirred for 1 h at 25° C., concentrated, and the residue was purified by flash column chromatography (PE/EA=30/1, v/v) to afford compound 5 (10.8 g, 86.8% yield).

Synthesis of Compound 6

To a solution of 5 (500 mg, 1.6 mmol, 1.0 eq.) in isopropanol (10 mL) were added 3-methylbenzenethiol (596 mg, 4.8 mmol, 3.0 eq.), ethylene glycol (397 mg, 6.4 mmol, 4.0 eq.), CuI (31 mg, 0.16 mmol, 0.1 eq) and $K_2CO_3$ (441 mg, 3.2 mol, 2.0 eq.). The resulting mixture was warmed to 80° C. and stirred for 18 h, before being concentrated. The residue was purified by flash column chromatography (PE/EA=10/1 to PE/EA=4:1, v/v) to provide compound 6 (295 mg, 60.1% yield).

Synthesis of Compound 7

To a solution of 6 (295 mg, 0.98 mmol, 1.0 eq.) in DCM (25 mL) at 0° C. was added m-CPBA (422 mg, 2.45 mol, 2.5 eq.). The resulting mixture was stirred at 25° C. for 18 h, before being diluted with DCM (100 mL) and washed with 10% aq. $NaHCO_3$. The organic layer was dried ($Na_2SO_4$), filtered and concentrated. The residue was purified by flash column chromatography (PE/EA=5/1 to PE/EA=3:1, v/v) to give compound 7 (225 mg, 67.6% yield) as a white solid.

Synthesis of Compound 8

NaOH (106 mg, 2.64 mol, 4.0 eq) was added to a solution of 7 (225 mg, 0.66 mmol, 1.0 eq.) in MeOH (6 mL) and $H_2O$ (6 mL). The resulting reaction mixture was warmed to 80° C. and stirred for 2 h, before being cooled to 0° C. and adjusting the pH to 2 with 2 N HCl. The resulting mixture was extracted with EtOAc (50 mL×3) and the combined organic layers were dried ($Na_2SO_4$) and concentrated to afford compound 8 (170 mg, 79.1% yield).

Synthesis of Compound 9

To a solution of 8 (170 mg, 0.52 mmol, 1.0 eq.) in DMF (5 mL) at 25° C. was added $NH_2$—OTHP (122 mg, 1.04 mmol, 2.0 eq.), HATU (217 mg, 0.57 mmol, 1.1 eq.) and DIEA (335 mg, 2.6 mmol, 5.0 eq.). The resulting mixture was stirred at 25° C. for 18 h, diluted with $H_2O$ (25 mL) and extracted with EtOAc (50 mL×3). The combined organic layers were washed with brine (50 mL×3), dried ($Na_2SO_4$) and concentrated. The residue was purified by flash column chromatography (PE/EA=4/1 to PE/EA=2:1, v/v) to afford compound 9 (147 mg, 57.5% yield).

Synthesis of Compound 10

CDI (247 mg, 3.5 mmol, 5.0 eq.) was added to a solution of 9 (147 mg, 0.35 mmol, 1.0 eq.) in DCM (20 mL) at 25° C. The resulting solution was then maintained at 50° C. for 18 h, allowed to cool to 25° C., and washed with brine (20 mL). The organic layer was dried ($Na_2SO_4$) and concentrated. The residue was purified by flash column chromatography (PE/EA=4/1 to DCM/MeOH=10:1, /v) to provide compound 10 (114 mg, 72.2% yield).

Synthesis of Compound 48

2 N HCl/MeOH (0.26 mL, 0.52 mol, 4.0 eq.) was added to a solution of 10 (60 mg, 0.13 mol, 1.0 eq.) in DCM (8 mL) and MeOH (8 mL) and was maintained at at 25° C. for 30 mins. before being concentrated and purified by prep-HPLC to afford compound 11 (16.0 mg, 33.5% yield) as a white solid. LR-MS: 366.7 $[M+1]^+$ m/z calculated 367.0, found 366.7. $^1$HNMR (400 MHz, DMSO-d6): δ 10.93 (s, 1H), 10.01 (s, 1H), 8.19 (d, 1H), 7.85-7.87 (m, 2H), 7.57-7.60 (m, 2H), 7.47 (d, 1H), 2.40 (s, 3H).

Enzymatic Assays

Fluorogenic biochemical assays used recombinant full-length FEN-1 or catalytic domains of Exo1, XPG or GEN1 and 200 nM of a DNA substrate (formed by annealing three oligonucleotides—quencher (5'-CAC GTT GAC TAC CGC TCA ATC CTG ACG AAC ACA TC-BHQ2), flap (5'-TAMRA-GA TGT CAA GCA GTC CTA ACT TTG AGG CAG AGT CCG C) and template (5'-GC GGA CTC TGC CTC AAG ACG GTA GTC AAC GTG-3') (PMID: 21062821)) in 50 mM Tris pH 8.0, 10 mM $MgCl_2$, 1 mM DTT, and 0.01% Tween-20. Inhibitors arrayed in dose response were added from DMSO stocks (using a V&P 384-pintool head) to the enzyme solution in low volume, black polystyrene 384-well plates (Corning #3677) 15 minutes prior to the addition of the DNA substrate. Reactions were allowed to proceed for 2-4 hours at 25° C. or 37° C. Fluorescence data (Excitation: 530 nm/10 nm bandwidth; Emission: 590 nm/20 nm bandwith) were measured with an Infinite M1000 plate reader (Tecan).

Table 1 provides select scaffold compounds and $IC_{50}$ data. Table 2 provides still more exemplary compounds.

TABLE 1

Selected Scaffold Compounds and $IC_{50}$ data.

| No. | Compound | SMD FEN-1 $IC_{50}$ (µM) |
|---|---|---|
| 11 | (structure: 5-chloro-3-hydroxyquinazoline-2,4(1H,3H)-dione) | 0.0208 |
| 12 | (structure: 3-hydroxyquinazoline-2,4(1H,3H)-dione) | 0.2407 |
| 13 | (structure: 3-hydroxypyrido[3,2-d]pyrimidine-2,4(1H,3H)-dione) | 1.3101 |
| 14 | (structure: 3-hydroxypyrido[2,3-d]pyrimidine-2,4(1H,3H)-dione) | 0.1062 |
| 15 | (structure: 3-hydroxy-7-phenylquinazoline-2,4(1H,3H)-dione) | 0.3561 |

TABLE 1-continued

Selected Scaffold Compounds and IC$_{50}$ data.

| No. | Compound | SMD FEN-1 IC$_{50}$ (μM) |
|---|---|---|
| 16 | | 0.3922 |
| 17 | | 3.3375 |
| 18 | | 0.1130 |
| 19 | | 0.1339 |
| 20 | | 2.8325 |
| 21 | | 0.0238 |
| 22 | | 0.0795 |
| 23 | | 0.01103 |
| 24 | | 0.0538 |
| 25 | | 1.6415 |
| 26 | | 0.0373 |

TABLE 1-continued

Selected Scaffold Compounds and IC$_{50}$ data.

| No. | Compound | SMD FEN-1 IC$_{50}$ (μM) |
|---|---|---|
| 27 | 7-benzyl-3-hydroxyquinazoline-2,4-dione | 0.0973 |
| 28 | 5-chloro-8-benzyl-3-hydroxyquinazoline-2,4-dione | 0.0772 |
| 29 | 7-(benzylsulfonyl)-3-hydroxyquinazoline-2,4-dione | 0.1601 |
| 30 | 8-(benzylsulfonyl)-3-hydroxyquinazoline-2,4-dione | 0.1288 |
| 31 | 8-((4-methylphenyl)sulfonyl)-3-hydroxyquinazoline-2,4-dione | 0.0242 |
| 32 | 8-((3-methylphenyl)sulfonyl)-3-hydroxyquinazoline-2,4-dione | 0.0145 |
| 33 | 8-((4-chlorophenyl)sulfonyl)-3-hydroxyquinazoline-2,4-dione | 0.0261 |
| 34 | 8-((3-chlorophenyl)sulfonyl)-3-hydroxyquinazoline-2,4-dione | 0.0264 |
| 35 | 5-bromo-3-hydroxyquinazoline-2,4-dione | 0.0196 |
| 36 | 8-fluoro-3-hydroxyquinazoline-2,4-dione | 0.0420 |

TABLE 1-continued

Selected Scaffold Compounds and IC$_{50}$ data.

| No. | Compound | SMD FEN-1 IC$_{50}$ (μM) |
|---|---|---|
| 37 | (7-fluoro-3-hydroxyquinazoline-2,4-dione) | 0.1710 |
| 38 | (6-fluoro-3-hydroxyquinazoline-2,4-dione) | 0.2165 |
| 39 | (5-fluoro-3-hydroxyquinazoline-2,4-dione) | 0.0544 |
| 40 | (6-fluoro-8-(phenylsulfonyl)-3-hydroxyquinazoline-2,4-dione) | 0.0156 |
| 41 | (3-hydroxy-8-((3-(trifluoromethyl)phenyl)sulfonyl)quinazoline-2,4-dione) | 0.0133 |
| 42 | (3-hydroxy-8-((3-methoxyphenyl)sulfonyl)quinazoline-2,4-dione) | 0.0165 |
| 43 | (5-chloro-3-hydroxy-8-(phenylsulfonyl)quinazoline-2,4-dione) | 0.0099 |
| 44 | (6-chloro-3-hydroxy-8-(m-tolylsulfonyl)quinazoline-2,4-dione) | 0.0109 |
| 45 | (8-((4-bromophenyl)sulfonyl)-3-hydroxyquinazoline-2,4-dione) | 0.0140 |

TABLE 1-continued

Selected Scaffold Compounds and IC$_{50}$ data.

| No. | Compound | SMD FEN-1 IC$_{50}$ (μM) |
|---|---|---|
| 46 | 8-(3-bromophenylsulfonyl)-3-hydroxyquinazoline-2,4(1H,3H)-dione | 0.0129 |
| 47 | 8-(3-hydroxyphenylsulfonyl)-3-hydroxyquinazoline-2,4(1H,3H)-dione | 0.0157 |
| 48 | 5-chloro-3-hydroxy-8-(3-methylphenylsulfonyl)quinazoline-2,4(1H,3H)-dione | 0.0093 |
| 49 | 8-(3-aminophenylsulfonyl)-3-hydroxyquinazoline-2,4(1H,3H)-dione | 0.0354 |
| 50 | 3-hydroxy-8-(3,5-dimethylphenylsulfonyl)quinazoline-2,4(1H,3H)-dione | 0.0116 |
| 51 | 7-fluoro-3-hydroxy-8-(3-methylphenylsulfonyl)quinazoline-2,4(1H,3H)-dione | 0.0192 |
| 52 | 7-chloro-3-hydroxy-8-(3-methylphenylsulfonyl)quinazoline-2,4(1H,3H)-dione | 0.1389 |
| 53 | 6-fluoro-3-hydroxy-8-(3-methylphenylsulfonyl)quinazoline-2,4(1H,3H)-dione | 0.0137 |

TABLE 1-continued
Selected Scaffold Compounds and IC$_{50}$ data.
| No. | Compound | SMD FEN-1 IC$_{50}$ (μM) |
|---|---|---|
| 54 | 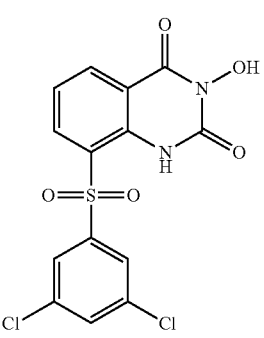 [SMILES: O=c1[nH]c2c(S(=O)(=O)c3cc(Cl)cc(Cl)c3)cccc2c(=O)n1O] | 0.0181 |
| 55 | 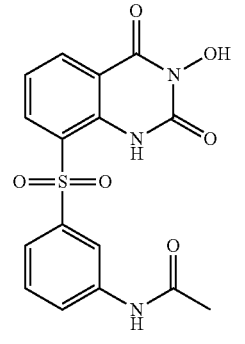 [SMILES: CC(=O)Nc1cccc(S(=O)(=O)c2cccc3c(=O)n(O)c(=O)[nH]c23)c1] | 0.0165 |
| 56 | 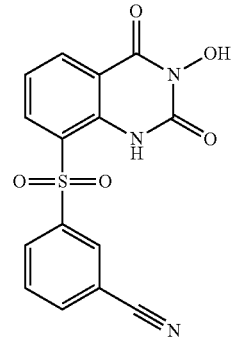 [SMILES: N#Cc1cccc(S(=O)(=O)c2cccc3c(=O)n(O)c(=O)[nH]c23)c1] | 0.0148 |
| 57 | 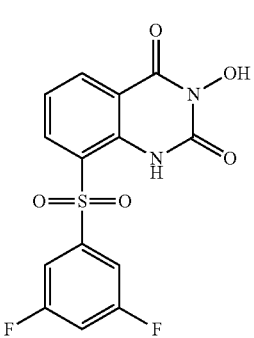 | 0.0128 |
| 58 | 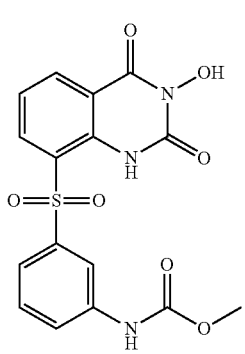 | 0.0128 |
| 59 | 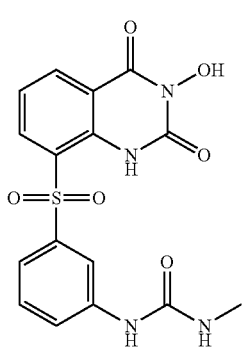 [SMILES: CNC(=O)Nc1cccc(S(=O)(=O)c2cccc3c(=O)n(O)c(=O)[nH]c23)c1] | 0.0141 |
| 60 | 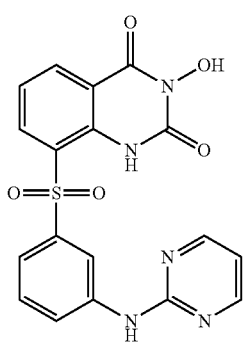 [SMILES: O=c1[nH]c2c(S(=O)(=O)c3cccc(Nc4ncccn4)c3)cccc2c(=O)n1O] | 0.0160 |
| 61 | 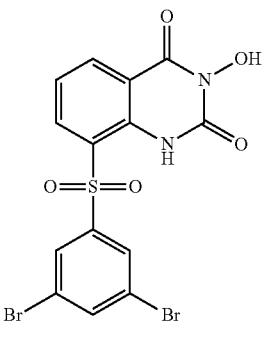 | 0.0166 |

TABLE 1-continued

Selected Scaffold Compounds and IC$_{50}$ data.

| No. | Compound | SMD FEN-1 IC$_{50}$ (μM) |
|---|---|---|
| 62 | 3-hydroxy-8-[(3-(pyridin-2-ylamino)phenyl)sulfonyl]quinazoline-2,4(1H,3H)-dione | 0.0289 |
| 63 | 1-(3-((3-hydroxy-2,4-dioxo-1,2,3,4-tetrahydroquinazolin-8-yl)sulfonyl)phenyl)urea | 0.0169 |
| 64 | 8-((3-(dimethylamino)phenyl)sulfonyl)-3-hydroxyquinazoline-2,4(1H,3H)-dione | 0.0149 |
| 65 | 8-((3,5-dimethoxyphenyl)sulfonyl)-3-hydroxyquinazoline-2,4(1H,3H)-dione | 0.0170 |
| 66 | 8-((3,5-dihydroxyphenyl)sulfonyl)-3-hydroxyquinazoline-2,4(1H,3H)-dione | 0.0093 |
| 67 | 5-fluoro-3-hydroxy-8-(m-tolylsulfonyl)quinazoline-2,4(1H,3H)-dione | 0.0178 |
| 68 | 7-fluoro-3-hydroxy-8-(phenylsulfonyl)quinazoline-2,4(1H,3H)-dione | 0.0944 |
| 69 | 8-((3-fluorophenyl)sulfonyl)-3-hydroxyquinazoline-2,4(1H,3H)-dione | 0.0100 |

TABLE 1-continued

Selected Scaffold Compounds and IC$_{50}$ data.

| No. | Compound | SMD FEN-1 IC$_{50}$ (μM) |
|---|---|---|
| 70 | (structure: 5-Cl, 8-(3-fluorophenylsulfonyl) 3-hydroxyquinazoline-2,4-dione) | 0.0098 |
| 71 | (structure: 5-Cl, 8-(3,5-difluorophenylsulfonyl) 3-hydroxyquinazoline-2,4-dione) | 0.0067 |
| 72 | (structure: 8-(1H-benzimidazol-5-ylsulfonyl) 3-hydroxyquinazoline-2,4-dione) | 0.0056 |
| 73 | (structure: 8-(3,5-diacetamidophenylsulfonyl) 3-hydroxyquinazoline-2,4-dione) | 0.0076 |
| 74 | (structure: 8-(3,5-diaminophenylsulfonyl) 3-hydroxyquinazoline-2,4-dione) | 0.0085 |
| 75 | (structure: 8-(thiophen-2-ylsulfonyl) 3-hydroxyquinazoline-2,4-dione) | 0.0116 |
| 76 | (structure: 5-Cl, 8-(3-chloro-5-methylphenylsulfonyl) 3-hydroxyquinazoline-2,4-dione) | 0.0094 |
| 77 | (structure: 5-Cl, 8-(3-fluoro-5-methylphenylsulfonyl) 3-hydroxyquinazoline-2,4-dione) | 0.0085 |

TABLE 1-continued

Selected Scaffold Compounds and IC₅₀ data.

| No. | Compound | SMD FEN-1 IC₅₀ (μM) |
|---|---|---|
| 78 | (structure) | 0.0066 |
| 79 | (structure) | 0.0166 |
| 80 | (structure) | 0.0094 |
| 81 | (structure) | 0.0184 |

TABLE 2

Selected Scaffold Compounds 82 (structure)

83 (structure)

84 (structure)

TABLE 2-continued
Selected Scaffold Compounds
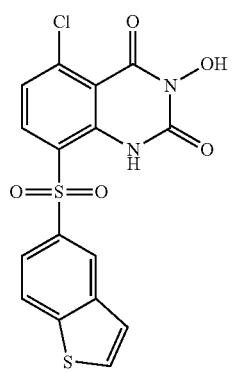
85
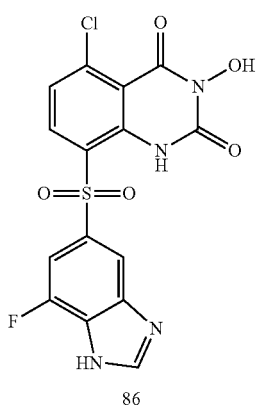 [SMILES: O=c1[nH]c2c(S(=O)(=O)c3cc(F)c4[nH]cnc4c3)ccc(Cl)c2c(=O)n1O]
86
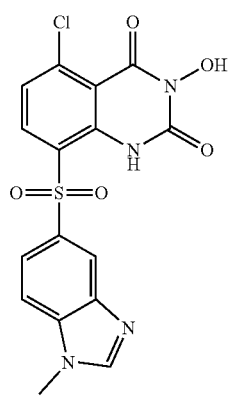
87
TABLE 2-continued
Selected Scaffold Compounds
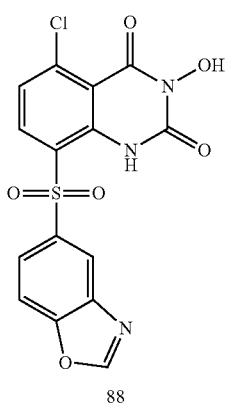 [SMILES: O=c1[nH]c2c(S(=O)(=O)c3ccc4ocnc4c3)ccc(Cl)c2c(=O)n1O]
88
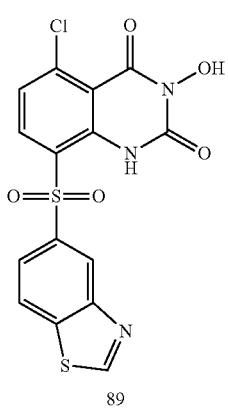
89
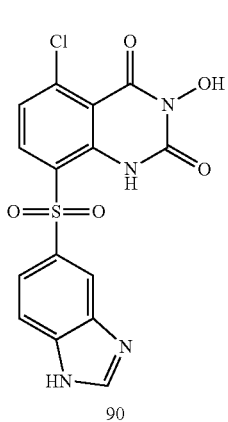 [SMILES: O=c1[nH]c2c(S(=O)(=O)c3ccc4scnc4c3)ccc(Cl)c2c(=O)n1O]
90

TABLE 2-continued
Selected Scaffold Compounds
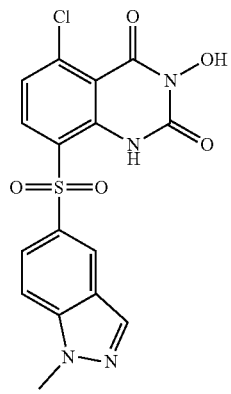
91
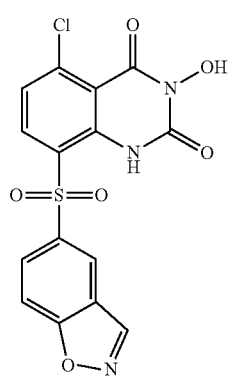
92
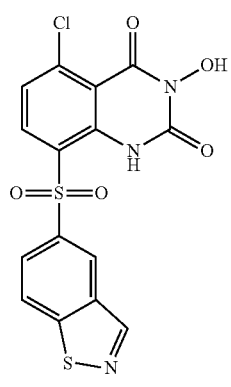
93
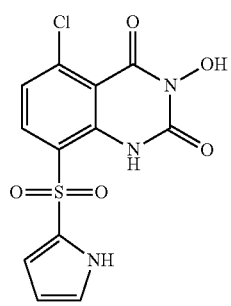
94
TABLE 2-continued
Selected Scaffold Compounds
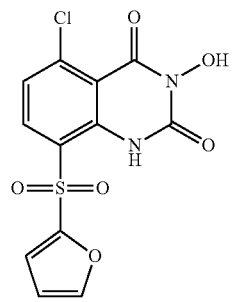
95
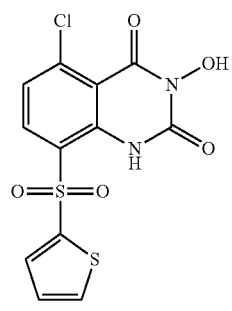
96
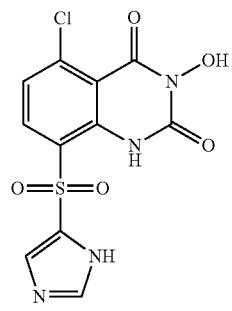
97
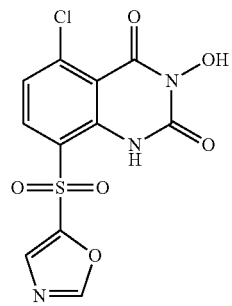
98

TABLE 2-continued
Selected Scaffold Compounds
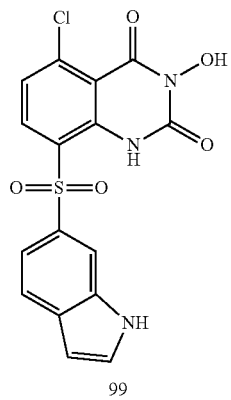 [SMILES: O=c1[nH]c2c(S(=O)(=O)c3ccc4cc[nH]c4c3)ccc(Cl)c2c(=O)n1O]
99
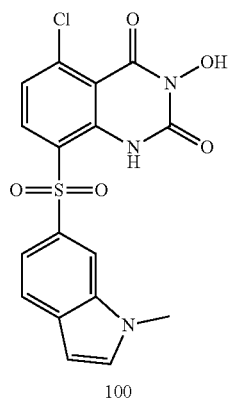 [SMILES: Cn1ccc2ccc(S(=O)(=O)c3ccc(Cl)c4c(=O)n(O)c(=O)[nH]c34)cc21]
100
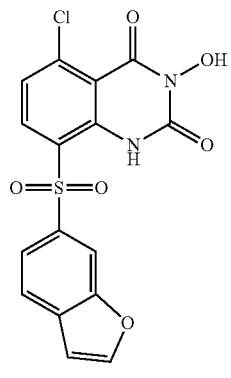
101
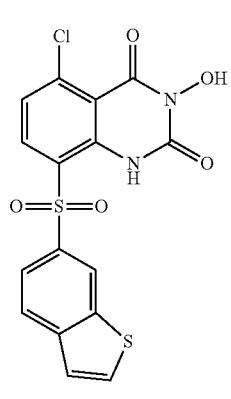
102
TABLE 2-continued
Selected Scaffold Compounds
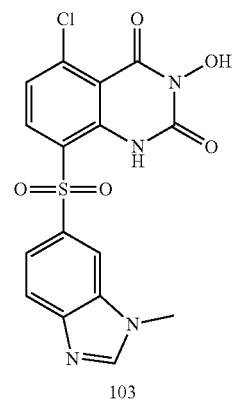 [SMILES: Cn1cnc2ccc(S(=O)(=O)c3ccc(Cl)c4c(=O)n(O)c(=O)[nH]c34)cc21]
103
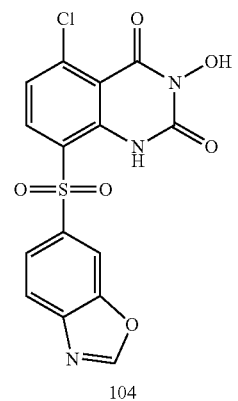 [SMILES: O=c1[nH]c2c(S(=O)(=O)c3ccc4ncoc4c3)ccc(Cl)c2c(=O)n1O]
104
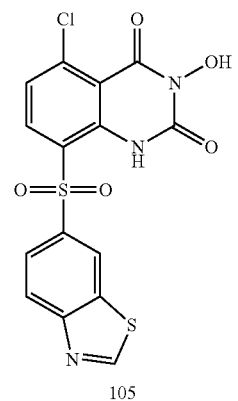 [SMILES: O=c1[nH]c2c(S(=O)(=O)c3ccc4ncsc4c3)ccc(Cl)c2c(=O)n1O]
105

TABLE 2-continued
Selected Scaffold Compounds
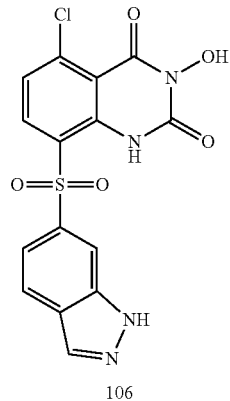 [SMILES: O=c1[nH]c2c(S(=O)(=O)c3ccc4cn[nH]c4c3)ccc(Cl)c2c(=O)n1O]
106
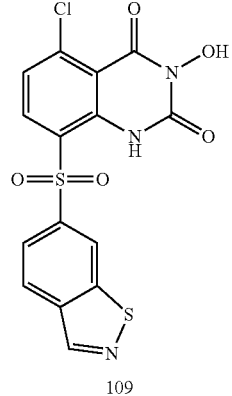
109
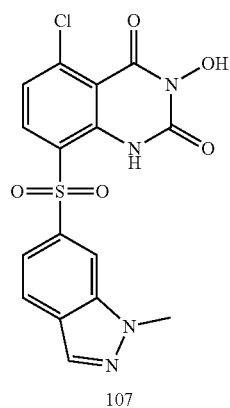 [SMILES: Cn1ncc2ccc(S(=O)(=O)c3ccc(Cl)c4c(=O)n(O)c(=O)[nH]c34)cc21]
107
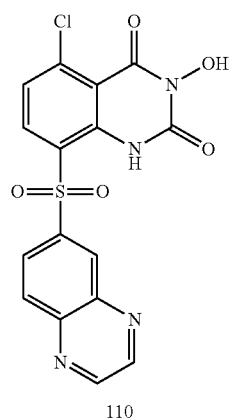 [SMILES: O=c1[nH]c2c(S(=O)(=O)c3ccc4nccnc4c3)ccc(Cl)c2c(=O)n1O]
110
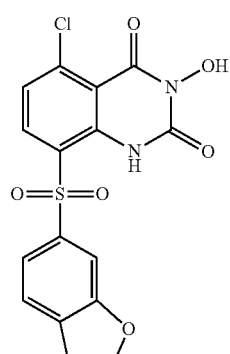
108
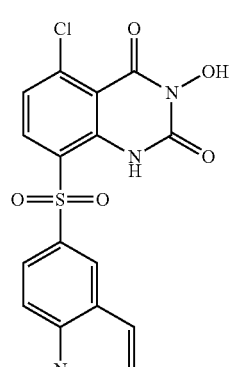
111

TABLE 2-continued
Selected Scaffold Compounds
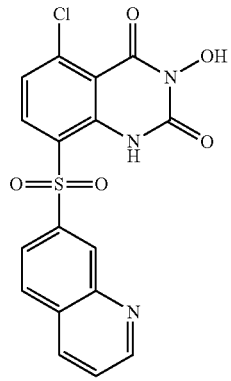
112
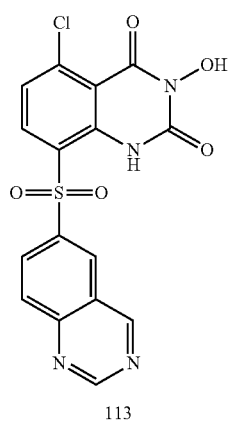 [SMILES: O=c1[nH]c2c(S(=O)(=O)c3ccc4ncccc4c3)ccc(Cl)c2c(=O)n1O]
113
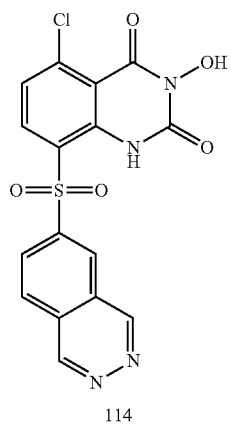 [SMILES: O=c1[nH]c2c(S(=O)(=O)c3ccc4cnncc4c3)ccc(Cl)c2c(=O)n1O]
114
TABLE 2-continued
Selected Scaffold Compounds
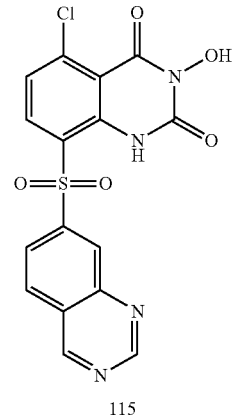 [SMILES: O=c1[nH]c2c(S(=O)(=O)c3ccc4cncnc4c3)ccc(Cl)c2c(=O)n1O]
115
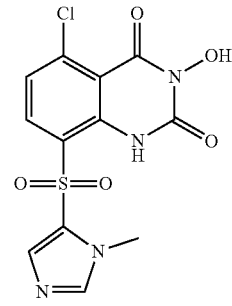
116
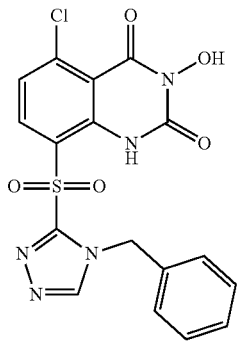
117
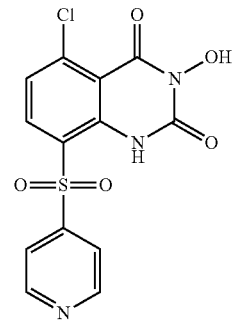
118

TABLE 2-continued
Selected Scaffold Compounds
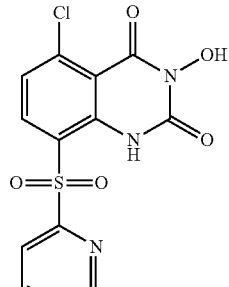
119
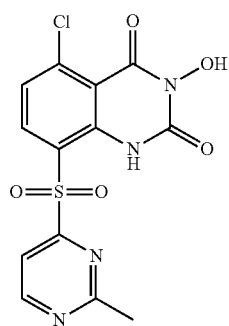
120
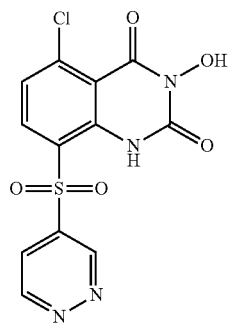
121
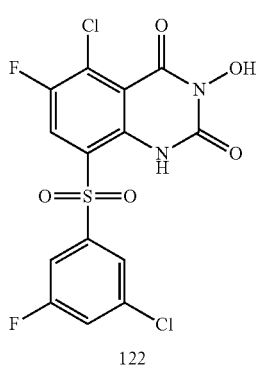 [SMILES: O=c1[nH]c2c(S(=O)(=O)c3cc(F)cc(Cl)c3)cc(F)c(Cl)c2c(=O)n1O]
122
TABLE 2-continued
Selected Scaffold Compounds
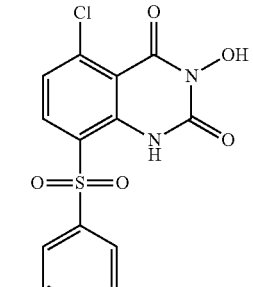
123
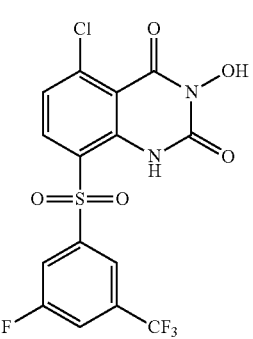
124
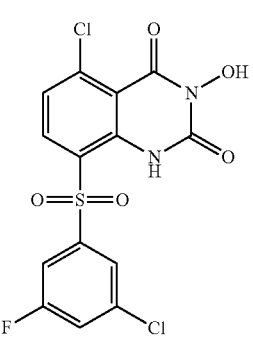
125
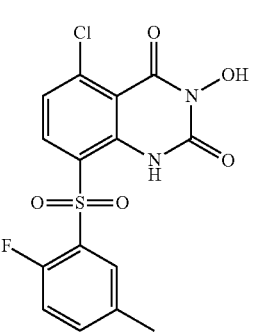
126

TABLE 2-continued

Selected Scaffold Compounds

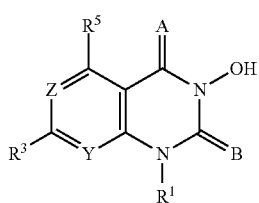

127

128

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula (I):

(I)

or a pharmaceutically acceptable salt thereof wherein,
A is independently O, S, or $NR^A$;
B is independently O, S, or $NR^B$;
Y is $CR^2$;
Z is independently $CR^4$ or N;
$R^1$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is independently $-SO_{n2}R^9$ or $-SO_{v2}NR^6R^7$;
$R^3$ is independently hydrogen, halogen, $-CX^3_3$, $-CHX^3_2$, $-CH_2X^3$, $-CN$, $-SO_{n3}R^{13}$, $-SO_{v3}NR^{10}R^{11}$, $-NHC(O)NR^{10}R^{11}$, $-N(O)_{m3}$, $-NR^{10}R^{11}$, $-C(O)R^{12}$, $-C(O)-OR^{12}$, $-OR^{13}$, $-NR^{10}SO_2R^{13}$, $-NR^{10}C(O)R^{12}$, $-NR^{10}C(O)OR^{12}$, $-NR^{10}OR^{12}$, $-OCX^3_3$, $-OCHX^3_2$, substituted or unsubstituted alkyl, substituted or unsubstituted heteroalkyl, substituted or unsubstituted cycloalkyl, substituted or unsubstituted aryl, or substituted or unsubstituted heteroaryl;
$R^4$ is independently hydrogen, halogen, $-CX^4_3$, $-CHX^4_2$, $-CH_2X^4$, $-CN$, $-SO_{n4}R^{17}$, $-SO_{v4}NR^{14}R^{15}$, $-NHC(O)NR^{14}R^{15}$, $-N(O)_{m4}$, $-NR^{14}R^{15}$, $-C(O)R^{16}$, $-C(O)-OR^{16}$, $-C(O)NR^{14}R^{15}$, $-OR^{17}$, $-NR^{14}SO_2R^{17}$, $-NR^{14}C(O)R^{16}$, $-NR^{14}C(O)OR^{16}$, $-NR^{14}R^{16}$, $-OCX^4_3$, $-OCHX^4_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is independently hydrogen, halogen, $-CX^5_3$, $-CHX^5_2$, $-CH_2X^5$, $-CN$, $-SO_{n5}R^{21}$, $-SO_{v5}NR^{18}R^{19}$, $-NHC(O)NR^{18}R^{19}$, $-N(O)_{m5}$, $-NR^{18}R^{19}$, $-C(O)R^{20}$, $-C(O)-OR^{20}$, $-C(O)NR^{18}R^{19}$, $-OR^{21}$, $-NR^{18}SO_2R^{21}$, $-NR^{18}C(O)R^{20}$, $-NR^{18}C(O)OR^{20}$, $-NR^{18}OR^{20}$, $-OCX^5_3$, $-OCHX^5_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
each $R^A$, $R^B$, $R^6$, $R^7$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ and $R^7$, $R^{10}$, and $R^{11}$, $R^{14}$ and $R^{15}$, and $R^{18}$ and $R^{19}$ substituents bonded to the same nitrogen atom may optionally be joined to form a substituted or unsubstituted heterocycloalkyl or substituted or unsubstituted heteroaryl;
each X, $X^3$, $X^4$, and $X^5$ is independently $-F$, $-Cl$, $-Br$, or $-I$;
each m3, m4, and m5 is independently an integer from 1 to 2;
each n3, n4, and n5 is independently an integer from 0 to 3;
n2 is an integer from 1 to 3; and
each v2, v3, v4, and v5 is independently an integer from 1 to 2.

2. The compound of claim 1, wherein $R^1$ is hydrogen.
3. The compound of claim 1, wherein:
A is O, S, or $NR^A$;
B is O, S, or $NR^B$; and
$R^A$ and $R^B$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.
4. A pharmaceutical composition comprising the compound of claim 1, or a pharmaceutically acceptable salt thereof, and a pharmaceutically acceptable excipient.

5. A method of inhibiting Flap structure-specific endonuclease 1(FEN-1) activity, said method comprising contacting the FEN-1 with an effective amount of the compound of claim 1, or a pharmaceutically acceptable salt thereof.

6. A method of treating cancer, said method comprising administering to a subject in need thereof an effective amount of a compound of claim 1, or a pharmaceutically acceptable salt thereof.

7. The compound of claim 1, or a pharmaceutically acceptable salt thereof, wherein the compound has structural Formula (II):

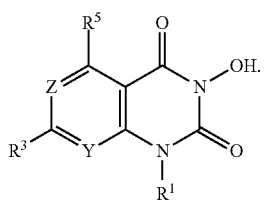

(II)

8. The compound of claim 1, or a pharmaceutically acceptable salt thereof, wherein the compound has structural Formula (III):

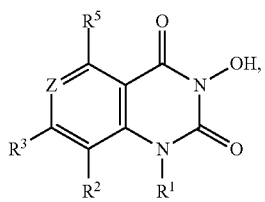

(III)

wherein $R^1$ is hydrogen, substituted or unsubstituted alkyl, substituted or unsubstituted heteroalkyl, substituted or unsubstituted aryl or substituted or unsubstituted heteroary; and $R^2$ is $-SO_{n2}R^9$ or $-SO_{v2}NR^6R^7-$.

9. The compound of claim 1, or a pharmaceutically acceptable salt thereof, wherein the compound has structural Formula (IV):

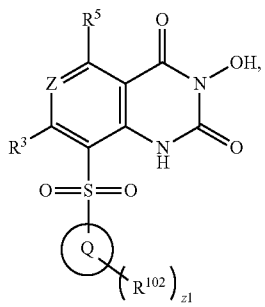

(IV)

wherein:

Q is substituted or unsubstituted cycloalkyl, substituted or unsubstituted heterocycloalkyl, substituted or unsubstituted aryl or substituted or unsubstituted heteroaryl;

z1 is an integer from 0 to 6;

m102 is an integer from 1 to 2;

n102 is an integer from 0 to 3;

v102 is an integer from 1 to 2;

$R^{102}$ is hydrogen halogen, $-CX^{102}_3$, $-CHX^{102}_2$, $-CH_2X^{102}$, $-CN$, $-SO_{n102}R^{102D}$, $-SO_{v102}NR^{102A}R^{102B}$, $-NHC(O)NR^{102A}R^{102B}$, $-N(O)_{m102}$, $-NR^{102A}R^{102B}$, $-C(O)R^{102C}$, $-C(O)-OR^{102C}$, $-C(O)NR^{102A}R^{102B}$, $-OR^{102D}$, $-NR^{102A}SO_2R^{102D}$, $-NR^{102A}C(O)R^{102C}$, $-NR^{102A}C(O)OR^{102C}$, $-NR^{102A}OR^{102C}$, $-OCX^{102}_3$, $-OCHX^{102}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102B}$ and $R^{102C}$ substituents bonded to the same nitrogen atom may optionally be joined to form a substituted or unsubstituted heterocycloalkyl or substituted or unsubstituted heteroaryl;

$R^{102A}$, $R^{102B}$, $R^{102C}$ and $R^{102D}$ are independtly hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102B}$ and $R^{102C}$ substiuents bonded to the same nitrogen atom may optionally be joined to form a substituted or unsubstituted heterocycloalkyl or substituted or unsubstituted heteroaryl;

$X^{102}$ is independently $-F$, $-Cl$, $-Br$, or $-I$; and

Z is N.

10. The compound of claim 9, or a pharmaceutically acceptable salt thereof, wherein the compound has structural Formula (V):

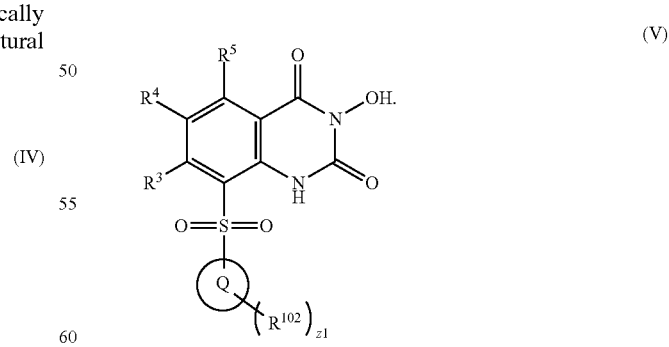

(V)

11. The compound of claim 10, or a pharmaceutically acceptable salt thereof, wherein the compound has structural Formula (VI):

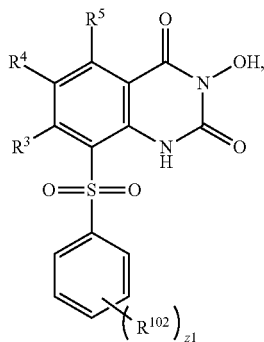

(VI)

wherein:
z1 is an integer from 0 to 5; and
$R^{102}$ is hydrogen, halogen, —CN, —NHC(O)NR$^{102A}$R$^{102B}$, —NR$^{102A}$R$^{102B}$, —OR$^{102D}$, substituted or unsubstituted alkyl, substituted or unsubstituted heteroalkyl, substituted or unsubstituted aryl or substituted or unsubstituted heteroaryl.

12. The compound of claim 1, or a pharmaceutically acceptable salt thereof, wherein the compound has structural Formula (VII):

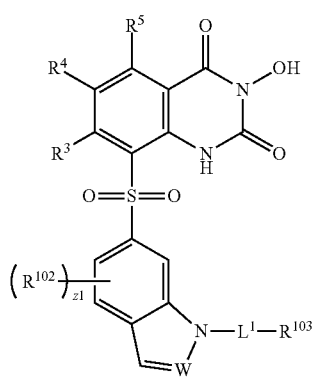

(VII)

wherein:
W is independently CR$^{102.4}$ or N;
$L^1$ is a bond, substituted or unsubstituted alkylene or substituted or unsubstituted heteroalkylene, substituted or unsubstituted cycloalkylene or substituted or unsubstituted heterocycloalkylene, substituted or unsubstituted arylene or substituted or unsubstituted heteroarylene;
z1 is an integer from 0 to 3;
$m^{102}$, $m^{102.4}$ and $m^{103}$ are independently an integer from 1 to 2;
$n^{102}$, $n^{102.4}$ and $n^{103}$ are independently an integer from 0 to 3;
$v^{102}$, $v^{102.4}$ and $v^{103}$ are independently an integer from 1 to 2;
$R^{102}$ is hydrogen, halogen, —CX$^{102}_3$, —CHX$^{102}_2$, —CH$_2$X$^{102}$, —CN, —SO$_{n102}$R$^{102D}$, —SO$_{v102}$NR$^{102A}$R$^{102B}$, —NHC(O)NR$^{102A}$R$^{102B}$, —N(O)$_{m102}$, —NR$^{102A}$R$^{102B}$, —C(O)R$^{102C}$, —C(O)—OR$^{102C}$, —C(O)NR$^{102A}$R$^{102B}$, —OR$^{102D}$, —NR$^{102A}$SO$_2$R$^{102D}$, —NR$^{102A}$C(O)R$^{102C}$, —NR$^{102A}$C(O)OR$^{102C}$, —NR$^{102A}$OR$^{102C}$, —OCX$^{102}_3$, —OCHX$^{102}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102B}$ and $R^{102C}$ substituents bonded to the same nitrogen atom may optionally be joined to form a substituted or unsubstituted heterocycloalkyl or substituted or unsubstituted heteroaryl;

$R^{102.4}$ is hydrogen, halogen, —CX$^{102.4}_3$, —CHX$^{102.4}_2$, —CH$_2$X$^{102.4}$, —CN, —SO$_{n102.4}$R$^{102.4D}$, —SO$_{v102.4}$NR$^{102.4A}$R$^{102.4B}$, —NHC(O)NR$^{102.4A}$R$^{102.4B}$, —N(O)$_{m102.4}$, —NR$^{102.4A}$R$^{102.4B}$, —C(O)R$^{102.4C}$, —C(O)—OR$^{102.4C}$, —C(O)NR$^{102.4A}$R$^{102.4B}$, —OR$^{102.4D}$, —NR$^{102.4A}$SO$_2$R$^{102.4D}$, —NR$^{102.4A}$C(O)R$^{102.4C}$, —NR$^{102.4A}$C(O)OR$^{102.4C}$, —NR$^{102.4A}$OR$^{102.4C}$, —OCX$^{102.4}_3$, —OCHX$^{102.4}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.4B}$ and $R^{102.4C}$ substituents bonded to the same nitrogen atom may optionally be joined to form a substituted or unsubstituted heterocycloalkyl or substituted or unsubstituted heteroaryl;

$R^{103}$ is hydrogen, halogen, —CX$^{103}_3$, —CHX$^{103}_2$, —CH$_2$X$^{103}$, —CN, —SO$_{n103}$R$^{103D}$, —SO$_{v103}$NR$^{103A}$R$^{103B}$, —NHC(O)NR$^{103A}$R$^{103B}$, —N(O)$_{m103}$, —NR$^{103A}$R$^{103B}$, —C(O)R$^{103C}$, —C(O)—OR$^{103C}$, —C(O)NR$^{103A}$R$^{103B}$, —OR$^{103D}$, —NR$^{103A}$SO$_2$R$^{103D}$, —NR$^{103A}$C(O)R$^{103C}$, —NR$^{103A}$C(O)OR$^{103C}$, —NR$^{103A}$OR$^{103C}$, —OCX$^{103}_3$, —OCHX$^{103}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{103B}$ and $R^{103C}$ substituents bonded to the same nitrogen atom may optionally be joined to form a substituted or unsubstituted heterocycloalkyl or substituted or unsubstituted heteroaryl;

$R^{102A}$, $R^{102B}$, $R^{102C}$, $R^{102D}$, $R^{102.4A}$, $R^{102.4B}$, $R^{102.4C}$, $R^{102.4D}$, $R^{103A}$, $R^{103B}$, $R^{103C}$ and, $R^{103D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102B}$ and $R^{102C}$, $R^{102.4B}$ and $R^{102.4C}$ and $R^{103B}$ and $R^{103C}$ and substituents bonded to the same nitrogen atom may optionally be joined to form a substituted or unsubstituted heterocycloalkyl or substituted or unsubstituted heteroaryl;

$X^{102}$, $X^{102.4}$ and $X^{103}$ are independently —F, —Cl, —Br, or —I; and $R^3$, $R^4$ and $R^5$ are independently hydrogen, halogen, substituted or unsubstituted alkyl or substituted or unsubstituted heteroalkyl.

13. The compound of claim 1, or a pharmaceutically acceptable salt thereof, wherein the compound has structural Formula (VIII):

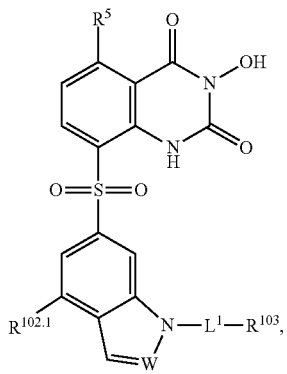

(VIII)

wherein:

W is independently $CR^{102.4}$ or N;

$L^1$ is a bond, substituted or unsubstituted alkylene or substituted or unsubstituted heteroalkylene, substituted or unsubstituted cycloalkylene or substituted or unsubstituted heterocycloalkylene, substituted or unsubstituted arylene or substituted or unsubstituted heteroarylene;

m102.1, $m^{102.4}$ and $m^{103}$ are independently an integer from 1 to 2;

$n^{102.1}$, $n^{102.4}$ and $n^{103}$ are independently an integer from 0 to 3;

$v^{102.1}$, $v^{102.4}$ and $v^{103}$ are independently an integer from 1 to 2;

$R^{102.1}$ is hydrogen, halogen, —$CX^{102.1}_3$, —$CHX^{102.1}_2$, —$CH_2X^{102.1}$, —CN, —$SO_{n102.1}R^{102.1D}$, —$SO_{v102.1}NR^{102.1A}R^{102.1B}$, —NHC(O)$NR^{102.1A}R^{102.1B}$, —N(O)$_{m102.1}$, —$NR^{102.1A}R^{102.1B}$, —C(O)$R^{102.1C}$, —C(O)—$OR^{102.1C}$, —C(O)$NR^{102.1A}R^{102.1B}$, —$OR^{102.1D}$, —$NR^{102.1A}SO_2R^{102.1D}$, —$NR^{102.1A}C(O)R^{102.1C}$, —$NR^{102.1A}C(O)OR^{102.1C}$, —$NR^{102.1A}OR^{102.1C}$, —$OCX^{102.1}_3$, —$OCHX^{102.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.1B}$ and $R^{102.1C}$ substituents bonded to the same nitrogen atom may optionally be joined to form a substituted or unsubstituted heterocycloalkyl or substituted or unsubstituted heteroaryl; $R^{102.1}$ and $R^{102.2}$ or $R^{102.2}$ and $R^{102.1}$ may optionally be joined to form a substituted or unsubstituted cycloalkyl, substituted or unsubstituted heterocycloalkyl, substituted or unsubstituted aryl or substituted or unsubstituted heteroaryl;

$R^{102.4}$ is hydrogen, halogen, —$CX^{102.4}_3$, —$CHX^{102.4}_2$, —$CH_2X^{102.4}$, —CN, —$SO_{n102.4}R^{102.4D}$, —$SO_{v102.4}NR^{102.4A}R^{102.4B}$, —NHC(O)$NR^{102.4A}R^{102.4B}$, —N(O)$_{m102.4}$, —$NR^{102.4A}R^{102.4B}$, —C(O)$R^{102.4C}$, —C(O)—$OR^{102.4C}$, —C(O)$NR^{102.4A}R^{102.4B}$, —$OR^{102.4D}$, —$NR^{102.4A}SO_2R^{102.4D}$, —$NR^{102.4A}C(O)R^{102.4C}$, —$NR^{102.4A}C(O)OR^{102.4C}$, —$NR^{102.4A}OR^{102.4C}$, —$OCX^{102.4}_3$, —$OCHX^{102.4}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.4B}$ and $R^{102.4C}$ substituents bonded to the same nitrogen atom may optionally be joined to form a substituted or unsubstituted heterocycloalkyl or substituted or unsubstituted heteroaryl;

$R^{103}$ is hydrogen, halogen, —$CX^{103}_3$, —$CHX^{103}_2$, —$CH_2X^{103}$, —CN, —$SO_{n103}R^{103D}$, —$SO_{v103}NR^{103A}R^{103B}$, —NHC(O)$NR^{103A}R^{103B}$, —N(O)$_{m103}$, —$NR^{103A}R^{103B}$, —C(O)$R^{103C}$, —C(O)—$OR^{103C}$, —C(O)$NR^{103A}R^{103B}$, —$OR^{103D}$, —$NR^{103A}SO_2R^{103D}$, —$NR^{103A}C(O)R^{103C}$, —$NR^{103A}C(O)OR^{103C}$, —$NR^{103A}OR^{103C}$, —$OCX^{103}_3$, —$OCHX^{103}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{103B}$ and $R^{103C}$ substituents bonded to the same nitrogen atom may optionally be joined to form a substituted or unsubstituted heterocycloalkyl or substituted or unsubstituted heteroaryl;

$R^{102.1A}$, $R^{102.1B}$, $R^{102.1C}$, $R^{102.1D}$, $R^{102.4A}$, $R^{102.4B}$, $R^{102.4C}$, $R^{102.4D}$, $R^{103A}$, $R^{103B}$, $R^{103C}$, and $R^{103D}$ are independently hydrogen, halogen, —$CF_3$, —$CCl_3$, —$CBr_3$, —$Cl_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{102.1B}$ and $R^{102.1C}$ and $R^{102.4B}$ and $R^{102.4C}$ and $R^{103B}$ and $R^{103C}$ substituents bonded to the same nitrogen atom may optionally be joined to form a substituted or unsubstituted heterocycloalkyl or substituted or unsubstituted heteroaryl;

$X^{102.1}$, $X^{102.4}$ and $X^{103}$ are independently —F, —Cl, —Br, or —I; and $R^5$ is halogen, substituted or unsubstituted alkyl or substituted or unsubstituted heteroalkyl.

14. A pharmaceutical composition comprising the compound of claim 7, or a pharmaceutically acceptable salt thereof, and a pharmaceutically acceptable excipient.

15. A method of inhibiting nuclease activity comprising contacting the nuclease with an effective amount of the compound of claim 1, or a pharmaceutically acceptable salt thereof.

16. The method of claim 15, wherein the nuclease is an endonuclease; an exonuclease, or a resolvase.

17. A method of treating cancer comprising administering to a subject in need thereof a therapeutically effective amount of a compound, or pharmaceutically acceptable salt thereof, of claim 7.

18. The method of claim 17, further comprising administering at least one additional anticancer agent.

19. The method of claim 18, wherein the anticancer agent is an immunotherapeutic anticancer agent.

20. A pharmaceutical composition, comprising a combination of a compound of claim 7 and at least one an additional anticancer agent.

* * * * *